US007425444B2

(12) United States Patent
Jestin et al.

(10) Patent No.: US 7,425,444 B2
(45) Date of Patent: Sep. 16, 2008

(54) CIRCOVIRUS SEQUENCES ASSOCIATED WITH PIGLET WEIGHT LOSS DISEASE (PWD)

(75) Inventors: André Jestin, Saint-Brieuc (FR); Emmanuel Albina, Trégueux (FR); Pierre Le Cann, Plédran (FR); Philippe Blanchard, Plérin (FR); Evelyne Hutet, Plérin (FR); Claire Arnauld, Saint-Brieuc (FR); Catherine Truong, Saint-Brieuc (FR); Dominique Mahe, Saint-Carreuc (FR); Roland Cariolet, Ploufragan (FR); François Madec, Saint-Brieuc (FR)

(73) Assignee: Wyeth

(*) Notice: Subject to any disclaimer, the term of this patent is extended or adjusted under 35 U.S.C. 154(b) by 4 days.

(21) Appl. No.: 11/588,306

(22) Filed: Oct. 27, 2006

(65) Prior Publication Data

US 2007/0041990 A1 Feb. 22, 2007

Related U.S. Application Data

(60) Division of application No. 10/718,264, filed on Nov. 21, 2003, now Pat. No. 7,179,472, which is a division of application No. 09/514,245, filed on Feb. 28, 2000, now Pat. No. 6,703,023, which is a continuation-in-part of application No. PCT/FR98/02634, filed on Dec. 4, 1998.

(30) Foreign Application Priority Data

Dec. 5, 1997 (FR) .................................. 97 15396

(51) Int. Cl.
*C12N 15/00* (2006.01)

(52) U.S. Cl. .................. 435/320.1; 435/235.1; 435/325

(58) Field of Classification Search ............. 435/320.1, 435/235.1, 325; 514/44
See application file for complete search history.

(56) References Cited

U.S. PATENT DOCUMENTS

| | | | |
|---|---|---|---|
| 4,946,787 | A | 8/1990 | Eppstein et al. |
| 5,106,733 | A | 4/1992 | Baker et al. |
| 5,382,425 | A | 1/1995 | Cochran et al. |
| 5,459,127 | A | 10/1995 | Felgner et al. |
| 5,498,413 | A | 3/1996 | Casal Alvarez et al. |
| 5,545,412 | A | 8/1996 | Eppstein et al. |
| 5,580,859 | A | 12/1996 | Felgner et al. |
| 5,587,164 | A | 12/1996 | Sanderson et al. |
| 5,703,055 | A | 12/1997 | Felgner et al. |
| 5,705,385 | A | 1/1998 | Bally et al. |
| 5,719,131 | A | 2/1998 | Harris et al. |
| 5,756,103 | A | 5/1998 | Paoletti et al. |
| 5,770,212 | A | 6/1998 | Falkner et al. |
| 5,795,872 | A | 8/1998 | Ricigliano et al. |
| 5,811,103 | A | 9/1998 | Meyers et al. |
| 5,820,869 | A | 10/1998 | Wasmoen et al. |
| 5,833,975 | A | 11/1998 | Paoletti et al. |
| 5,888,513 | A | 3/1999 | Plana Duran et al. |
| 5,910,488 | A | 6/1999 | Nabel et al. |
| 5,990,091 | A | 11/1999 | Tartaglia et al. |
| 6,004,777 | A | 12/1999 | Tartaglia et al. |
| 6,015,694 | A | 1/2000 | Dubensky, Jr. et al. |
| 6,019,980 | A | 2/2000 | Li et al. |
| 6,033,904 | A | 3/2000 | Cochran et al. |
| 6,143,333 | A | 11/2000 | Gordon et al. |
| 6,143,334 | A | 11/2000 | Reinbold et al. |
| 6,143,734 | A | 11/2000 | Garvey et al. |
| 6,165,493 | A | 12/2000 | Neurath et al. |
| 6,207,165 | B1 | 3/2001 | Audonnet et al. |
| 6,217,883 | B1 | 4/2001 | Allan et al. |
| 6,287,856 | B1 | 9/2001 | Poet et al. |
| 6,368,601 | B1 | 4/2002 | Allan |
| 6,391,314 | B1 | 5/2002 | Allan et al. |
| 6,475,779 | B2 | 11/2002 | Mathiowitz et al. |
| 6,497,883 | B1 | 12/2002 | Bublot et al. |
| 6,517,843 | B1 | 2/2003 | Ellis et al. |
| 6,573,081 | B2 | 6/2003 | Bernhardt et al. |
| 6,660,272 | B2 | 12/2003 | Allan et al. |
| 6,703,023 | B1 | 3/2004 | Jestin et al. |
| 6,794,163 | B2 | 9/2004 | Liu et al. |

(Continued)

FOREIGN PATENT DOCUMENTS

| | | |
|---|---|---|
| DE | 10/044648 | 3/2002 |
| EP | 0 737 750 | 10/1996 |
| FR | 2 422 956 | 11/1979 |
| FR | 2518 755 | 6/1983 |
| FR | 2769322 | 4/1999 |

(Continued)

OTHER PUBLICATIONS

U.S. Appl. No. 60/069,750, filed Dec. 16, 1997, Wang et al.
U.S. Appl. No. 60/069,233, filed Dec. 11, 1997, Wang et al.
Allan, G. M. et al., "Isolation of Procine Circovirus-like Viruses from Pigs with a Wasting Disease in the USA and Europe", Journal of Veterinary Diagnostic Investigation, vol. 10, pp. 3-10, Jan. 1998, XP 002068503.
Allan, G.M. et al., 1995, Vet. Microbiol., 44: 49-64.

(Continued)

*Primary Examiner*—Ali R. Salimi
(74) *Attorney, Agent, or Firm*—Bingham McCutchen, LLP

(57) ABSTRACT

The genome sequences and the nucleotide sequences coding for the PWD circovirus polypeptides, such as the circovirus structural and non-structural polypeptides, vectors including the sequences, and cells and animals transformed by the vectors are provided. Methods for detecting the nucleic acids or polypeptides, and kits for diagnosing infection by a PWD circovirus, also are provided. Method for selecting compounds capable of modulating the viral infection are further provided. Pharmaceutical, including vaccine, compositions for preventing and/or treating viral infections caused by PWD circovirus and the use of vectors for preventing and/or treating diseases also are provided.

68 Claims, 29 Drawing Sheets

U.S. PATENT DOCUMENTS

| | | | |
|---|---|---|---|
| 7,148,015 | B2 | 12/2006 | Jestin et al. |
| 7,179,472 | B2 | 2/2007 | Jestin et al. |
| 7,223,407 | B2 | 5/2007 | Jestin et al. |
| 7,223,594 | B2 | 5/2007 | Jestin et al. |
| 7,244,433 | B2 | 7/2007 | Jestin et al. |
| 7,258,865 | B2 | 8/2007 | Jestin et al. |
| 7,261,898 | B2 | 8/2007 | Jestin et al. |
| 7,297,537 | B2 | 11/2007 | Jestin et al. |
| 7,314,628 | B2 | 1/2008 | Jestin et al. |
| 2002/0055189 | A1 | 5/2002 | Bernhardt et al. |
| 2002/0106639 | A1 | 8/2002 | Li et al. |
| 2002/0177216 | A1 | 11/2002 | Phillip et al. |
| 2003/0170616 | A1 | 9/2003 | Wang et al. |
| 2005/0058653 | A1 | 3/2005 | Ellis et al. |

FOREIGN PATENT DOCUMENTS

| | | |
|---|---|---|
| FR | 2772047 | 6/1999 |
| SU | 1 538 305 | 12/1994 |
| WO | WO 90/11092 | 10/1990 |
| WO | 92/05255 | 4/1992 |
| WO | 94/01133 | 1/1994 |
| WO | 94/21797 | 9/1994 |
| WO | WO 94/27238 | 11/1994 |
| WO | 94/27435 | 12/1994 |
| WO | WO 95/11307 | 4/1995 |
| WO | 96/34109 | 10/1996 |
| WO | 96/40931 | 12/1996 |
| WO | 96/40945 | 12/1996 |
| WO | 98/40499 | 9/1998 |
| WO | WO 99/18214 | 4/1999 |
| WO | 99/29717 | 6/1999 |
| WO | 99/29871 | 6/1999 |
| WO | 00/01409 | 1/2000 |
| WO | 00/24428 | 5/2000 |
| WO | 00/77216 | 12/2000 |
| WO | WO 00/77188 | 12/2000 |
| WO | WO 01/96377 | 6/2002 |
| WO | WO 02/102999 | 12/2002 |

OTHER PUBLICATIONS

Author Unknown, GenBank info on AF027217 (Revised Jul. 5, 2002).
Author Unknown, NCBI Sequence Revision History of AF027217 (Revised Jul. 5, 2002).
Barany, F., 1991, PNAS. USA, 88: 189-193.
Blanchard et al., 2003, "An ORF2 Protein-Based ELISA for Procine Circovirus Type 2 Antobodies in Post-Weaning Multisystemic Wasting Syndrome", Veterinary Microbiology, 94: 183-184.
Blanchard et al., 2003, "Protection of Swine Against Post-Weaning Multisystemic Wasting Syndrome (PMWS) by Porcine Circovirus Type 2 (PCV2) Proteins", Vaccine 21: 4565-4575.
Buckholz, R.G., 1993, Yeast systems for the expression of heterologous gene products. Curr. Op. Biotechnology 4: 538-542.
Burg, J.L. et al., 1996, Mol. and Cell. Probes, 10: 257-271.
Chu, B.C.F. et al., 1986, NAR, 14: 5591-5603.
Chu, P.W.G. et al., 1993, Virus Research, 27: 161-171.
Chu, Te-hua Terina et al., 1997, "Toward Highly Efficient Cell-Type-Specific Gene Transfer with Retroviral Vectors Displaying Single-Chain Antibodies", J. Virol., 71(1): 720-725.
Clark, E.G., 1997, American Association of Swine Practitioners, 499-501.
Cosset, Francois-Loic et al., 1995, "Retroviral by Envelopes Expressing an N-Terminal Binding Domain", J. Virol., 69:6314-6322.
Daft, B. et al., 1996, American Association of Veterinary Laboratory Diagnosticians, 32.
Derse, D. et al., 1995, J. Virol., 69(3): 1907-1912.
Derwent Abstract of French Patent Appl. No. 2422956, 1979.
Derwent Abstract of French Patent Appl. No. 2518755, 1983.
Dialog Inpadoc Family and Legal Status Search for German Patent Appl. No. 10044648, 2000.
Dialog Inpadoc Family and Legal Status Search for WO 01/96377, 2001.
Dialog Inpadoc Family and Legal Status Search for WO 02/102999, 2002.
Duck, P. et al., 1990, Biotechniques, 9: 142-147.
Dulac, G.C. et al., 1989, Can. J. Vet. Res., 53: 431-433.
Edwards, C.P., and Aruffo, A., 1993, Current applications of COS cell based transient expression systems. Curr. Op. Biotechnology 4: 558-563.
Edwards, S. et al., 1994, Vet. Rec., 134: 680-681.
Ellis, J. et al., "Isolation of Circovirus from legions of Pigs with Postweaning Multisystemic Wasting Syndrome", Canadian Veterinary Journal, col. 39, pp. 44-51, Jan. 1998, XP-002068502.
Erlich, H.A., 1989, In PCR Technology. Principles and Applications for DNA Amplification. New York: Stockton Press.
Felgner, et al., 1987, Proc. Natl. Acad. Sci., 84:7413-7417.
Fontes, E.P.B. et al., 1994, J. Biol. Chem., vol. 269, No. 11:8459-8465.
Fraley et al., 1980, J. Biol. Chem., 255: 10431-10435.
Guateli, J.C. et al., 1990, Proc. Nat'l Acad. Sci., USA, 87: 1874-1878.
Hackland, A.F. et al., 1994, Arch. Virol., 139: 1-22.
Hamel, A. et al., "Nucleotide Sequence of Procine Circovirus Associated with Postweaning Multisystemic Wasting Syndrome in Pigs", Journal of Virology, vol. 72, No. 6, pp. 5262-5267, Jun. 1998, XP-002078783.
Hanson, S.F. et al., 1995, Virology, 211: 1-9.
Harding, J.C. and Clark, E.G., 1997, Swine Health and Production, vol. 5, No. 5: 201-203.
Harding, J.C., 1997, American Association of Swine Practitioners, 503.
Harding, R.M. et al., 1993, Journal of General Virology, 74: 323-328.
Heyraud-Nitschke, F. et al., 1995, Nucleic Acids Research, vol. 23, No. 6: 910-916.
Horner, G.W., 1991, Surveillance 18(5): 23.
Huygen, K. et al., 1996, Nature Medicine, 2(8): 893-898.
Innis, M.A. et al., 1990, in PCR Protocols. A guide to Methods and Applications, San Diego, Academic Press.
Kaneda, et al., 1989, Science, 243: 375-378.
Kasahara, Noriyuki et al., 1994, "Tissue-Specific Targeting of Retroviral Vectors Through Ligan-Receptor Interactions", Science, 266: 1373-1376.
Kessler, C., "Overview of Amplification on Systems" in Non-radioactive Labeling and Detection of Biomolecules, 1992, Springer Verlag, Berlin, New-York: 197-205.
Kievitis, T. et al., 1991, J. Virol. Methods, 35: 273-286.
Kohler, G. & Milstein, 1975, Nature, 256(5517): 495-497.
Kwoh, D.Y. et al., 1989, Proc. Nat'l Acad. Sci., USA, 86: 1173-1177.
Ladany, S. et al., 1989, J. Clin. Microbiol. 27: 2778-2783.
Lazarowitz, S.G. et al., 1989, The EMBO Journal, vol. 8 No. 4: 1023-1032.
Liu et al., 1997, J. Gen. Virol., 78 (Pt 6), 1265-1270.
Luckow, V.A., 1993, Baculovirus systems for the expression of human gene products. Curr. Op. Biotechnol. 4: 564-572.
Mankertz, A. et al., 1997, J. Virol., 71: 2562-2566.
Marglin, A. and Merrifield, R.B., 1966, J. Am. Chem. Soc., 88(21): 5051-5052.
Matthews, J.A. et al., 1988, Anal. Biochem., 169: 1-25.
McNeilly, F. et al., 1996, Vet. Immunol. Immunopathol., 49: 295-306.
Meehan, B.M. et al., 1997, J. Gen. Virol. 78: 221-227.
Midoux, 1993, Nucleic Acids Research, 21: 871-878.
Miele, E.A. et al., 1983, J. Mol. Biol. 171: 281-295.
Morozov, I. et al., "Detection of a Novel Strain of Procine Circovirus in Pigs with Postweaning Multisystemic Wasting Syndrome", Journal of Clinical Microbiology, col. 36, No. 9, pp. 2535-2541, Sep. 1998, XP-002090921.
Müller, 1974, in Methode der Organischen Chemie, E. Wunsch Ed., vol. 15-I and 15-II, Thieme, Stuttgart.
Nayar, G.P. et al., 1997, Can. Vet. J. 38(6): 385-386.
Neddleman, Saul B. et al., 1970, "A General Method Applicable to the Search for Similarities in the Amino Acid Sequence of Two Proteins", J. Mol. Biol., 48(3): 443-453.

Olins, P.O., and Lee, S.C., 1993, Curr. Op. Biotechnol. 4: 520-525.
Pagano et al., 1967 , J. Virol., 1: 891-897.
Pearson, William R. et al., 1988, "Improved Tools for Biological Sequence Comparison", Proc. Nat'l Acad, Sci., USA, 85: 2444-2448.
Rolfs, A. et al., "Usage of Polymerase Chain Reaction in Genetic and Infectious Disease" in PCR Topics, 1991, Springer-Verlag, Berlin.
Rose, N. et al., 2002, "Risk Factors for Porcine Post-Weaning Multisystemic Wasting Syndrome (PMWS) in 149 French Farrow-to-Finish Herds", Preventive Veterinary Microbiology, 61: 209-225.
Sambrook, J. et al., 1989, Molecular cloning: A Laboratory Manual. Cold Spring Harbor, NY: Cold Spring Harbor Laboratory Press.
Sanchez-Pescador, R., 1988, J. Clin. Microbiol., 26(10): 1934-1938.
Ségales, J. et al., "First Report of Post-Weaning Multisystemic Wasting Syndrome in Pigs in Spain", Beterinary Record, col. 141, No. 23, pp. 600-601, Dec. 1997, XP-002068504.
Shiver, J.W., "Immune Responses to HIV gp 120 Elicited by DNA Vaccination," in Vaccines, 1995, eds Chanock, et al., pp. 95-98, Cold Spring Harbor Laboratory Press, Cold Spring Harbor, New York.
Smith, Temple F. et al., 1981, "Comparison of Biosequences", Advances in Applied Mathematics, 2: 482-489.
Tascon, R.E. et al., 1996, Nature Medicine, 2(8): 888-892.
Tischer, I. and Bohk, H.J., 1988, Zentralbl Bakteriol Mikrobiol Hyg [A] 270: 280-287.
Tischer, I. et al., 1982, Nature, 295: 64-66.
Tischer, I. et al., 1986, Arch. Virol., 91: 271-276.
Tischer, I. et al., 1995, Arch. Virol., 140: 737-743.
Urdea, M.S., 1988, Nucleic Acids Research, 11: 4937-4957.
Valsesia-Whittmann, Sandrine et al., 1996, "Improvement of Retroviral Retargeting by Using Amino Acid Spacers between an Additional Binding Domain and the N Terminus of Moloney Nurine Leukemia Virus SU", J. Virol. 70(3): 2059-2064.
Virus Taxonomy, Murphy, F.A. et al., Ed. 1995, Sixth Report of the International Committee on Taxonomy of Viruses, Springer-Verlag Wien New York.
Walker, G.T. et al., 1992, Nucleic Acids Res. 20: 1691-1696.
Walker, G.T. et al., 1992, Proc. Nat'l Acad. Sci., USA, 89: 392-396.
White, B.A. et al. Eds., "PCR Cloning Protocol" in Methods in Molecular Biology, 67, Humana Press, Towota, 1997.
Young, John A. T. et al., "Efficient Incorporation of Human CD4 Protein into Avian Leukosis Virus Particles", Reports, 1421-1423, 1990.
Zhao, T.M. et al., 1996, Proc. Natl. Acad. Sci., USA 96(13): 6653-6648.
ABI-Prism, "Automated DNA Sequencing, Chemistry Guide", Applied Biosystems, product manual, applicable to automated sequencers ABI Prism 310, 377 and 373 (2000).
Adams, Mark D. et al. "Complementary DNA Sequencing: Expressed Sequence Tags and Human Genome Project," Science, 1651-1656. (1991).
Albina et al., "Premiers Résultats du CNEVA sur le dépérissement fatal du porcelet en fin de post-sevrage" La Semaine Veterinaire des Filieres, 26:1-2, Nov. 30, 1996.
Allan et al., "Porcine Circoviruses: A Review," J Vet Diagn Invest. 12: 3-14 (2000).
Allan et al., "Immunostimulation, PCV-2 and PMWS," Veterinary Record (2000); 147(6):170-171.
Allan, G.M., et al., "Production, preliminary characterisation and applications of monoclonal antibodies to porcine circovirus," Veterianry Immunology and Immunopathology, 43 (1994) 357-371.
Altmann, Curtis R. et al. "Microarray-Based Analysis of Early Development in Xenopus Iaevis," Developmental Biology, 236:64-75 (2001).
Bantle, John A. et al. "Phase III Interlaboratory Study of FETAX Part 3. FETAX Validation using 12 Compounds with and without an Exogenous Metabolic Activation System," Journal of Applied Toxicology, 19:447-472 (1999).
Behr, J.P., "Gene Transfer with Synthetic Cationic Amphiphiles: Prospects for Gene Therapy" Bioconjugate Chem. 5(5):382-389 (1994).
Bei, R. et al., "The Use of a Cationic Liposome Formulation (DOTAP) Mixed with a Recombinant Tumor-Associated Antigen to Induce Immune Responses and Protective Immunity in Mice," Journal of Immunotherapy, 21(3):159-169 (1998).

Cho et al., "Enhanced cellular immunity of hepatitis C virus nonstructural proteins by codelivery of granulocyte macrophage-colony stimulating facotr gene in intramuscular DNA immunization," Vaccine 17:1136-1144 (1999).
Cruse et al., "The Illustrated Dictionary of Immunology," Boca Raton: CRC Press (1995) p. 156.
Cruse et al., "The Illustrated Dictionary of Immunology," 2nd edition. Boca Raton: CRC Press (2003) p613.
Dedet, V., "Seule certitude: un maladle à part entière," La Semaine Veterinaire p. 54, May 24, 1997.
DMRIE structure, Printed from PubChem Compound Summary 2008.
Donnelly, John J. et al., "Immunization with DNA" Journal of Immunological Methods, 176: 145-152 (1994).
Dorland's Illustrated Medical Dictionary, 28th edition. Philadelphia. WB Saunders p. 1787 (1994).
Ellis et al., "Reproduction of lesions of Post eaning Multisystemic wasting syndrome in gnotobiotic piglets," J. Vet. Diagn. Invest. 11:3-14 (1999).
Ellis et al., "Coinfection by porcine circoviruses and porcine parvovirus in pigs with naturally acquired postweaning multisystemic wasting syndrome" J. Vet. Diagn. Invest. 12(1):21-27 (2000).
Ertl, H.C.J. et al., "Genetic Immunization" Viral Immunology, 9(1):1-9 (1996).
Felgner J.H. et al., "Enhanced gene delivery and mechanism studies with a novel series of cationic lipid formulations," The journal of biological chemistry, 269(4)2550-2561 (1994).
Fenaux, M. et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2," Journal of Clinical Microbiology, Jul. 2000, 38(7):2494-2503.
Fort, Douglas J. et al. "Evaluation of the Developmental Toxicity of Thalidomide Using Frog Embryo Teratogenesis Assay--Xenopus (FETAX): Biotransformation and Detoxification," Teratogensis, Carcinogenesis, and Mutagenesis, 20:35-47 (2000).
GenBank Accession No. AF027217; May 14, 1998.
Gregoriadis G. et al., "Liposome-mediated DNA vaccination" FEBS Letters, Feb. 3, 1997; 402:107-110.
Gregoriadis, Gregory, "Genetic vaccines: strategies for optimization" Pharmaceutical Research, 15( 5):661-670 (1998).
Grierson, S.S., et al., "Genome sequence analysis of 10 Dutch porcine circovirus type 2 (PCV-2) isolates from a PMWS case-control study," Research in Veterinary Science,77 (2004) pp. 265-268.
Haddad, D. et al., "Comparative study of DNA-based immunization vectors: effect of secretion signals on the antibody responses in mice," FEMS Immunology and Medical Microbiology, 18(3):193-202 (1997).
Hamel et al., "Porcine Circovirus," (Sequence Alignments for SEQ ID No:s 1-4 and 6) Genbank Acc No: 027217, Dec. 19, 1997.
Inumaru, S. et al., "cDNA Cloning of Porcine Granulocyte-Macrophage Colony-Stimulating Factor" Immunology and Cell Biology, 73:474-476, XP-000946635 (1995).
Ishii N. et al., "Cationic liposomes are a strong adjuvant for a DNA vaccine of human immunodeficiency virus type 1" AIDS Res Hum Retroviruses, Nov. 1, 1997 13(6):1421-1428.
Izumida, et al., "Establishment of the Attenuated Strain of Porcine Parvovirus of the Live Vaccine and its Biological-Immunological Characteristics," Japanese Veterinary Science, 48(2):293-303 (1996).
Klavinskis, Linda S. et al., "Intranasal Immunization with Plasmid DNA-Lipid Complexes Elicits Mucosal Immunity in the Female Genital and Rectal Tracts" J. Immunol 1999, pp. 254-262.
Knell, S. et al., "Comparative genetic charaterization of Porcine Circovirus type 2 samples from German wild boar populations," Veterinary Microbiology, 109 (2005) pp. 169-177.
Krakowka et al., "Activation of the Immune System in the Pivotal Event in the Production of Wasting Disease in Pigs Infected with Porcine Circovirus-2 (PCV-2)," Vet Pathology. 38:31-42 (2001).

Krakowka et al., "Immunologic Features of Porcine Circovirus Type-2 Infection," *Viral Immunology*. 15(4): 567-582 (2002).

LeCann et al., "Piglet Wasting disease," *Veterinary Record*, p. 660, Dec. 20/27 1997.

Lekcharoensuk, P. et al., "Epitope Mapping of the Major Capsid Protein of Type 2 Porcine Circovirus (PCV2) by Using Chimeric PCV1 and PCV2," *Journal of Virology*, vol. 78, No. 15, Aug. 2004, pp. 8135-8145.

Mahé et al., "Differential Recognition of ORF 2 Protein from Type 1 and Type 2 Porcine circoviruses and Identification of Immunorelevant Epitopes", *Journal of General Virology* 81:1815-1824 (2000).

Mankerts et al., "Porcine Circovirus Complete Genome", EMBL Sequence Database XP-002104869 May 22, 1997.

McCluskie, Michael J. et al., "Route and Method of Delivery of DNA Vaccine Influence Immune Responses in Mice and Non-Human Primates" *Molecular Medicine* 5:287-300 (1999).

McInnes, C.J. et al., "Cloning and Expression of a cDNA Encoding Ovine Granulocyte-Macrophage Colony-Stimulating Factor" *Gene*, 105: 275-279, XP-002148815 (1991).

Meehan et al., "Putative PCV Replication-Associated Protein (REP)", EMBL Sequence Database XP 002104867 (1997).

Meehan et al., "Porcine Circovirus Complete Genome", EMBL Sequence Database XP-002104868 (1997).

Meehan, B.M. et al., "Characterization of noval circovirus DNAs associated with wasting syndromes in pigs." , *Journal of General Virology*, vol. 79, No. 9, pp. 2171-2179, Sep. 1998, XP-002090386.

Miller, J.S. et al., "The nucleotide sequence of RNA-1 of Indian peanut clump furovirus" *Arch. Virol.* 141:2301-2312, (1996).

Mumford J.A. et al., "Antigenicity and immunogenicity of equine infleuenza vaccine containing a Carbomer adjuvant,"*Epidemiol. Infect.* 112: 421-437 (1994).

Nakakura, Norihiko et al. "Synthesis of Heterogenous mRNA-like RNA and Low-Molecular-Weight RNA before the Midblastula Transition in Embryos of *Xenopus laevis*,"*Developmental Biology*, 123:421-429 (1987).

Nash RA et al., "Molecular cloning and in vivo evaluation of canine granulocyte-macrophage colony-stimulating factor" *Blood* 78(4):930-937, XP 002133949 (1991).

Nawagtigul et al., "Open Reading Frame 2 of Porcine Circovirus Type 2 Encodes a Major Capsid Protein", *Journal of General Virology* 81:2281-2287 (2000).

Nayer et al., "Detection and Characterization of Porcine Circovirus Associated With Postweaving Multisystemic Wasting Syndrome Pigs", *Can Vet. J.* 38:385-386 (1997).

Newport, John et al., "Major Developmental Transition in Early Xenopus Embryos: I. Characterization and Timing of Cellular Changes at the Midblastula Stage," *Cell* 30:675-686 (1982).

Newport, John et al. "A Major Developmental Transition in Early Xenopus Embryos: II. Control of the Onset of Transactions," *Cell* 30:687-696 (1982).

Nieuwkoop and Faber "Normal Table of Xenopus laevis (Daudin) - A Systematic and chronological survey of the development from the fertilized egg to the end of metamorposis, " Chapter VII, 162-188 Garland Publishing(1994).

Norman, JA et al., "Development of Improved Vectors for DNA-Based Immunization and other Gene Therapy Applications," *Vaccine*, 15(8): 801-803 (1997).

Nuwaysir, Emile F. et al. "Microarrays and Toxicology: The Advent of Toxicogenomics," *Molecular Carcinogenesis*, 24:153-159 (1999).

Okada, E. et al., "Intranasal immunization of a DNA vaccine with IL-I2 and Granulocyte-macrophage colony-stimulating Factor (GM-(SF)) - expressing plasmids in Liposomes Induces Strong Mucosal and Cell-Mediated immune responses against HIV-1 antigens," *The Journal of Immunology*, 159:3638-3647 (1997).

Parker, SE et al., "Plasmid DNA gene therapy: Studies with the human interleukin-2 gene in tumor cells in vitro and in the murine B16 melanoma model in vivo," *Cancer Gene Therapy*, 3(3):175-185 (1996).

Restifo, N P et al., "The promises of nucelic acid vaccines,", *Gene Therapy*, 7:89-92 (2000).

Ruitenberg, K. M. et al., "DNA-Mediated Immunization with Glycoprotein D of Equine Herpesvirus 1 (EHV-1) in a Murine Model of EHV-1 Respiratory Infection," *Vaccine*, 17:237-244 (1999).

Schena, Mark, et al., "Quantitative Monitoring of Gene Expression Patterns with a Complementary DNA Microarray," *Science*, 270: 467-470 (1995).

Schena, Mark et al. "Parallel human genome analysis: Microarray-based expression monitoring of 1000 genes," *Proc. Natl. Acad. Sci. USA*, 93:10614-10619 (1999).

Schultz, J et al., "Update on Antiviral DNA Vaccine Research (1998-2000)," *Intervirology*, 43: 197-217 (2000).

Sin, J-I et al., "Protective Immunity Against Heterologous Challenge with Encephalomyocarditis Virus by VP1 DNA Vaccination: Effect on Coinjection with a Granulocyte-Macrophage Colony Stimulating Factor Gene," *Vaccine* 15:1827-1833 (1997).

Somasundaram, C. et al., "Enhanced Protective Response and Immuno-Adjuvant Effects of Porcine GM-CSF on DNA Vaccination of Pigs against Aujeszky's Disease Virus," *Veterinary Immunology and Immunopathology* 70:277-287 (1999).

Terpestra et al., "Potentcy control of modified live viral vaccines for veterinary use," *Vaccine* 14(6):570-575 (1996).

Todd et al., "Comparision of Three Animal Viruses with Circular Single-Stranded DNA Genomes," *Arch Virol.*, 117:129-135 (1991).

Vannier, et al., "Study of the Efficacy of an Inactivated Virus Vaccine Against Porcine Parvovirus," *Ann. Rech. Vet.* 17(4):425-432 (1986).

Vogel, et al., "Nucleic Acid Vaccines," *Clinical Microbiology Reviews* 8(3):406-410 (1995).

Walker, G.T. et al., *Nucleic Acids Res.* (1992) 20: 1691-1696.

Watanabe, Y et al., "Highly Efficient Transfection into Primary Cultured Mouse Hepatocytes by Use of Cation-Liposomes: An Application for Immunization," *J. Biochem.* 116:1220-1226 (1994).

Wen, L. et al., "Genotyping of porcine circovirus type 2 from a variety of clinical conditions in China," *Veterinary Microbiology*, 110(2005) pp. 141-146.

West et al., "Myocarditis and abortion associated with intrauterine infection of sows with porcine circovirus 2" *J Vet Diagn Invest.* 11: 530-532 (1999).

Wheeler, C.J. et al., "Converting an alcohol to an amine in a cationic lipid dramatically alters the co-lipid requirement, cellular transfection activity and the ultrastructure of DNA-cytofectin complexes," *Biochemica et Biophysica Acta* 1280:1-11, XP 002035803 (1996).

Xiang Z. et al., "Manipulation of the immune response to a plasmid-encoded viral antigen by coinoculation with plasmids expressing cytokines," *Immunity*, 2:129-135 (1995).

Yokoyama et al. "DNA immunization: Effects of vehicle and route of administration on the induction of protective antviral immunity," *FEMS Immunology and Medical Microbiology*, 14:221-230 (1996).

Young, "Fields Virology" 3rd ed. Philadelphia: Lippencott-Raven Publishers Chapter 70- Parvoviruses; vol. 2, p2199-2220 (1996).

Zhang, Michael Q. "Large-Scale Gene Expression Data Analysis: A New Challenge to Computational Biologists," *Genome Research*, 9(8):681-688 (1999).

```
         Leu Ala Ser Arg Cys Arg Cys Cys Arg Pro Leu Thr Leu Ser Phe Ala Leu Cys
          Trp Arg Val Glu Ala Ala Ala Gly Arg Cys Arg *** His Phe His Trp Ala
          Gly Ala Cys Lys Pro Leu Pro Leu Val Glu Ala Ala Asp Thr Phe Ile Gly Leu
          --- --- --- --- --- --- --- --- --- --- --- --- --- --- --- --- --- ---
3'        TGG TCG CGT GAA GCC GTC GCC GTC GTG GAG CCG TCG CAG TCA CTT TTA CGG TTC
                  9              18              27              36          45              54
5'        ACC AGC GCA CTT CGG CAG CGG CAG CAC CTC GGC AGC GTC AGT GAA AAT GCC AAG
          Thr Ser Ala Leu Arg Gln Arg Gln His Leu Gly Ser Val Ser Glu Asn Ala Lys
          Pro Ala His Phe Gly Ser Gly Ser Thr Ser Ala Ala Ser Val Lys Met Pro Ser
          Gln Arg Thr Ser Ala Ala Ala Ala Pro Arg Gln Arg Gln *** Lys Cys Gln Ala

Ser Phe Arg Gly Ala Val Gly Tyr Ser Thr Pro Thr *** Gly *** Tyr Asp Lys
          Leu Phe Ala Ala Arg Leu Gly Met Leu Pro Pro His Glu Gly Lys Ile Ile Arg
          Leu Phe Leu Pro Gly Cys Gly Trp Leu Leu His Thr Asn Val Arg Leu Leu Gly
          --- --- --- --- --- --- --- --- --- --- --- --- --- --- --- --- --- ---
          GTT CTT TTC GCC GGG CGT TGG GGT ATT CTC CAC CCA CAA GTG GGA ATT ATT AGG
                  63              72              81              90              99             108
          CAA GAA AAG CGG CCC GCA ACC CCA TAA GAG GTG GGT GTT CAC CCT TAA TAA TCC
          --- --- --- --- --- --- --- --- --- --- --- --- --- --- --- --- --- ---
          Gln Glu Lys Arg Pro Ala Thr Pro *** Glu Val Gly Val His Pro *** *** Ser
          Lys Lys Ser Gly Pro Gln Pro His Lys Arg Trp Val Phe Thr Leu Asn Asn Pro
          Arg Lys Ala Ala Arg Asn Pro Ile Arg Gly Gly Cys Ser Pro Leu Ile Ile Leu

Arg Pro Pro Ser Phe Cys Phe Val Pro Ala Glu Leu Arg Gly Lys Gln Asn Asn
          Gly Leu Leu Leu Phe Val Phe Tyr Pro Leu Lys Trp Asp Gly Lys Lys Ile Ile
          Glu Ser Ser Ser Phe Phe Leu Ile Arg Ser Ser Gly Ile Glu Arg Lys Ser ***
          --- --- --- --- --- --- --- --- --- --- --- --- --- --- --- --- --- ---
          AAG GCT CCT CCT CTT TTT GTT TTA TGC CCT CGA AGG TTA GAG GGA AAA ACT AAT
                 117             126             135             144             153             162
          TTC CGA GGA GGA GAA AAA CAA AAT ACG GGA GCT TCC AAT CTC CCT TTT TGA TTA
          --- --- --- --- --- --- --- --- --- --- --- --- --- --- --- --- --- ---
          Phe Arg Gly Gly Glu Lys Gln Asn Thr Gly Ala Ser Asn Leu Pro Phe *** Leu
          Ser Glu Glu Glu Lys Asn Lys Ile Arg Glu Leu Pro Ile Ser Leu Phe Asp Tyr
          Pro Arg Arg Arg Lys Thr Lys Tyr Gly Ser Phe Gln Ser Pro Phe Leu Ile Ile

Gln Lys His Arg Pro Leu Asn Pro Leu Pro Tyr Phe Glu Glu Gly Gly Pro Thr
          Lys Asn Thr Ala Leu Phe Thr Gln Phe Leu Thr Ser Ser Arg Val Glu Leu Pro
          Lys Thr Gln Pro Ser Ser Pro Lys Ser Ser Pro Leu Val Gly *** Arg Trp Pro
          --- --- --- --- --- --- --- --- --- --- --- --- --- --- --- --- --- ---
          AAA ACA AAC ACC GCT CCT TCC AAA CCT TCT CCC ATC TTG AGG AGT GGA GGT CCC
                 171             180             189             198             207             216
          TTT TGT TTG TGG CGA GGA AGG TTT GGA AGA GGG TAG AAC TCC TCA CCT CCA GGG
          --- --- --- --- --- --- --- --- --- --- --- --- --- --- --- --- --- ---
          Phe Cys Leu Trp Arg Gly Arg Phe Gly Arg Gly *** Asn Ser Ser Pro Pro Gly
          Phe Val Cys Gly Glu Glu Gly Leu Glu Glu Gly Arg Thr Pro His Leu Gln Gly
          Leu Phe Val Ala Arg Lys Val Trp Lys Arg Val Glu Leu Leu Thr Ser Arg Gly

Gln Ser Asn Gln *** Ser Ala Ser Lys *** Cys Pro Ser Thr Thr Asn Gln His
          Lys Arg Ile Lys Ser Leu Leu Leu Ser Lys Val Leu His Leu Pro Ile Lys Thr
          Asn Ala Phe Lys Ala Leu Phe Cys Val Lys Leu Leu Thr Phe His Tyr Lys Pro
          --- --- --- --- --- --- --- --- --- --- --- --- --- --- --- --- --- ---
          CAA ACG CTT AAA ACG ATT CTT CGT CTG AAA ATT GTT CCA CTT CAC CAT AAA ACC
                 225             234             243             252             261             270
          GTT TGC GAA TTT TGC TAA GAA GCA GAC TTT TAA CAA GGT GAA GTG CTA TTT TGG
          --- --- --- --- --- --- --- --- --- --- --- --- --- --- --- --- --- ---
          Val Cys Glu Phe Cys *** Glu Ala Asp Phe *** Gln Gly Glu Val Val Phe Trp
          Phe Ala Asn Phe Ala Lys Lys Gln Thr Phe Asn Lys Val Lys Trp Tyr Phe Gly
          Leu Arg Ile Leu Leu Arg Ser Arg Leu Leu Thr Arg *** Ser Gly Ile Leu Val
```

FIG. 2a

```
  Gly Ser Gly Cys Arg Ser Leu Ser Leu Phe Arg Gly Ala Ser Tyr Leu Ile Ser
   Gly Ala Ala Val Asp Leu Phe Arg Phe Ser Gly Val Leu Leu Ile Phe Phe Val
Ala Arg Gln Trp Met Ser Phe Ala Phe Pro Val Ser Trp Cys Phe Leu Ser Tyr
--- --- --- --- --- --- --- --- --- --- --- --- --- --- --- --- --- ---
ACG GGC GAC GGT GTA GCT CTT TCG CTT TCC TTG GCT GGT CGT CTT ATT TCT TAT
    279         288         297         306         315         324
TGC CCG CTG CCA CAT CGA GAA AGC GAA AGG AAC CGA CCA GCA GAA TAA AGA ATA
--- --- --- --- --- --- --- --- --- --- --- --- --- --- --- --- --- ---
Cys Pro Leu Pro His Arg Glu Ser Glu Arg Asn Arg Pro Ala Glu *** Arg Ile
 Ala Arg Cys His Ile Glu Lys Ala Lys Gly Thr Asp Gln Gln Asn Lys Glu Tyr
  Pro Ala Ala Thr Ser Arg Lys Arg Lys Glu Pro Thr Ser Arg Ile Lys Asn Thr

Cys Tyr Leu Leu Gly Cys Val *** Arg Thr His Leu Glu Ala Ser Gly Pro Ser
   Ala Thr Phe Phe Ala Val Tyr Lys Asp Leu Thr Ser Ser Arg Pro Val Leu Pro
Gln Leu Leu Ser Pro Trp Met Ser Ile Ser His Pro Ala Gly Arg Phe Trp Pro
--- --- --- --- --- --- --- --- --- --- --- --- --- --- --- --- --- ---
GAC GTC ATT TCT TCC GGT GTA TGA ATA GCT CAC ACC TCG AGG CGC CTT GGT CCC
    333         342         351         360         369         378
CTG CAG TAA AGA AGG CCA CAT ACT TAT CGA GTG TGG AGC TCC GCG GAA CCA GGG
--- --- --- --- --- --- --- --- --- --- --- --- --- --- --- --- --- ---
Leu Gln *** Arg Arg Pro His Thr Tyr Arg Val Trp Ser Ser Ala Glu Pro Gly
 Cys Ser Lys Glu Gly His Ile Leu Ile Glu Cys Gly Ala Pro Arg Asn Gln Gly
  Ala Val Lys Lys Ala Thr Tyr Leu Ser Ser Val Glu Leu Arg Gly Thr Arg Gly

Ala Cys Arg Gly Thr *** Gln Gln Ser Tyr Gly Lys Pro Ser Pro Thr Lys Pro
   Leu Ala Ala Val Gln Arg Ser Ser His Thr Gly Lys Gln Leu Arg Pro Arg Gln
Phe Arg Leu Ser Arg Asp Val Ala Thr Leu Val Arg Lys Ser Val Pro Asp Lys
--- --- --- --- --- --- --- --- --- --- --- --- --- --- --- --- --- ---
CTT CGC GTC GCT GGA CAG ATG ACG ACA CTC ATG GGA AAA CCT CTG CCC CAG AAA
    387         396         405         414         423         432
GAA GCG CAG CGA CCT GTC TAC TGC TGT GAG TAC CCT TTT GGA GAC GGG GTC TTT
--- --- --- --- --- --- --- --- --- --- --- --- --- --- --- --- --- ---
Glu Ala Gln Arg Pro Val Tyr Cys Cys Glu Tyr Pro Phe Gly Asp Gly Val Phe
 Lys Arg Ser Asp Leu Ser Thr Ala Val Ser Thr Leu Leu Glu Thr Gly Ser Leu
  Ser Ala Ala Thr Cys Leu Leu Leu *** Val Pro Phe Trp Arg Arg Gly Leu Trp

Ser Gln Leu Arg Ala Thr Glu Gln Leu Thr His Ser Phe Asn Gly Arg Ala Pro
   His Ser Tyr Gly Leu Leu Lys Arg Tyr Arg Ile His Ser Ile Glu Ala Pro Gln
Thr Val Thr Ala Ser Cys Asn Gly Thr Val Tyr Thr Leu Phe Lys Arg Pro Ser
--- --- --- --- --- --- --- --- --- --- --- --- --- --- --- --- --- ---
CCA CTG ACA TCG GCT CGT CAA AGG ACA TTG CAT ACA CTC TTT AAA GGC GCC CGA
    441         450         459         468         477         486
GGT GAC TGT AGC CGA GCA GTT TCC TGT AAC GTA TGT GAG AAA TTT CCG CGG GCT
--- --- --- --- --- --- --- --- --- --- --- --- --- --- --- --- --- ---
Gly Asp Cys Ser Arg Ala Val Ser Cys Asn Val Cys Glu Lys Phe Pro Arg Ala
 Val Thr Val Ala Glu Gln Phe Pro Val Thr Tyr Val Arg Asn Phe Arg Gly Leu
  *** Leu *** Pro Ser Ser Phe Leu *** Arg Met *** Glu Ile Ser Ala Gly Trp

Gln Val Lys Ser Leu Ser Arg Ser Ser Ala Ala Ala His Asn Ser Ser Leu Gln
   Ser Phe Lys Gln Phe His Ala Pro Leu His Leu Leu Thr Ile Pro Leu Cys Ser
Ala Ser Ser Lys Phe Thr Leu Pro Phe Ile Cys Cys Arg Ser Gln Phe Val Ala
--- --- --- --- --- --- --- --- --- --- --- --- --- --- --- --- --- ---
CCG ACT TGA AAA CTT TCA CTC GCC CTT CTA CGT CGT CGC ACT AAC CTT CTG TCG
    495         504         513         522         531         540
GGC TGA ACT TTT GAA AGT GAG CGG GAA GAT GCA GCA GCG TGA TTG GAA GAC AGC
--- --- --- --- --- --- --- --- --- --- --- --- --- --- --- --- --- ---
Gly *** Thr Phe Glu Ser Glu Arg Glu Asp Ala Ala Ala *** Leu Glu Asp Ser
 Ala Glu Leu Leu Lys Val Ser Gly Lys Met Gln Gln Arg Asp Trp Lys Thr Ala
  Leu Asn Phe *** Lys *** Ala Gly Arg Cys Ser Ser Val Ile Gly Arg Gln Leu
```

FIG. 2b

```
  Val Arg *** Leu Pro Gly Ala Arg Asn His Ser Ser Gly Thr Pro Gly Tyr Asn
 Tyr Val Asp Tyr His Ala Arg Gly Thr Thr Pro Leu Ala Leu Pro Gly Thr Ile
Thr Cys Thr Met Thr Pro Gly Gly Pro Gln Pro Phe Leu Trp His Ala Arg Leu
--- --- --- --- --- --- --- --- --- --- --- --- --- --- --- --- --- ---
ACA TGT GCA GTA TCA CCC GGG CGG GCC AAC ACC CTT CTC GGT CAC CCG GGC ATT
        549         558         567         576         585         594
TGT ACA CGT CAT AGT GGG CCC GCC CGG TTG TGG GAA GAG CCA GTG GGC CCG TAA
--- --- --- --- --- --- --- --- --- --- --- --- --- --- --- --- --- ---
Cys Thr Arg His Ser Gly Pro Ala Arg Leu Trp Glu Glu Pro Val Gly Pro ***
 Val His Val Ile Val Gly Pro Pro Gly Cys Gly Lys Ser Gln Trp Ala Arg Asn
  Tyr Thr Ser *** Trp Ala Arg Pro Val Val Gly Arg Ala Ser Gly Pro Val Ile

Gln Gln Ala * Pro Cys Arg Ser Ser Ala * Tyr Phe Tyr Thr Thr Pro His
 Lys Ser Leu Arg Pro Val Gly Val Pro Leu Arg Thr Ser Ile Leu Pro Pro Ile
Lys Ala Ser Gly Leu Ser Val *** Gln Phe Gly Leu Leu Phe Leu His His Ser
--- --- --- --- --- --- --- --- --- --- --- --- --- --- --- --- --- ---
AAA ACG ACT CGG ATC CCT GTG GAT GAC CTT CGG ATC ATC TTT ATT CAC CAC CCT
        603         612         621         630         639         648
TTT TGC TGA GCC TAG GGA CAC CTA CTG GAA GCC TAG TAG AAA TAA GTG GTG GGA
--- --- --- --- --- --- --- --- --- --- --- --- --- --- --- --- --- ---
Phe Cys * Ala * Gly His Leu Leu Glu Ala * * Lys *** Val Val Gly
 Phe Ala Glu Pro Arg Asp Thr Tyr Trp Lys Pro Ser Arg Asn Lys Trp Trp Asp
  Leu Leu Ser Leu Gly Thr Pro Thr Gly Ser Leu Val Glu Ile Ser Gly Gly Met

Ile Asp His Leu Leu Leu Gln Gln Lys Pro His Asn Lys His Ser Thr Val Lys
 Ser Ile Met Ser Phe Phe Asn Asn Asn Gln Ile Ile Lys Ile Ala Pro *** Arg
Pro Tyr *** Pro Ser Ser Thr Thr Thr Lys Ser Ser Lys *** Pro Gln Asn Gly
--- --- --- --- --- --- --- --- --- --- --- --- --- --- --- --- --- ---
ACC TAT AGT ACC TCT TCT TCA ACA ACA AAA CCT ACT AAA AAT ACC GAC CAA TGG
        657         666         675         684         693         702
TGG ATA TCA TGG AGA AGA AGT TGT TGT TTT GGA TGA TTT TTA TGG CTG GTT ACC
--- --- --- --- --- --- --- --- --- --- --- --- --- --- --- --- --- ---
Trp Ile Ser Trp Arg Arg Ser Cys Cys Phe Gly *** Phe Leu Trp Leu Val Thr
 Gly Tyr His Gly Glu Glu Val Val Val Leu Asp Asp Phe Tyr Gly Trp Leu Pro
  Asp Ile Met Glu Lys Lys Leu Leu Phe Trp Met Ile Phe Met Ala Gly Tyr Leu

Pro His Asp Val Ser Val Thr His Gly Thr Asp Met Ser Gln Leu Ser *** Leu
 Pro Ile Ile *** Gln Ser Gln Thr Val Pro Ile Trp Gln Ser Tyr Leu Ser Phe
Gln Ser Ser Arg Ser Leu Ser His Ser Arg Tyr Gly Asn Val Thr Ser Val Leu
--- --- --- --- --- --- --- --- --- --- --- --- --- --- --- --- --- ---
AAC CCT ACT AGA TGA CTC TGA CAC ACT GGC CAT AGG TAA CTG ACA TCT CTG ATT
        711         720         729         738         747         756
TTG GGA TGA TCT ACT GAG ACT GTG TGA CCG GTA TCC ATT GAC TGT AGA GAC TAA
--- --- --- --- --- --- --- --- --- --- --- --- --- --- --- --- --- ---
Leu Gly * Ser Thr Glu Thr Val * Pro Val Ser Ile Asp Cys Arg Asp ***
 Trp Asp Asp Leu Leu Arg Leu Cys Asp Arg Tyr Pro Leu Thr Val Glu Thr Lys
  Gly Met Ile Tyr * Asp Cys Val Thr Gly Ile His * Leu *** Arg Leu Lys

Pro Tyr Gln Glu Lys Lys Pro Gly Cys Tyr Lys Ser *** Trp Cys Asp Pro Gly
 Pro Thr Ser Asn Arg Lys Gln Gly Ala Thr Asn Gln Asn Gly Ala Ile Leu Gly
Pro Pro Val Thr Gly Lys Lys Ala Arg Leu Ile Lys Ile Val Leu Leu *** Ala
--- --- --- --- --- --- --- --- --- --- --- --- --- --- --- --- --- ---
TCC CCC ATG ACA AGG AAA AAA CCG GGC GTC ATA AAA CTA ATG GTC GTT AGT CCG
        765         774         783         792         801         810
AGG GGG TAC TGT TCC TTT TTT GGC CCG CAG TAT TTT GAT TAC CAG CAA TCA GGC
--- --- --- --- --- --- --- --- --- --- --- --- --- --- --- --- --- ---
Arg Gly Tyr Cys Ser Phe Phe Gly Pro Gln Tyr Phe Asp Tyr Gln Gln Ser Gly
 Gly Gly Thr Val Pro Phe Leu Ala Arg Ser Ile Leu Ile Thr Ser Asn Gln Ala
  Gly Val Leu Phe Leu Phe Trp Pro Ala Val Phe *** Leu Pro Ala Ile Arg Pro
```

FIG. 2c

```
Gly Pro Ile Thr Ser Arg Leu Gln Gln Gly Leu Gln Leu Leu Glu Arg Asp Ser
 Gly Leu Phe Pro Val Gly *** Ser Ser Asp Trp Ser Tyr Phe Ser Glu Ile Pro
Gly Trp Ser His Tyr Glu Glu Val Ala Thr Gly Ala Thr Ser Ala Arg *** Arg
--- --- --- --- --- --- --- --- --- --- --- --- --- --- --- --- --- ---
GGG GGT CCT TAC CAT GAG GAG TTG ACG ACA GGG TCG ACA TCT TCG AGA GAT AGC
     819         828         837         846         855         864
CCC CCA GGA ATG GTA CTC CTC AAC TGC TGT CCC AGC TGT AGA AGC TCT CTA TCG
--- --- --- --- --- --- --- --- --- --- --- --- --- --- --- --- --- ---
Pro Pro Gly Met Val Leu Leu Asn Cys Cys Pro Ser Cys Arg Ser Ser Leu Ser
 Pro Gln Glu Trp Tyr Ser Ser Thr Ala Val Pro Ala Val Glu Ala Leu Tyr Arg
  Pro Arg Asn Gly Thr Pro Gln Leu Leu Ser Gln Leu *** Lys Leu Ser Ile Gly

Ser *** *** Lys Ala Ile Lys Ser Ser Gln Gln Leu Val Ile Trp Pro Pro Val
 Pro Asn Ser Ser Gln Leu Lys Pro Leu Ser Ser Ser Phe Leu Gly Arg Leu Tyr
  Leu Ile Val Val Lys Cys Asn Gln Phe Val Ala Pro Ser Cys Asp Val Ser Thr
--- --- --- --- --- --- --- --- --- --- --- --- --- --- --- --- --- ---
CTC CTA ATG ATG AAA CGT TAA AAC CTT CTG ACG ACC TCT TGT TAG GTG CCT CCA
     873         882         891         900         909         918
GAG GAT TAC TAC TTT GCA ATT TTG GAA GAC TGC TGG AGA ACA ATC CAC GGA GGT
--- --- --- --- --- --- --- --- --- --- --- --- --- --- --- --- --- ---
Glu Asp Tyr Tyr Phe Ala Ile Leu Glu Asp Cys Trp Arg Thr Ile His Gly Gly
 Arg Ile Thr Thr Leu Gln Phe Trp Lys Thr Ala Gly Glu Gln Ser Thr Glu Val
  Gly Leu Leu Leu Cys Asn Phe Gly Arg Leu Leu Glu Asn Asn Pro Arg Arg Tyr

Arg Leu Gly Ile Gln Leu Leu Pro Gly Val Arg His Gly Lys Gly Met Tyr Phe
 Gly Phe Ala Ser Lys Phe Cys His Val Trp Gly Thr Gly Lys Glu Trp Ile Phe
  Gly Ser Pro Arg Asn Ser Ala Thr Ser Gly Gly Gln Ala Arg Lys Gly Tyr Leu
--- --- --- --- --- --- --- --- --- --- --- --- --- --- --- --- --- ---
TGG GCT TCC GGC TAA ACT TCG TCA CCT GGG TGG GAC ACG GGA AAA GGG TAT ATT
     927         936         945         954         963         972
ACC CGA AGG CCG ATT TGA AGC AGT GGA CCC ACC CTG TGC CCT TTT CCC ATA TAA
--- --- --- --- --- --- --- --- --- --- --- --- --- --- --- --- --- ---
Thr Arg Arg Pro Ile *** Ser Ser Gly Pro Thr Leu Cys Pro Phe Pro Ile ***
 Pro Glu Gly Arg Phe Glu Ala Val Asp Pro Pro Cys Ala Leu Phe Pro Tyr Lys
  Pro Lys Ala Asp Leu Lys Gln Trp Thr His Pro Val Pro Phe Ser His Ile Lys

Leu Asn Ser Leu Arg Lys Gln *** *** Met Thr Ile Thr Lys Ile Lys Ile ***
 Tyr Ile Val Ser Asp Lys Lys Asn Asp Cys Arg Leu Pro Lys *** Lys *** Glu
  Ile Phe *** Gln Thr Lys Lys Thr Ile Val Asp Tyr His Asn Lys Asn Lys Asn
--- --- --- --- --- --- --- --- --- --- --- --- --- --- --- --- --- ---
TTA TTT AAT GAC TCA GAA AAA ACA ATA GTG TAG CAT TAC CAA AAA TAA AAA TAA
     981         990         999        1008        1017        1026
AAT AAA TTA CTG AGT CTT TTT TGT TAT CAC ATC GTA ATG GTT TTT ATT TTT ATT
--- --- --- --- --- --- --- --- --- --- --- --- --- --- --- --- --- ---
Asn Lys Leu Leu Ser Leu Phe Cys Tyr His Ile Val Met Val Phe Ile Phe Ile
 Ile Asn Tyr *** Val Phe Phe Val Ile Thr Ser *** Trp Phe Leu Phe Leu Phe
  *** Ile Thr Glu Ser Phe Leu Leu Ser His Arg Asn Gly Phe Tyr Phe Tyr Ser

Lys Ser Pro Arg Glu Pro Tyr Ile Arg Gln Ile Thr Cys Leu Tyr Asp Val Lys
 Asn Leu Pro Asp Lys Leu Ile Phe Glu Arg Phe Gln Val Tyr Ile Thr Leu Arg
  Met *** Leu Thr Lys *** Ser Leu Asn Glu Ser Asn Tyr Met Phe Leu *** Gly
--- --- --- --- --- --- --- --- --- --- --- --- --- --- --- --- --- ---
GTA AAT CTC CCA GAA AGT CCT ATT TAA GAG ACT TAA CAT GTA TTT ATC AGT TGG
    1035        1044        1053        1062        1071        1080
CAT TTA GAG GGT CTT TCA GGA TAA ATT CTC TGA ATT GTA CAT AAA TAG TCA ACC
--- --- --- --- --- --- --- --- --- --- --- --- --- --- --- --- --- ---
His Leu Glu Gly Leu Ser Gly *** Ile Leu *** Ile Val His Lys *** Ser Thr
 Ile *** Arg Val Phe Gln Asp Lys Phe Ser Glu Leu Tyr Ile Asn Ser Gln Pro
  Phe Arg Gly Ser Phe Arg Ile Asn Ser Leu Asn Cys Thr *** Ile Val Asn Leu
```

FIG. 2d

```
      Gly Cys Leu Lys Pro Ser His Asn Cys Lys Pro Ala Cys Leu Gly Pro Arg His
      Val Val Tyr Asn Gln Ala Thr Thr Ala Asn Gln Leu Ala Tyr Gly Leu Gly Thr
      *** Trp Met Ile Lys Pro Gln Pro Gln Met Lys Ser Arg Met Ala Trp Ala Gln
      --- --- --- --- --- --- --- --- --- --- --- --- --- --- --- --- --- ---
      AAT GGT GTA TTA AAA CCC GAC ACC AAC GTA AAA CCT CGC GTA TCG GGT CCG GAC
          1089        1098        1107        1116        1125        1134
      TTA CCA CAT AAT TTT GGG CTG TGG TTG CAT TTT GGA GCG CAT AGC CCA GGC CTG
      --- --- --- --- --- --- --- --- --- --- --- --- --- --- --- --- --- ---
      Leu Pro His Asn Phe Gly Leu Trp Leu His Phe Gly Ala His Ser Pro Gly Leu
      Tyr His Ile Ile Leu Gly Cys Gly Cys Ile Leu Glu Arg Ile Ala Gln Ala Cys
      Thr Thr *** Phe Trp Ala Val Val Ala Phe Trp Ser Ala *** Pro Arg Pro Val

Ala Arg Cys Gln His Pro Tyr Lys Phe Pro Ala Val Ala Pro Lys Lys *** ***
      His Glu Val Asn Thr His Thr Asn Leu His Leu Trp Leu Gln Asn Arg Lys Asn
      Thr Ser Ser Met Pro Thr Pro Ile *** Ile Ser Gly Cys Ser Thr Glu Lys Ile
      --- --- --- --- --- --- --- --- --- --- --- --- --- --- --- --- --- ---
      ACA CGA GCT GTA ACC ACA CCC ATA AAT TTA CCT CGG TGT CGA CCA AAG AAA ATA
          1143        1152        1161        1170        1179        1188
      TGT GCT CGA CAT TGG TGT GGG TAT TTA AAT GGA GCC ACA GCT GGT TTC TTT TAT
      --- --- --- --- --- --- --- --- --- --- --- --- --- --- --- --- --- ---
      Cys Ala Arg His Trp Cys Gly Tyr Leu Asn Gly Ala Thr Ala Gly Phe Phe Tyr
      Val Leu Asp Ile Gly Val Gly Ile *** Met Glu Pro Gln Leu Val Ser Phe Ile
      Cys Ser Thr Leu Val Trp Val Phe Lys Trp Ser His Ser Trp Phe Leu Leu Leu

Lys Ala Pro Val Leu *** Asn Asn Pro Arg Ala Arg Thr Gln Pro His Leu Val
      Asn Pro Gln Phe Trp Asp Ile Thr Gln Asp Leu Glu Pro Lys Pro Thr Phe Tyr
      Ile Gln Ser Ser Gly Ile Leu Gln Lys Thr *** Ser Gln Asn Pro Pro Ser Thr
      --- --- --- --- --- --- --- --- --- --- --- --- --- --- --- --- --- ---
      ATA AAC CGA CCT TGG TTA GTT AAC AAA CCA GAT CGA GAC CAA ACC CCC ACT TCA
          1197        1206        1215        1224        1233        1242
      TAT TTG GCT GGA ACC AAT CAA TTG TTT GGT CTA GCT CTG GTT TGG GGG TGA AGT
      --- --- --- --- --- --- --- --- --- --- --- --- --- --- --- --- --- ---
      Tyr Leu Ala Gly Thr Asn Gln Leu Phe Gly Leu Ala Leu Val Trp Gly *** Ser
      Ile Trp Leu Glu Pro Ile Asn Cys Leu Val *** Leu Trp Phe Gly Gly Gly Val
      Phe Gly Trp Asn Gln Ser Ile Val Trp Ser Ser Ser Gly Leu Gly Val Lys Tyr

Gln Leu Pro Leu Tyr Leu Ala Ala Lys His His Pro Pro Leu Leu Leu *** Tyr
      Arg Ser His Tyr Thr Phe Pro Gln Arg Ile Thr His Arg Ser Ser Tyr Asn Ile
      Gly Pro Thr Thr Pro Leu Pro Ser Gly *** Pro Thr Ala Pro Pro Thr Thr Leu
      --- --- --- --- --- --- --- --- --- --- --- --- --- --- --- --- --- ---
      TGG ACC TCA CCA TCC ATT TCC CGA CGG AAT ACC ACA CCG CCC TCC TCA TCA ATT
          1251        1260        1269        1278        1287        1296
      ACC TGG AGT GGT AGG TAA AGG GCT GCC TTA TGG TGT GGC GGG AGG AGT AGT TAA
      --- --- --- --- --- --- --- --- --- --- --- --- --- --- --- --- --- ---
      Thr Trp Ser Gly Arg *** Arg Ala Ala Leu Trp Cys Gly Gly Arg Ser Ser ***
      Pro Gly Val Val Gly Lys Gly Leu Pro Tyr Gly Val Ala Gly Gly Val Val Asn
      Leu Glu Trp *** Val Lys Gly Cys Leu Met Val Trp Arg Glu Glu *** Leu Ile

Leu Pro *** Leu Gly Leu Gln His Leu Pro Asn Cys Leu Gln Cys Gly Leu Tyr
      Tyr Pro Asp Tyr Ala Leu Asn Thr Ser Pro Thr Val Phe Asn Ala Asp Leu Ile
      Ile Pro Thr Met Pro Trp Thr Pro Pro Pro Pro *** Leu Thr Pro Met Trp Ser
      --- --- --- --- --- --- --- --- --- --- --- --- --- --- --- --- --- ---
      ATA TCC CCA GTA TCC GGT TCA ACC ACC TCC CCC AAT GTT TCA ACC GTA GGT TCT
          1305        1314        1323        1332        1341        1350
      TAT AGG GGT CAT AGG CCA AGT TGG TGG AGG GGG TTA CAA AGT TGG CAT CCA AGA
      --- --- --- --- --- --- --- --- --- --- --- --- --- --- --- --- --- ---
      Tyr Arg Gly His Arg Pro Ser Trp Trp Arg Gly Leu Gln Ser Trp His Pro Arg
      Ile Gly Val Ile Gly Gln Val Gly Gly Gly Gly Tyr Lys Val Gly Ile Gln Asp
      *** Gly Ser *** Ala Lys Leu Val Glu Gly Val Thr Lys Leu Ala Ser Lys Ile
```

FIG. 2e

```
 Cys Cys His Val Trp Cys Arg Lys Ser *** Leu His His Pro Arg Gln Pro Leu
  Val Val Thr Ser Gly Val Gly Arg Gln Asn Ser Thr Ile Pro Asp Arg Pro Tyr
   Leu Leu Leu Pro Gly Leu Val Glu Lys Ile Leu Pro Ser Pro Thr Glu Pro Thr
   --- --- --- --- --- --- --- --- --- --- --- --- --- --- --- --- --- ---
   ATT GTT GTC ACC TGG GTT GTG GAG AAA CTA ATC TCC ACT ACC CCA GAG ACC CCA
       1359        1368        1377        1386        1395        1404
   TAA CAA CAG TGG ACC CAA CAC CTC TTT GAT TAG AGG TGA TGG GGT CTC TGG GGT
   --- --- --- --- --- --- --- --- --- --- --- --- --- --- --- --- --- ---
      Gln Gln Trp Thr Gln His Leu Phe Asp *** Arg *** Trp Gly Leu Trp Gly
   Asn Asn Ser Gly Pro Asn Thr Ser Leu Ile Arg Gly Asp Gly Val Ser Gly Val
    Thr Thr Val Asp Pro Thr Pro Leu *** Leu Glu Val Met Gly Ser Leu Gly ***

Ile *** Ile *** Gly Lys *** Tyr Pro Leu Ile Pro Phe Thr Pro Thr Pro Pro
   Phe Glu Tyr Lys Ala Lys Arg Ile Arg Tyr Tyr Gln Phe Pro Leu Pro Leu Pro
   Phe Asn Met Asn Leu Arg Glu Leu Val Thr Thr Asn Ser Leu Tyr Pro Tyr Pro
   --- --- --- --- --- --- --- --- --- --- --- --- --- --- --- --- --- ---
   TTT TAA GTA TAA ATC GGA AAG ATT ATG CCA TCA TAA CCT TTC CAT CCC CAT CCC
       1413        1422        1431        1440        1449        1458
   AAA ATT CAT ATT TAG CCT TTC TAA TAC GGT AGT ATT GGA AAG GTA GGG GTA GGG
   --- --- --- --- --- --- --- --- --- --- --- --- --- --- --- --- --- ---
   Lys Ile His Ile *** Pro Phe *** Tyr Gly Ser Ile Gly Lys Val Gly Val Gly
    Lys Phe Ile Phe Ser Leu Ser Asn Thr Val Val Leu Glu Arg *** Gly *** Gly
     Asn Ser Tyr Leu Ala Phe Leu Ile Arg *** Tyr Trp Lys Gly Arg Gly Arg Gly

Gln His Arg Arg Leu Pro Pro Pro Val Pro Arg His Gln Ile Glu Ala Arg ***
   Asn Thr Gly Gly Ser Pro Pro Leu Phe Gln Gly Ile Asn Phe Arg Leu Glu Asn
   Thr Pro Ala Ala Gln Pro Pro Ser Ser Ser Ala Ser Thr Ser Asp *** Ser Thr
   --- --- --- --- --- --- --- --- --- --- --- --- --- --- --- --- --- ---
   CCA ACC ACG GCG GAC TCC CCC CCT CCT TGA CCG GCT ACA ACT TAG AGT CGA GCA
       1467        1476        1485        1494        1503        1512
   GGT TGG TGC CGC CTG AGG GGG GGA GGA ACT GGC CGA TGT TGA ATC TCA GCT CGT
   --- --- --- --- --- --- --- --- --- --- --- --- --- --- --- --- --- ---
   Gly Trp Cys Arg Leu Arg Gly Gly Gly Thr Gly Arg Cys *** Ile Ser Ala Arg
    Val Gly Ala Ala *** Gly Gly Glu Glu Leu Ala Asp Val Glu Ser Gln Leu Val
     Leu Val Pro Pro Glu Gly Gly Arg Asn Trp Pro Met Leu Asn Leu Ser Ser Leu

Cys Glu Leu Ile Ala Ala Leu Thr Arg Arg Lys His His Thr Cys Ile Arg ***
    Val Asn Trp Ser Pro Gln Ser His Gly Gly Arg Ile Thr Leu Val Phe Glu Arg
   Leu Met Gly Leu His Ser Arg Thr Asp Glu Glu *** Pro Ser Tyr Leu Asn Glu
   --- --- --- --- --- --- --- --- --- --- --- --- --- --- --- --- --- ---
   ATT GTA AGG TTC TAC CGA CGC TCA CAG GAG GAG AAT ACC ACT CAT GTT TAA GAG
       1521        1530        1539        1548        1557        1566
   TAA CAT TCC AAG ATG GCT GCG AGT GTC CTC CTC TTA TGG TGA GTA CAA ATT CTC
   --- --- --- --- --- --- --- --- --- --- --- --- --- --- --- --- --- ---
   *** His Ser Lys Met Ala Ala Ser Val Leu Leu Leu Trp *** Val Gln Ile Leu
    Asn Ile Pro Arg Trp Leu Arg Val Ser Ser Ser Tyr Gly Glu Tyr Lys Phe Ser
     Thr Phe Gln Asp Gly Cys Glu Cys Pro Pro Leu Met Val Ser Thr Asn Ser Leu

Phe Pro Pro Phe Gln Leu Tyr Gly Asp Lys Pro Ala Met Gln Leu Pro Lys Gln
    Ser Leu Arg Ser Asn Phe Ile Gly Thr Lys Arg Arg Trp Arg Tyr Arg Asn Arg
   Leu Phe Ala Pro Ile Ser Ser Val Arg Arg Glu Ala Gly Asp Thr Val Thr Glu
   --- --- --- --- --- --- --- --- --- --- --- --- --- --- --- --- --- ---
   ATC TTT CCG CCC TTA ACT TCT ATG GGC AGA AAG CCG CGG TAG ACA TTG CCA AAG
       1575        1584        1593        1602        1611        1620
   TAG AAA GGC GGG AAT TGA AGA TAC CCG TCT TTC GGC GCC ATC TGT AAC GGT TTC
   --- --- --- --- --- --- --- --- --- --- --- --- --- --- --- --- --- ---
   *** Lys Gly Gly Asn *** Arg Tyr Pro Ser Phe Gly Ala Ile Cys Asn Gly Phe
    Arg Lys Ala Gly Ile Glu Asp Thr Arg Leu Ser Ala Pro Ser Val Thr Val Ser
     Glu Arg Arg Glu Leu Lys Ile Pro Val Phe Arg Arg His Leu *** Arg Phe Leu
```

FIG. 2f

```
  Leu Arg Pro Thr Gly Phe Ile Thr Lys Glu Pro Pro His Lys Trp Ser Pro Gln
   Phe Ala Pro His Val Leu Tyr Pro Arg Arg Arg Leu Ile Asn Gly Leu His Ser
  Ser Pro Pro Thr Tyr Trp Ile His Asp Glu Gly Ser Ser Thr Glu Leu Ile Ala
  --- --- --- --- --- --- --- --- --- --- --- --- --- --- --- --- --- ---
  ACT TCC GCC CCA CAT GGT TTA TAC CAG AAG AGG CCT CCT ACA AAG GTT CTA CCG
       1629        1638        1647        1656        1665        1674
  TGA AGG CGG GGT GTA CCA AAT ATG GTC TTC TCC GGA GGA TGT TTC CAA GAT GGC
  --- --- --- --- --- --- --- --- --- --- --- --- --- --- --- --- --- ---
  *** Arg Arg Gly Val Pro Asn Met Val Phe Ser Gly Gly Cys Phe Gln Asp Gly
   Glu Gly Gly Val Tyr Gln Ile Trp Ser Ser Pro Glu Asp Val Ser Lys Met Ala
  Lys Ala Gly Cys Thr Lys Tyr Gly Leu Leu Arg Arg Met Phe Pro Arg Trp Leu

Pro Pro Pro Asp Thr Lys Gln Pro Leu Ala Glu Lys Ala Val Asp Asp *** Leu
  Arg Pro Arg Thr Arg Arg Arg Arg Tyr Arg Arg Arg Pro Trp Thr Met Arg Tyr
  Ala Pro Ala Pro Gly Asp Glu Ala Thr Val Gly Gly Gln Gly Arg *** Gly Ile
  --- --- --- --- --- --- --- --- --- --- --- --- --- --- --- --- --- ---
  ACG CCC CCG CCC AGG CAG AAG ACG CCA TTG CGG AGG AAC CGG TGC AGT AGG ATA
       1683        1692        1701        1710        1719        1728
  TGC GGG GGC GGG TCC GTC TTC TGC GGT AAC GCC TCC TTG GCC ACG TCA TCC TAT
  --- --- --- --- --- --- --- --- --- --- --- --- --- --- --- --- --- ---
  Cys Gly Gly Gly Ser Val Phe Cys Gly Asn Ala Ser Leu Ala Thr Ser Ser Tyr
   Ala Gly Ala Gly Pro Ser Ser Ala Val Thr Pro Pro Trp Pro Arg His Pro Ile
    Arg Gly Arg Val Arg Leu Leu Arg *** Arg Leu Leu Gly His Val Ile Leu ***

Leu Ser Leu Leu Ala Ser Ser Tyr Tyr
    Phe His Phe Phe His Ala Ala Thr Thr Asn
  Phe Thr Phe Ser Thr Arg Gln Gln Leu Ile
  --- --- --- --- --- --- --- --- --- -
  TTT TCA CTT TCT TCA CGC GAC GAC ATC ATA A  5'
       1737        1746        1755
  AAA AGT GAA AGA AGT GCG CTG CTG TAG TAT T  3'
  --- --- --- --- --- --- --- --- --- ---
  Lys Ser Glu Arg Ser Ala Leu Leu *** Tyr
   Lys Val Lys Glu Val Arg Cys Cys Ser Ile
    Lys *** Lys Lys Cys Cys Ala Ala Val Val
```

FIG. 2g

|  | 10 | 20 | 30 | 40 | 50 | |
|---|---|---|---|---|---|---|
| circopormank | 1 ACCAGCGCAC | TTCGGCAGCG | GCAGCACCTC | GGCAGCGTCA | GTGAAAATGC | 50 |
| circopormeeh | 1 ACCAGCGCAC | TTCGGCAGCG | GCAGCACCTC | GGCAGCGTCA | GTGAAAATGC | 50 |
| circopordfp | 1 ACCAGCGCAC | TTCGGCAGCG | GCAGCACCTC | GGCAGCGTCA | GTGAAAATGC | 50 |

|  | 60 | 70 | 80 | 90 | 100 | |
|---|---|---|---|---|---|---|
| circopormank | 51 CAAGCAAGAA | AAGCGGCCCG | CAACCCCATA | AGAGGTGGGT | GTTCACCCTT | 100 |
| circopormeeh | 51 CAAGCAAGAA | AAGCGGCCCG | CAACCCCATA | AGAGGTGGGT | GTTCACCCTT | 100 |
| circopordfp | 51 CAAGCAAGAA | AAGCGGCCCG | CAACCCCATA | AGAGGTGGGT | GTTCACCCTT | 100 |

|  | 110 | 120 | 130 | 140 | 150 | |
|---|---|---|---|---|---|---|
| circopormank | 101 AATAATCCTT | CCGAGGAGGA | GAAAAACAAA | ATACGGGAGC | TTCCAATCTC | 150 |
| circopormeeh | 101 AATAATCCTT | CCGAGGAGGA | GAAAAACAAA | ATACGGGAGC | TTCCAATCTC | 150 |
| circopordfp | 101 AATAATCCTT | CCGAGGAGGA | GAAAAACAAA | ATACGGGAGC | TTCCAATCTC | 150 |

|  | 160 | 170 | 180 | 190 | 200 | |
|---|---|---|---|---|---|---|
| circopormank | 151 CCTTTTTGAT | TATTTTGTTT | GCGGAGAGGA | AGGTTTGGAA | GAGGGTAGAA | 200 |
| circopormeeh | 151 CCTTTTTGAT | TATTTTGTTT | GCGGAGAGGA | AGGTTTGGAA | GAGGGTAGAA | 200 |
| circopordfp | 151 CCTTTTTGAT | TATTTTGTTT | GTGGCGAGGA | AGGTTTGGAA | GAGGGTAGAA | 200 |

|  | 210 | 220 | 230 | 240 | 250 | |
|---|---|---|---|---|---|---|
| circopormank | 201 CTGCTCACCT | CCAGGGGTTT | GCTAATTTTG | CTAAGAAGCA | GACTTTTAAC | 250 |
| circopormeeh | 201 CTCCTCACCT | CCAGGGGTTT | GCGAATTTTG | CTAAGAAGCA | GACTTTTAAC | 250 |
| circopordfp | 201 CTCCTCACCT | CCAGGGGTTT | GCGAATTTTG | CTAAGAAGCA | GACTTTTAAC | 250 |

|  | 260 | 270 | 280 | 290 | 300 | |
|---|---|---|---|---|---|---|
| circopormank | 251 AAGGTGAAGT | GGTATTTTGG | TGCCCGCTGC | CACATCGAGA | AAGCGAAAGG | 300 |
| circopormeeh | 251 AAGGTGAAGT | GGTATTTTGG | TGCCCGCTGC | CACATCGAGA | AAGCGAAAGG | 300 |
| circopordfp | 251 AAGGTGAAGT | GGTATTTTGG | TGCCCGCTGC | CACATCGAGA | AAGCGAAAGG | 300 |

|  | 310 | 320 | 330 | 340 | 350 | |
|---|---|---|---|---|---|---|
| circopormank | 301 AACCGACCAG | CAGAATAAAG | AATACTGCAG | TAAAGAAGGC | CACATACTTA | 350 |
| circopormeeh | 301 AACCGACCAG | CAGAATAAAG | AATACTGCAG | TAAAGAAGGC | CACATACTTA | 350 |
| circopordfp | 301 AACCGACCAG | CAGAATAAAG | AATACTGCAG | TAAAGAAGGC | CACATACTTA | 350 |

|  | 360 | 370 | 380 | 390 | 400 | |
|---|---|---|---|---|---|---|
| circopormank | 351 TCGAGTGTGG | AGCTCCGCGG | AACCAGGGGA | AGCGCAGCGA | CCTGTCTACT | 400 |
| circopormeeh | 351 TCGAGTGTGG | AGCTCCGCGG | AACCAGGGGA | AGCGCAGCGA | CCTGTCTACT | 400 |
| circopordfp | 351 TCGAGTGTGG | AGCTCCGCGG | AACCAGGGGA | AGCGCAGCGA | CCTGTCTACT | 400 |

|  | 410 | 420 | 430 | 440 | 450 | |
|---|---|---|---|---|---|---|
| circopormank | 401 GCTGTGAGTA | CCCTTTTGGA | GACGGGGTCT | TTGGTGACTG | TAGCCGAGCA | 450 |
| circopormeeh | 401 GCTGTGAGTA | CCCTTTTGGA | GACGGGGTCT | TTGGTGACTG | TAGCCGAGCA | 450 |
| circopordfp | 401 GCTGTGAGTA | CCCTTTTGGA | GACGGGGTCT | TTGGTGACTG | TAGCCGAGCA | 450 |

|  | 460 | 470 | 480 | 490 | 500 | |
|---|---|---|---|---|---|---|
| circopormank | 451 GTTCCCTGTA | ACGTATGTGA | GAAATTTCCG | CGGGCTGGCT | GAACTTTTGA | 500 |
| circopormeeh | 451 GTTCCCTGTA | ACGTATGTGA | GAAATTTCCG | CGGGCTGGCT | GAACTTTTGA | 500 |
| circopordfp | 451 GTTTCCTGTA | ACGTATGTGA | GAAATTTCCG | CGGGCTGGCT | GAACTTTTGA | 500 |

|  | 510 | 520 | 530 | 540 | 550 | |
|---|---|---|---|---|---|---|
| circopormank | 501 AAGTGAGCGG | GAAGATGCAG | CAGCGTGATT | GGAAGACAGC | TGTACACGTC | 550 |
| circopormeeh | 501 AAGTGAGCGG | GAAGATGCAG | CAGCGTGATT | GGAAGACAGC | TGTACACGTC | 550 |
| circopordfp | 501 AAGTGAGCGG | GAAGATGCAG | CAGCGTGATT | GGAAGACAGC | TGTACACGTC | 550 |

|  | 560 | 570 | 580 | 590 | 600 | |
|---|---|---|---|---|---|---|
| circopormank | 551 ATAGTGGGCC | CGCCCGGTTG | TGGGAAGAGC | CAGTGGGCCC | GTAATTTTGC | 600 |
| circopormeeh | 551 ATAGTGGGCC | CGCCCGGTTG | TGGGAAGAGC | CAGTGGGCCC | GTAATTTTGC | 600 |
| circopordfp | 551 ATAGTGGGCC | CGCCCGGTTG | TGGGAAGAGC | CAGTGGGCCC | GTAATTTTGC | 600 |

FIG. 3a

```
                         610        620        630        640        650
circopormank   601 TGAGCCTAGC GACACCTACT GGAAGCCTAG TAGAAATAAG TGGTGGGATG  650
circopormeeh   601 TGAGCCTAGG GACACCTACT GGAAGCCTAG TAGAAATAAG TGGTGGGATG  650
circopordfp    601 TGAGCCTAGG GACACCTACT GGAAGCCTAG TAGAAATAAG TGGTGGGATG  650

660        670        680        690        700
circopormank   651 GATATCATGG AGAAGAAGTT GTTGTTTTGG ATGATTTTTA TGACTGGTTA  700
circopormeeh   651 GATATCATGG AGAAGAAGTT GTTGTTTTGG ATGATTTTTA TGACTGGTTA  700
circopordfp    651 GATATCATGG AGAAGAAGTT GTTGTTTTGG ATGATTTTTA TGACTGGTTA  700

710        720        730        740        750
circopormank   701 CCTTGGGATG ATCTACTGAG ACTGTGTGAC CGGTATCCAT TGACTGTAGA  750
circopormeeh   701 CCTTGGGATG ATCTACTGAG ACTGTGTGAC CGGTATCCAT TGACTGTAGA  750
circopordfp    701 CCTTGGGATG ATCTACTGAG ACTGTGTGAC CGGTATCCAT TGACTGTAGA  750

760        770        780        790        800
circopormank   751 GACTAAAGGC GGTACTGTTC CTTTTTTGGC TCGCAGTATT TTGATTACCA  800
circopormeeh   751 GACTAAAGGG GGTACTGTTC CTTTTTTGGC CCGCAGTATT TTGATTACCA  800
circopordfp    751 GACTAAAGGG GGTACTGTTC CTTTTTTGGC CCGCAGTATT TTGATTACCA  800

810        820        830        840        850
circopormank   801 GCAATCAGGC CCCCCAGGAA TGGTACTCCT CAACTGCTGT CCCAGCTGTA  850
circopormeeh   801 GCAATCAGGC CCCCCAGGAA TGGTACTCCT CAACTGCTGT CCCAGCTGTA  850
circopordfp    801 GCAATCAGGC CCCCCAGGAA TGGTACTCCT CAACTGCTGT CCCAGCTGTA  850

860        870        880        890        900
circopormank   851 GAAGCTCTCT ATCGGAGGAT TACTACTTTG CAATTTTGGA AGACTGCTGG  900
circopormeeh   851 GAAGCTCTCT ATCGGAGGAT TACTACTTTG CAATTTTGGA AGACTGCTGG  900
circopordfp    851 GAAGCTCTCT ATCGGAGGAT TACTACTTTG CAATTTTGGA AGACTGCTGG  900

910        920        930        940        950
circopormank   901 AGAACAATCA ACGGAGGTAC CCGAAGGCCG ATTTGAAGCA GTGGACCCAC  950
circopormeeh   901 AGAACAATCC ACGGAGGTAC CCGAAGGCCG ATTTGAAGCA GTGGACCCAC  950
circopordfp    901 AGAACAATCC ACGGAGGTAC CCGAAGGCCG ATTTGAAGCA GTGGACCCAC  950

960        970        980        990       1000
circopormank   951 CCTGTGCCCT TTTCCCATAT AAAATAAATT ACTGAGTCTT TTTTGTTATC 1000
circopormeeh   951 CCTGTGCCCT TTTCCCATAT AAAATAAATT ACTGAGTCTT TTTTGTTATC 1000
circopordfp    951 CCTGTGCCCT TTTCCCATAT AAAATAAATT ACTGAGTCTT TTTTGTTATC 1000

1010       1020       1030       1040       1050
circopormank  1001 ACATCGTAAT GGTTTTTATT TTTATTTATT TAGAGGGTCT TTTAGGATAA 1050
circopormeeh  1001 ACATCGTAAT GGTTTTTATT TTTATTTATT TAGAGGGTCT TTTAGGATAA 1050
circopordfp   1001 ACATCGTAAT GGTTTTTATT TTTATTCATT TAGAGGGTCT TTCAGGATAA 1050

1060       1070       1080       1090       1100
circopormank  1051 ATTCTCTGAA TTGTACATAA ATAGTCAGCC TTACCACATA ATTTTGGGCT 1100
circopormeeh  1051 ATTCTCTGAA TTGTACATAA ATAGTCAGCC TTACCACATA ATTTTGGGCT 1100
circopordfp   1051 ATTCTCTGAA TTGTACATAA ATAGTCAACC TTACCACATA ATTTTGGGCT 1100

1110       1120       1130       1140       1150
circopormank  1101 GTGGCTGCAT TTTGGAGCGC ATAGCCGAGG CCTGTGTGCT CGACATTGGT 1150
circopormeeh  1101 GTGGCTGCAT TTTGGAGCGC ATAGCCGAGG CCTGTGTGCT CGACATTGGT 1150
circopordfp   1101 GTGGTTGCAT TTTGGAGCGC ATAGCCCAGG CCTGTGTGCT CGACATTGGT 1150

1160       1170       1180       1190       1200
circopormank  1151 GTGGGTATTT AAATGGAGCC ACAGCTGGTT TCTTTTATTA TTTGGGTGGA 1200
circopormeeh  1151 GTGGGTATTT AAATGGAGCC ACAGCTGGTT TCTTTTATTA TTTGGGTGGA 1200
circopordfp   1151 GTGGGTATTT AAATGGAGCC ACAGCTGGTT TCTTTTATTA TTTGGCTGGA 1200
```

FIG. 3b

|  | | 1210 | 1220 | 1230 | 1240 | 1250 | |
|---|---|---|---|---|---|---|---|
| circopormank | 1201 | ACCAATCAAT | TGTTTGGTCC | AGCTCAGGTT | TGGGGGTGAA | GTACCTGGAG | 1250 |
| circopormeeh | 1201 | ACCAATCAAT | TGTTTGGTCC | AGCTCAGGTT | TGGGGGTGAA | GTACCTGGAG | 1250 |
| circopordfp  | 1201 | ACCAATCAAT | TGTTTGGTCT | AGCTCTGGTT | TGGGGGTGAA | GTACCTGGAG | 1250 |
|  |  | 1260 | 1270 | 1280 | 1290 | 1300 |  |
| circopormank | 1251 | TGGTAGGTAA | AGGGCTGCCT | TATGGTGTGG | CGGGAGGAGT | AGTTAATATA | 1300 |
| circopormeeh | 1251 | TGGTAGGTAA | AGGGCTGCCT | TATGGTGTGG | CGGGAGGAGT | AGTTAATATA | 1300 |
| circopordfp  | 1251 | TGGTAGGTAA | AGGGCTGCCT | TATGGTGTGG | CGGGAGGAGT | AGTTAATATA | 1300 |
|  |  | 1310 | 1320 | 1330 | 1340 | 1350 |  |
| circopormank | 1301 | GGGGTCATAG | GCCAAGTTGG | TGGAGGGGGT | TACAAAGTTG | GCATCCAAGA | 1350 |
| circopormeeh | 1301 | GGGGTCATAG | GCCAAGTTGG | TGGAGGGGGT | TACAAAGTTG | GCATCCAAGA | 1350 |
| circopordfp  | 1301 | GGGGTCATAG | GCCAAGTTGG | TGGAGGGGGT | TACAAAGTTG | GCATCCAAGA | 1350 |
|  |  | 1360 | 1370 | 1380 | 1390 | 1400 |  |
| circopormank | 1351 | TAACAACAGT | GGACCCAACA | CCTCTTTGAT | TAGAGGTGAT | GGGGTCTCTG | 1400 |
| circopormeeh | 1351 | TAACAACAGT | GGACCCAACA | CCTCTTTGAT | TAGAGGTGAT | GGGGTCTCTG | 1400 |
| circopordfp  | 1351 | TAACAACAGT | GGACCCAACA | CCTCTTTGAT | TAGAGGTGAT | GGGGTCTCTG | 1400 |
|  |  | 1410 | 1420 | 1430 | 1440 | 1450 |  |
| circopormank | 1401 | GGGTAAAATT | CATATTTAGC | CTTTCTAATA | CGGTAGTATT | GGAAAGGTAG | 1450 |
| circopormeeh | 1401 | GGGTAAAATT | CATATTTAGC | CTTTCTAATA | CGGTAGTATT | GGAAAGGTAG | 1450 |
| circopordfp  | 1401 | GGGTAAAATT | CATATTTAGC | CTTTCTAATA | CGGTAGTATT | GGAAAGGTAG | 1450 |
|  |  | 1460 | 1470 | 1480 | 1490 | 1500 |  |
| circopormank | 1451 | GGGTAGGGGG | TTGGTGCCGC | CTGAGGGGGG | GAGGAACTGG | CCGATGTTGA | 1500 |
| circopormeeh | 1451 | GGGTAGGGGG | TTGGTGCCGC | CTGAGGGGGG | GAGGAACTGG | CCGATGTTGA | 1500 |
| circopordfp  | 1451 | GGGTAGGGGG | TTGGTGCCGC | CTGAGGGGGG | GAGGAACTGG | CCGATGTTGA | 1500 |
|  |  | 1510 | 1520 | 1530 | 1540 | 1550 |  |
| circopormank | 1501 | ATCTGAGGTG | GTTAACATGC | CAAGATGGCT | GCGAGTATCC | TCCTTTTATG | 1550 |
| circopormeeh | 1501 | ATTTGAGGTA | GTTAACATTC | CAAGATGGCT | GCGAGTATCC | TCCTTTTATG | 1550 |
| circopordfp  | 1501 | ATCTCAGCTC | GTTAACATTC | CAAGATGGCT | GCGAGTGTCC | TCCTCTTATG | 1550 |
|  |  | 1560 | 1570 | 1580 | 1590 | 1600 |  |
| circopormank | 1551 | GTGATTACAA | ATTCTTTAGA | AAGGCGGCAA | TTGAAGATAC | CCGTCTTTCG | 1600 |
| circopormeeh | 1551 | GTGAGTACAA | ATTCTGTAGA | AAGGCGGGAA | TTGAAGATAC | CCGTCTTTCG | 1600 |
| circopordfp  | 1551 | GTGAGTACAA | ATTCTCTAGA | AAGGCGGGAA | TTGAAGATAC | CCGTCTTTCG | 1600 |
|  |  | 1610 | 1620 | 1630 | 1640 | 1650 |  |
| circopormank | 1601 | GCGCCATCTG | TAACGGTTTC | TGAAGGCGGG | GTGTGCCAAA | TATGGTCTTC | 1650 |
| circopormeeh | 1601 | GCGCCATCTG | TAACGGTTTC | TGAAGGCGGG | GTGTGCCAAA | TATGGTCTTC | 1650 |
| circopordfp  | 1601 | GCGCCATCTG | TAACGGTTTC | TGAAGGCGGG | GTGTACCAAA | TATGGTCTTC | 1650 |
|  |  | 1660 | 1670 | 1680 | 1690 | 1700 |  |
| circopormank | 1651 | TCCGGAGGAT | GTTTCCAAGA | TGGCTGCGGG | GGCGGGTCCT | TCTTCTGCGG | 1700 |
| circopormeeh | 1651 | TCCGGAGGAT | GTTTCCAAGA | TGGCTGCGGG | GGCGGGTCCT | TCTTCTGCGG | 1700 |
| circopordfp  | 1651 | TCCGGAGGAT | GTTTCCAAGA | TGGCTGCGGG | GGCGGGTCCG | TCTTCTGCGG | 1700 |
|  |  | 1710 | 1720 | 1730 | 1740 | 1750 |  |
| circopormank | 1701 | TAACGCCTCC | TTGGCCACGT | CATCCTATAA | AAGTGAAAGA | AGTGCGCTGC | 1750 |
| circopormeeh | 1701 | TAACGCCTCC | TTGGCCACGT | CATCCTATAA | AAGTGAAAGA | AGTGCGCTGC | 1750 |
| circopordfp  | 1701 | TAACGCCTCC | TTGGCCACGT | CATCCTATAA | AAGTGAAAGA | AGTGCGCTGC | 1750 |
|  |  | 1760 | 1770 | 1780 | 1790 | 1800 |  |
| circopormank | 1751 | TGTAGTATT | .......... | .......... | .......... | .......... | 1800 |
| circopormeeh | 1751 | TGTAGTATT | .......... | .......... | .......... | .......... | 1800 |
| circopordfp  | 1751 | TGTAGTATT | .......... | .......... | .......... | .......... | 1800 |

FIG. 3c

|  |  | 10 | 20 | 30 | 40 | 50 |  |
|---|---|---|---|---|---|---|---|
| circopormank | 1 | NPSKKSGPQP | HKRWVFTLNN | PSEEEKNKIR | ELPISLFDYF | VCGEEGLEEG | 50 |
| circopormeeh | 1 | NPSKKSGPQP | HKRWVFTLNN | PSEEEKNKIR | ELPISLFDYF | VCGEEGLEEG | 50 |
| circopordfp[ | 1 | NPSKKSGPQP | HKRWVFTLNN | PSEEEKNKIR | ELPISLFDYF | VCGEEGLEEG | 50 |

|  |  | 60 | 70 | 80 | 90 | 100 |  |
|---|---|---|---|---|---|---|---|
| circopormank | 51 | RTAHLQGFAN | FAKKQTFNKV | KWYFGARCHI | EKAKGTDQQN | KEYCSKEGHI | 100 |
| circopormeeh | 51 | RTPHLQGFAN | FAKKQTFNKV | KWYFGARCHI | EKAKGTDQQN | KEYCSKEGHI | 100 |
| circopordfp[ | 51 | RTPHLQGFAN | FAKKQTFNKV | KWYFGARCHI | EKAKGTDQQN | KEYCSKEGHI | 100 |

|  |  | 110 | 120 | 130 | 140 | 150 |  |
|---|---|---|---|---|---|---|---|
| circopormank | 101 | LIECGAPRNQ | GKRSDLSTAV | STLLETGSLV | TVAEQFPVTY | VRNFRGLAEL | 150 |
| circopormeeh | 101 | LIECGAPRNQ | GKRSDLSTAV | STLLETGSLV | TVAEQFPVTY | VRNFRGLAEL | 150 |
| circopordfp[ | 101 | LIECGAPRNQ | GKRSDLSTAV | STLLETGSLV | TVAEQFPVTY | VRNFRGLAEL | 150 |

|  |  | 160 | 170 | 180 | 190 | 200 |  |
|---|---|---|---|---|---|---|---|
| circopormank | 151 | LKVSGKMQQR | DWKTAVHVIV | GPPGCGKSQW | ARNFAEPSQT | YWKPSRNKWH | 200 |
| circopormeeh | 151 | LKVSGKMQQR | DWKTAVHVIV | GPPGCGKSQW | ARNFAEPROT | YWKPSRNKWH | 200 |
| circopordfp[ | 151 | LKVSGKMQQR | DWKTAVHVIV | GPPGCGKSQW | ARNFAEPROT | YWKPSRNKWH | 200 |

|  |  | 210 | 220 | 230 | 240 | 250 |  |
|---|---|---|---|---|---|---|---|
| circopormank | 201 | DGYHGEEVVV | LDDFYGWLPW | DDLLRLCDRY | PLTVETKGGT | VPFLARSILI | 250 |
| circopormeeh | 201 | DGYHGEEVVV | LDDFYGWLPW | DDLLRLCDRY | PLTVETKGGT | VPFLARSILI | 250 |
| circopordfp[ | 201 | DGYHGEEVVV | LDDFYGWLPW | DDLLRLCDRY | PLTVETKGGT | VPFLARSILI | 250 |

|  |  | 260 | 270 | 280 | 290 | 300 |  |
|---|---|---|---|---|---|---|---|
| circopormank | 251 | TSNQAPQEWY | SSTAVPAVEA | LYRRITTLQF | WKTAGEQSTE | VPEGRFEAVD | 300 |
| circopormeeh | 251 | TSNQAPQEWY | SSTAVPAVEA | LYRRITTLQF | WKTAGEQSTE | VPEGRFEAVD | 300 |
| circopordfp[ | 251 | TSNQAPQEWY | SSTAVPAVEA | LYRRITTLQF | WKTAGEQSTE | VPEGRFEAVD | 300 |

|  |  | 310 | 320 | 330 | 340 | 350 |  |
|---|---|---|---|---|---|---|---|
| circopormank | 301 | PPCALFPYKI | NY | | | | 350 |
| circopormeeh | 301 | PPCALFPYKI | NY | | | | 350 |
| circopordfp[ | 301 | PPCALFPYKI | NY | | | | 350 |

FIG. 4

```
                    10         20         30         40         50
circopormank   1 MTWPRRRYRR RRTRPRSHLG NILRRRPYLA HPAFRNRYRW RRKTGIFNCR   50
circopormeeh   1 MTWPRRRYRR RRTRPRSHLG NILRRRPYLA HPAFRNRYRW RRKTGIFNSR   50
circopordfp[   1 MTWPRRRYRR RRTRPRSHLG NILRRRPYLV HPAFRNRYRW RRKTGIFNSR   50

60         70         80         90        100
circopormank  51 LSKEFVLTIK GGYSQPSWNV NILRFNIGQF LPPSGGTNPL PLPFQYYRIR  100
circopormeeh  51 LSTEFVLTIK GGYSQPSWNV NYLKFNIGQF LPPSGGTNPL PLPFQYYRIR  100
circopordfp[  51 LSREFVLTIR GGTSQPSWNV NFLRFNIGQF LPPSGGTNPL PLPFQYYRIR  100

110        120        130        140        150
circopormank 101 KAKYEFYPRD PITSNERGVG STVVILDANF VTPSTNLAYD PYINYSSRHT  150
circopormeeh 101 KAKYEFYPRD PITSNQRGVG STVVILDANF VTPSTNLAYD PYINYSSRHT  150
circopordfp[ 101 KAKYEFYPRD PITSNQRGVG STVVILDANF VTPSTNLAYD PYINYSSRHT  150

160        170        180        190        200
circopormank 151 IRQPFTYHSR YFTPKPELDQ TIDWFHPNNK RNQLWLHLNT HTNVEHTGLG  200
circopormeeh 151 IRQPFTYHSR YFTPKPELDQ TIDWFHPNNK RNQLWLHLNT HTNVEHTGLG  200
circopordfp[ 151 IRQPFTYHSR YFTPKPELDQ TIDWFQPNNK RNQLWLHLNT HTNVEHTGLG  200

210        220        230        240        250
circopormank 201 YALQNAATAQ NYVVRLTIYV QFREFILKDP LNK*.......  ..........  250
circopormeeh 201 YALQNAATAQ NYVVRLTIYV QFREFILKDP LNK*.......  ..........  250
circopordfp[ 201 YALQNATTAQ NYVVRLTIYV QFREFILKDP LNE*.......  ..........  250
```

FIG. 5

```
                    10         20         30         40         50
circopormank   1 MISIPPLIST RLPVGVARLS KITGPLALPT TGRAHYDVYS CLPITLLHLP   50
circopormeeh   1 MISIPPLIST RLPVGVPRLS KITGPLALPT TGRAHYDVYS CLPITLLHLP   50
circopordfp[   1 MISIPPLIST RLPVGVPRLS KITGPLALPT TGRAHYDVYS CLPITLLHLP   50

60         70         80         90        100
circopormank  51 AHFQKFSQPA EISHIRYREL LGYSHQRPRL QKGTHSSRQV AALPLVPRSS  100
circopormeeh  51 AHFQKFSQPA EISHIRYREL LGYSHQRPRL QKGTHSSRQV AALPLVPRSS  100
circopordfp[  51 AHFQKFSQPA EISHIRYRKL LGYSHQRPRL QKGTHSSRQV AALPLVPRSS  100

110        120        130        140        150
circopormank 101 TLDKYVAFFT AVFFILLVGS FRFLDVAAGT KIPLHLVKSL LLSKISKPLE  150
circopormeeh 101 TLDKYVAFFT AVFFILLVGS FRFLDVAAGT KIPLHLVKSL LLSKIRKPLE  150
circopordfp[ 101 TLDKYVAFFT AVFFILLVGS FRFLDVAAGT KIPLHLVKSL LLSKIRKPLE  150

160        170        180        190        200
circopormank 151 VSSSTLFQTF LSANKIIKKG DWKLPYFVFL LLGRIIKGEH PPLMGLRAAF  200
circopormeeh 151 VRSSTLFQTF LSANKIIKKG DWKLPYFVFL LLGRIIKGEH PPLMGLRAAF  200
circopordfp[ 151 VRSSTLFQTF LATNKIIKKG DWKLPYFVFL LLGRIIKGEH PPLMGLRAAF  200

210        220        230        240        250
circopormank 201 LAWHFH*.... ..........  ..........  ..........  ..........  250
circopormeeh 201 LAWHFH..... ..........  ..........  ..........  ..........  250
circopordfp[ 201 LAWHFH-.... ..........  ..........  ..........  ..........  250
```

FIG. 6

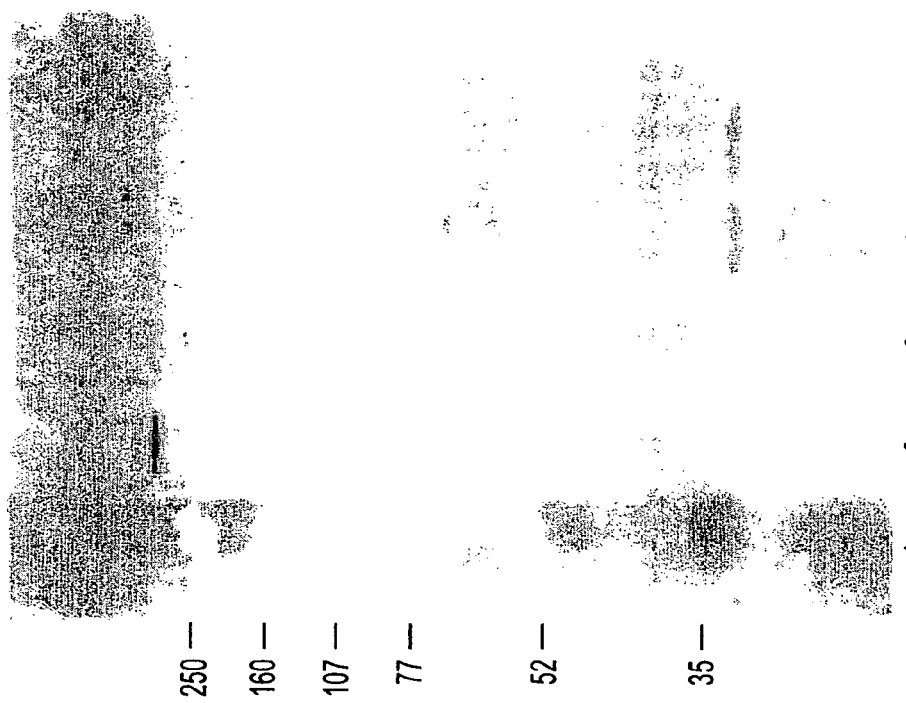

```
         Leu Ala Ser Arg Cys Arg Cys Cys Arg Pro Leu Val Glu Ala Ala Val His Gly
          Trp Arg Val Glu Ala Ala Ala Ala Gly Arg Cys Cys Arg Leu Leu Leu Met Gly
          Gly Ala Cys Lys Pro Leu Pro Leu Val Glu Ala Ala Gly *** Cys Cys Cys Ala
          --- --- --- --- --- --- --- --- --- --- --- --- --- --- --- --- --- ---
3'        TGG TCG CGT GAA GCC GTC GCC GTC GTG GAG CCG TCG TGG AGT CGT CGT TGT ACG
                   9          18          27          36          45          54
5'        ACC AGC GCA CTT CGG CAG CGG CAG CAC CTC GGC AGC ACC TCA GCA GCA ACA TGC
          --- --- --- --- --- --- --- --- --- --- --- --- --- --- --- --- --- ---
          Thr Ser Ala Leu Arg Gln Arg Gln His Leu Gly Ser Thr Ser Ala Ala Thr Cys
           Pro Ala His Phe Gly Ser Gly Ser Thr Ser Ala Ala Pro Gln Gln Gln His Ala
            Gln Arg Thr Ser Ala Ala Ala Ala Pro Arg Gln His Leu Ser Ser Asn Met Pro

Ala Leu Leu Ile Ser Ser Ala Ser Gly Leu Gly Met Phe Pro Pro His Glu Ser
           Leu Leu Phe Phe Pro Leu Leu Pro Gly Trp Gly Trp Leu Leu His Thr Asn Val
            Trp Cys Ser Ser His Phe Phe Arg Val Gly Val Gly Tyr Phe Thr Pro Thr ***
          --- --- --- --- --- --- --- --- --- --- --- --- --- --- --- --- --- ---
          GGT CGT TCT TCT TAC CTT CTT CGC CTG GGG TTG GGG TAT TTT CCA CCC ACA AGT
                  63          72          81          90          99         108
          CCA GCA AGA AGA ATG GAA GAA GCG GAC CCC AAC CCC ATA AAA GGT GGG TGT TCA
          --- --- --- --- --- --- --- --- --- --- --- --- --- --- --- --- --- ---
          Pro Ala Arg Arg Met Glu Glu Ala Asp Pro Asn Pro Ile Lys Gly Gly Cys Ser
           Gln Gln Glu Glu Trp Lys Lys Arg Thr Pro Thr Pro *** Lys Val Gly Val His
            Ser Lys Lys Asn Gly Arg Ser Gly Pro Gln Pro His Lys Arg Trp Val Phe Thr

Gln Ile Ile Arg Gly Phe Val Leu Ala Leu Phe Tyr Pro Ile Lys Trp Tyr Gly
           Arg Phe Leu Gly Glu Ser Ser Ser Arg Leu Phe Ile Arg Ser Arg Gly Ile Asp
            Glu Ser Tyr Asp Lys Arg Leu Arg Ala Cys Ser Phe Val Pro Asp Glu Leu Ile
          --- --- --- --- --- --- --- --- --- --- --- --- --- --- --- --- --- ---
          GAG ACT TAT TAG GAA GGC TTC TGC TCG CGT TCT TTT ATG CCC TAG AAG GTT ATA
                 117         126         135         144         153         162
          CTC TGA ATA ATC CTT CCG AAG ACG AGC GCA AGA AAA TAC GGG ATC TTC CAA TAT
          --- --- --- --- --- --- --- --- --- --- --- --- --- --- --- --- --- ---
          Leu *** Ile Ile Leu Pro Lys Thr Ser Ala Arg Lys Tyr Gly Ile Phe Gln Tyr
           Ser Glu *** Ser Phe Arg Arg Arg Ala Gln Glu Asn Thr Gly Ser Ser Asn Ile
            Leu Asn Asn Pro Ser Glu Asp Glu Arg Lys Lys Ile Arg Asp Leu Pro Ile Ser

*** Lys Ile Ile Lys Asn Asn Ala Leu Leu Thr Ile Leu Phe Ser Ser Cys Arg
           Arg Asn Ser *** Lys Ile Thr Pro Ser Ser Pro Leu Ser Ser Pro Arg Val Gly
            Gly Ile Gln Asn Asn *** Gln Gln Arg Pro Pro Tyr His Pro Leu Val Phe Val
          --- --- --- --- --- --- --- --- --- --- --- --- --- --- --- --- --- ---
          GGG ATA AAC TAA TAA AAT AAC AAC CGC TCC TCC CAT TAC TCC TTC CTG CTT GTG
                 171         180         189         198         207         216
          CCC TAT TTG ATT ATT TTA TTG TTG GCG AGG AGG GTA ATG AGG AAG GAC GAA CAC
          --- --- --- --- --- --- --- --- --- --- --- --- --- --- --- --- --- ---
          Pro Tyr Leu Ile Ile Leu Leu Leu Ala Arg Arg Val Met Arg Lys Asp Glu His
           Pro Ile *** Leu Phe Tyr Cys Trp Arg Gly Gly *** *** Gly Arg Thr Asn Thr
            Leu Phe Asp Tyr Phe Ile Val Gly Glu Glu Gly Asn Glu Glu Gly Arg Thr Pro

Val Glu Leu Pro Glu Ser Ile Lys His Leu Leu Leu Ser Lys Ile Phe His Leu
          *** Arg Trp Pro Asn Ala Leu Lys Thr Phe Phe Cys Val Lys Leu Leu Thr Phe
           Glu Gly Gly Pro Thr Arg *** Asn Gln Ser Ser Ala Ser Lys *** Tyr Leu Ser
          --- --- --- --- --- --- --- --- --- --- --- --- --- --- --- --- --- ---
          GAG TGG AGG TCC CCA AGC GAT TAA AAC ACT TCT TCG TCT GAA AAT TAT TTC ACT
                 225         234         243         252         261         270
          CTC ACC TCC AGG GGT TCG CTA ATT TTG TGA AGA AGC AGA CTT TTA ATA AAG TGA
          --- --- --- --- --- --- --- --- --- --- --- --- --- --- --- --- --- ---
          Leu Thr Ser Arg Gly Ser Leu Ile Leu *** Arg Ser Arg Leu Leu Ile Lys ***
           Ser Pro Pro Gly Val Arg *** Phe Cys Glu Glu Ala Asp Phe *** *** Ser Glu
            His Leu Gln Gly Phe Ala Asn Phe Val Lys Lys Gln Thr Phe Asn Lys Val Lys
```

FIG. 8a

```
  Pro Ile Gln Thr Gly Ala Ala Val Asp Leu Phe Arg Phe Ser Cys Ile Leu Leu
   His Tyr Lys Pro Ala Arg Gln Trp Met Ser Phe Ala Phe Pro Val Ser *** Cys
    Thr Thr Asn Pro His Gly Ser Gly Cys Arg Ser Leu Ser Leu Phe Leu Asp Ala
   --- --- --- --- --- --- --- --- --- --- --- --- --- --- --- ---
   TCA CCA TAA ACC CAC GGG CGA CGG TGT AGC TCT TTC GCT TTC CTT GTC TAG TCG
         279         288         297         306         315         324
   AGT GGT ATT TGG GTG CCC GCT GCC ACA TCG AGA AAG CGA AAG GAA CAG ATC AGC
   --- --- --- --- --- --- --- --- --- --- --- --- --- --- --- ---
  Ser Gly Ile Trp Val Pro Ala Ala Thr Ser Arg Lys Arg Lys Glu Gln Ile Ser
   Val Val Phe Gly Cys Pro Leu Pro His Arg Glu Ser Glu Arg Asn Arg Ser Ala
    Trp Tyr Leu Gly Ala Arg Cys His Ile Glu Lys Ala Lys Gly Thr Asp Gln Gln

Ile Phe Phe Val Ala Thr Phe Phe Ala Val *** Gln His Leu Thr Ser Ser Arg
    Phe Leu Ser Tyr Gln Leu Leu Ser Pro Leu Lys Ser His Ser His Pro Ala Gly
     Ser Tyr Leu Ile Ser Cys Tyr Leu Leu Cys Ser Val Ser Pro Thr His Leu Glu
   --- --- --- --- --- --- --- --- --- --- --- --- --- --- --- ---
   TCT TAT TTC TTA TGA CGT CAT TTC TTC CGT TGA ATG ACT ACC TCA CAC CTC GAG
         333         342         351         360         369         378
   AGA ATA AAG AAT ACT GCA GTA AAG AAG GCA ACT TAC TGA TGG AGT GTG GAG CTC
   --- --- --- --- --- --- --- --- --- --- --- --- --- --- --- ---
  Arg Ile Lys Asn Thr Ala Val Lys Lys Ala Thr Tyr *** Trp Ser Val Glu Leu
   Glu *** Arg Ile Leu Gln *** Arg Arg Gln Leu Thr Asp Gly Val Trp Ser Ser
    Asn Lys Glu Tyr Cys Ser Lys Glu Gly Asn Leu Leu Met Glu Cys Gly Ala Pro

Ser Arg Leu Ser Leu Pro Thr Val Gln Arg Ser Ser His Thr Gly Gln Gln Leu
    Leu Asp *** Pro Cys Arg Leu Ser Arg Asp Val Ala Thr Leu Val Lys Asn Ser
     *** Ile Glu Pro Val Val Ser His Gly Thr *** Gln Gln Ser Tyr Arg Thr Pro
   --- --- --- --- --- --- --- --- --- --- --- --- --- --- --- ---
   GAT CTA GAG TCC CTG TTG CCT CAC TGG ACA GAT GAC GAC ACT CAT GGA ACA ACC
         387         396         405         414         423         432
   CTA GAT CTC AGG GAC AAC GGA GTG ACC TGT CTA CTG CTG TGA GTA CCT TGT TGG
   --- --- --- --- --- --- --- --- --- --- --- --- --- --- --- ---
  Leu Asp Leu Arg Asp Asn Gly Val Thr Cys Leu Leu Leu *** Val Pro Cys Trp
   *** Ile Ser Gly Thr Thr Glu *** Pro Val Tyr Cys Cys Glu Tyr Leu Val Gly
    Arg Ser Gln Gly Gln Arg Ser Asp Leu Ser Thr Ala Val Ser Thr Leu Leu Glu

Ala Pro Thr Gln His Gly Asn Cys Leu Leu Val Arg Tyr Arg Lys Asp Ser Ile
    Leu Pro Leu Arg Thr Val Thr Ala Ser Cys Cys Gly Thr Val Asn Thr Leu Phe
     Ser Arg Ser Asp Pro Ser Arg Gln Leu Ala Ala Gly Gln Leu Thr Gln *** Phe
   --- --- --- --- --- --- --- --- --- --- --- --- --- --- --- ---
   TCT CGC CCT CAG ACC ACT GGC AAC GTC TCG TCG TGG GAC ATT GCA AAC AGT CTT
         441         450         459         468         477         486
   AGA GCG GGA GTC TGG TGA CCG TTG CAG AGC AGC ACC CTG TAA CGT TTG TCA GAA
   --- --- --- --- --- --- --- --- --- --- --- --- --- --- --- ---
  Arg Ala Gly Val Trp *** Pro Leu Gln Ser Ser Thr Leu *** Arg Leu Ser Glu
   Glu Arg Glu Ser Gly Asp Arg Cys Arg Ala Ala Pro Cys Asn Val Cys Gln Lys
    Ser Gly Ser Leu Val Thr Val Ala Glu Gln His Pro Val Thr Phe Val Arg Asn

Glu Ala Pro Gln Ser Phe Lys Gln Phe His Ala Pro Phe His Leu Leu Thr Ile
    Lys Arg Pro Ser Ala Ser Ser Lys Phe Thr Leu Pro Phe Ile Cys Phe Arg Ser
     Asn Gly Arg Ala Pro Gln Val Lys Ser Leu Ser Arg Ser Phe Ala Ser Ala His
   --- --- --- --- --- --- --- --- --- --- --- --- --- --- --- ---
   TAA AGG CGC CCG ACC GAC TTG AAA ACT TTC ACT CGC CCT TTT ACG TCT TCG CAC
         495         504         513         522         531         540
   ATT TCC GCG GGC TGG CTG AAC TTT TGA AAG TGA GCG GGA AAA TGC AGA AGC GTG
   --- --- --- --- --- --- --- --- --- --- --- --- --- --- --- ---
  Ile Ser Ala Gly Trp Leu Asn Phe *** Lys *** Ala Gly Lys Cys Arg Ser Val
   Phe Pro Arg Ala Gly *** Thr Phe Glu Ser Glu Arg Glu Asn Ala Glu Ala ***
    Phe Arg Gly Leu Ala Glu Leu Leu Lys Val Ser Gly Lys Met Gln Lys Arg Asp
```

FIG. 8b

```
Pro Leu Ser Ile Tyr Val Asp Asn His Pro Trp Arg Pro Thr Thr Phe Ala Phe
Gln Phe Val Leu Thr Cys Thr Met Thr Pro Gly Gly Pro His Pro Leu Leu Leu
Asn Ser Ser *** His Val Arg *** Gln Pro Ala Val Gln Thr His Tyr Phe Cys
--- --- --- --- --- --- --- --- --- --- --- --- --- --- --- --- --- ---
TAA CCT TCT GAT TAC ATG TGC AGT AAC ACC CCG GTG GAC CCA CAC CAT TTT CGT
    549         558         567         576         585         594
ATT GGA AGA CTA ATG TAC ACG TCA TTG TGG GGC CAC CTG GGT GTG GTA AAA GCA
--- --- --- --- --- --- --- --- --- --- --- --- --- --- --- --- --- ---
Ile Gly Arg Leu Met Tyr Thr Ser Leu Trp Gly His Leu Gly Val Val Lys Ala
 Leu Glu Asp *** Cys Thr Arg His Cys Gly Ala Thr Trp Val Trp *** Lys Gln
  Trp Lys Thr Asn Val His Val Ile Val Gly Pro Pro Gly Cys Gly Lys Ser Lys

Pro Ser Ser Ile Lys Cys Val Arg Phe Gly Cys Val Pro Phe Trp Arg Ser Val
 His Ala Ala Leu Lys Ala Ser Gly Ser Val Val Tyr Gln Phe Gly Gly Leu Phe
Ile Pro Gln *** Asn Gln Leu Gly Pro Phe Trp Met Ser Ser Val Val *** Phe
--- --- --- --- --- --- --- --- --- --- --- --- --- --- --- --- --- ---
TTA CCC GAC GAT TAA AAC GTC TGG GCC TTT GGT GTA TGA CCT TTG GTG GAT CTT
    603         612         621         630         639         648
AAT GGG CTG CTA ATT TTG CAG ACC CGG AAA CCA CAT ACT GGA AAC CAC CTA GAA
--- --- --- --- --- --- --- --- --- --- --- --- --- --- --- --- --- ---
Asn Gly Leu Leu Ile Leu Gln Thr Arg Lys Pro His Thr Gly Asn His Leu Glu
 Met Gly Cys *** Phe Cys Arg Pro Gly Asn His Ile Leu Glu Thr Thr *** Lys
  Trp Ala Ala Asn Phe Ala Asp Pro Glu Thr Thr Tyr Trp Lys Pro Pro Arg Asn

Leu Pro Pro Ile Thr Val Met Thr Phe Phe His Asn Asn Asn Ile Val Lys Ile
 Leu His His Ser Pro *** Trp Pro Ser Ser Thr Thr Thr Ile Ser Ser Lys ***
  Cys Thr Thr Pro His Asn Gly His His Leu Leu Pro Gln *** Gln His Ser Lys
--- --- --- --- --- --- --- --- --- --- --- --- --- --- --- --- --- ---
TGT TCA CCA CCC TAC CAA TGG TAC CAC TTC TTC ACC AAC AAT AAC TAC TGA AAA
    657         666         675         684         693         702
ACA AGT GGT GGG ATG GTT ACC ATG GTG AAG AAG TGG TTG TTA TTG ATG ACT TTT
--- --- --- --- --- --- --- --- --- --- --- --- --- --- --- --- --- ---
Thr Ser Gly Gly Met Val Thr Met Val Lys Lys Trp Leu Leu Leu Met Thr Phe
 Gln Val Val Gly Trp Leu Pro Trp *** Arg Ser Gly Cys Tyr *** *** Leu Leu
  Lys Trp Trp Asp Gly Tyr His Gly Glu Glu Val Val Val Ile Asp Asp Phe Tyr

Ala Pro Gln Gly Pro Ile Ile *** Gln Ser Gln Thr Ile Ser Ile Trp Gln Ser
 Pro Gln Ser Gly Gln Ser Ser Arg Ser Leu Ser His Ser Arg Tyr Gly Asn Val
  His Ser Ala Ala Arg Pro His Asp Val Ser Val Thr His Asp Ile Asp Met Ser
--- --- --- --- --- --- --- --- --- --- --- --- --- --- --- --- --- ---
TAC CGA CCG ACG GGA CCC TAC TAG ATG ACT CTG ACA CAC TAG CTA TAG GTA ACT
    711         720         729         738         747         756
ATG GCT GGC TGC CCT GGG ATG ATC TAC TGA GAC TGT GTG ATC GAT ATC CAT TGA
--- --- --- --- --- --- --- --- --- --- --- --- --- --- --- --- --- ---
Met Ala Gly Cys Pro Gly Met Ile Tyr *** Asp Cys Val Ile Asp Ile His ***
 Trp Leu Ala Ala Leu Gly *** Ser Thr Glu Thr Val *** Ser Ile Ser Ile Asp
  Gly Trp Leu Pro Trp Asp Asp Leu Leu Arg Leu Cys Asp Arg Tyr Pro Leu Thr

Tyr Leu Ser Phe Thr Ser Ser Tyr Arg Lys Gln Gly Ala Thr Asn Gln Asn Gly
 Thr Ser Val Leu Pro Pro Val Thr Gly Lys Lys Ala Arg Leu Ile Arg Ile Val
  Gln Leu Ser *** Leu His Phe Gln Val Lys Lys Pro Gly Cys Tyr Glu Ser ***
--- --- --- --- --- --- --- --- --- --- --- --- --- --- --- --- --- ---
GAC ATC TCT GAT TTC CAC CTT GAC ATG GAA AAA ACC GGG CGT CAT AAG ACT AAT
    765         774         783         792         801         810
CTG TAG AGA CTA AAG GTG GAA CTG TAC CTT TTT TGG CCC GCA GTA TTC TGA TTA
--- --- --- --- --- --- --- --- --- --- --- --- --- --- --- --- --- ---
Leu *** Arg Leu Lys Val Glu Leu Tyr Leu Phe Trp Pro Ala Val Phe *** Leu
 Cys Arg Asp *** Arg Trp Asn Cys Thr Phe Phe Gly Pro Gln Tyr Ser Asp Tyr
  Val Glu Thr Lys Gly Gly Thr Val Pro Phe Leu Ala Arg Ser Ile Leu Ile Thr
```

FIG. 8c

```
  Ala Ile Leu Gly Arg Gln Phe Pro Val Gly *** Ser Ser Asp Trp Ser Tyr Phe
  Leu Leu *** Val Gly Asn Ser His Tyr Glu Glu Val Ala Thr Gly Ala Thr Ser
  Trp Cys Asp Ser Gly Thr Pro Ile Thr Ser Arg Leu Gln Gln Gly Leu Gln Leu
  --- --- --- --- --- --- --- --- --- --- --- --- --- --- --- --- --- ---
  GGT CGT TAG TCT GGG GCA ACC TTA CCA TGA GGA GTT GAC GAC AGG GTC GAC ATC
      819         828         837         846         855         864
  CCA GCA ATC AGA CCC CGT TGG AAT GGT ACT CCT CAA CTG CTG TCC CAG CTG TAG
  --- --- --- --- --- --- --- --- --- --- --- --- --- --- --- --- --- ---
  Pro Ala Ile Arg Pro Arg Trp Asn Gly Thr Pro Gln Leu Leu Ser Gln Leu ***
    Gln Gln Ser Asp Pro Val Gly Met Val Leu Leu Asn Cys Cys Pro Ser Cys Arg
     Ser Asn Gln Thr Pro Leu Glu Trp Tyr Ser Ser Thr Ala Val Pro Ala Val Glu

Ser Lys Ile Pro Pro Asn Ser Gly Gln Tyr Lys Pro Leu Ile Ser Cys Phe Leu
   Ala Arg *** Arg Leu Ile Val Glu Lys Thr Asn Gln Phe Phe Ala Val Ser Cys
    Leu Glu Lys Asp Ser Ser *** Lys Arg Pro Ile Lys Ser Ser His *** Leu Val
  --- --- --- --- --- --- --- --- --- --- --- --- --- --- --- --- --- ---
  TTC GAG AAA TAG CCT CCT AAT GAA GGA ACC ATA AAA CCT TCT TAC GAT GTC TTG
      873         882         891         900         909         918
  AAG CTC TTT ATC GGA GGA TTA CTT CCT TGG TAT TTT GGA AGA ATG CTA CAG AAC
  --- --- --- --- --- --- --- --- --- --- --- --- --- --- --- --- --- ---
  Lys Leu Phe Ile Gly Gly Leu Leu Pro Trp Tyr Phe Gly Arg Met Leu Gln Asn
   Ser Ser Leu Ser Glu Asp Tyr Phe Leu Gly Ile Leu Glu Glu Cys Tyr Arg Thr
    Ala Leu Tyr Arg Arg Ile Thr Ser Leu Val Phe Trp Lys Asn Ala Thr Glu Gln

Gly Arg Leu Phe Pro Ala Leu Glu Asp Gly Lys Gly Gly Trp Ala Arg Phe Lys
   Asp Val Ser Ser Pro Pro Trp Asn Thr Val Arg Glu Gly Gly His Gly Ser Asn
    Ile Trp Pro Pro Leu Pro Gly Thr Arg *** Gly Lys Gly Gly Met Gly Gln Ile
  --- --- --- --- --- --- --- --- --- --- --- --- --- --- --- --- --- ---
  TTA GGT GCC TCC TTC CCC CGG TCA AGC AGT GGG AAA GGG GGG GTA CGG GAC TTA
      927         936         945         954         963         972
  AAT CCA CGG AGG AAG GGG GCC AGT TCG TCA CCC TTT CCC CCC CAT GCC CTG AAT
  --- --- --- --- --- --- --- --- --- --- --- --- --- --- --- --- --- ---
  Asn Pro Arg Arg Lys Gly Ala Ser Ser Ser Pro Phe Pro Pro His Ala Leu Asn
   Ile His Gly Gly Arg Gly Pro Val Arg His Pro Phe Pro Pro Met Pro *** Ile
    Ser Thr Glu Glu Gly Gly Gln Phe Val Thr Leu Ser Pro Pro Cys Pro Glu Phe

Trp Ile Phe Tyr Ile Val Ser Asp Lys Lys Asp Ser Arg Leu Pro Lys *** ***
   Gly Tyr Ser Ile Phe *** Gln Thr Lys Lys Ile Val Glu Tyr His Asn Lys Asn
    Glu Met His Phe Leu Asn Ser Leu Arg Lys *** *** Lys Thr Ile Thr Lys Ile
  --- --- --- --- --- --- --- --- --- --- --- --- --- --- --- --- --- ---
  AAG GTA TAC TTT ATT TAA TGA CTC AGA AAA AAT AGT GAA GCA TTA CCA AAA ATA
      981         990         999         1008        1017        1026
  TTC CAT ATG AAA TAA ATT ACT GAG TCT TTT TTA TCA CTT CGT AAT GGT TTT TAT
  --- --- --- --- --- --- --- --- --- --- --- --- --- --- --- --- --- ---
  Phe His Met Lys *** Ile Thr Glu Ser Phe Leu Ser Leu Arg Asn Gly Phe Tyr
   Ser Ile *** Asn Lys Leu Leu Ser Leu Phe Tyr His Phe Val Met Val Phe Ile
    Pro Tyr Glu Ile Asn Tyr *** Val Phe Phe Ile Thr Ser *** Trp Phe Leu Leu

Glu Asn Leu Thr Leu His Pro Thr Lys Leu Ile Leu Asn Glu Ser Asn Tyr Met
   Asn Met Leu Pro *** Thr Pro Pro Arg *** Phe *** Ile Arg Gln Ile Thr Cys
    Ile *** *** Pro Asn Leu Pro Pro Asp Lys Phe Asn Phe Glu Arg Phe Gln Val
  --- --- --- --- --- --- --- --- --- --- --- --- --- --- --- --- --- ---
  ATA AGT AAT TCC CAA TTC ACC CCC CAG AAA TTT TAA TTT AAG AGA CTT AAC ATG
      1035        1044        1053        1062        1071        1080
  TAT TCA TTA AGG GTT AAG TGG GGG GTC TTT AAA ATT AAA TTC TCT GAA TTG TAC
  --- --- --- --- --- --- --- --- --- --- --- --- --- --- --- --- --- ---
  Tyr Ser Leu Arg Val Lys Trp Gly Val Phe Lys Ile Lys Phe Ser Glu Leu Tyr
   Ile His *** Gly Leu Ser Gly Gly Ser Leu Lys Leu Asn Ser Leu Asn Cys Thr
    Phe Ile Lys Gly *** Val Gly Gly Leu *** Asn *** Ile Leu *** Ile Val His
```

FIG. 8d

```
  Cys Pro *** Val Ser Ile Thr Asn Arg Thr Thr Tyr Val Thr Lys Ser Arg Leu
  Val His Asn Cys Pro Tyr Gln Ile Gly Pro Arg Ile Tyr Gln Lys Arg Val Cys
  Tyr Met Thr Val Arg Ile Asn Tyr Glu Gln Asp Tyr Ile Ser Asn Glu Phe Ala
  --- --- --- --- --- --- --- --- --- --- --- --- --- --- --- --- --- ---
  TAT GTA CCA ATG TGC CTA TAA CAT AAG GAC CAG CAT ATA TGA CAA AAG CTT GCG
      1089        1098        1107        1116        1125        1134
  ATA CAT GGT TAC ACG GAT ATT GTA TTC CTG GTC GTA TAT ACT GTT TTC GAA CGC
  --- --- --- --- --- --- --- --- --- --- --- --- --- --- --- --- --- ---
  Ile His Gly Tyr Thr Asp Ile Val Phe Leu Val Val Tyr Thr Val Phe Glu Arg
   Tyr Met Val Thr Arg Ile Leu Tyr Ser Trp Ser Tyr Ile Leu Phe Ser Asn Ala
    Thr Trp Leu His Gly Tyr Cys Ile Pro Gly Arg Ile Tyr Cys Phe Arg Thr Gln

Ala Ser Ala *** Thr Thr *** Met Glu Leu Leu Lys Tyr Asp *** Gly Cys Ser
   His Arg Pro Arg Arg Pro Arg Cys Lys Trp Cys Asn Thr Thr Glu Ala Val Ala
    Thr Gly Leu Gly Val His Asp Val Asn Gly Ala Thr Gln Leu Arg Leu Trp Leu
  --- --- --- --- --- --- --- --- --- --- --- --- --- --- --- --- --- ---
  TCA CGG CTC CGG ATG CAC CAG ATG TAA AGG TCG TCA AAC ATC AGA GTC GGT GTC
      1143        1152        1161        1170        1179        1188
  AGT GCC GAG GCC TAC GTG GTC TAC ATT TCC AGC AGT TTG TAG TCT CAG CCA CAG
  --- --- --- --- --- --- --- --- --- --- --- --- --- --- --- --- --- ---
  Ser Ala Glu Ala Tyr Val Val Tyr Ile Ser Ser Ser Leu *** Ser Gln Pro Gln
   Val Pro Arg Pro Thr Trp Ser Thr Phe Pro Ala Val Cys Ser Leu Ser His Ser
    Cys Arg Gly Leu Arg Gly Leu His Phe Gln Gln Phe Val Val Ser Ala Thr Ala

Thr Glu Lys Thr Thr Gln Asn Ser Thr Ile Leu Leu Ser Ile *** Ser Leu Asn
   Pro Lys Lys Gln Gln Lys Thr Pro Leu Leu *** Tyr His Phe Arg Pro Cys Thr
    Gln Asn Arg Lys Asn Asn Pro Gln Phe Tyr Asp Ile Thr Phe Asp Leu Val Pro
  --- --- --- --- --- --- --- --- --- --- --- --- --- --- --- --- --- ---
  GAC CAA AGA AAA CAA CAA ACC AAC CTT CAT TAG TTA TCA CTT TAG ATC CTG TCC
      1197        1206        1215        1224        1233        1242
  CTG GTT TCT TTT GTT GTT TGG TTG GAA GTA ATC AAT AGT GAA ATC TAG GAC AGG
  --- --- --- --- --- --- --- --- --- --- --- --- --- --- --- --- --- ---
  Leu Val Ser Phe Val Val Trp Leu Glu Val Ile Asn Ser Glu Ile *** Asp Arg
   Trp Phe Leu Leu Leu Phe Gly Trp Lys *** Ser Ile Val Lys Ser Arg Thr Gly
    Gly Phe Phe Cys Cys Leu Val Gly Ser Asn Gln *** *** Asn Leu Gly Gln Val

Pro Pro Leu Thr Gly Pro Thr Thr Pro Ser Pro Ser Pro *** Pro Ile Ala Pro
   Gln Pro Tyr Leu Val Pro Leu Pro Leu Leu Leu Ala Pro Asn His Tyr Pro Pro
    Lys Pro Thr Phe Tyr Arg Ser His Tyr Ser Phe Pro Gln Thr Ile Thr His Arg
  --- --- --- --- --- --- --- --- --- --- --- --- --- --- --- --- --- ---
  AAA CCC CCA TTT CAT GGC CCT CAC CAT CCT CTT CCC GAC CCA ATA CCA TAC CGC
      1251        1260        1269        1278        1287        1296
  TTT GGG GGT AAA GTA CCG GGA GTG GTA GGA GAA GGG CTG GGT TAT GGT ATG GCG
  --- --- --- --- --- --- --- --- --- --- --- --- --- --- --- --- --- ---
  Phe Gly Gly Lys Val Pro Gly Val Val Gly Glu Gly Leu Gly Tyr Gly Met Ala
   Leu Gly Val Lys Tyr Arg Glu Trp *** Glu Lys Gly Trp Val Met Val Trp Arg
    Trp Gly *** Ser Thr Gly Ser Gly Arg Arg Arg Ala Gly Leu Trp Tyr Gly Gly

Pro Thr Thr *** Met Pro Thr Met Pro Ser Pro Gln Pro Arg Gln *** Leu Thr
   Leu Leu Leu Lys Cys Leu Pro *** Leu His Pro Ser His Gly Lys Asn Cys Leu
    Ser Ser Tyr Asn Val Tyr Pro Asp Tyr Thr Leu Ala Thr Ala Lys Thr Val Phe
  --- --- --- --- --- --- --- --- --- --- --- --- --- --- --- --- --- ---
  CCT CCT CAT CAA ATG TAT CCC CAG TAT CCA CTC CCG ACA CCG AAA ACA ATG TTT
      1305        1314        1323        1332        1341        1350
  GGA GGA GTA GTT TAC ATA GGG GTC ATA GGT GAG GGC TGT GGC TTT TGT TAC AAA
  --- --- --- --- --- --- --- --- --- --- --- --- --- --- --- --- --- ---
  Gly Gly Val Val Tyr Ile Gly Val Ile Gly Glu Gly Cys Gly Leu Cys Tyr Lys
   Glu Glu *** Phe Thr *** Gly Ser *** Val Arg Ala Val Ala Phe Val Thr Lys
    Arg Ser Ser Leu His Arg Gly His Arg *** Gly Leu Trp Pro Leu Leu Gln Ser
```

FIG. 8e

```
  Ile Met *** Phe Leu Leu Val Pro Ala Trp Glu Gly Thr Val Arg Pro Ser Arg
  *** *** Arg Phe Tyr Cys Cys Gln Leu Gly Ser Gly Gln *** Gly Pro His Asp
 Asn Asp Asp Leu Ile Val Ala Ser Ser Gly Val Gly Arg Asp Gly Gln Thr Ile
 --- --- --- --- --- --- --- --- --- --- --- --- --- --- --- --- --- ---
 CAA TAG TAG ATT TTA TTG TCG TGA CCT CGG GTG AGG GGA CAG TGG GAC CCA CTA
     1359        1368        1377        1386        1395        1404
 GTT ATC ATC TAA AAT AAC AGC ACT GGA GCC CAC TCC CCT GTC ACC CTG GGT GAT
 --- --- --- --- --- --- --- --- --- --- --- --- --- --- --- --- --- ---
 Val Ile Ile *** Asn Asn Ser Thr Gly Ala His Ser Pro Val Thr Leu Gly Asp
 Leu Ser Ser Lys Ile Thr Ala Leu Glu Pro Thr Pro Leu Ser Pro Trp Val Ile
 Tyr His Leu Lys *** Gln His Trp Ser Pro Leu Pro Cys His Pro Gly *** Ser

Pro Ala Pro Gly Ser Asn Leu Arg Leu Arg Glu *** Glu Thr Thr Asn Leu Pro
 Pro Leu Leu Ala Leu Ile *** Gly *** Gly Lys Lys Asn Gln Leu Ile *** Leu
 Pro Ser Cys Pro Trp Phe Glu Val Lys Val Lys Arg Ile Arg Tyr Tyr Glu Phe
 --- --- --- --- --- --- --- --- --- --- --- --- --- --- --- --- --- ---
 GCC CCT CGT CCC GGT CTT AAG TTG GAA TTG AAA AGA ATA AGA CAT CAT AAG TTT
     1413        1422        1431        1440        1449        1458
 CGG GGA GCA GGG CCA GAA TTC AAC CTT AAC TTT TCT TAT TCT GTA GTA TTC AAA
 --- --- --- --- --- --- --- --- --- --- --- --- --- --- --- --- --- ---
 Arg Gly Ala Gly Pro Glu Phe Asn Leu Asn Leu Ser Tyr Ser Val Val Phe Lys
 Gly Glu Gln Gly Gln Asn Ser Thr Leu Thr Phe Leu Ile Leu *** Tyr Ser Lys
 Gly Ser Arg Ala Arg Ile Gln Pro *** Pro Phe Leu Phe Cys Ser Ile Gln Arg

Cys Leu Ala Pro Thr Gln Gly Gly Glu Gln Pro Phe Phe Thr Met Leu Ile Ser
 Ala Cys Leu Pro Pro Lys Val Gly Arg Arg Pro Ser Ser Leu *** *** Tyr Gln
 Pro Val Ser Arg Pro Asn Ser Gly Gly Gly Pro Pro Leu Phe Asp Asn Ile Asn
 --- --- --- --- --- --- --- --- --- --- --- --- --- --- --- --- --- ---
 CCC GTG TCT CGC CCC CAA ACT GGG GGG AGG ACC CCC TTC TTT CAG TAA TTA TAA
     1467        1476        1485        1494        1503        1512
 GGG CAC AGA GCG GGG GTT TGA CCC CCC TCC TGG GGG AGG AAA GTC ATT AAT ATT
 --- --- --- --- --- --- --- --- --- --- --- --- --- --- --- --- --- ---
 Gly His Arg Ala Gly Val *** Pro Pro Ser Trp Gly Lys Lys Val Ile Asn Ile
 Gly Thr Glu Arg Gly Phe Asp Pro Pro Pro Gly Gly Arg Lys Ser Leu Ile Leu
 Ala Gln Ser Gly Gly Leu Thr Pro Leu Leu Gly Glu Glu Ser His *** Tyr ***

Asp *** *** Thr Trp Arg Gly Pro Pro Arg Glu Ser Gln Pro Glu Ser Ser Leu
 Ile Glu Asp His Gly Gly Gly Leu Leu Ala Asn Gln Ser His Asn Ala Gln Cys
 Phe Arg Met Met Asp Val Ala Trp Ser Pro Thr Arg Val Thr Thr Arg Lys Val
 --- --- --- --- --- --- --- --- --- --- --- --- --- --- --- --- --- ---
 CCT AGA GTA GTA CAG GTG GCG GGT CCT CCC GCA AGA CTG ACA CCA AGC GAA CTG
     1521        1530        1539        1548        1557        1566
 GAA TCT CAT CAT GTC CAC CGC CCA GGA GGG CGT TCT GAC TGT GGT TCG CTT GAC
 --- --- --- --- --- --- --- --- --- --- --- --- --- --- --- --- --- ---
 Glu Ser His His Val His Arg Pro Gly Gly Arg Ser Asp Cys Gly Ser Leu Asp
 Asn Leu Ile Met Ser Thr Ala Gln Glu Gly Val Leu Thr Val Val Arg Leu Thr
 Ile Ser Ser Cys Pro Pro Pro Arg Arg Ala Phe *** Leu Trp Phe Ala *** Gln

Ile Asp Ser Pro Ala Pro Ser Ala Pro Thr Ser Ser Ala Met Lys Gly Glu Gly
 Tyr Ile Arg Leu His Pro Leu Pro Pro His Gln Leu His Trp Lys Glu Lys Glu
 Thr Tyr Gly Phe Thr Arg Ser Leu Arg Thr Asn Phe Ile Gly Asn Lys Arg Arg
 --- --- --- --- --- --- --- --- --- --- --- --- --- --- --- --- --- ---
 TCA TAT AGG CTT CCA CGC CCT CTC CGC CCA CAA CTT CTA CGG TAA AAA GGA AGA
     1575        1584        1593        1602        1611        1620
 AGT ATA TCC GAA GGT GCG GGA GAG GCG GGT GTT GAA GAT GCC ATT TTT CTT TCT
 --- --- --- --- --- --- --- --- --- --- --- --- --- --- --- --- --- ---
 Ser Ile Ser Glu Gly Ala Gly Glu Ala Gly Val Glu Asp Ala Ile Phe Pro Ser
 Val Tyr Pro Lys Val Arg Glu Arg Arg Val Leu Lys Met Pro Phe Phe Leu Leu
 Tyr Ile Arg Arg Cys Gly Arg Gly Gly Cys *** Arg Cys His Phe Ser Phe Ser
```

FIG. 8f

```
  Ala Thr Val Thr Ala Pro Thr Ser Ser Gly Pro Ala Ala Ala Ser Ser Arg Ala
   Leu Pro Leu Pro Pro Pro Pro Pro Arg Ala Leu Pro Pro Pro Pro Pro Asp Pro
  Trp Arg Tyr Arg His Arg Pro His Val Leu Trp Pro Arg Arg Arg Leu Ile Gln
  --- --- --- --- --- --- --- --- --- --- --- --- --- --- --- --- --- ---
  GGT CGC CAT TGC CAC CGC CCC CAC CTG CTC GGT CCC CGC CGC CGC CTC CTA GAC
       1629         1638         1647         1656         1665         1674
  CCA GCG GTA ACG GTG GCG GGG GTG GAC GAG CCA GGG GCG GCG GCG GAG GAT CTG
  --- --- --- --- --- --- --- --- --- --- --- --- --- --- --- --- --- ---
  Pro Ala Val Thr Val Ala Gly Val Asp Glu Pro Gly Ala Ala Ala Glu Asp Leu
   Gln Arg *** Arg Trp Arg Gly Trp Thr Ser Gln Gly Arg Arg Arg Arg Ile Trp
    Ser Gly Asn Gly Gly Gly Gly Gly Arg Ala Arg Gly Gly Gly Gly Gly Ser Gly

Leu Ile Ala Ala Pro Ala Thr Asp Glu Glu Glu Thr Val Gly Gly Gln Ile Arg
   Trp Ser Pro Gln Pro Pro Pro Thr Lys Lys Lys Pro Leu Ala Glu Lys Ser Val
  Gly Leu His Ser Arg Pro Arg His Arg Arg Arg Arg Tyr Arg Arg Arg Pro Tyr
  --- --- --- --- --- --- --- --- --- --- --- --- --- --- --- --- --- ---
  CGG TTC TAC CGA CGC CCC CGC CAC AGA AGA AGA AGC CAT TGC GGA GGA ACC TAT
       1683         1692         1701         1710         1719         1728
  GCC AAG ATG GCT GCG GGG GCG GTG TCT TCT TCT TCG GTA ACG CCT CCT TGG ATA
  --- --- --- --- --- --- --- --- --- --- --- --- --- --- --- --- --- ---
  Ala Lys Met Ala Ala Gly Ala Val Ser Ser Ser Ser Val Thr Pro Pro Thr Ile
   Pro Arg Trp Leu Arg Gly Arg Cys Leu Leu Leu Arg *** Arg Leu Leu Gly Tyr
    Gln Asp Gly Cys Gly Gly Gly Val Phe Phe Phe Gly Asn Ala Ser Leu Asp Thr

*** Ile Gln Phe Arg Phe Phe His Ala Thr Leu Ile
   Asp Tyr Arg Phe Val Phe Ser Thr Arg Gln Leu Tyr
  Thr Met Asp Ser Phe Ser Leu Leu Ala Ser Tyr Thr Asn
  --- --- --- --- --- --- --- --- --- --- --- --- ---
  GCA GTA TAG ACT TTT GCT TTC TTC ACG CGA CAT TCA TAA  5'
       1737         1746         1755         1764
  CGT CAT ATC TGA AAA CGA AAG AAG TGC GCT GTA AGT ATT  3'
  --- --- --- --- --- --- --- --- --- --- --- --- ---
  Arg His Ile *** Lys Arg Lys Lys Cys Ala Val Ser Ile
   Val Ile Ser Glu Asn Glu Arg Ser Ala Leu *** Val
    Ser Tyr Leu Lys Thr Lys Glu Val Arg Cys Lys Tyr
```

FIG. 8g

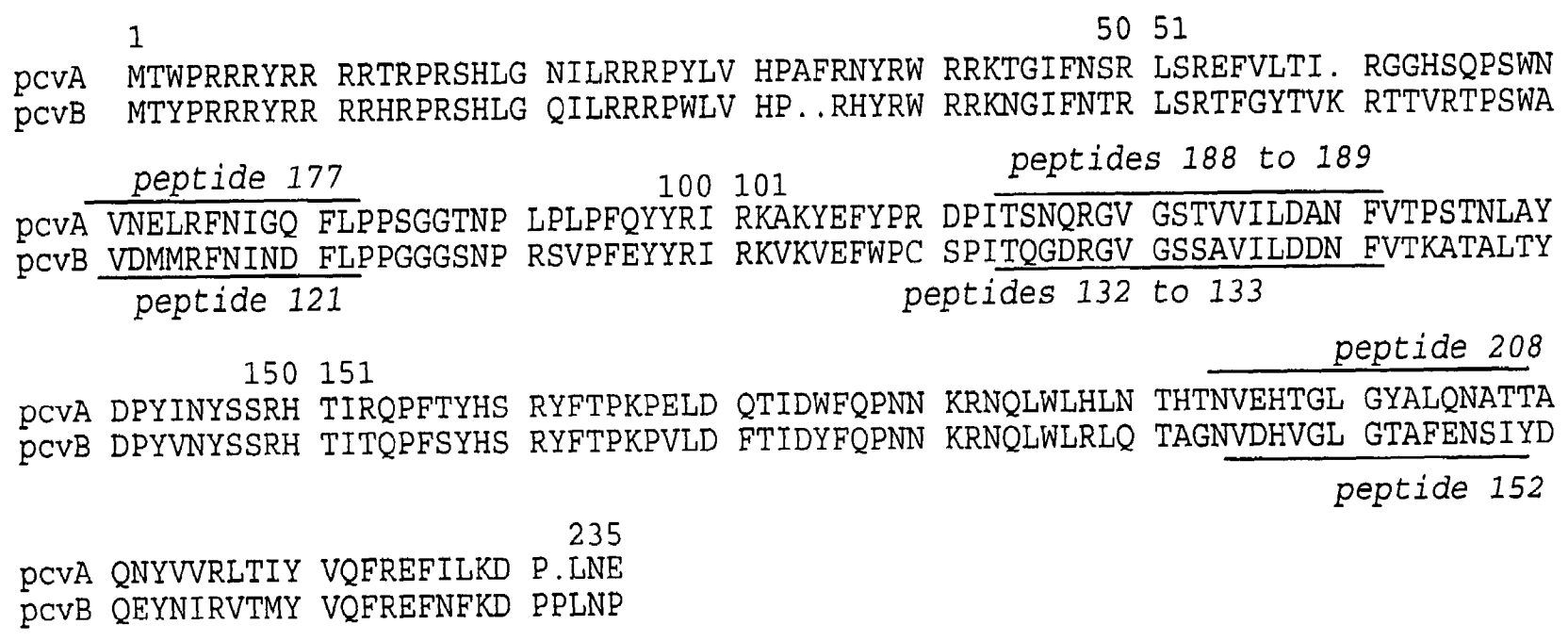

```
          1                                                    50 51
pcvA   MTWPRRRYRR RRTRPRSHLG NILRRRPYLV HPAFRNYRW RRKTGIFNSR LSRE ated with Piglet Weight Loss Disease (PWD)

CIRCOVIRUS SEQUENCES ASSOCIATED WITH PIGLET WEIGHT LOSS DISEASE (PWD)

INFORMATION ON RELATED APPLICATIONS

This application is a divisional of U.S. patent application Ser. No. 10/718,264, filed Nov. 21, 2003, now U.S. Pat. No. 7,179,472, which is a divisional of U.S. patent application Ser. No. 09/514,245, filed Feb. 28, 2000, now U.S. Pat. No. 6,703,023, which is a continuation-in-part of International Patent Application No. PCT/FR98/02634, filed Dec. 4, 1998, published in a non-English language, the specifications of which are incorporated herein by reference in their entireties.

BACKGROUND OF THE INVENTION

The invention relates to the genomic sequence and nucleotide sequences coding for polypeptides of PWD circovirus, such as the structural and nonstructural polypeptides of said circovirus, as well as vectors including said sequences and cells or animals transformed by these vectors. The invention likewise relates to methods for detecting these nucleic acids or polypeptides and kits for diagnosing infection by the PWD circovirus. The invention is also directed to a method for selecting compounds capable of modulating the viral infection. The invention further comprises pharmaceutical compositions, including vaccines, for the prevention and/or the treatment of viral infections by PWD circovirus as well as the use of a vector according to the invention for the prevention and/or the treatment of diseases by gene therapy.

Piglet weight loss disease (PWD), alternatively called fatal piglet wasting (FPW) has been widely described in North America (Harding, J. C., 1997), and authors have reported the existence of a relationship between this pathology and the presence of porcine circovirus (Daft, B. et al., 1996; Clark, E. G., 1997; Harding, J. C., 1997; Harding, J. C. and Clark, E. G., 1997; Nayar, G. P. et al., 1997). A porcine circovirus has already been demonstrated in established lines of cell cultures derived from pigs and chronically infected (Tischer, I., 1986, 1988, 1995; Dulac, G. C., 1989; Edwards, S., 1994; Allan, G. M., 1995 and McNeilly, F., 1996). This virus, during experimental infection of piglets, does not prove pathogenic for pigs (Tischer, I., 1986, Horner, G. W., 1991) and its nucleotide sequence has been determined and characterized (Tischer, I., 1982; Meehan, B. M. et al., 1997; Mankertz., A., 1997). The porcine circovirus, called PCV virus, is part of the circovirus genus of the circoviridae family (Murphy, F. A. et al., 1995) whose virion has a circular DNA of size between 1.7 and 2.3 kb, which DNA comprises three open reading frames (ORF1 to ORF3), coding for a replication protein REP involved in the initiation and termination phase of rolling circular replication (RCR) (Heyraud-Nitschke, F., et al., 1995; Harding, M. R. et al., 1993; Hanson, S. F. et al., 1995; Fontes, E. P. B. et al., 1994), coding for a capsid protein (Boulton, L. H. et al., 1997; Hackland, A. F. et al., 1994; Chu, P. W. G. et al., 1993) and coding for a nonstructural protein called a dissemination protein (Lazarowitz., S. G. et al., 1989).

The inventors of the present invention have noticed that the clinical signs perceptible in pigs and linked to infection by the PWD circovirus are very distinctive. These manifestations in general appear in pigs of 8 to 12 weeks of age, weaned for 4 to 8 weeks. The first signs are hypotonia without it being possible to speak of prostration. Rapidly (48 hours), the flanks hollow, the line of the spine becomes apparent, and the pigs "blanch." These signs are in general accompanied by hyperthermia, anorexia and most often by respiratory signs (coughing, dyspnea, polypnea). Transitory diarrhea can likewise appear. The disease state phase lasts approximately one month at the end of which the rate of mortality varies from 5 to 20%. To these mortalities, it is expedient to add a variable proportion (5-10%) of cadaveric animals which are no longer able to present an economic future. It is to be noted that outside of this critical stage of the end of post-weaning, no anomaly appears on the farms. In particular, the reproductive function is totally maintained.

On the epidemiological level, the first signs of this pathology appeared at the start of 1995 in the east of the Côtes d'Armor region in France, and the farms affected are especially confined to this area of the region. In December 1996, the number of farms concerned could not be evaluated with precision because of the absence of a specific laboratory diagnostic method or of an epidemiological surveillance system of the livestock. Based on the clinical facts as well as on results of postmortem examinations supplied by veterinarians, it is possible to estimate this number as several dozen (80-100). The contagiousness of the disease is weak to moderate. Cases are being reported outside the initial area and for the majority are following the transfer of animals coming from farms familiar with the problem. On the other hand, a characteristic of the condition is its strong remanence. Thus, farms which have been affected for a year are still affected in spite of the massive administration of therapeutics. Farms with clinical expression are drawn from various categories of specialization (breeders/fatteners, post-weaners/fatteners) and different economic structures are concerned. In addition, the disorders appear even in farms where the rules of animal husbandry are respected.

Numerous postmortem examinations have been carried out either on farms or in the laboratory. The elements of the lesional table are disparate. The most constant macroscopic lesions are pneumonia which sometimes appears in patchy form as well as hypertrophy of the lymphatic ganglia. The other lesions above all affect the thoracic viscera including, especially, pericarditis and pleurisy. However, arthritis and gastric ulcers are also observed. The lesions revealed in the histological examination are essentially situated at the pulmonary level (interstitial pneumonia), ganglionic level (lymphoid depletion of the lymph nodes, giant cells) and renal level (glomerulonephritis, vasculitis). The infectious agents have been the subject of wide research. It has been possible to exclude the intervention of pestiviruses and Aujeszky's disease. The disorders appear in the seropositive PDRS (Porcine Dysgenic and Respiratory Syndrome, an infection linked to an arteriovirus) herds, but it has not been possible to establish the role of the latter in the genesis of the disorders (the majority of the farms in Brittany are PDRS seropositive).

The inventors of the present invention, with the aim of identifying the etiological agent responsible for PWD, have carried out "contact" tests between piglets which are obviously "ill" and SPF pigs (specific pathogen-free) from CNEVA (Centre National d'Etudes Vétérinaires et Alimentaires, France). These tests allow the development of signs comparable to those observed on the farm to be observed in protected animal houses. The discrete signs such as moderate hyperthermia, anorexia and intermittent diarrhea appeared after one week of contact. It must be noted that the PDRS virus only diffused subsequent to the clinical signs. In addition, inoculations of organ homogenates of sick animals to healthy pigs allowed signs related to those observed on the farms to be reproduced, although with a lower incidence, linked to the favorable conditions of upkeep of the animals in the experimental installations.

Thus, the inventors of the present invention have been able to demonstrate that the pathological signs appear as a well-defined entity affecting the pig at a particular stage of its growth.

This pathology has never been described in France. However, sparse information, especially Canadian, relates to similar facts.

The disorders cannot be mastered with the existing therapeutics.

The data collected both on the farm and by experimentation have allowed the following points to be highlighted:

PWD is transmissible but its contagiousness is not very high, its etiological origin is of infectious and probably viral nature, PWD has a persistent character in the affected farms.

Considerable economic consequences ensue for the farms.

Thus, there is currently a significant need for a specific and sensitive diagnostic, whose production is practical and rapid, allowing the early detection of the infection.

A reliable, sensitive and practical test which allows the distinction between strains of porcine circovirus (PCV) is thus strongly desirable.

On the other hand, a need for efficient and well-tolerated treatment of infections with PWD circovirus likewise remains desirable, no vaccine currently being available against PWD circovirus.

Concerning PWD circovirus, it will probably be necessary to understand the role of the immune defense in the physiology and the pathology of the disease to develop satisfactory vaccines.

Fuller information concerning the biology of these strains, their interactions with their hosts, the associated infectivity phenomena and those of escape from the immune defenses of the host especially, and finally their implication in the development of associated pathologies, will allow a better understanding of these mechanisms. Taking into account the facts which have been mentioned above and which show in particular the limitations of combating infection by the PWD circovirus, it is thus essential today on the one hand to develop molecular tools, especially starting from a better genetic knowledge of the PWD circovirus, and likewise to perfect novel preventive and therapeutic treatments, novel methods of diagnosis and specific, efficacious and tolerated novel vaccine strategies. This is precisely the subject of the present invention.

SUMMARY OF THE INVENTION

The present invention relates to vaccines comprising a nucleotide sequence of the genome of Porcine circovirus type B, or a homologue or fragment thereof, and an acceptable pharmaceutical or veterinary vehicle. In one embodiment of the invention, the nucleotide sequence is selected from SEQ ID No. 15, SEQ ID No. 19 SEQ ID No. 23, or SEQ ID No. 25, or a homologue or fragment thereof. In another embodiment of the invention, the homologue has at least 80% sequence identity to SEQ ID No. 15, SEQ ID No. 19, SEQ ID No. 23 or SEQ ID No. 25. In yet another embodiment, the vaccines further comprising an adjuvant The present invention also relates to vaccines comprising a polypeptide encoded by a nucleotide sequence of the genome of PCVB, or a homologue or fragment thereof, and an acceptable pharmaceutical or veterinary vehicle. In one embodiment, the homologue has at least 80% sequence identity to SEQ ID No. 15, SEQ ID No. 19, SEQ ID No. 23 or SEQ ID No. 25. In another embodiment of the invention, the nucleotide sequence is selected from SEQ ID No. 23 or SEQ ID No. 25, or a homologue or fragment thereof. In still another embodiment, the polypeptide has the amino acid sequence of SEQ ID No. 24 or SEQ ID No. 26. In yet another embodiment, the homologue has at least 80% sequence identity to SEQ ID No. 24 or SEQ ID No. 26. In another embodiment, the polypeptide has the amino acid sequence of SEQ ID No. 29, SEQ ID No. 30, SEQ ID No. 31, or SEQ ID No. 32.

A further aspect of the invention relates to vaccines comprising a vector and an acceptable pharmaceutical or veterinary vehicle, the vector comprising a nucleotide sequence of the genome of Porcine circovirus type B, or a homologue or fragment thereof. In one embodiment, the vaccine further comprises a gene coding for an expression product capable of inhibiting or retarding the establishment or development of a genetic or acquired disease.

The present invention also relates to vaccines comprising a cell and an acceptable pharmaceutical or veterinary vehicle, wherein the cell is transformed with a nucleotide sequence of the genome of Porcine circovirus type B, or a homologue or fragment thereof.

Still further, the present invention relates to vaccines comprising a pharmaceutically acceptable vehicle and a single polypeptide, wherein the single polypeptide consists of SEQ ID No. 26.

Additionally, the present invention relates to methods of immunizing a mammal against piglet weight loss disease comprising administering to a mammal an effective amount of the vaccines described above.

These and other aspects of the invention will become apparent to the skilled artisan in view of the teachings contained herein.

Test 1: experimental reproduction of the PWD by inoculation of pig organ homogenates from farms affected by PWD.

Test 2: experimental reproduction of PWD.

Test 3: experimental reproduction of PWD.

Test 4: no experimental reproduction of PWD.

FIG. 2: Organization of the genome of the circovirus associated with PWD of type A (PCVA)

strand of (+) polarity (SEQ ID No. 1);

strand of (−) polarity (SEQ ID No. 5, represented according to the orientation 3'→5');

sequences of amino acids of proteins encoded by the two DNA strands in the three possible reading frames SEQ ID NOS: 2-4 and 6-8 respectively.

FIG. 3: Alignment of the nucleotide sequence SEQ ID No. 1 of the PWD circovirus of type A (PCVA) and of the MEEHAN SEQ ID No. 163 strain and MANKERTZ SEQ ID No. 164 strain circoviruses of the porcine cell lines.

FIG. 4: Alignment of the sequence of amino acids SEQ ID No. 10 of a polypeptide encoded by the nucleotide sequence SEQ ID No. 9 (ORF1) of the PWD circovirus of type A (PCVA) and of corresponding nucleotide sequences of the MEEHAN SEQ ID No. 165 strain and MANKERTZ SEQ ID No. 166 strain circoviruses of the porcine cell lines.

FIG. 5: Alignment of the sequence of amino acids SEQ ID No. 12 of a polypeptide encoded by the nucleotide sequence SEQ ID No. 11 (ORF2) of the PWD circovirus of type A (PCVA) and of corresponding nucleotide sequences of the MEEHAN SEQ ID No. 167 strain and MANKERTZ SEQ ID No. 168 strain circoviruses of the porcine cell lines.

FIG. 6: Alignment of the sequence of amino acids SEQ ID No. 14 of a polypeptide encoded by the nucleotide sequence SEQ ID No. 13 (ORF3) of the PWD circovirus of type A (PCVA) and of corresponding nucleotide sequences of the MEEHAN SEQ ID No. 169 strain and MANKERTZ SEQ ID No. 170 strain circoviruses of the porcine cell lines.

FIG. 7: Western blot analysis of recombinant proteins of the PWD circovirus of type A (PCVA).

The analyses were carried out on cell extracts of Sf9 cells obtained after infection with recombinant baculovirus PCF ORF 1.

FIG. 8: Organization of the genome of the circovirus associated with the PWD of type B (PCVB)
  strand of (+) polarity (SEQ ID No. 15);
  strand of (−) polarity (SEQ ID No. 19, represented according to the orientation 3'→5');
  sequence of amino acids of proteins encoded by the two DNA strands in the three possible reading frames SEQ ID NOS: 16-18 and 20-22 respectively.

Figure 9:
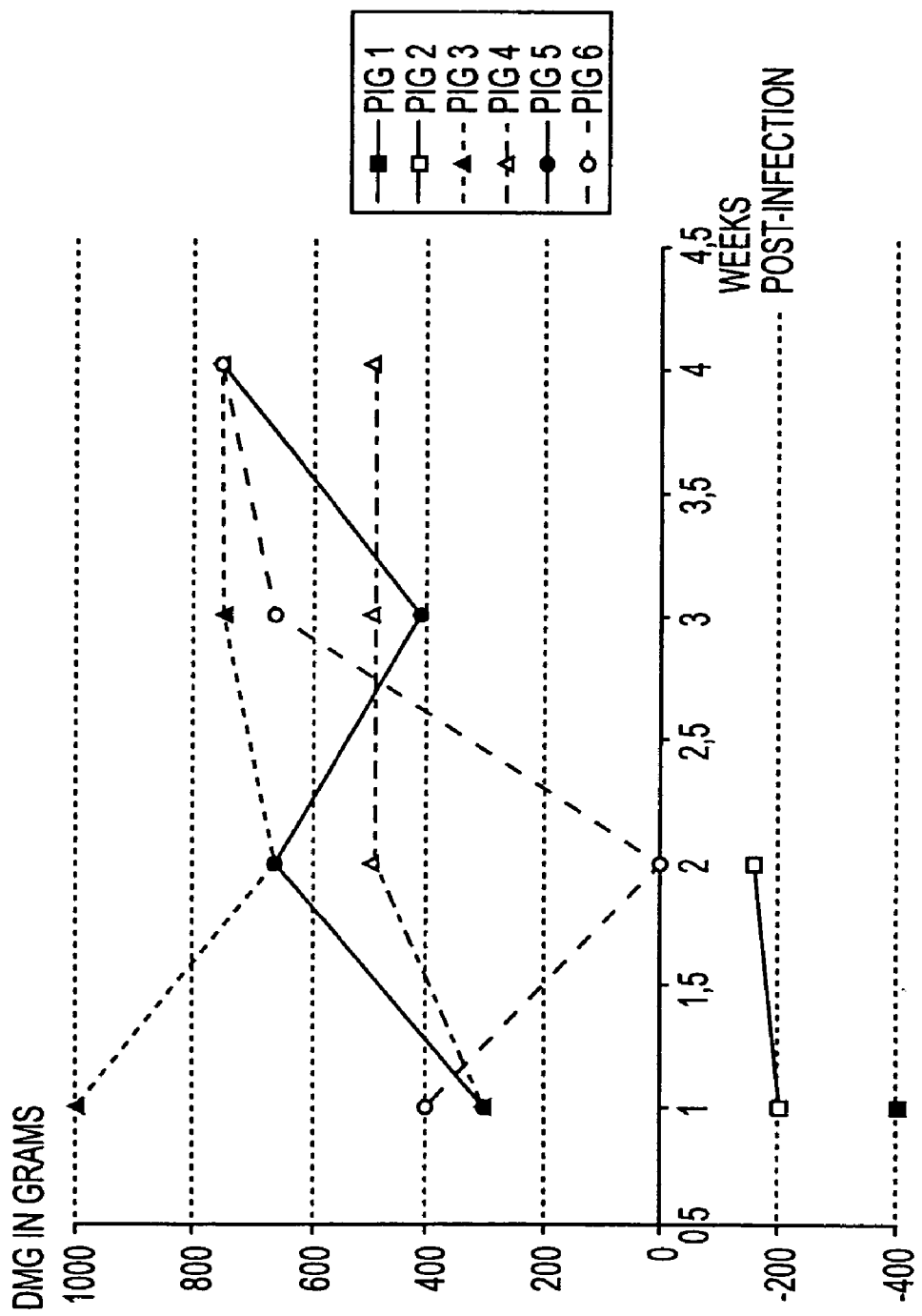

FIG. 9: Evolution of the daily mean gain (DMG) of pig farms affected by piglet weight loss disease (PWD), placed under experimental conditions.

Figure 10:
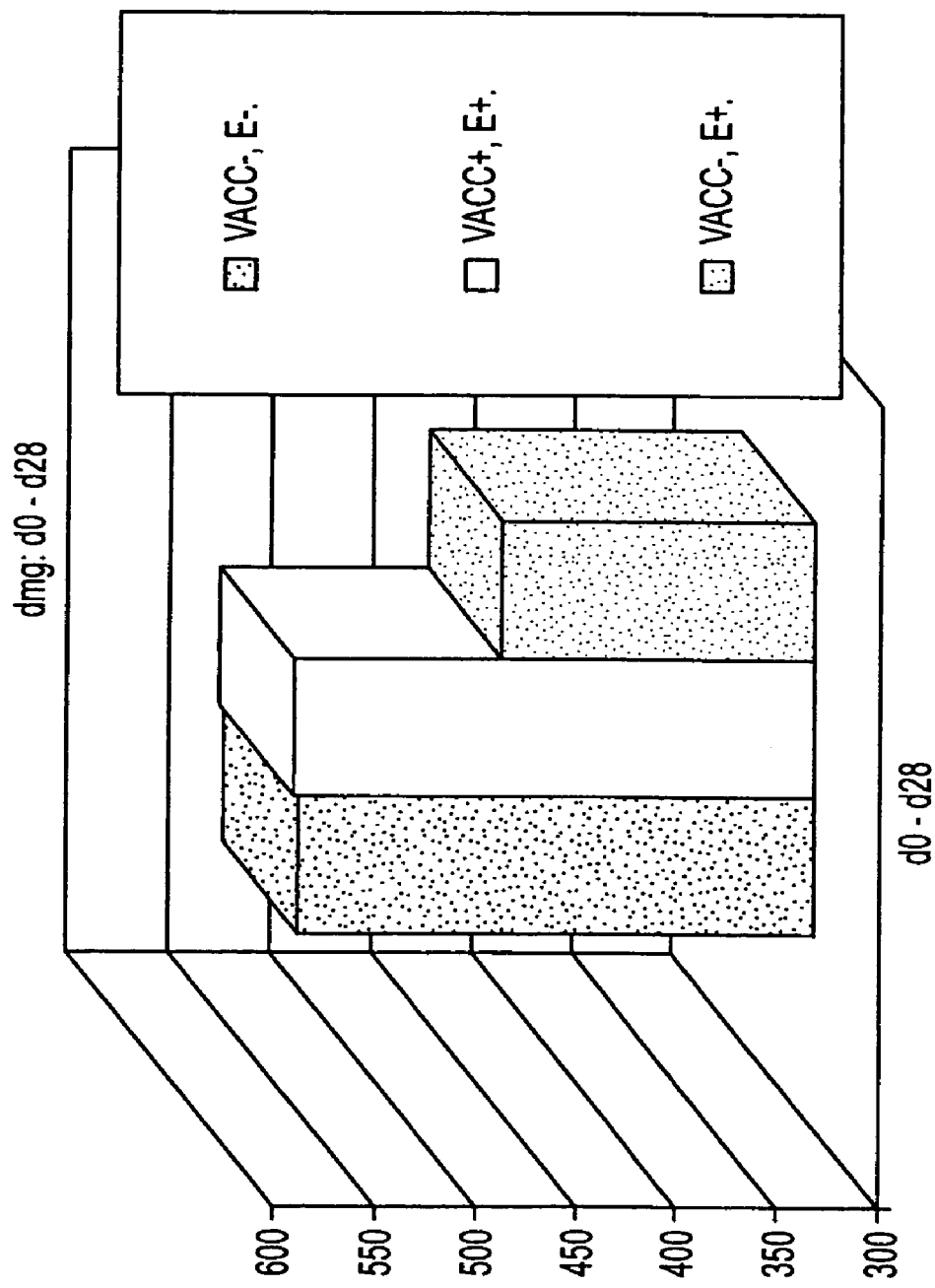

FIG. 10: DMG compared for the 3 batches of pigs (F1, F3 and F4) calculated over a period of 28 days, after vaccination test.

Figure 11:
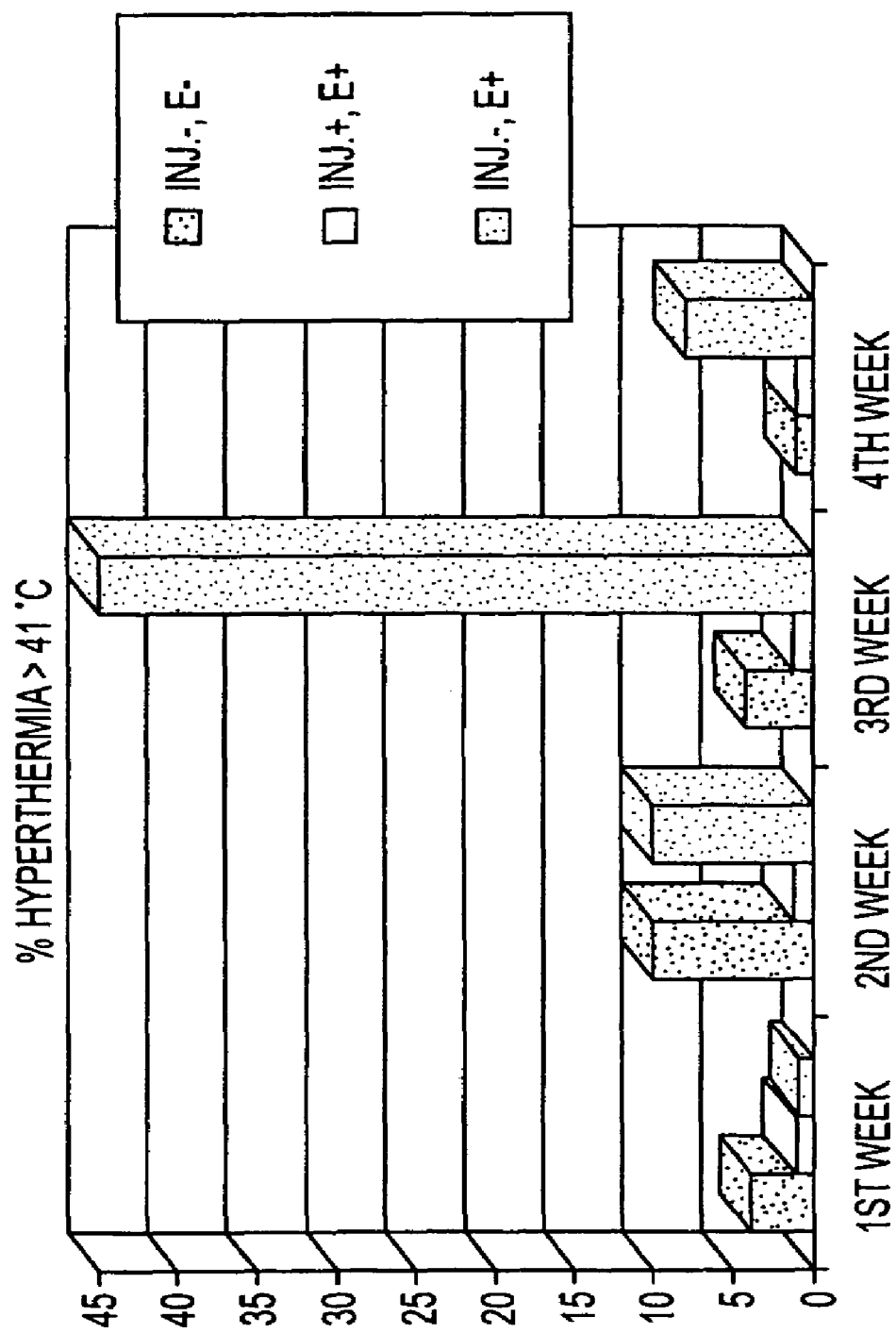

FIG. 11: Hyperthermia greater than 41° C., expressed as a percentage compared for the 3 batches of pigs (F1, F3 and F4) calculated per week over a period of 28 days, after vaccination test.

Figure 12:
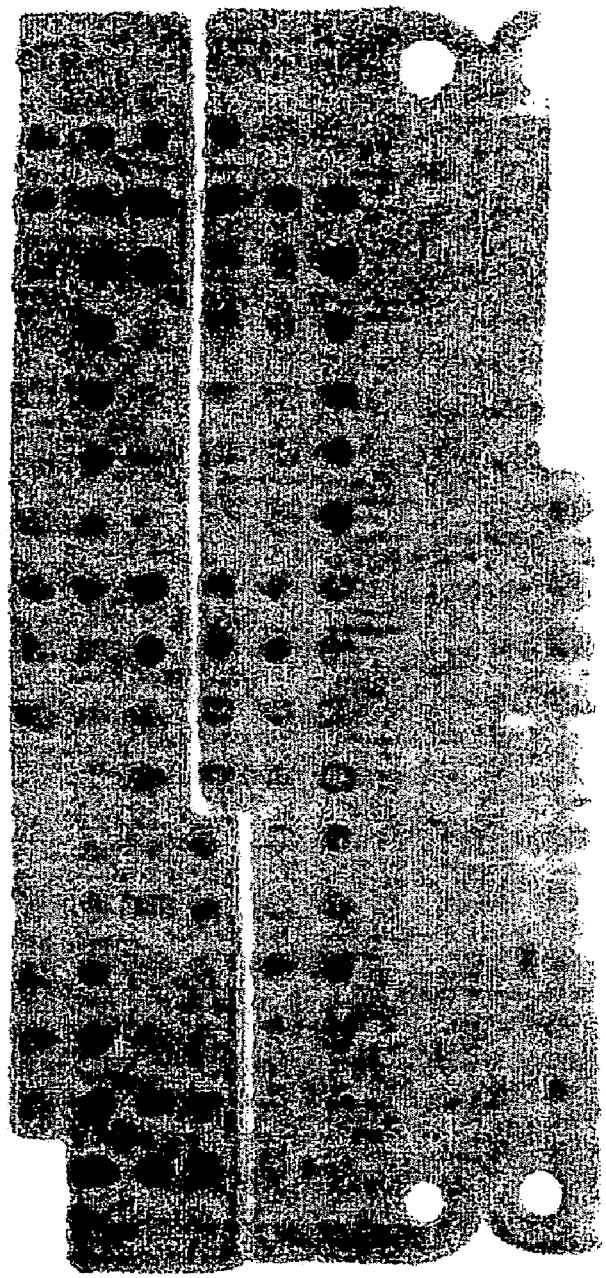

FIG. 12: Membranes of peptide spots corresponding to the ORF2s revealed with the aid of an infected pig serum, originating from a conventional farm.

The numbers of specific peptides of the circovirus of type B as well as their nonreactive homologs (type A) are indicated in bold.

The nonspecific immunogenic peptides are indicated in italics.

FIG. 13: Alignment of amino acid sequences of proteins encoded by the ORF2 of the PWD circovirus of type A SEQ ID No. 12 and by the ORF'2 of the PWD circovirus of type B SEQ ID No. 26. The position of 4 peptides corresponding to specific epitopes of the PWD circovirus of type B is indicated on the corresponding sequence by a bold line, their homolog on the sequence of the PWD circovirus of type A is likewise indicated by an ordinary line.

Figure 14:
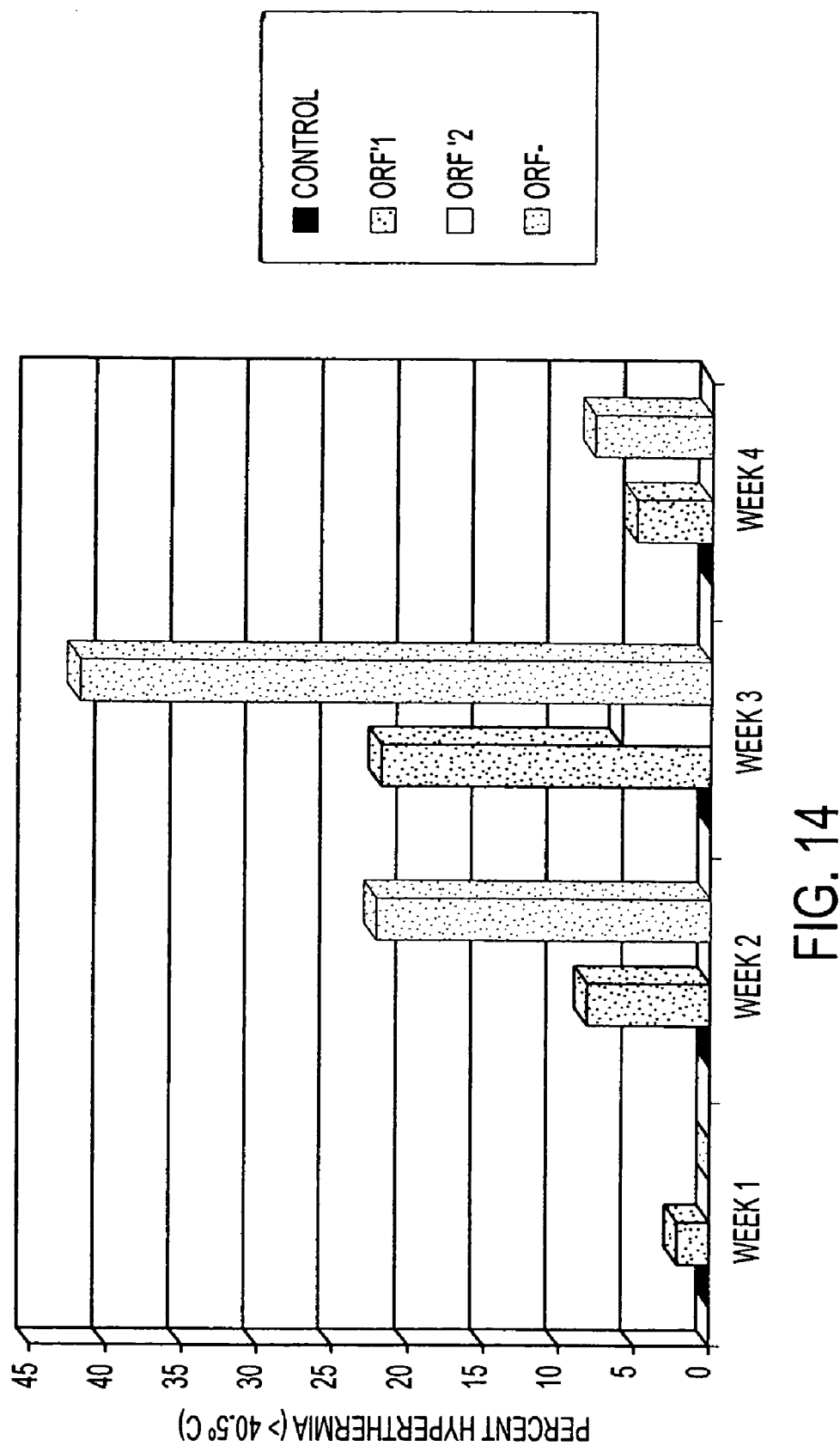

FIG. 14: Charts the results of experiments that demonstrate, in terms of percent hyperthermia, that vaccination with ORF'1 and ORF'2 of PCV-B enhances the level of protection in swine challenged with PCV-B (Percent hyperthermia: >40.5 C, control: not vaccinated and not challenged, ORF'1: vaccinated and challenged, ORF'2: vaccinated and challenged, ORF: not vaccinated, challenged).

Figure 15:
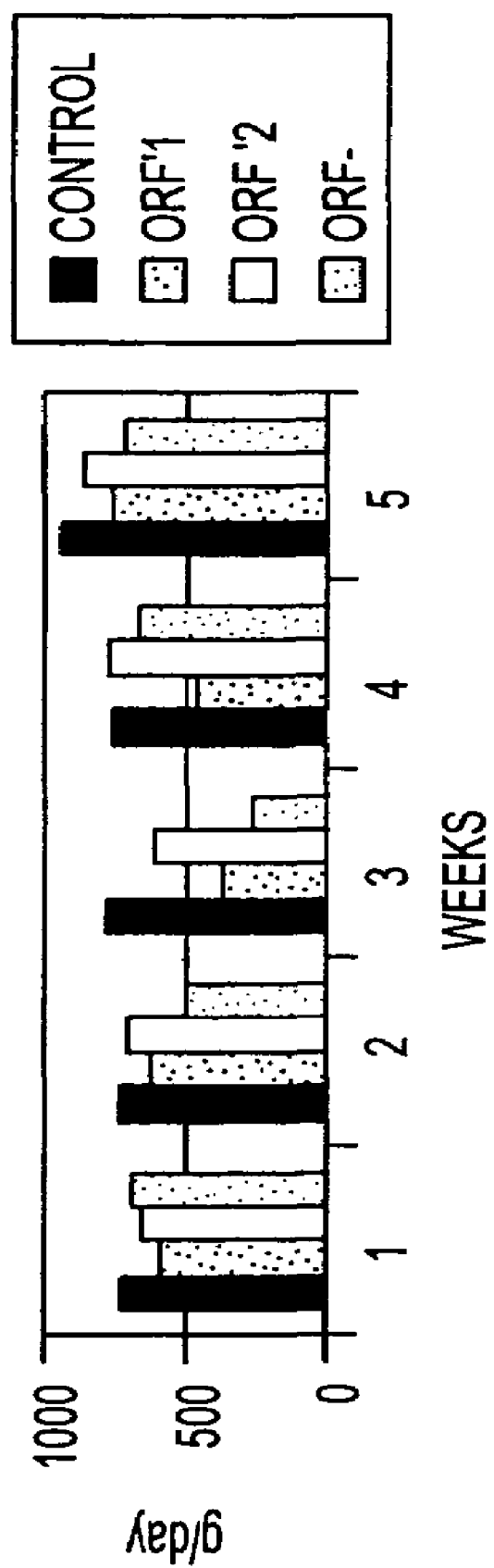

FIG. 15: Charts the results of experiments that demonstrate, in terms of animal growth, that vaccination with ORF'1 and ORF'2 of PCV-B enhances the level of protection in swine challenged with PCV-B (Control: not vaccinated, not challenged, ORF'1: vaccinated and challenged, ORF'2: vaccinated and challenged, ORF: not vaccinated, challenged).

Figure 16:
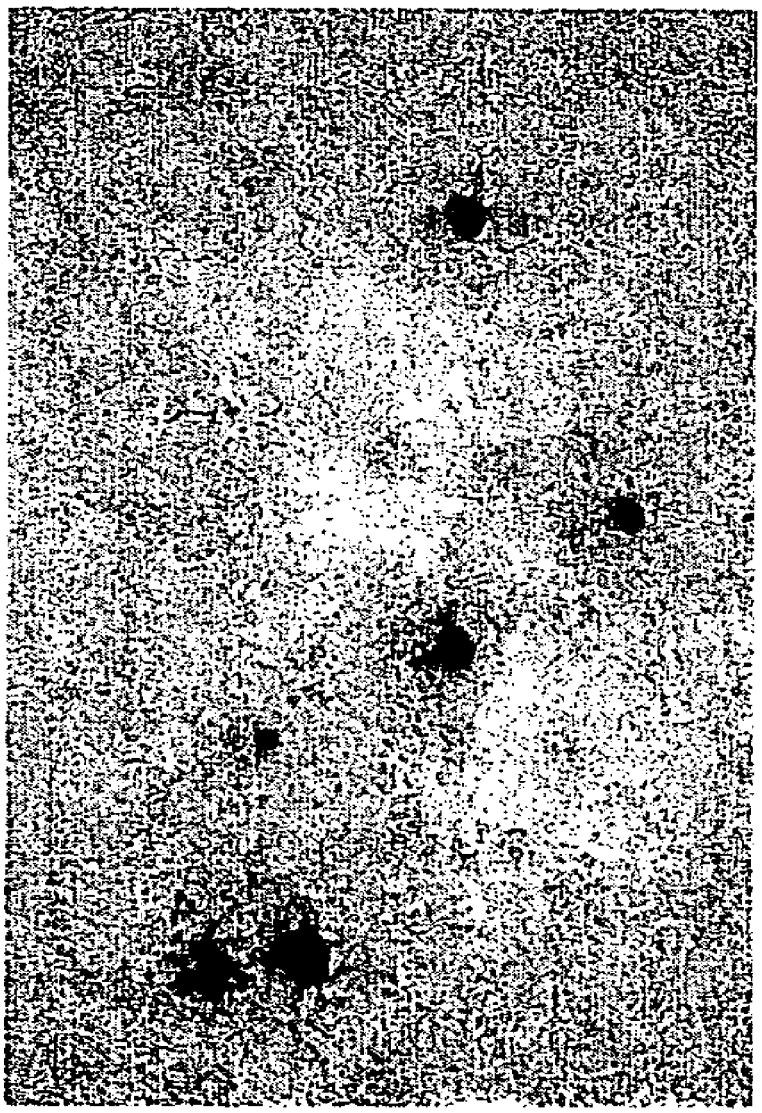

FIG. 16: Immunoperoxidase staining of PK15 cells at 24 h post-transfection with the pcDNA3/ORF'2 plasmid. Expression of PCVB ORF'2 was confirmed by IPMA following incubation in the presence of the swine anti-PCVB monospecific serum.

DETAILED DESCRIPTION OF THE INVENTION

The present invention relates to nucleotide sequences of the genome of PWD circovirus selected from the sequences SEQ ID No. 1, SEQ ID No. 5, SEQ ID No. 15, SEQ ID No. 19 or one of their fragments.

The nucleotide sequences of sequences SEQ ID No. 1 and SEQ ID No. 5 correspond respectively to the genome sequence of the strand of (+) polarity and of the strand of (−) polarity of the PWD circovirus of type A (or PCVA), the sequence SEQ ID No. 5 being represented according to the orientation 5'→3'.

The nucleotide sequences of sequences SEQ ID No. 15 and SEQ ID No. 19 correspond respectively to the genome sequence of the strand of (+) polarity and of the strand of (−) polarity of the PWD circovirus of type B (or PCVB), the sequence SEQ ID No. 19 being represented according to the orientation 5'→3'.

The present invention likewise relates to nucleotide sequences, characterized in that they are selected from:
  a) a nucleotide sequence of a specific fragment of the sequence SEQ ID No. 1, SEQ ID No. 5, SEQ ID No. 15, SEQ ID No. 19 or one of their fragments;
  b) a nucleotide sequence homologous to a nucleotide sequence such as defined in a);
  c) a nucleotide sequence complementary to a nucleotide sequence such as defined in a) or b), and a nucleotide sequence of their corresponding RNA;
  d) a nucleotide sequence capable of hybridizing under stringent conditions with a sequence such as defined in a), b) or c);
  e) a nucleotide sequence comprising a sequence such as defined in a), b), c) or d); and
  f) a nucleotide sequence modified by a nucleotide sequence such as defined in a), b), c), d) or e).

Nucleotide, polynucleotide or nucleic acid sequence will be understood according to the present invention as meaning both a double-stranded or single-stranded DNA in the monomeric and dimeric (so-called in tandem) forms and the transcription products of said DNAs.

It must be understood that the present invention does not relate to the genomic nucleotide sequences taken in their natural environment, that is to say in the natural state. It concerns sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning and subcloning, it being possible for the sequences of the invention to be carried by vectors.

The nucleotide sequences SEQ ID No. 1 and SEQ ID No. 15 were obtained by sequencing of the genome by the Sanger method.

Nucleotide sequence fragment according to the invention will be understood as designating any nucleotide fragment of the PWD circovirus, type A or B, of length of at least 8 nucleotides, preferably at least 12 nucleotides, and even more preferentially at least 20 consecutive nucleotides of the sequence from which it originates.

Specific fragment of a nucleotide sequence according to the invention will be understood as designating any nucleotide fragment of the PWD circovirus, type A or B, having, after alignment and comparison with the corresponding fragments of known porcine circoviruses, at least one nucleotide or base of different nature. For example, the specific nucleotide fragments of the PWD circovirus of type A can easily be determined by referring to FIG. 3 of the present invention in which the nucleotides or bases of the sequence SEQ ID No. 1 (circopordfp) are shown which are of different nature, after alignment of said sequence SEQ ID No. 1 with the other two sequences of known porcine circovirus (circopormeeh and circopormank).

Homologous nucleotide sequence in the sense of the present invention is understood as meaning a nucleotide sequence having at least a percentage identity with the bases of a nucleotide sequence according to the invention of at least 80%, preferably 90% or 95%, this percentage being purely statistical and it being possible to distribute the differences between the two nucleotide sequences at random and over the whole of their length.

Specific homologous nucleotide sequence in the sense of the present invention is understood as meaning a homologous nucleotide sequence having at least one nucleotide sequence of a specific fragment, such as defined above. Said "specific" homologous sequences can comprise, for example, the sequences corresponding to the genomic sequence or to the sequences of its fragments representative of variants of PWD circovirus of type A or B. These specific homologous sequences can thus correspond to variations linked to mutations within strains of PWD circovirus of type A and B, and especially correspond to truncations, substitutions, deletions and/or additions of at least one nucleotide. Said homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotidic sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, Ad. App. Math 2: 482 (1981), by the homology alignment algorithm of Neddleman and Wunsch, J. Mol. Biol. 48: 443 (1970), by the search for similarity method of Pearson and Lipman, Proc. Natl. Acad. Sci. (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree or identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would use one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

In the BLAST N or BLAST P "BLAST 2 sequence", software which is available in the web site http://www.ncbi.nlm.nih.gov/gorf/b12.html, and habitually used by the inventors and in general by the skilled man for comparing and determining the identity between two sequences, gap cost which depends on the sequence length to be compared is directly selected by the software (i.e. 11.2 for substitution matrix BLOSUM-62 for length >85).

In the present description, PWD circovirus will be understood as designating the circoviruses associated with piglet weight loss disease (PWD) of type A (PCVA) or type B (PCVB), defined below by their genomic sequence, as well as the circoviruses whose nucleic sequences are homologous to the sequences of PWD circoviruses of type A or B, such as in particular the circoviruses corresponding to variants of the type A or of the type B.

Complementary nucleotide sequence of a sequence of the invention is understood as meaning any DNA whose nucleotides are complementary to those of the sequence of the invention, and whose orientation is reversed (antiparallel sequence).

Hybridization under conditions of stringency with a nucleotide sequence according to the invention is understood as meaning a hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following:

2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example a temperature of 37° C. in the presence of a 2×SSC buffer, respectively require a globally less significant complementarity for the hybridization between the two sequences.

The stringent hybridization conditions described above for a polynucleotide with a size of approximately 350 bases will be adapted by the person skilled in the art for oligonucleotides of greater or smaller size, according to the teaching of Sambrook et al., 1989.

Among the nucleotide sequences according to the invention, those are likewise preferred which can be used as a primer or probe in methods allowing the homologous sequences according to the invention to be obtained, these methods, such as the polymerase chain reaction (PCR), nucleic acid cloning and sequencing, being well known to the person skilled in the art.

Among said nucleotide sequences according to the invention, those are again preferred which can be used as a primer or probe in methods allowing the presence of PWD circovirus or one of its variants such as defined below to be diagnosed.

The nucleotide sequences according to the invention capable of modulating, of inhibiting or of inducing the expression of PWD circovirus gene, and/or capable of modulating the replication cycle of PWD circovirus in the host cell and/or organism are likewise preferred. Replication cycle will be understood as designating the invasion and the multiplication of PWD circovirus, and its propagation from host cell to host cell in the host organism.

Among said nucleotide sequences according to the invention, those corresponding to open reading frames, called ORF sequences, and coding for polypeptides, such as, for example, the sequences SEQ ID No. 9 (ORF1), SEQ ID No. 11 (ORF2) and SEQ ID No. 13 (ORF3) respectively corresponding to the nucleotide sequences between the positions 47 and 985 determined with respect to the position of the nucleotides on the sequence SEQ ID No. 1, the positions 1723 and 1022 and the positions 658 and 38 with respect to the position of the nucleotides on the sequence SEQ ID No. 5 (represented according to the orientation 3'→5'), the ends being included, or alternatively the sequences SEQ ID No. 23 (ORF'1), SEQ ID No. 25 (ORF'2) and SEQ ID No. 27 (ORF'3), respectively corresponding to the sequences between the positions 51 and 995 determined with respect to the position of the nucleotides on the sequence SEQ ID No. 15, the positions 1734 and 1033 and the positions 670 and 357, the positions being determined with respect to the position of the nucleotides on the sequence SEQ ID No. 19 (represented according to the orientation 3'→5'), the ends being included, are finally preferred.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Said representative fragments can likewise be obtained by chemical synthesis when their size is not very large and according to methods well known to persons skilled in the art.

Modified nucleotide sequence will be understood as meaning any nucleotide sequence obtained by mutagenesis according to techniques well known to the person skilled in the art, and containing modifications with respect to the normal sequences according to the invention, for example mutations in the regulatory and/or promoter sequences of polypeptide expression, especially leading to a modification of the rate of expression of said polypeptide or to a modulation of the replicative cycle.

Modified nucleotide sequence will likewise be understood as meaning any nucleotide sequence coding for a modified polypeptide such as defined below.

The present invention relates to nucleotide sequences of PWD circovirus according to the invention, characterized in that they are selected from the sequences SEQ ID No. 9, SEQ D No. 11, SEQ ID No. 13, SEQ ID No. 23, SEQ ID No. 25, SEQ ID No. 27 or one of their fragments.

The invention likewise relates to nucleotide sequences characterized in that they comprise a nucleotide sequence selected from:
  a) a nucleotide sequence SEQ ID No. 9, SEQ ID No. 11, SEQ ID No. 13, SEQ ID No. 23, SEQ ID No. 25, SEQ ID No. 27 or one of their fragments;
  b) a nucleotide sequence of a specific fragment of a sequence such as defined in a);
  c) a homologous nucleotide sequence having at least 80% identity with a sequence such as defined in a) or b);
  d) a complementary nucleotide sequence or sequence of RNA corresponding to a sequence such as defined in a), b) or c); and
  e) a nucleotide sequence modified by a sequence such as defined in a), b), c) or d).

As far as homology with the nucleotide sequences SEQ ID No. 9, SEQ ID No. 11, SEQ ID No. 13, SEQ ID No. 23, SEQ ID No. 25, SEQ ID No. 27 or one of their fragments is concerned, the homologous, especially specific, sequences having a percentage identity with one of the sequences SEQ ID No. 9, SEQ ID No. 11, SEQ ID No. 13, SEQ ID No. 23, SEQ ID No. 25, SEQ ID No. 27 or one of their fragments of at least 80%, preferably 90% or 95%, are preferred. Said specific homologous sequences can comprise, for example, the sequences corresponding to the sequences ORF1, ORF2, ORF3, ORF'1, ORF'2 and ORF'3 of PWD circovirus variants of type A or of type B. In the same manner, these specific homologous sequences can correspond to variations linked to mutations within strains of PWD circovirus of type A or of type B and especially correspond to truncations, substitutions, deletions and/or additions of at least one nucleotide.

Among nucleotide sequences according to the invention, the sequence SEQ ID No. 23 which has a homology having more than 80% identity with the sequence SEQ ID No. 9, as well as the sequence SEQ ID No. 25, are especially preferred.

Preferably, the invention relates to the nucleotide sequences according to the invention, characterized in that they comprise a nucleotide sequence selected from the following sequences:

a)     SEQ ID No. 33   170 5' TGT<u>G</u>GC<u>C</u>GA 3';

b)     SEQ ID No. 34   450 5' AG<u>T</u>TTCCT 3';

c)     SEQ ID No. 35 1026 5' T<u>C</u>ATTTAGAGGGTCTTT<u>C</u>AG 3';

d)     SEQ ID No. 36 1074 5' GTCA<u>A</u>CCT 3';

e)     SEQ ID No. 37 1101 5' GTGG<u>T</u>TGC 3';

f)     SEQ ID No. 38 1123 5' AGCC<u>C</u>AGG 3';

g)     SEQ ID No. 39 1192 5' TTGG<u>C</u>TGG 3';

h)     SEQ ID No. 40 1218 5' TC<u>T</u>AGCTC<u>T</u>GGT 3';

i)     SEQ ID No. 41 1501 5' ATCT<u>C</u>AG<u>C</u>T<u>C</u>GT 3';

j)     SEQ ID No. 42 1536 5' T<u>G</u>TCCTCCT<u>C</u>TT 3';

k)     SEQ ID No. 43 1563 5' TCT<u>C</u>TAGA 3';

l)     SEQ ID No. 44 1623 5' TGT<u>A</u>CCAA 3';

m)     SEQ ID No. 45 1686 5' TCC<u>G</u>TCTT 3';

and their complementary sequences.

In the list of nucleotide sequences a)-m) above, the underlined nucleotides are mutated with respect to the two known sequences of circovirus which are nonpathogenic to pigs. The number preceding the nucleotide sequence represents the position of the first nucleotide of said sequence in the sequence SEQ ID No. 1.

The invention comprises the polypeptides encoded by a nucleotide sequence according to the invention, preferably a polypeptide whose sequence is represented by a fragment, especially a specific fragment, of one of the six sequences of amino acids represented in FIG. 2, these six amino acid sequences corresponding to the polypeptides which can be encoded according to one of the three possible reading frames of the sequence SEQ ID No. 1 or of the sequence SEQ ID No. 5, or a polypeptide whose sequence is represented by a fragment, especially a specific fragment, of one of the six sequences of amino acids shown in FIG. 8, these six sequences of amino acids corresponding to the polypeptides which can be encoded according to one of the three possible reading frames of the sequence SEQ ID No. 15 or of the sequence SEQ ID No. 19.

The invention likewise relates to the polypeptides, characterized in that they comprise a polypeptide selected from the amino acid sequences SEQ ID No. 10, SEQ ID No. 12, SEQ ID No. 14, SEQ ID No. 24, SEQ ID No. 26, SEQ ID No. 28 or one of their fragments.

Among the polypeptides according to the invention, the polypeptide of amino acid sequence SEQ ID No. 24 which has a homology having more than 80% identity with the sequence SEQ ID No. 10, as well as the polypeptide of sequence SEQ ID No. 26, are especially preferred.

The invention also relates to the polypeptides, characterized in that they comprise a polypeptide selected from:
a) a specific fragment of at least 5 amino acids of a polypeptide of an amino acid sequence according to the invention;
b) a polypeptide homologous to a polypeptide such as defined in a);
c) a specific biologically active fragment of a polypeptide such as defined in a) or b); and
d) a polypeptide modified by a polypeptide such as defined in a), b) or c).

Among the polypeptides according to the invention, the polypeptides of amino acid sequences SEQ ID No. 29, SEQ ID No. 30, SEQ ID No. 31 and SEQ ID No. 32 are also preferred, these polypeptides being especially capable of specifically recognizing the antibodies produced during infection by the PWD circovirus of type B. These polypeptides thus have epitopes specific for the PWD circovirus of type B and can thus be used in particular in the diagnostic field or as immunogenic agent to confer protection in pigs against infection by PWD circovirus, especially of type B.

In the present description, the terms polypeptide, peptide and protein are interchangeable.

It must be understood that the invention does not relate to the polypeptides in natural form, that is to say that they are not taken in their natural environment but that they can be isolated or obtained by purification from natural sources, or else obtained by genetic recombination, or alternatively by chemical synthesis and that they can thus contain unnatural amino acids, as will be described below.

Polypeptide fragment according to the invention is understood as designating a polypeptide containing at least 5 consecutive amino acids, preferably 10 consecutive amino acids or 15 consecutive amino acids.

In the present invention, specific polypeptide fragment is understood as designating the consecutive polypeptide fragment encoded by a specific fragment nucleotide sequence according to the invention.

Homologous polypeptide will be understood as designating the polypeptides having, with respect to the natural polypeptide, certain modifications such as, in particular, a deletion, addition or substitution of at least one amino acid, a truncation, a prolongation, a chimeric fusion, and/or a mutation. Among the homologous polypeptides, those are preferred whose amino acid sequence has at least 80%, preferably 90%, homology with the sequences of amino acids of polypeptides according to the invention.

Specific homologous polypeptide will be understood as designating the homologous polypeptides such as defined above and having a specific fragment of polypeptide according to the invention.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following.

These equivalent amino acids can be determined either by depending on their structural homology with the amino acids which they substitute, or on results of comparative tests of biological activity between the different polypeptides, which are capable of being carried out.

By way of example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

The specific homologous polypeptides likewise correspond to polypeptides encoded by the specific homologous nucleotide sequences such as defined above and thus comprise in the present definition the polypeptides which are mutated or correspond to variants which can exist in PWD circovirus, and which especially correspond to truncations, substitutions, deletions and/or additions of at least one amino acid residue.

Specific biologically active fragment of a polypeptide according to the invention will be understood in particular as designating a specific polypeptide fragment, such as defined above, having at least one of the characteristics of polypeptides according to the invention, especially in that it is:

capable of inducing an immunogenic reaction directed against a PWD circovirus; and/or capable of being recognized by a specific antibody of a polypeptide according to the invention; and/or capable of linking to a polypeptide or to a nucleotide sequence of PWD circovirus; and/or capable of exerting a physiological activity, even partial, such as, for example, a dissemination or structural (capsid) activity; and/or capable of modulating, of inducing or of inhibiting the expression of PWD circovirus gene or one of its variants, and/or capable of modulating the replication cycle of PWD circovirus in the cell and/or the host organism.

The polypeptide fragments according to the invention can correspond to isolated or purified fragments naturally present in a PWD circovirus or correspond to fragments which can be obtained by cleavage of said polypeptide by a proteolytic enzyme, such as trypsin or chymotrypsin or collagenase, or by a chemical reagent, such as cyanogen bromide (CNBr) or alternatively by placing said polypeptide in a very acidic environment, for example at pH 2.5. Such polypeptide fragments can likewise just as easily be prepared by chemical synthesis, from hosts transformed by an expression vector according to the invention containing a nucleic acid allowing the expression of said fragments, placed under the control of appropriate regulation and/or expression elements.

"Modified polypeptide" of a polypeptide according to the invention is understood as designating a polypeptide obtained by genetic recombination or by chemical synthesis as will be described below, having at least one modification with respect to the normal sequence. These modifications will especially be able to bear on amino acids at the origin of a specificity, of pathogenicity and/or of virulence, or at the origin of the structural conformation, and of the capacity of membrane insertion of the polypeptide according to the invention. It will thus be possible to create polypeptides of equivalent, increased or decreased activity, and of equivalent, narrower, or wider specificity. Among the modified polypeptides, it is necessary to mention the polypeptides in which up to 5 amino acids can be modified, truncated at the N- or C-terminal end, or even deleted or added.

As is indicated, the modifications of the polypeptide will especially have as objective:

to render it capable of modulating, of inhibiting or of inducing the expression of PWD circovirus gene and/or capable of modulating the replication cycle of PWD circovirus in the cell and/or the host organism, of allowing its incorporation into vaccine compositions,
of modifying its bioavailability as a compound for therapeutic use.

The methods allowing said modulations on eukaryotic or prokaryotic cells to be demonstrated are well known to the person skilled in the art. It is likewise well understood that it will be possible to use the nucleotide sequences coding for said modified polypeptides for said modulations, for example through vectors according to the invention and described below, in order, for example, to prevent or to treat the pathologies linked to the infection.

The preceding modified polypeptides can be obtained by using combinatorial chemistry, in which it is possible to systematically vary parts of the polypeptide before testing them on models, cell cultures or microorganisms for example, to select the compounds which are most active or have the properties sought.

Chemical synthesis likewise has the advantage of being able to use:
unnatural amino acids, or
nonpeptide bonds.

Thus, in order to improve the duration of life of the polypeptides according to the invention, it may be of interest to use unnatural amino acids, for example in D form, or else amino acid analogs, especially sulfur-containing forms, for example.

Finally, it will be possible to integrate the structure of the polypeptides according to the invention, its specific or modified homologous forms, into chemical structures of polypeptide type or others. Thus, it may be of interest to provide at the N- and C-terminal ends compounds not recognized by the proteases.

The nucleotide sequences coding for a polypeptide according to the invention are likewise part of the invention.

The invention likewise relates to nucleotide sequences utilizable as a primer or probe, characterized in that said sequences are selected from the nucleotide sequences according to the invention.

Among the pairs of nucleotide sequences utilizable as a pair of primers according to the invention, the pairs of primers selected from the following pairs are preferred:

a) SEQ ID No. 46 5' GTG TGC TCG ACA TTG GTG TG 3',
and
   SEQ ID No. 47 5' TGG AAT GTT AAC GAG CTG AG 3';
b) SEQ ID No. 46 5' GTG TGC TCG ACA TTG GTG TG 3',
and
   SEQ ID No. 48 5' CTC GCA GCC ATC TTG GAA TG 3';
c) SEQ ID No. 49 5' CGC GCG TAA TAC GAC TCA CT 3',
and
   SEQ ID No. 46 5' GTG TGC TCG ACA TTG GTG TG 3';
d) SEQ ID No. 49 5' CGC GCG TAA TAC GAC TCA CT 3',
and
   SEQ ID No. 48 5' CTC GCA GCC ATC TTG GAA TG 3';
and
e) SEQ ID No. 50 5' CCT GTC TAC TGC TGT GAG TAC CTT
        GT 3', and SEQ ID No. 51  5' GCA GTA GAC AGG TCA CTC CGT TGT
        CC 3'.

The cloning and the sequencing of the PWD circovirus, type A and B, has allowed it to be identified, after comparative analysis with the nucleotide sequences of other porcine circoviruses, that, among the sequences of fragments of these nucleic acids, were those which are strictly specific to the PWD circovirus of type A, of type B or of type A and B, and those which correspond to a consensus sequence of porcine circoviruses other than the PWD circoviruses of type A and/or B.

There is likewise a great need for nucleotide sequences utilizable as a primer or probe specific to the whole of the other known and nonpathogenic porcine circoviruses.

Said consensus nucleotide sequences specific to all circoviruses, other than PWD circovirus of type A and B, are easily identifiable from FIG. 3 and the sequence SEQ ID No. 15, and are part of the invention.

Among said consensus nucleotide sequences, that which is characterized in that it is part of the following pair of primers is preferred:

a) SEQ ID No. 46 5' GTG TGC TCG ACA TTG GTG TG 3',
and
   SEQ ID No. 52 5' TGG AAT GTT AAC TAC CTC AA 3'.

The invention likewise comprises a nucleotide sequence according to the invention, characterized in that said sequence is a specific consensus sequence of porcine circovirus other than PWD circovirus of type B and in that it is one of the primers of the following pairs of primers:

a)   SEQ ID No. 53 5' GGC GGC GCC ATC TGT AAC GGT
              TT 3',
and
     SEQ ID No. 54 5' GAT GGC GCC GAA AGA CGG GTA
              TC 3'.

It is well understood that the present invention likewise relates to specific polypeptides of known porcine circoviruses other than PWD circovirus, encoded by said consensus nucleotide sequences, capable of being obtained by purification from natural polypeptides, by genetic recombination or by chemical synthesis by procedures well known to the person skilled in the art and such as described in particular below. In the same manner, the labeled or unlabeled mono- or polyclonal antibodies directed against said specific polypeptides encoded by said consensus nucleotide sequences are also part of the invention.

It will be possible to use said consensus nucleotide sequences, said corresponding polypeptides as well as said antibodies directed against said polypeptides in procedures or sets for detection and/or identification such as described below, in place of or in addition to nucleotide sequences, polypeptides or antibodies according to the invention, specific to PWD circovirus type A and/or B.

These protocols have been improved for the differential detection of the circular monomeric forms of specific replicative forms of the virion or of the DNA in replication and the dimeric forms found in so-called in-tandem molecular constructs.

The invention additionally relates to the use of a nucleotide sequence according to the invention as a primer or probe for the detection and/or the amplification of nucleic acid sequences.

The nucleotide sequences according to the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially at least 20 nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as:

the TAS technique (Transcription-based Amplification System), described by Kwoh et al. in 1989;

the 3SR technique (Self-Sustained Sequence Replication), described by Guatelli et al. in 1990;

the NASBA technique (Nucleic Acid Sequence Based Amplification), described by Kievitis et al. in 1991;

the SDA technique (Strand Displacement Amplification) (Walker et al., 1992);

the TMA technique (Transcription Mediated Amplification).

The polynucleotides of the invention can also be employed in techniques of amplification or of modification of the nucleic acid serving as a probe, such as:

the LCR technique (Ligase Chain Reaction), described by Landegren et al. in 1988 and improved by Barany et al. in 1991, which employs a thermostable ligase;

the RCR technique (Repair Chain Reaction), described by Segev in 1992;

the CPR technique (Cycling Probe Reaction), described by Duck et al. in 1990;

the amplification technique with Q-beta replicase, described by Miele et al. in 1983 and especially improved by Chu et al. in 1986, Lizardi et al. in 1988, then by Burg et al. as well as by Stone et al. in 1996.

In the case where the target polynucleotide to be detected is possibly an RNA, for example an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

The invention also comprises the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive element ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes which are utilizable for numerous applications.

Examples of nonradioactive labeling of nucleotide sequences are described, for example, in French Patent No. 78.10975 or by Urdea et al. or by Sanchez-Pescador et al. in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between said capture probe and the target nucleic acid is then detected with the aid of a second probe, a so-called detection probe, labeled with an easily detectable element.

Another subject of the present invention is a vector for the cloning and/or expression of a sequence, characterized in that it contains a nucleotide sequence according to the invention.

The vectors according to the invention, characterized in that they contain the elements allowing the expression and/or the secretion of said nucleotide sequences in a determined host cell, are likewise part of the invention.

The vector must then contain a promoter, signals of initiation and termination of translation, as well as appropriate regions of regulation of transcription. It must be able to be maintained stably in the host cell and can optionally have particular signals specifying the secretion of the translated protein. These different elements are chosen as a function of the host cell used. To this end, the nucleotide sequences according to the invention can be inserted into autonomous replication vectors within the chosen host, or integrated vectors of the chosen host.

Such vectors will be prepared according to the methods currently used by the person skilled in the art, and it will be possible to introduce the clones resulting therefrom into an appropriate host by standard methods, such as, for example, lipofection, electroporation and thermal shock.

The vectors according to the invention are, for example, vectors of plasmid or viral origin.

A preferred vector for the expression of polypeptides of the invention is baculovirus.

The vector pBS KS in which is inserted the in-tandem DNA sequence of the PWD circovirus type A (or DFP) as deposited at the CNCM on 3 Jul. 1997, under the number I-1891, is likewise preferred.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector such as defined above, then the culturing of said cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as animal cells, in particular the cultures of mammalian cells (Edwards and Aruffo, 1993), and especially Chinese hamster ovary (CHO) cells, but likewise the cells of insects in which it is possible to use procedures employing baculoviruses, for example (Luckow, 1993).

A preferred host cell for the expression of the proteins of the invention is constituted by sf9 insect cells.

A more preferred host cell according to the invention is *E. coli*, such as deposited at the CNCM on 3 Jul. 1997, under the number I-1891.

The invention likewise relates to animals comprising one of said transformed cells according to the invention.

The obtainment of transgenic animals according to the invention overexpressing one or more of the genes of PWD circovirus or part of the genes will be preferably carried out in rats, mice or rabbits according to methods well known to the person skilled in the art, such as by viral or nonviral transfections. It will be possible to obtain the transgenic animals overexpressing one or more of said genes by transfection of multiple copies of said genes under the control of a strong promoter of ubiquitous nature, or selective for one type of tissue. It will likewise be possible to obtain the transgenic animals by homologous recombination in embryonic cell strains, transfer of these cell strains to embryos, selection of the affected chimeras at the level of the reproductive lines, and growth of said chimeras.

The transformed cells as well as the transgenic animals according to the invention are utilizable in procedures for preparation of recombinant polypeptides.

It is today possible to produce recombinant polypeptides in relatively large quantity by genetic engineering using the cells transformed by expression vectors according to the invention or using transgenic animals according to the invention.

The procedures for preparation of a polypeptide of the invention in recombinant form, characterized in that they employ a vector and/or a cell transformed by a vector according to the invention and/or a transgenic animal comprising one of said transformed cells according to the invention, are themselves comprised in the present invention.

Among said procedures for preparation of a polypeptide of the invention in recombinant form, the preparation procedures employing a vector, and/or a cell transformed by said vector and/or a transgenic animal comprising one of said transformed cells, containing a nucleotide sequence according to the invention coding for a polypeptide of PWD circovirus, are preferred.

The recombinant polypeptides obtained as indicated above can just as well be present in glycosylated form as in nonglycosylated form and can or cannot have the natural tertiary structure.

A preferred variant consists in producing a recombinant polypeptide used to a "carrier" protein (chimeric protein). The advantage of this system is that it allows a stabilization of and a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps:

a) culture of transformed cells under conditions allowing the expression of a recombinant polypeptide of nucleotide sequence according to the invention;

b) if need be, recovery of said recombinant polypeptide.

When the procedure for preparation of a polypeptide of the invention employs a transgenic animal according to the invention, the recombinant polypeptide is then extracted from said animal.

The invention also relates to a polypeptide which is capable of being obtained by a procedure of the invention such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques which are conventional in the field of the synthesis of peptides. This synthesis can be carried out in homogeneous solution or in solid phase.

For example, recourse can be made to the technique of synthesis in homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

According to another preferred technique of the invention, recourse will be made to the technique described by Merrifield.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids which are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated form used with a view to obtaining immunogenic compositions capable of inducing the synthesis of antibodies directed against multiple epitopes. Said polypeptides or their glycosylated fragments are likewise part of the invention.

These hybrid molecules can be formed, in part, of a polypeptide carrier molecule or of fragments thereof according to the invention, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

Said hybrid nucleotide sequences coding for a hybrid polypeptide as well as the hybrid polypeptides according to the invention characterized in that they are recombinant polypeptides obtained by the expression of said hybrid nucleotide sequences are likewise part of the invention.

The invention likewise comprises the vectors characterized in that they contain one of said hybrid nucleotide sequences. The host cells transformed by said vectors, the transgenic animals comprising one of said transformed cells as well as the procedures for preparation of recombinant polypeptides using said vectors, said transformed cells and/or said transgenic animals are, of course, likewise part of the invention.

The polypeptides according to the invention, the antibodies according to the invention described below and the nucleotide sequences according to the invention can advantageously be employed in procedures for the detection and/or identification of PWD circovirus, or of porcine circovirus other than a PWD circovirus, in a biological sample (biological tissue or fluid) capable of containing them. These procedures, according to the specificity of the polypeptides, the antibodies and the nucleotide sequences according to the invention which will be used, will in particular be able to detect and/or to identify a PWD circovirus or a porcine circovirus other than a PWD circovirus or other than the PWD circovirus of type B.

The polypeptides according to the invention can advantageously be employed in a procedure for the detection and/or the identification of PWD circovirus of type A, of type B, of type A or B, or porcine circovirus other than the PWD circovirus of type B, or of porcine circovirus other than the PWD circovirus of type A or B, in a biological sample (biological tissue or fluid) capable of containing them, characterized in that it comprises the following steps:

a) contacting of this biological sample with a polypeptide or one of its fragments according to the invention (under conditions allowing an immunological reaction between said polypeptide and the antibodies possibly present in the biological sample);

b) demonstration of the antigen-antibody complexes possibly formed.

In the present description, PWD circovirus, except if a particular mention is indicated, will be understood as designating a PWD circovirus of type A or of type B, and porcine circovirus other than PWD, except if a particular mention is indicated, will be understood as designating a porcine circovirus other than a PWD circovirus of type A and B.

Preferably, the biological sample is formed by a fluid, for example a pig serum, whole blood or biopsies.

Any conventional procedure can be employed for carrying out such a detection of the antigen-antibody complexes possibly formed.

By way of example, a preferred method brings into play immunoenzymatic processes according to the ELISA technique, by immunofluorescence, or radioimmunological processes (RIA) or their equivalent.

Thus, the invention likewise relates to the polypeptides according to the invention, labeled with the aid of an adequate label such as of the enzymatic, fluorescent or radioactive type.

Such methods comprise, for example, the following steps:
  deposition of determined quantities of a polypeptide composition according to the invention in the wells of a microtiter plate,
  introduction into said wells of increasing dilutions of serum, or of a biological sample other than that defined previously, having to be analyzed,
  incubation of the microplate,
  introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example at 550 nm,
  detection, by comparison with a control test, of the quantity of hydrolyzed substrate.

The invention likewise relates to a kit or set for the detection and/or identification of PWD circovirus, of porcine circovirus other than a PWD circovirus or of porcine circovirus other than the PWD circovirus of type B, characterized in that it comprises the following elements:
  a polypeptide according to the invention,
  if need be, the reagents for the formation of the medium favorable to the immunological or specific reaction,
  if need be, the reagents allowing the detection of the antigen-antibody complexes produced by the immunological reaction between the polypeptide(s) of the invention and the antibodies possibly present in the biological sample, these reagents likewise being able to carry a label, or to be recognized in their turn by a labeled reagent, more particularly in the case where the polypeptide according to the invention is not labeled,
  if need be, a biological reference sample (negative control) devoid of antibodies recognized by a polypeptide according to the invention,
  if need be, a biological reference sample (positive control) containing a predetermined quantity of antibodies recognized by a polypeptide according to the invention.

The polypeptides according to the invention allow monoclonal or polyclonal antibodies to be prepared which are characterized in that they specifically recognize the polypeptides according to the invention. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide which has served as an antigen has previously been immobilized. The polyclonal antibodies according to the invention can also be prepared by purification, on an affinity column on which a polypeptide according to the invention has previously been immobilized, of the antibodies contained in the serum of pigs infected by a PWD circovirus.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of PWD circovirus, of porcine circovirus other than a PWD circovirus, or other than the PWD circovirus of type B, in a biological sample, characterized in that it comprises the following steps:
  a) contacting of the biological sample (biological tissue or fluid) with a mono- or polyclonal antibody according to the invention (under conditions allowing an immunological reaction between said antibodies and the polypeptides of PWD circovirus, of porcine circovirus other than a PWD circovirus, of porcine circovirus other than the PWD circovirus of type B, possibly present in the biological sample);
  b) demonstration of the antigen-antibody complex possibly formed.

Likewise within the scope of the invention is a kit or set for the detection and/or the identification of PWD circovirus, of porcine circovirus other than a PWD circovirus or of porcine circovirus other than the PWD circovirus of type B, characterized in that it comprises the following components:
  a polyclonal or monoclonal antibody according to the invention, if need be labeled;
  if need be, a reagent for the formation of the medium favorable to the carrying out of the immunological reaction;
  if need be, a reagent allowing the detection of the antigen-antibody complexes produced by the immunological reaction, this reagent likewise being able to carry a label, or being capable of being recognized in its turn by a labeled reagent, more particularly in the case where said monoclonal or polyclonal antibody is not labeled;
  if need be, reagents for carrying out the lysis of cells of the sample tested.

The present invention likewise relates to a procedure for the detection and/or the identification of PWD, of porcine circovirus other than a PWD circovirus or of porcine circovirus other than the PWD circovirus of type B, in a biological sample, characterized in that it employs a nucleotide sequence according to the invention.

More particularly, the invention relates to a procedure for the detection and/or the identification of PWD circovirus, of porcine circovirus other than a PWD circovirus or of porcine circovirus other than the PWD circovirus of type B, in a biological sample, characterized in that it contains the following steps:
  a) if need be, isolation of the DNA from the biological sample to be analyzed;
  b) specific amplification of the DNA of the sample with the aid of at least one primer, or a pair of primers, according to the invention;
  c) demonstration of the amplification products.

These can be detected, for example, by the technique of molecular hybridization utilizing a nucleic probe according to the invention. This probe will advantageously be labeled with a nonradioactive (cold probe) or radioactive element.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in said biological sample.

Another aim of the present invention consists in a procedure according to the invention, characterized in that it comprises the following steps:
  a) contacting of a nucleotide probe according to the invention with a biological sample, the DNA contained in the biological sample having, if need be, previously been made accessible to hybridization under conditions allowing the hybridization of the probe with the DNA of the sample;
  b) demonstration of the hybrid formed between the nucleotide probe and the DNA of the biological sample.

The present invention also relates to a procedure according to the invention, characterized in that it comprises the following steps:
  a) contacting of a nucleotide probe immobilized on a support according to the invention with a biological sample, the DNA of the sample having, if need be, previously been made accessible to hybridization, under conditions allowing the hybridization of the probe with the DNA of the sample;
  b) contacting of the hybrid formed between the nucleotide probe immobilized on a support and the DNA contained in the biological sample, if need be after elimination of the DNA of the biological sample which has not hybridized with the probe, with a nucleotide probe labeled according to the invention;
  c) demonstration of the novel hybrid formed in step b).

According to an advantageous embodiment of the procedure for detection and/or identification defined previously, this is characterized in that, prior to step a), the DNA of the biological sample is first amplified with the aid of at least one primer according to the invention.

The invention is additionally directed at a kit or set for the detection and/or the identification of PWD circovirus, of porcine circovirus other than the PWD circovirus or of porcine circovirus other than the PWD circovirus of type B, characterized in that it comprises the following elements:
  a) a nucleotide probe according to the invention;
  b) if need be, the reagents necessary for the carrying out of a hybridization reaction;
  c) if need be, at least one primer according to the invention as well as the reagents necessary for an amplification reaction of the DNA.

The invention likewise relates to a kit or set for the detection and/or the identification of PWD circovirus, of porcine circovirus other than a PWD circovirus or of porcine circovirus other than the PWD circovirus of type B, characterized in that it comprises the following components:
  a) a nucleotide probe, called a capture probe, according to the invention;
  b) an oligonucleotide probe, called a revealing probe, according to the invention,
  c) if need be, at least one primer according to the invention, as well as the reagents necessary for an amplification reaction of the DNA.

The invention also relates to a kit or set for the detection and/or identification of PWD circovirus, of porcine circovirus other than a PWD circovirus or of porcine circovirus other than the PWD circovirus of type B, characterized in that it comprises the following elements:
  a) at least one primer according to the invention;
  b) if need be, the reagents necessary for carrying out a DNA amplification reaction;
  c) if need be, a component allowing the sequence of the amplified fragment to be verified, more particularly an oligonucleotide probe according to the invention.

The invention additionally relates to the use of a nucleotide sequence according to the invention, of a polypeptide according to the invention, of an antibody according to the invention, of a cell according to the invention, and/or of an animal transformed according to the invention, for the selection of an organic or inorganic compound capable of modulating, inducing or inhibiting the expression of genes, and/or of modifying the cellular replication of PWD circovirus or capable of inducing or of inhibiting the pathologies linked to an infection by a PWD circovirus.

The invention likewise comprises a method of selection of compounds capable of binding to a polypeptide or one of its fragments according to the invention, capable of binding to a nucleotide sequence according to the invention, or capable of recognizing an antibody according to the invention, and/or capable of modulating, inducing or inhibiting the expression of genes, and/or of modifying the cellular replication of PWD circovirus or capable of inducing or inhibiting the pathologies linked to an infection by a PWD circovirus, characterized in that it comprises the following steps:

a) contacting of said compound with said polypeptide, said nucleotide sequence, or with a cell transformed according to the invention and/or administration of said compound to an animal transformed according to the invention;

b) determination of the capacity of said compound to bind to said polypeptide or said nucleotide sequence, or to modulate, induce or inhibit the expression of genes, or to modulate the growth or the replication of PWD circovirus, or to induce or inhibit in said transformed animal the pathologies linked to an infection by PWD circovirus (designated activity of said compound).

The compounds capable of being selected can be organic compounds such as polypeptides or carbohydrates or any other organic or inorganic compounds already known, or novel organic compounds elaborated by molecular modeling techniques and obtained by chemical or biochemical synthesis, these techniques being known to the person skilled in the art.

It will be possible to use said selected compounds to modulate the cellular replication of PWD circovirus and thus to control infection by this virus, the methods allowing said modulations to be determined being well known to the person skilled in the art.

This modulation can be carried out, for example, by an agent capable of binding to a protein and thus of inhibiting or of potentiating its biological activity, or capable of binding to an envelope protein of the external surface of said virus and of blocking the penetration of said virus into the host cell or of favoring the action of the immune system of the infected organism directed against said virus. This modulation can likewise be carried out by an agent capable of binding to a nucleotide sequence of a DNA of said virus and of blocking, for example, the expression of a polypeptide whose biological or structural activity is necessary for the replication or for the proliferation of said virus host cells to host cells in the host animal.

The invention relates to the compounds capable of being selected by a selection method according to the invention.

The invention likewise relates to a pharmaceutical composition comprising a compound selected from the following compounds:

a) a nucleotide sequence according to the invention;

b) a polypeptide according to the invention;

c) a vector, a viral particle or a cell transformed according to the invention;

d) an antibody according to the invention;

e) a compound capable of being selected by a selection method according to the invention;

possibly in combination with a pharmaceutically acceptable vehicle and, if need be, with one or more adjuvants of the appropriate immunity.

The invention also relates to an immunogenic and/or vaccine composition, characterized in that it comprises a compound selected from the following compounds:

a) a nucleotide sequence according to the invention;

b) a polypeptide according to the invention;

c) a vector or a viral particle according to the invention; and d) a cell according to the invention.

In one embodiment, the vaccine composition according to the invention is characterized in that it comprises a mixture of at least two of said compounds a), b), c) and d) above and in that one of the two said compounds is related to the PWD circovirus of type A and the other is related to the PWD circovirus of type B.

In another embodiment of the invention, the vaccine composition is characterized in that it comprises at least one compound a), b), c), or d) above which is related to PWD circovirus of type B. In still another embodiment, the vaccine composition is characterized in that it comprises at least one compound a), b), c), or d) above which is related to PWD circovirus of type B ORF'2.

A compound related to the PWD circovirus of type A or of type B is understood here as respectively designating a compound obtained from the genomic sequence of the PWD circovirus of type A or of type B.

The invention is additionally aimed at an immunogenic and/or vaccine composition, characterized in that it comprises at least one of the following compounds:

a nucleotide sequence SEQ ID No. 23, SEQ ID No. 25, or one of their fragments or homologues;

a polypeptide of sequence SEQ ID No. 24, SEQ ID No. 26, or one of their fragments, or a modification thereof;

a vector or a viral particle comprising a nucleotide sequence SEQ ID No. 23, SEQ ID No. 25, or one of their fragments or homologues;

a transformed cell capable of expressing a polypeptide of sequence SEQ ID No. 24, SEQ ID No. 26, or one of their fragments, or a modification thereof; or a mixture of at least two of said compounds.

The invention also comprises an immunogenic and/or vaccine composition according to the invention, characterized in that it comprises said mixture of at least two of said compounds as a combination product for simultaneous, separate or protracted use for the prevention or the treatment of infection by a PWD circovirus, especially of type B.

In a preferred embodiment, the vaccine composition according to the invention comprises the mixture of the following compounds:

a pcDNA3 plasmid containing a nucleic acid of sequence SEQ ID No. 23;

a pcDNA3 plasmid containing a nucleic acid of sequence SEQ ID No. 25;

a pcDNA3 plasmid containing a nucleic acid coding for the GM-CSF protein;

a recombinant baculovirus containing a nucleic acid of sequence SEQ ID No. 23;

a recombinant baculovirus containing a nucleic acid of sequence SEQ ID No. 25; and if need be, an adjuvant of the appropriate immunity, especially the adjuvant AIF™.

The invention is likewise directed at a pharmaceutical composition according to the invention, for the prevention or the treatment of an infection by a PWD circovirus.

The invention is also directed at a pharmaceutical composition according to the invention for the prevention or the treatment of an infection by the PWD circovirus of type B.

The invention likewise concerns the use of a composition according to the invention, for the preparation of a medicament intended for the prevention or the treatment of infection by a PWD circovirus, preferably by the PWD circovirus of type B.

Under another aspect, the invention relates to a vector, a viral particle or a cell according to the invention, for the treatment and/or the prevention of a disease by gene therapy.

Finally, the invention comprises the use of a vector, of a viral particle or of a cell according to the invention for the preparation of a medicament intended for the treatment and/or the prevention of a disease by gene therapy.

The polypeptides of the invention entering into the immunogenic or vaccine compositions according to the invention can be selected by techniques known to the person skilled in the art such as, for example, depending on the capacity of said polypeptides to stimulate the T cells, which is translated, for example, by their proliferation or the secretion of interleukins, and which leads to the production of antibodies directed against said polypeptides.

In pigs, as in mice, in which a weight dose of the vaccine composition comparable to the dose used in man is administered, the antibody reaction is tested by taking of the serum followed by a study of the formation of a complex between the antibodies present in the serum and the antigen of the vaccine composition, according to the usual techniques.

The pharmaceutical compositions according to the invention will contain an effective quantity of the compounds of the invention, that is to say in sufficient quantity of said compound(s) allowing the desired effect to be obtained, such as, for example, the modulation of the cellular replication of PWD circovirus. The person skilled in the art will know how to determine this quantity, as a function, for example, of the age and of the weight of the individual to be treated, of the state of advancement of the pathology, of the possible secondary effects and by means of a test of evaluation of the effects obtained on a population range, these tests being known in these fields of application.

According to the invention, said vaccine combinations will preferably be combined with a pharmaceutically acceptable vehicle and, if need be, with one or more adjuvants of the appropriate immunity.

Today, various types of vaccines are available for protecting animals or man against infectious diseases: attenuated living microorganisms (*M. bovis*—BCG for tuberculosis), inactivated microorganisms (influenza virus), acellular extracts (*Bordetella pertussis* for whooping cough), recombined proteins (surface antigen of the hepatitis B virus), polysaccharides (pneumococcal). Vaccines prepared from synthetic peptides or genetically modified microorganisms expressing heterologous antigens are in the course of experimentation. More recently still, recombined plasmid DNAs carrying genes coding for protective antigens have been proposed as an alternative vaccine strategy. This type of vaccination is carried out with a particular plasmid originating from a plasmid of *E. coli* which does not replicate in vivo and which codes uniquely for the vaccinating protein. Animals have been immunized by simply injecting the naked plasmid DNA into the muscle. This technique leads to the expression of the vaccine protein in situ and to an immune response of cellular type (CTL) and of humoral type (antibody). This double induction of the immune response is one of the principal advantages of the vaccination technique with naked DNA.

The vaccine compositions comprising nucleotide sequences or vectors into which are inserted said sequences are especially described in the international application No. WO 90/11092 and likewise in the international application No. WO 95/11307.

The constitutive nucleotide sequence of the vaccine composition according to the invention can be injected into the host after having been coupled to compounds which favor the penetration of this polynucleotide into the interior of the cell or its transport to the cell nucleus. The resultant conjugates can be encapsulated in polymeric microparticles, as described in the international application No. WO 94/27238 (Medisorb Technologies International).

According to another embodiment of the vaccine composition according to the invention, the nucleotide sequence, preferably a DNA, is complexed with DEAE-dextran (Pagano et al., 1967) or with nuclear proteins (Kaneda et al., 1989), with lipids (Felgner et al., 1987) or encapsulated in liposomes (Fraley et al., 1980) or else introduced in the form of a gel facilitating its transfection into the cells (Midoux et al., 1993, Pastore et al., 1994). The polynucleotide or the vector according to the invention can also be in suspension in a buffer solution or be combined with liposomes.

Advantageously, such a vaccine will be prepared according to the technique described by Tacson et al. or Huygen et al. in 1996 or alternatively according to the technique described by Davis et al. in the international application No. WO 95/11307.

Such a vaccine can likewise be prepared in the form of a composition containing a vector according to the invention, placed under the control of regulation elements allowing its expression in man or animal. It will be possible, for example, to use, by way of in vivo expression vector of the polypeptide antigen of interest, the plasmid pcDNA3 or the plasmid pcDNA1/neo, both marketed by Invitrogen (R&D Systems, Abingdon, United Kingdom). It is also possible to use the plasmid V1Jns.tPA, described by Shiver et al. in 1995. Such a vaccine will advantageously comprise, apart from the recombinant vector, a saline solution, for example a sodium chloride solution.

Pharmaceutically acceptable vehicle is understood as designating a compound or a combination of compounds entering into a pharmaceutical composition or vaccine which does not provoke secondary reactions and which allows, for example, the facilitation of the administration of the active compound, an increase in its duration of life and/or its efficacy in the body, an increase in its solubility in solution or alternatively an improvement in its conservation. These pharmaceutically acceptable vehicles are well known and will be adapted by the person skilled in the art as a function of the nature and of the mode of administration of the chosen active compound.

As far as the vaccine formulations are concerned, these can comprise adjuvants of the appropriate immunity which are known to the person skilled in the art, such as, for example, aluminum hydroxide, a representative of the family of muramyl peptides such as one of the peptide derivatives of N-acetyl muramyl, a bacterial lysate, or alternatively Freund's incomplete adjuvant.

These compounds can be administered by the systemic route, in particular by the intravenous route, by the intramuscular, intradermal or subcutaneous route, or by the oral route. In a more preferred manner, the vaccine composition comprising polypeptides according to the invention will be administered by the intramuscular route, through the food or by nebulization several times, staggered over time.

Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present invention is administered in an amount that is protective against piglet weight loss disease.

For example, in the case of a vaccine according to the present invention comprising a polypeptide encoded by a nucleotide sequence of the genome of PCV, or a homologue or fragment thereof, the polypeptide will be administered one time or several times, spread out over time, directly or by means of a transformed cell capable of expressing the polypeptide, in an amount of about 0.1 to 10 μg per kilogram weight of the animal, preferably about 0.2 to about 5 μg/kg, more preferably about 0.5 to about 2 μg/kg for a dose.

The present invention likewise relates to the use of nucleotide sequences of PWD circovirus according to the invention for the construction of autoreplicative retroviral vectors and the therapeutic applications of these, especially in the field of human gene therapy in vivo.

The feasibility of gene therapy applied to man no longer needs to be demonstrated and this relates to numerous therapeutic applications like genetic diseases, infectious diseases and cancers. Numerous documents of the prior art describe the means of employing gene therapy, especially through viral vectors. Generally speaking, the vectors are obtained by deletion of at least some of the viral genes which are replaced by the genes of therapeutic interest. Such vectors can be propagated in a complementation line which supplies in trans the deleted viral functions in order to generate a defective viral vector particle for replication but capable of infecting a host cell. To date, the retroviral vectors are amongst the most widely used and their mode of infection is widely described in the literature accessible to the person skilled in the art.

The principle of gene therapy is to deliver a functional gene, called a gene of interest, of which the RNA or the corresponding protein will produce the desired biochemical effect in the targeted cells or tissues. On the one hand, the insertion of genes allows the prolonged expression of complex and unstable molecules such as RNAs or proteins which can be extremely difficult or even impossible to obtain or to administer directly. On the other hand, the controlled insertion of the desired gene into the interior of targeted specific cells allows the expression product to be regulated in defined tissues. For this, it is necessary to be able to insert the desired therapeutic gene into the interior of chosen cells and thus to have available a method of insertion capable of specifically targeting the cells or the tissues chosen.

Among the methods of insertion of genes, such as, for example, microinjection, especially the injection of naked plasmid DNA (Derse, D. et al., 1995, and Zhao, T. M. et al., 1996), electroporation, homologous recombination, the use of viral particles, such as retroviruses, is widespread. However, applied in vivo, the gene transfer systems of recombinant retroviral type at the same time have a weak infectious power (insufficient concentration of viral particles) and a lack of specificity with regard to chosen target cells.

The production of cell-specific viral vectors, having a tissue-specific tropism, and whose gene of interest can be translated adequately by the target cells, is realizable, for example, by fusing a specific ligand of the target host cells to the N-terminal part of a surface protein of the envelope of PWD circovirus. It is possible to mention, for example, the construction of retroviral particles having the CD4 molecule on the surface of the envelope so as to target the human cells infected by the HIV virus (YOUNG, J. A. T. et al., Sciences 1990, 250, 1421-1423), viral particles having a peptide hormone fused to an envelope protein to specifically infect the cells expressing the corresponding receptor (KASAHARA, N. et al., Sciences 1994, 266, 1373-1376) or else alternatively viral particles having a fused polypeptide capable of immobilizing on the receptor of the epidermal growth factor (EGF) (COSSET, F. L. et al., J. of Virology 1995, 69, 10, 6314-6322). In another approach, single-chain fragments of antibodies directed against surface antigens of the target cells are inserted by fusion with the N-terminal part of the envelope protein (VALSESIA-WITTMAN, S. et al., J. of Virology 1996, 70, 3, 2059-2064; TEARINA CHU, T. H. et al., J. of Virology 1997, 71, 1, 720-725).

For the purposes of the present invention, a gene of interest in use in the invention can be obtained from a eukaryotic or prokaryotic organism or from a virus by any conventional technique. It is, preferably, capable of producing an expression product having a therapeutic effect and it can be a product homologous to the cell host or, alternatively, heterologous. In the scope of the present invention, a gene of interest can code for an (i) intracellular or (ii) membrane product present on the surface of the host cell or (iii) secreted outside the host cell. It can therefore comprise appropriate additional elements such as, for example, a sequence coding for a secretion signal. These signals are known to the person skilled in the art.

In accordance with the aims pursued by the present invention, a gene of interest can code for a protein corresponding to all or part of a native protein as found in nature. It can likewise be a chimeric protein, for example arising from the fusion of polypeptides of various origins or from a mutant having improved and/or modified biological properties. Such a mutant can be obtained, by conventional biological techniques, by substitution, deletion and/or addition of one or more amino acid residues.

It is very particularly preferred to employ a gene of therapeutic interest coding for an expression product capable of inhibiting or retarding the establishment and/or the development of a genetic or acquired disease. A vector according to the invention is in particular intended for the prevention or for the treatment of cystic fibrosis, of hemophilia A or B, of Duchenne's or Becker's myopathy, of cancer, of AIDS and of other bacteria or infectious diseases due to a pathogenic organism: virus, bacteria, parasite or prion. The genes of interest utilizable in the present invention are those which code, for example, for the following proteins:

- a cytokine and especially an interleukin, an interferon, a tissue necrosis factor and a growth factor and especially a hematopoietic growth factor (G-CSF, GM-CSF),
- a factor or cofactor involved in clotting and especially factor VIII, von Willebrand's factor, antithrombin III, protein C, thrombin and hirudin,
- an enzyme or an enzyme inhibitor such as the inhibitors of viral proteases,
- an expression product of a suicide gene such as thymidine kinase of the HSV virus (herpesvirus) of type 1,
- an activator or an inhibitor of ion channels,
- a protein of which the absence, the modification or the deregulation of expression is responsible for a genetic disease, such as the CFTR protein, dystrophin or minidystrophin, insulin, ADA (adenosine diaminose), glucocerebrosidase and phenylhydroxylase,
- a protein capable of inhibiting the initiation or the progression of cancers, such as the expression products of tumor suppressor genes, for example the P53 and Rb genes,
- a protein capable of stimulating an immune or an antibody response, and a protein capable of inhibiting a viral infection or its development, for example the antigenic epitopes of the virus in question or altered variants of viral proteins capable of entering into competition with the native viral proteins.

The invention thus relates to the vectors characterized in that they comprise a nucleotide sequence of PWD circovirus according to the invention, and in that they additionally comprise a gene of interest.

The present invention likewise relates to viral particles generated from said vector according to the invention. It additionally relates to methods for the preparation of viral particles according to the invention, characterized in that they employ a vector according to the invention, including viral pseudoparticles (VLP, virus-like particles).

The invention likewise relates to animal cells transfected by a vector according to the invention.

Likewise comprised in the invention are animal cells, especially mammalian, infected by a viral particle according to the invention.

The present invention likewise relates to a vector, a viral particle or a cell according to the invention, for the treatment and/or the prevention of a genetic disease or of an acquired disease such as cancer or an infectious disease. The invention is likewise directed at a pharmaceutical composition comprising, by way of therapeutic or prophylactic agent, a vector or a cell according to the invention, in combination with a vehicle acceptable from a pharmaceutical point of view.

Other characteristics and advantages of the invention appear in the examples and the figures.

The invention is described in more detail in the following illustrative examples. Although the examples may represent only selected embodiments of the invention, it should be understood that the following examples are illustrative and not limiting.

EXAMPLES

Example 1

Cloning, Sequencing and Characterization of the PWD Circovirus of Type A (PCVA)

1. Experimental Procedures

Figure 1:
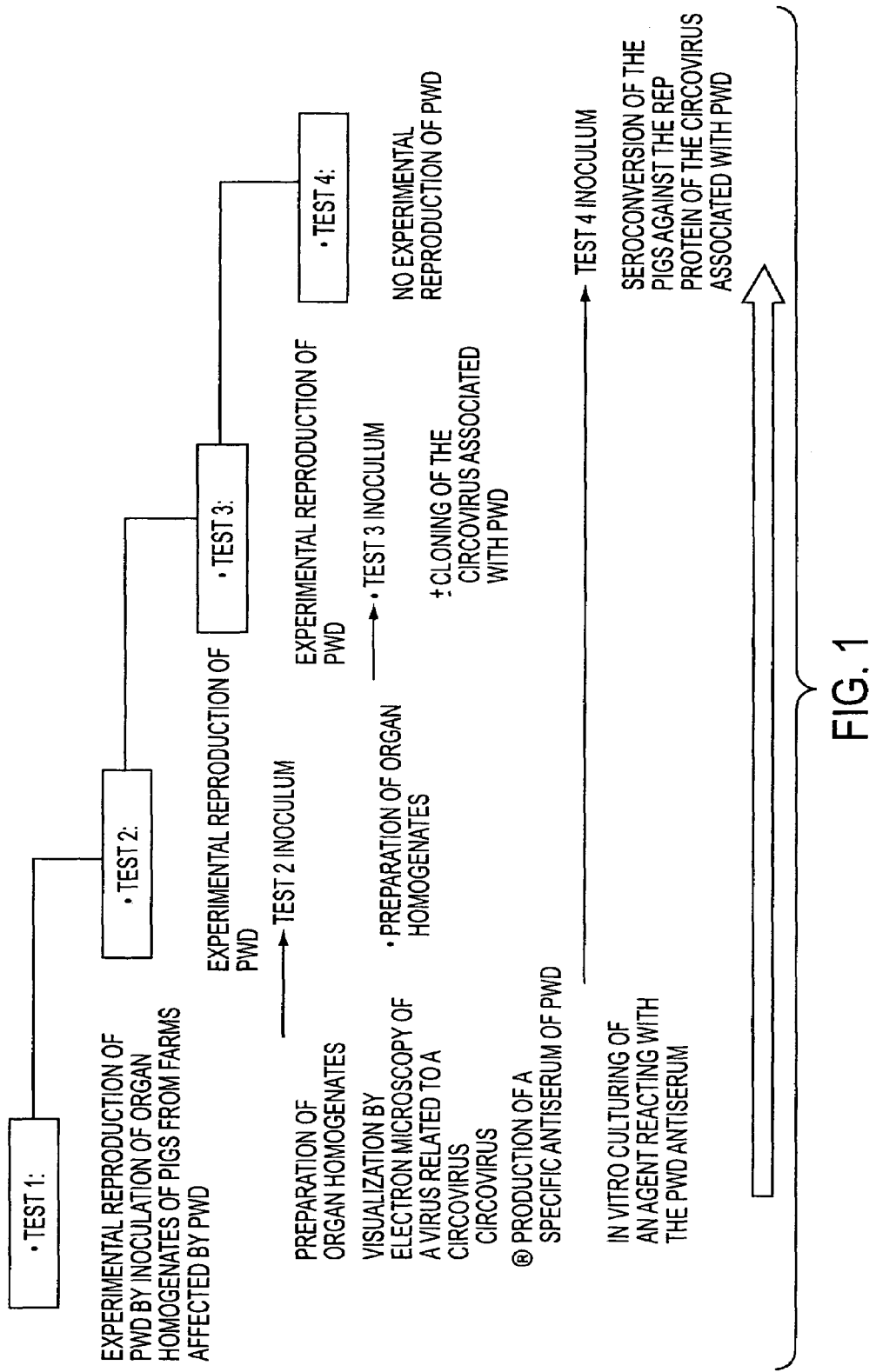
FIG. 1: Experimental scheme which has made it possible to bring about the isolation and the identification of the circovirus associated with PWD of type A and B.

Experimental reproduction of the infection and its syndrome are provided (cf. FIG. 1).

A first test was carried out with pigs from a very well-kept farm, but affected by piglet weight loss disease (PWD), likewise called fatal piglet wasting (FPW). Tests carried out with SPF (specific pathogen-free) pigs showed a transfer of contaminant(s) finding expression in a complex pathology combining hyperthermia, retardation of growth, diarrhea and conjunctivitis. The PDRS (porcine dysgenic and respiratory syndrome) virus, an infectious disease due to an arteriovirus) was rapidly isolated from breeding pigs and contact pigs. It should have been possible to attribute all the clinical signs to the presence of the PDRS virus. However, two farm pigs presented signs of FPW without the PDRS virus being isolated. The histological analyses and blood formulas, however, showed that these pigs were suffering from an infectious process of viral origin.

In a second test, 8-week SPF pigs were inoculated by the intratracheal route with organ homogenates of two farm pigs suffering from FPW. The inoculated pigs exhibited hyperthermia 8 to 9 days post-infection, then their growth was retarded. Other SPF pigs, placed in contact, had similar, attenuated signs 30 days after the initial experiment. No seroconversion with respect to a European or Canadian strain of PDRS virus was recorded in these animals.

A third test allowed the syndrome to be reproduced from samples taken from the pigs of the second test.

Conclusion

The syndrome is reproduced under the experimental conditions. It is determined by at least one infectious agent, which is transmittable by direct contact. The clinical constants are a sometimes high hyperthermia (greater than or equal to 41.5° C.) which develops 8 to 10 days after infection. Retardation of the growth can be observed. The other signs are a reversal of the blood formula (reversal of the lymphocyte/polynuclear ratio from 70/30 to 30/70) and frequent lesions on the ganglia, especially those draining the respiratory apparatus (ganglionic hypertrophy, loss of structure with necrosis and infiltration by mononucleated or plurinucleated giant cells).

2. Laboratory Studies

Various cell supports including primary pig kidney cells or cell lines, pig testicle cells, monkey kidney cells, pig lymphocytes, pig alveolar macrophages and circulating blood monocytes were used to demonstrate the possible presence of a virus. No cytopathic effect was demonstrated in these cells. On the other hand, the use of a serum of a pig sick after experimental infection allowed an intracellular antigen to be revealed in the monocytes, the macrophages and approximately 10% of pig kidney (PK) cells infected with organ homogenates. This indirect revealing was carried out kinetically at different culture times. It is evident from this that the antigen initially appears in the nucleus of the infected cells before spreading into the cytoplasm. The successive passages in cell culture did not allow the signal to be amplified.

Under electron microscopy on organ homogenates, spherical particles labeled specifically by the serum of sick pigs, infected under the experimental conditions, were visualized. The size of these particles is estimated at 20 nm.

After two passages of these organ homogenates over pig lymphocytes and then three passages over pig kidney or testicle cells, a cytopathic effect developed and was amplified. An adenovirus was visualized in the electron microscope, which, under the experimental conditions, did not reproduce FPW (only a hyperthermia peak was noted 24 to 48 hours after infection, and then nothing more).

It has been possible to demonstrate DNA bands in certain samples of pigs infected under the experimental conditions and having exhibited signs of the disease (results not shown). A certain connection exists between the samples giving a positive result in cell culture and those having a DNA band.

Conclusion

At least two types of virus were demonstrated in the organ homogenates from pigs suffering from FPW. One is an adenovirus, but by itself alone it does not reproduce the disease. The other type of virus is a circovirus and is associated with FPW. This circovirus, of which two types have been isolated and sequenced, designated below PWD circovirus type A (or PCVA) and PWD circovirus of type B (or PCVB) have mutations with respect to the known sequences of circovirus which are nonpathogenic for the pig.

3. Cloning and Sequencing of the DNA of the PWD Circovirus of Type A

Cloning and sequencing of the DNA of PHD circovirus Type A is accomplished by extraction of the replicative form (RF) DNA, followed by cleavage by the Kpn I enzyme and amplification by a pair of primers flanking the Kpn I restriction site. The two strands of DNA are sequenced at least twice by the Sanger method.

The nucleic sequence of the strand of (+) polarity of the genome of the PWD circovirus of type A (or PCVA), strain FPW, is represented by the sequence SEQ ID No. 1 in the list of sequences, the nucleic acid sequence of the strand of (−)

polarity of the genome of the PWD circovirus of type A (or PCVA) being represented by the nucleic acid sequence 3'→5' of FIG. 3 or by the sequence SEQ ID No. 5 (represented according to the orientation 5'→3') in the list of sequences.

The amino acid sequences SEQ ID No. 10, SEQ ID No. 12 and SEQ ID No. 14 of the list of sequences respectively represent the sequences of proteins encoded by the nucleic sequences of the 3 open reading frames SEQ ID No. 9 (ORF1), corresponding to the REP protein, SEQ ID No. 11 (ORF2) and SEQ ID No. 13 (ORF3), determined from the sequence SEQ ID No. 1 of the strand of (+) polarity or of the nucleic sequence SEQ ID No. 5 of the strand of (−) polarity of the genome of the PWD circovirus of type A.

4. Comparison of the Nucleotide Sequences and Amino Acids of the PWD Circovirus of Type A (or Associated with PWD) which are Obtained with the Corresponding Sequences of MEEHAN and MANKERTZ Circoviruses of Porcine Cell Lines.

DNA sequences are analyzed using, DNASIS software.

Sequences of Oligonucleotides used as Primers or Probes in the Detection and/or Identification Procedures 1. Specific Detection of the PWD Circovirus of Type A:

SEQ ID No. 46 primer PCV 5:   5' GTG TGC TCG ACA TTG
                                 GTG TG 3';

SEQ ID No. 47 primer PCV 10:  5' TGG AAT GTT AAC GAG
                                 CTG AG 3';

2. Specific Detection of the Circovirus of the Cell Lines:

SEQ ID No. 46  primer PCF 5: 5' GTG TGC TCG ACA TTG
                                GTG TG 3';

SEQ ID No. 52  primer MEE 1: 5' TGG AAT GTT AAC TAC
                                CTC AA 3';

3. Differential Detection:
the pairs of primers used are those described, for example, in the paragraphs 1 and 2 above;

4. Detection of the Monomeric Circular Replicative Forms RF:

SEQ ID No. 46  primer PCV 5: 5' GTG TGC TCG ACA TTG
                                GTG TG 3';

SEQ ID No. 48  primer PCV 6: 5' CTC GCA GCC ATC TTG
                                GAA TG 3';

5. Detection of the Vectors Carrying the Dimers in Tandem:
Nar Dimer:

SEQ ID No. 49 primer KS 620:  5' CGC GCG TAA TAC GAC
                                 TCA CT 3';

SEQ ID No. 46 primer PCV 5:   5' GTG TGC TCG ACA TTG
                                 GTG TG 3';

Kpn Dimer:

SEQ ID No. 49 primer KS 620:  5' CGC GCG TAA TAC GAC
                                 TCA CT 3';

SEQ ID No. 48 primer PCV 6:   5' CTC GCA GCC ATC TTG
                                 GAA TG 3';

6. Differential Detection:

The pairs of primers used are those described, for example, in paragraphs 4 and 5 above.

The procedures using the pairs or primers described in paragraphs 4 and 5 are of particular interest for differentially detecting the circular monomeric forms of specific replicative forms of the virion or of the DNA in replication and the dimeric forms found in the so-called in-tandem molecular constructs.

The in-tandem constructs of the viral genome (dimers) such as the constructs used for the preparation of the pBS KS+tandem PCV Kpn I vector, deposited at the CNCM under the number I-1891, 3 Jul. 1997 (*E. coli* transformed by said vector) are very interesting for their use in methods of production of sufficient quantity of an inoculum formed of DNA, intended for the virus production, this in the absence of a satisfactory virus production protocol in a cell system. These said methods of production using in-tandem constructs of the viral genome will allow the virulence factors to be studied by mutation and by way of consequence will be able to be used for the production of a collection of viruses carrying the mutations indicated in the construction of vectors which will have the appropriate tropism and virulence. These vectors with autoreplicative structure have the sought gene transfer properties, especially for their applications in gene therapy, and in vaccinology.

Western-Blot Analysis of Recombinant Proteins of the PWD Circovirus of Type A

The results were obtained using a specific antiserum of the PWD circovirus produced during test 1 (cf. FIG. 1).

Type of Products Analyzed

The analyses were carried out on cell extracts of Sf9 cells obtained after infection by the recombinant baculovirus PCV ORF 1.

The culture of Sf9 cells was carried out in a 25 cm$^2$ Petri dish according to the standard culture methods for these cells. After centrifugation, the cell pellets are taken up with 300 μl of PBS buffer (phosphate saline buffer).

Electrophoresis (PAGE-SDS)

The electrophoresis is carried out on the cell extracts of Sf9 cells obtained previously on 5 samples (cf. Table 1 below) under the following conditions:

% polyacrylamide gel: 8%; conditions: denaturing

Voltage: 80 V; duration: 135 mn.

TABLE 1

Nature of the samples subjected to electrophoresis

| | Well No. | | | | |
|---|---|---|---|---|---|
| | 1 | 2 | 3 | 4 | 5 |
| Sample applied | PM Rainbow | Raoul 24 h | Raoul 48 h | Raoul 72 h | Raoul 96 h |
| μl of sample | 10 | 15 | 15 | 15 | 15 |
| μl of Laemmli 4× | 0 | 5 | 5 | 5 | 5 |

Legends to Table 1:
Laemmli 4×: loading buffer
PM Rainbow: molecular-weight markers (35, 52, 77, 107, 160 and 250 kD)
Raoul 24 h, 48 h, 72 h and 96h: expression products of the ORF1 of the PWD circovirus of type A.

Western Blot

After electrophoresis, the bands obtained in the different wells are transferred to nitrocellulose membrane for 1 h at 100 v in a TGM buffer (tris-glycine-methanol).

The Western blot is carried out under the following conditions:
1) Saturation with a solution containing 5% of skimmed milk; 0.05% of Tween 20 in a TBS 1× buffer (tris buffer saline) for 30 min.
2) 1st Antibody:
10 ml of PWD anticircovirus antibody of type A are added diluted to 1/100, then the reaction mixture is incubated for one night at 4° C. Three washes of 10 min in TBS 1× are carried out.
3) 2nd Antibody:
10 ml of pig rabbit P164 antibody anti-immunoglobulins, coupled to peroxidase (Dakopath), are added diluted to 1/100, then the reaction medium is incubated for 3 hours at 37° C. Three washes of 10 min in TBS 1× are carried out.
4) Visualization
The substrate 4-chloro-1-naphthol in the presence of oxygenated water is used for visualization.
Results
The results are shown in FIG. 7.

Kinetics of Appearance of Antibodies Specific for the REP Recombinant Protein of the PWD Circovirus of Type A Expressed in Baculovirus After Infection of Pigs by the PWD Circovirus of Type A (Test 4, cf. FIG. 1)

After infection of the pigs, a sample of serum of each of the infected pigs is taken at different periods expressed in the table by the date of taking (carried out here in the same year) and is then analyzed by Western blot.

The visualization of the specific antibodies is carried out in the manner described previously.

The results obtained are shown by Table 2 below.

TABLE 2

Kinetics of appearance of specific antibodies

| Sample | Pigs | 10/6 | 16/06 | 23/06 | 01/07 | 08/07 | 15/07 | 21/07 |
|---|---|---|---|---|---|---|---|---|
| A3 Control | 1 | | | | | | Neg. | |
| | 2 | | | | | | Neg. | |
| B2 Infec. RP+ | 1 | Neg. | Neg. | Neg. | + | + | ++ | +++ |
| | 2 | Neg. | Neg. | Neg. | Neg. | Neg. | Neg. | Neg. |
| | 3 | Neg. | Neg. | Neg. | Neg. | + | + | + |
| | 4 | Neg. | Neg. | Neg. | Neg. | Neg. | Neg. | ++ |

Legends to Table 2:
A3 control: uninfected control animals;
B2 Infec. RP+: animals infected with pig kidney (PK) cells containing the circovirus;
Neg.: negative;
+, ++, +++: intensity scale of the positive reaction;
10/06, 16/06, 23/06, 01/07, 08/07, 15/07, 21/07: dates expressed in day/month on which the different withdrawals of serum were carried out.

Example 2

Cloning, Sequencing and Characterization of the Type B PWD Circovirus (PCVB)

The techniques used for cloning, sequencing and characterization of the type B PWD circovirus (PCVB) are those used in Example 1 above for the type A PWD circovirus (PCVA).

The nucleic acid sequence of the strand of (+) polarity of the genome of the PWD circovirus of type B (or PCVB) is represented by the sequence SEQ ID No. 15 in the sequence listing, the nucleic acid sequence of the strand of (−) polarity of the genome of the PWD circovirus of type B (or PCVB) being represented by the nucleic acid sequence 3'→5' of FIG. 8 or by the sequence SEQ ID No. 19 (represented according to the orientation 5'→3') in the sequence listing.

The amino acid sequences, SEQ ID No. 24, SEQ ID No. 26 and SEQ ID No. 28 of the sequence listing, respectively, represent the sequences of the proteins encoded by the nucleic sequences of the 3 open reading frames SEQ ID No. 23 (ORF'1), corresponding to the REP protein, SEQ ID No. 25 (ORF'2) and SEQ ID No. 27 (ORF'3), determined from the sequence SEQ ID No. 15 of the strand of (+) polarity or from the nucleic sequence SEQ ID No. 19 of the strand of (−) polarity of the genome of the PWD circovirus of type B.

Example 3

Comparative Analysis of Nucleotide Sequences (ORF1, ORF2 and Genomic) and Amino Acid Sequences Encoded by the ORF1 and the ORF2 of the PWD Circoviruses of Type A (PCVA) and of Type B (PCVB)

The results expressed in % of homology are shown in Tables 3 and 4 below.

TABLE 3

Compared analysis of the amino acid sequences

| % homology | ORF1 | ORF2 |
|---|---|---|
| PCVA/PCVB | 80.4 | 56.2 |

TABLE 4

Compared analysis of the nucleotide sequences

| % homology | Genomic | ORF1 | ORF2 | The remainder |
|---|---|---|---|---|
| PCVA/PCVB | 70.4 | 80.4 | 60.1 | 66.1 |

Example 4

Observation of the Disease and Reproduction of the Disease Under Experimental Conditions a) Test No. 1: Observation of the Disease The objective is to take breeding animals at the start of disease and to place them under experimental conditions to follow the progression of the pathology and describe all the clinical signs thereof. This first test was carried out on 3 breeding pigs aged 10 weeks of which 2 were already ill (suffering from wasting), and on 3 other pigs aged 13 weeks, not having signs of disease. The clinical observation was spread over a period of 37 days. Two pigs of 10 weeks wasted rapidly (pigs 1 and 2, FIG. 9) and had to be painlessly killed 5 and 6 days after their arrival. A single pig exhibited hyperthermia over 5 days and diarrhea. Two other pigs exhibited dyspnea and cough, of which one additionally had hyperthermia, greater than 41° C., for the two first days of its stay. Another pig had retarded growth in the second week (pig 6, FIG. 9), without any other clinical sign being recorded. On the lesional level, 5 pigs out of 6 exhibited macroscopic lesions of gray pneumonia, the sixth exhibited cicatricial lesions on the lung.

b) Test No. 2: Reproduction of the Disease from Inocula Prepared in Farm Pigs.

The two sick pigs in test 1 served to prepare inocula which were tested in test 2 on specific-pathogen-free (SPF) pigs. The SPF pigs were aged 9 weeks at the time of inoculation. The clinical and lesional results are shown in Table 5.

TABLE 5

Summary of the measurements carried out during experimental reproduction of PWD. (The values of the control animals are reported in brackets, the underlined values indicate a difference between infected animals and control animals)

| | Test Measurement | | | | | |
|---|---|---|---|---|---|---|
| | 2 | 3 | 4 | 5 | 6 | 7 |
| Status of the pigs | SPF CNEVA | SPF field | SPF CNEVA | SPF CNEVA | Conventional | Conventional |
| Age | 9 weeks | 6 weeks | 5 weeks | 5 weeks | 5 weeks | 6-7 weeks |
| Number | 4 | 6 | 12 | 8 | 8 | 8 |
| Inoculation route | Intratracheal route | Intratracheal route | Intratracheal + intramuscular route | Intratracheal + intramuscular route | Intratracheal + intramuscular route | Intratracheal + intramuscular route |
| Inoculum titer per pig | ND* | ND* | $10^{4.53}$ TCID$_{50}$ per ml: 1 ml IM + 5 ml IT | $10^{4.53}$ TCID$_{50}$ per ml: 1 ml IM + 5 ml IT | $10^{4.53}$ TCID$_{50}$ per ml: 1 ml IM + 5 ml IT | $10^{4.53}$ TCID$_{50}$ per ml: 1 ml IM + 5 ml IT |
| Start of hyperthermia | 10 days post-infection | 9-13 days post-infection | 12-13 days post-infection | 9-14 days post-infection | 8-12 days post-infection | 12 days post-infection |
| % of pigs in hyperthermia** | 100% | 83% | 92% | 100% | 75% | 88% |
| Number of days of hyperthermia per pig** | 7 | 4.5 | 3.3 | 5.8 | 7.5 | 11.6 |
| Maximum temperatures*** | 40.4 to 41.7° C. | 40.6 to 42.3° C. | 40.2 to 41.6° C. | 40.3 to 40.8° C. | 40.6 to 42° C. | 40.2 to 41.9° C. |
| Hyperthermia**** % per week | | | | | | |
| W1 | 3.5 (3.5) | 17 (36) | 7 (5) | 37 (17) | 16 (17) | 20 (28) |
| W2 | 42 (3.5) | 7 (13) | 13 (1) | 21 (3) | 52 (10) | 37 (28) |
| W3 | 35 (3.5) | 33 (10) | 28 (7) | 62 (2) | 34 (12) | 79 (17) |
| W4 | 21 (3.5) | 28 (7) | 5 (0) | 6 (3) | 25 (22) | 55 (3) |
| DMG: | | | | | | |
| W1 | 928 (1053) | 417 (357) | 564 (620) | 650 (589) | 401 (407) | 509 (512) |
| W2 | 678 (1028) | 428 (617) | 503 (718) | 612 (584) | 294 (514) | 410 (310) |
| W3 | 661 (1000) | 771 (642) | 381 (657) | 520 (851) | 375 (586) | 435 (440) |
| W4 | 786 (1100) | 550 (657) | 764 (778) | 641 (696) | 473 (610) | 451 (681) |
| Contact pigs transmission | Yes to 100% | Yes to 75% | Not tested | Not tested | Not tested | Not tested |
| % of pulmonary lesions | 25 | 75 | 0 | 25 | 25 | 12 |
| % of ganglionic lesions | 17 | 33 | 67 | 25 | 50 | 12 |

*ND: not determined,
**hyperthermia when the temperature is greater than 40° C.,
***range of maximum temperatures recorded at the individual level,
****the percentage corresponds to the number of temperature recordings greater than 40° C. divided by the total number of temperature recordings in the week on all of the pigs.

In this test, there was no wasting, at the very most a retardation of the growth in the second, third or fourth week after infection. These data illustrate that certain breeding conditions probably favor the expression of the disease.

c) Tests No. 3 to No. 7: Reproduction of the Experimental Tests

The increase in the number of the experimental tests on pigs had the mastering and better characterization of the experimental model as an objective. All of the results are presented in Table 5.

Under the experimental conditions, PWD is thus characterized by a long incubation, of 8 to 14 days, true hyperthermia over 2 to 8 days, a decrease in food consumption and a retardation of the increase in weight on the second, third or fourth week post-infection. The lesional table associated with this clinical expression includes, in the main, ganglionic hypertrophy and lesions of pneumonia.

Conclusion

The perfection of this experimental model allows the direct etiological role of the PWD circovirus in the disease to be indisputably demonstrated. In addition, this model is an indispensable tool for the understanding of pathogenic mechanisms and the study of future vaccine candidates.

Example 5

Demonstration of the Vaccine Composition Protective Efficacy Produced from Nucleic Fragments of PWD Circovirus Sequence 1) Animals Used for the Study Piglets having the PWD disease, reproduced under experimental conditions described in paragraph c) of Example 4, were used in a protocol for evaluating the vaccine composition efficacy, comprising nucleic fragments of PWD circovirus sequence.

2) Tested Vaccine Composition and Vaccination Protocol a) Components Used for the Study The plasmids were obtained from the pcDNA3 plasmid of INVITROGENE pcDNA3ORF–plasmids These plasmids are plasmids which do not carry a PWD circovirus nucleic acid insert and are used as a negative control plasmid.

pcDNA3ORF1+plasmid and pcDNA3ORF2+plasmid

The pcDNA3ORF1+ and pcDNA3ORF2+ plasmids are plasmids which carry a nucleic acid insert of the sequence of the PWD circovirus of TYPE B, and an insert comprising the nucleic acid fragment SEQ ID No. 23 (ORF'1) coding for the Rep protein of sequence SEQ ID No. 24 and an insert comprising the nucleic acid fragment SEQ ID No. 25 (ORF'2) coding for the protein of sequence SEQ ID No. 26, probably corresponding to the capsid protein, respectfully. These nucleic constructs further comprise the ATG initiation codon of the coding sequence of the corresponding protein.

GMCSF+Plasmid

GM-CSF (granulocyte/macrophage colony stimulating factor) is a cytokine which occurs in the development, the maturation and the activation of macrophages, granulocytes and dendritic cells which present an antigen. The beneficial contribution of the GM-CSF in vaccination is considered to be a cellular activation with, especially, the recruitment and the differentiation of cells which present an antigen.

This pcDNA3-GMCSF+ plasmid carries a nucleic acid insert coding for the granulocyte/macrophage colony stimulation factor, the GM-CSF protein.

The gene coding for this GM-CSF protein was cloned and sequenced by Inumaru et al. (*Immunol. Cell Biol*., 1995, 73 (5), 474-476). The pcDNA3-GMCSF+ plasmid was obtained by Dr. B. Charley of INRA of Jouy-en-Josas (78, France).

Recombinant Baculoviruses

The so-called ORF-baculoviruses are viruses not carrying any insert comprising a nucleic acid fragment capable of expressing a PWD circovirus protein.

The so-called ORF1+(BAC ORF1+) or ORF2+(BAC ORF2+) baculoviruses are recombinant baculoviruses carrying an insert comprising a nucleic acid fragment SEQ ID No. 23 (ORF'1) and an insert comprising the nucleic acid fragment SEQ ID No. 25 (ORF'2), respectively.

Adjuvant

The adjuvant supplied by the Seppic Company, a subsidiary of AIR LIQUIDE, is the adjuvant corresponding to the reference AIF SEPPIC.

b) Vaccination Protocol

Weaned piglets aged 3 weeks are divided into four batches A, B, C and D each comprising 8 piglets.

Batches A, B and C, aged 3 weeks, each receive a first injection (injection M1) of 1 ml containing 200 micrograms of plasmids (naked DNA) in PBS, pH: 7.2, by the intramuscular route for each of the plasmids mentioned below for each batch, then, at the age of 5 weeks, a second injection (injection M2) comprising these same plasmids. A third injection is carried out simultaneously on the other side of the neck. This third injection comprises 1 ml of a suspension containing $5\times10^6$ cells infected by recombinant baculoviruses and 1 ml of AIF SEPPIC adjuvant.

Batch A (F1) (Control Batch):

First Injection pcDNA3ORF1−plasmid, pcDNA3ORF2−plasmid and GMCSF+plasmid.

Second and Third Injection (Simultaneous)

pcDNA3ORF1−plasmid, pcDNA3ORF2−plasmid and GMCSF+plasmid;

Cells transformed by baculoviruses not containing any nucleic acid insert coding for a PWD circovirus protein;

AIF SEPPIC Adjuvant.

Batch B (F2) (Control Batch):

First Injection pcDNA3ORF1−plasmid, pcDNA3ORF2−plasmid and GMCSF+plasmid;

Second and Third Injection (Simultaneous)

pcDNA3ORF1−plasmid, pcDNA3ORF2−plasmid and GMCSF+plasmid;

Cells transformed by baculoviruses not containing any nucleic acid insert coding for a PWD circovirus protein;

AIF SEPPIC Adjuvant.

Batch C (F3):

First Injection pcDNA3ORF1+plasmid, pcDNA3ORF2+plasmid and GMCSF+plasmid;

Second and Third Injection (Simultaneous)

pcDNA3ORF1+plasmid, pcDNA3ORF2+plasmid and GMCSF+plasmid;

Cells transformed by BAC ORF1+ and BAC ORF2+ recombinant baculoviruses capable of respectively expressing the Rep protein of sequence SEQ ID No. 24 and the protein of sequence SEQ ID No. 26 of the PWD circovirus of TYPE B.

Batch D (F4) (Control Batch): No Injection

The batches of piglets B, C and D are infected (tested) at the age of 6 weeks although batch A is not subjected to the test.

3) Observation of the Batches counting of coughing/sneezing: 15 minutes/batch/day;

consistency of fecal matter: every day;

regular recordings: weekly taking of blood, weighing;

weighing of food refuse: 3 times per week;

calculation of the daily mean gain in weight (dmg);

The daily mean gains were calculated for each of the batches over a period of 28 days following testing (cf. FIG. 10), an intermediate calculation of the dmg was likewise carried out for each of the batches over the first and second periods of 14 days. The results obtained are reported below in Table 6.

TABLE 6

| | Daily mean gains | | | |
|---|---|---|---|---|
| | F1 | F2 | F3 | F4 |
| d0-d14 | 411 g | 450 g | 511 g | 461 g |
| d14-d28 | 623 g | 362 g | 601 g | 443 g |
| d0-d28 | 554 g | 406 g | 556 g | 452 g |

Measurement of Hyperthermia

The measurement of hyperthermia, of greater than 41° C. (cf. FIG. 11) and greater than 40.2° C., was carried out for each of the batches over a total period of 28 days following testing. The results obtained, corresponding to the ratio expressed as a percentage between the number of temperature recordings of greater than 41° C. (or greater than 40.2° C.) and the total number of temperature recordings carried out on all of the pigs per one-week period are reported below in Tables 7 and 8, respectively, for the hyperthermia measurements of greater than 41° C. and greater than 40.2° C.

TABLE 7

| | Hyperthermia > 41° C. | | | |
|---|---|---|---|---|
| | F1 | F2 | F3 | F4 |
| W1 | 4.1 | 0 | 0 | 0 |
| W2 | 10.7 | 16. | 0 | 8.9 |
| W3 | 4.7 | 27. | 0 | 45. |
| W4 | 0 | 0 | 0 | 7.5 |

TABLE 8

| | \multicolumn{4}{c}{Hyperthermia > 40.2} |
|---|---|---|---|---|
| | F1 | F2 | F3 | F4 |
| W1 | 29.1 | 10.41 | 29.1 | 20.8 |
| W2 | 28.5 | 39.2 | 10.7 | 37.5 |
| W3 | 14.3 | 68.7 | 25.0 | 81.2 |
| W4 | 3.3 | 17.5 | 20.0 | 55 |

4) Conclusion

The recordings carried out clearly show that the animals which received the three injections of a vaccine composition comprising nucleic acid fragments of PWD circovirus according to the invention and/or capable of expressing recombinant proteins of PWD circovirus, in particular of type B, did not exhibit hyperthermia (cf. FIG. 10). These animals additionally did not experience a decline in their growth, the dmgs being comparable to those of uninfected control animals (cf. FIG. 9). They did not exhibit any particular clinical sign.

These results demonstrate the efficacious protection of the piglets against infection with a PWD circovirus of the invention, the primary agent responsible for PWD or FPW, provided by a vaccine composition prepared from a nucleic acid fragment of the nucleic sequence of PWD circovirus according to the invention, in particular of type B, and/or from recombinant proteins encoded by these nucleic acid fragments.

These results in particular show that the proteins encoded by the ORF1 and ORF2 of PWD circovirus according to the invention are immunogenic proteins inducing an efficacious protective response for the prevention of infection by a PWD circovirus.

Example 6

Serological Diagnosis of PWD Circovirus by Immunodetermination using Recombinant Proteins or Synthetic Peptides of PWD Circovirus A. Serological Diagnosis with Recombinant Proteins The identification and the sequencing of porcine PWD circovirus allow recombinant proteins of PWD circovirus to be produced by the techniques of genetic recombination well known to the person skilled in the art. Using these techniques, recombinant proteins encoded, in particular, by the ORF'2 of the PWD circovirus, type B, were expressed by transformed Sf9 insect cells and then isolated.

These recombinant proteins encoded by the ORF'2 are extracted, after culture of the transformed Sf9 cells, by thermal cell lysis by means of 3 cycles of freezing/thawing to −70° C./+37° C. Healthy Sf9 cells or nontransformed control Sf9 cells are also lysed.

Two antigenic fractions originating from nontransformed control Sf9 cells and Sf9 cells expressing the ORF'2 are precipitated at 4° C. by a 60% plus or minus 5% saturated ammonium sulfate solution. Determination of total proteins is carried out with the aid of the Biorad kit. 500 ng of control Sf9 proteins and of semipurified Sf9 proteins expressing the ORF'2, in solution in 0.05 M bicarbonate buffer pH 9.6, are passively adsorbed at the bottom of 3 different wells of a Nunc Maxisorp microplate by incubation for one night at +4° C.

The reactivity of pig sera with respect to each of these antigenic fractions is evaluated by an indirect ELISA reaction of which the experimental protocol is detailed below:

Saturation step: 200 µl/well of PBS1×/3% semi-skimmed milk, 1 h 30 incubation at 37° C.

Washing: 200 µl/well of PBS1×/Tween 20: 0.05%, 3 rapid washes.

Serum incubation step: 100 µl/well of serum diluted to $\frac{1}{100}$ in PBS1×/semi-skimmed milk, 1%/Tween 20: 0.05%, 1 h incubation at 37° C.

Washing: 200 µl/well of PBS1×/Tween 20: 0.05%, 2 rapid washes followed by 2 washes of 5 min.

Conjugate incubation step: 50 µl/well of rabbit anti-pig conjugate diluted to $\frac{1}{1000}$ in PBS1×/semi-skimmed milk, 1%/Tween 20: 0.05%, 1 h incubation at 37° C.

Washing: 200 µl/well of PBS1×/Tween 20: 0.05%, 2 rapid washes followed by 2 washes of 5 min.

Visualization step: 100 µl/well of OPD substrate/citrate buffer/$H_2O_2$, 15 min incubation at 37° C.

Termination: 50 µl/well of 1 N $H_2SO_4$.

Read optical density in a spectrophotometer at 490 nm.

Results

The results obtained are shown below in Table 9.

TABLE 9

| Antigens | Reactivity of Pig Serum not inoculated with Circovirus | Reactivity of Pig Serum inoculated with Circovirus |
|---|---|---|
| Purified Sf9 control | 0.076 | 0.088 |
| Sf9 expressing purified ORF'2 | 0.071 | 1.035 |

The results are expressed in optical density measured in a spectrophotometer at 490 nm during analysis by ELISA of the reactivity of pig sera which are or are not inoculated with the type B PWD circovirus according to the protocol indicated above.

B. Serological Diagnosis by Synthetic Peptide

The epitopic mapping of the proteins encoded, for example, by the nucleic sequences ORF1 and ORF2 of the two types of PWD circovirus (types A and B) additionally allowed immunogenic circoviral epitopes to be identified on the proteins encoded by the nucleic sequences ORF'1 and ORF'2 as well as the specific epitopes of the protein encoded by the nucleic acid sequence ORF'2 of the type B PWD circovirus. Four specific epitopes of the type B PWD circovirus and one epitope common to the two types of PWD circovirus situated on the protein encoded by the nucleic sequence ORF'2 were synthesized in peptide form. The equivalent peptides in the circovirus of type A were likewise synthesized. All peptides were evaluated as diagnostic antigens within the context of carrying out a serological test.

Results

The results obtained are shown in Table 10, below.

TABLE 10

Results of the evaluation as a diagnostic antigen of synthetic peptides encoded
by the nucleic sequences ORF2 and ORF'2 of PWD circovirus of type A and B.

| | Peptide | Type PWD circovirus | Position | AA sequence | SPF D0/D54 | Infected pig serum reactivity Circovirus B Conventional 1 D0/D42 | Conventional 2 D0/D42 | Epitopic specificity |
|---|---|---|---|---|---|---|---|---|
| SEQ ID NO: 29 | 121 | B | 71-85 | VDMMRFNINDFLPPG | +/−, +++ | +/−, +++ | −, +++ | Circovirus B |
| SEQ ID NO: 55 | 177 | B | 70-84 | NVNELRFNIGQFLPP | +/−, + | +/−, +/− | +/−, − | |
| SEQ ID NO: 30 | 131 | B | 115-129 | QGDRGVGSSAVILDD | +/−, +/− | ++, ++ | +/−, + | Circovirus B |
| SEQ ID NO: 56 | 188 | A | 114-127 | TSNQRGVGSTVVIL | +/−, − | −, +/− | +/−, +/− | |
| SEQ ID NO: 31 | 133 | B | 119-134 | GVGSSAVILDDNVFTK | −, ++ | ++, +++ | +/−, ++ | |
| SEQ ID NO: 57 | 189 | A | 118-132 | RGVGSTVVILDANFV | +/−, − | −, +/− | +/−, +/− | |
| SEQ ID NO: 58 | 146 | B | 171-185 | FTIDYFQPNNKRNQL | −, +/− | −, ++ | −, ++ | Circovirus A&B |
| SEQ ID NO: 59 | 202 | A | 170-184 | DQTIDWFQPNNKRNQ | +++, +++ | +/−, ++ | +, ++ | |
| SEQ ID NO: 32 | 152 | B | 195-209 | VDHVGLGTAFENSIY | −, ++ | +++, +++ | +/−, + | Circovirus B |
| SEQ ID NO: 60 | 208 | A | 194-208 | NVEHTGLGYALQNAT | −, − | −, − | −, − | |

+/−, +, ++, +++. Increasing intensities of the reactivities observed in Spot peptides on a nitrocellulose membrane. The porcine sera tested are from animals experimentally infected with the circovirus of type B within the animal houses of the CNEVA. Samples are taken from the animals before inoculation on d0 and 42 days or 54 days after inoculation, on d42, d54.

Example 7

Characterization of the Specific Epitopes of the PWD Circovirus of Type B

The proteins encoded by the ORF2 of the porcine circoviruses of type A and B were chosen for this study. For each of the ORF2s (types A and B), 56 peptides of 15 amino acids which overlap every 4 amino acids were synthesized, thus covering the whole of the protein (cf. Table 11 below).

TABLE 11

Sequence of amino acids of the 56 peptides of 15 amino acids
synthesized from the nucleic sequence ORF2' (type B) and ORF2 (type
A) of PWD circovirus with their corresponding spot number (cf. FIG. 12)

| | Type B ORF'2 | | | Type A ORF2 | |
|---|---|---|---|---|---|
| | Spot No. | Sequence | | Spot No. | Sequence |
| SEQ ID NO: 61 | 107 | HRPRSHLGQILRRRP | SEQ ID NO: 84 | 163 | TRPRSHLGNILRRRP |
| SEQ ID NO: 62 | 108 | SHLGQILRRRPWLVH | SEQ ID NO: 85 | 164 | SHLGNILRRRPYLVH |
| SEQ ID NO: 63 | 109 | QILRRRPWLVHPRHR | SEQ ID NO: 86 | 165 | NILRRRPYLVHPAFR |
| SEQ ID NO: 64 | 110 | RRPWLVHPRHRYRWR | SEQ ID NO: 87 | 166 | RRPYLVHPAFRNRYR |
| SEQ ID NO: 65 | 111 | LVHPRHRYRWRRKNG | SEQ ID NO: 88 | 167 | LVHPAFRNRYRWRRK |
| SEQ ID NO: 66 | 112 | RHRYRWRRKNGIFNT | SEQ ID NO: 89 | 168 | AFRNRYRWRRKTGIF |
| SEQ ID NO: 67 | 113 | RWRRKNGIFNTRLSR | SEQ ID NO: 90 | 169 | RYRWRRKTGIFNSRL |
| SEQ ID NO: 68 | 114 | KNGIFNTRLSRTFGY | SEQ ID NO: 91 | 170 | RRKTGIFNSRLSREF |
| SEQ ID NO: 69 | 115 | FNTRLSRTFGYTVKR | SEQ ID NO: 92 | 171 | GIFNSRLSREFVLTI |
| SEQ ID NO: 70 | 116 | LSRTFGYTVKTTFVR | SEQ ID NO: 93 | 172 | SRLSREFVLTIRGGH |
| SEQ ID NO: 71 | 117 | FGYTVKRTTVRTPSW | SEQ ID NO: 94 | 173 | REFVLTIRGGHSQPS |
| SEQ ID NO: 72 | 118 | VKRTTVRTPSWAVDM | SEQ ID NO: 95 | 174 | LTIRGGHSQPSWNVN |
| SEQ ID NO: 73 | 119 | TVRTPSWAVDMMRFN | SEQ ID NO: 96 | 175 | GGHSQPSWNVNELRF |
| SEQ ID NO: 74 | 120 | PSWAVDMMRFNINDF | SEQ ID NO: 97 | 176 | QPSWNVNELRFNIGQ |
| SEQ ID NO: 29 | 121 | VDMMRFNINDFLPPG | SEQ ID NO: 98 | 177 | NVNELRFNIGQFLPP |

TABLE 11-continued

Sequence of amino acids of the 56 peptides of 15 amino acids synthesized from the nucleic sequence ORF'2 (type B) and ORF2 (type A) of PWD circovirus with TABLE 11-continued Sequence of amino acids of the 56 peptides of 15 amino acids synthesized from the nucleic sequence ORF2' (type B) and ORF2 (type A) of PWD circovirus with their corresponding spot number (cf. FIG. 12)

| Type B ORF'2 | | | Type A ORF2 | | |
|---|---|---|---|---|---|
| | Spot No. | Sequence | | Spot No. | Sequence |
| SEQ ID NO:133 | 157 | IRVTMYVQFREFNFK | SEQ ID NO:160 | 213 | VVRLTIYVQFREFIL |
| SEQ ID NO:134 | 158 | MYVQFREFNFKDPPL | SEQ ID NO:161 | 214 | TIYVQFREFILKDPL |
| SEQ ID NO:135 | 159 | VQFREFNFKDPPLNP | SEQ ID NO:162 | 215 | YVQFREFILKDPLNE |

These peptides were synthesized according to the "spot" method which consists of simultaneous synthesis of a large number of peptides on a cellulose solid support, each site of synthesis of a peptide constituting a spot (Synt:em, NIMES). This method involves orientation of the peptides on the plate, these being fixed covalently by the carboxy-terminal end. A spot represents approximately 50 nmol of peptide.

The reference of the spots and corresponding peptide sequences is given in Table 11.

These membranes were used for immunoreactivity tests with respect to serum of SPF pigs which were or were not infected experimentally with the type B PWD circoviral strain as well as with respect to sera of infected pigs from conventional farms (conventional farms 1 or 2). This study allowed specific immunoreactive peptides of the circovirus of type B corresponding to the spots No. 121, No. 132, No. 133 and No. 152 (respectively of amino acid sequences SEQ ID No. 29, SEQ ID No. 30, SEQ ID No. 31 and SEQ ID No. 32) to be demonstrated. An illustration is shown in FIG. 12 where the membranes are visualized with an infected pig serum coming from a conventional farm. Nonspecific immunoreactive peptides of type [lacuna] were likewise demonstrated, among which we shall keep the peptide No. 146 SEQ ID No. 123 which is strongly immunogenic.

A comparison between the peptide sequences of circoviruses of type A and B (FIG. 13) indicates a divergence ranging from 20 to 60% for the specific immunoreactive peptides of the type B, and a weaker divergence (13%) between the nonspecific peptides.

Example 8

Protection of Swine From Post-Weaning Multisystemic Wasting Syndrome (PMWS) Conferred by Procine Circovirus Type B (PCV-B) ORF'2 Protein The ORF'1-encoded protein (REP) and ORF'2-encoded putative capsid protein of PCV-B were expressed, either in insect cells by recombinant baculovirus vectors, or in mammalian cell lines by transfection with plasmidic expression vectors. These two circovirus-derived proteins were detectable in both expression systems. As evaluated by weight gains, hyperthermia and absence of lesions following challenge, the pigs were protected against a virulent circovirus challenge after one first DNA immunization with plasmids directing ORF'2 protein and GM-CSF expression and a second injection, 15 days later, with the same plasmid preparation plus the ORF'2 recombinant protein. A lower level of protection was observed when the pigs were vaccinated with ORF'1 protein, as opposed to pigs vaccinated with ORF'2 protein.

A. Development of an Experimental Model of PMWS in Swine:

Eight 3 week-old SPF pigs were inoculated intratracheally (5 ml) and intramuscularly (1 ml).

B. Production and Control of PCV-B Plasmids:

PCV-B ORF'1 and ORF'2 genes, isolated from PCV-B challenge strain, was cloned into vector plasmid pcDNA3.1. All constructs were validated through a partial sequencing of the PCV-B genes in the final plasmids and expression control by immunoperoxidase on PK15 cells respectively transfected with each plasmid, using swine polyclonal antibodies.

Plasmid Encoding GM-CSF has Been Co-Administered.

C. Construction of Recombinant Baculoviruses:

ORF'1 and ORF'2 proteins were expressed under polyhedrin promoter control. Recombinant proteins were detected by western-blot using swine polyclonal antibodies.

D. Vaccination and Challenge:

Four groups of 7 pigs were vaccinated intramuscularly at day 0 (Do), two weeks later, they received the same plasmid preparation plus the recombinant baculovirus.

E. Monitoring:

All groups of pigs were housed in isolated experimental units with air filtration and low air pressure. Clinical observations and rectal temperatures were recorded every day. The pigs were weighed weekly.

F. Conclusions

Expression of PCV-B ORF'2 or PCV-B ORF'1 in swine resulted in a significantly enhanced level of protection as evaluated by weight evolution and body temperature evolution following challenge with PCV-B circovirus. These results are summarized in FIGS. 14 and 15.

The invention described herein may be embodied in other specific forms without departing from the spirit or essential characteristics thereof. The specific embodiments previously described are therefore to be considered as illustrative of, and not limiting, the scope of the invention. Additionally, the disclosure of all publications and patent applications cited above and below, including International Patent Application No. PCT/FR98/02634, filed Dec. 4, 1998, and published as International Publication No. WO 99/29871 on Jun. 17, 1999, are expressly incorporated herein by reference in their entireties to the same extent as if each were incorporated by reference individually.

BIBLIOGRAPHIC REFERENCES

Allan, G. M. et al., 1995, Vet. Microbiol., 44: 49-64.

Barany, F., 1911, PNAS. USA, 88: 189-193.

Boulton, L. H. et al., 1997, J. Gen. Virol., 78 (Pt 6), 1265-1270.

Buckholz, R. G., 1993, Yeast systems for the expression of heterologous gene products. Curr. Op. Biotechnology 4: 538-542.
Burg, J. L. et al., 1996, Mol. and Cell. Probes, 10: 257-271.
Chu, B. C. F. et al., 1986, NAR, 14: 5591-5603.
Chu, P. W. G. et al., 1993, Virus Research, 27: 161-171.
Clark, E. G., 1997, American Association of Swine Practitioners, 499-501.
Daft, B. et al., 1996, American Association of Veterinary Laboratory Diagnosticians, 32.
Derse, D. et al., 1995, J. Virol., 69(3): 1907-1912.
Duck, P. et al., 1990, Biotechniques, 9: 142-147.
Dulac, G. C. et al., 1989, Can. J. Vet. Res., 53: 431-433.
Edwards, C. P., and Aruffo, A., 1993, Current applications of COS cell based transient expression systems. Curr. Op. Biotechnology 4: 558-563.
Edwards, S. et al., 1994, Vet. Rec., 134: 680-681.
Erlich, H. A., 1989, In PCR Technology. Principles and Applications for DNA Amplification. New York: Stockton Press.
Felgner, et al., 1987, Proc. Natl. Acad. Sci., 84: 7413.
Fontes, E. P. B. et al., 1994, J. Biol. Chem., Vol. 269, No. 11: 8459-8465.
Fraley et al., 1980, J. Biol. Chem., 255: 10431.
Guateli, J. C. et al., 1990, PNAS. USA, 87: 1874-1878.
Hackland, A. F. et al., 1994, Arch. Virol., 139: 1-22.
Hanson, S. F. et al., 1995, Virology, 211: 1-9.
Harding, J. C., 1997, American Association of Swine Practitioners, 503.
Harding, R. M. et al., 1993, Journal of General Virology, 74: 323-328.
Harding, J. C. and Clark, E. G., 1997, Swine Health and Production, Vol. 5, No. 5: 201-203.
Heyraud-Nitschke, F. et al., 1995, Nucleic Acids Research, Vol. 23, No. 6.
Homer, G. W., 1991, Surveillance 18(5): 23.
Houben-Weyl, 1974, in Methode der Organischen Chemie, E. Wunsch Ed., Volume 15-I and 15-II, Thieme, Stuttgart.
Huygen, K. et al., 1996, Nature Medicine, 2(8): 893-898.
Innis, M. A. et al., 1990, in PCR Protocols. A guide to Methods and Applications, San Diego, Academic Press.
Kaneda, et al., 1989, Science, 243: 375.
Kievitis, T. et al., 1991, J. Virol. Methods, 35: 273-286.
Kohler, G. et al., 1975, Nature, 256(5517): 495-497.
Kwoh, D. Y. et al., 1989, PNAS. USA, 86: 1173-1177.
Ladany, S. et al., 1989, J. Clin. Microbiol. 27: 2778-2783.
Lazarowitz, S. G. et al., 1989, The EMBO Journal, Vol. 8 No. 4: 1023-1032.
Luckow, V. A., 1993, Baculovirus systems for the expression of human gene products. Curr. Op. Biotechnology 4: 564-572.
Mankertz, A. et al., 1997, J. Virol., 71: 2562-2566.
Matthews, J. A. et al., 1988, Anal. Biochem., 169: 1-25.
McNeilly, F. et al., 1996, Vet. Immunol. Immunopathol., 49: 295-306.
Meehan, B. M. et al., 1997, J. Gen. Virol. 78: 221-227.
Merrifield, R. D., 1966, J. Am. Chem. Soc., 88(21): 5051-5052.
Midoux, 1993, Nucleic Acids Research, 21: 871-878.
Miele, E. A. et al., 1983, J. Mol. Biol., 171: 281-295.
Murphy, F. A. et al., 1995, Sixth Report of the International Committee on Taxonomy of Viruses. Springer-Verlag Wien N.Y.
Nayar, G. P. et al., 1997, Can. Vet. J. 38(6): 385-386.
Olins, P. O., and Lee, S. C., 1993, Recent advances in heterologous gene expression in E. coli. Curr. Op. Biotechnology 4: 520-525.
Pagano et al., 1967, J. Virol., 1: 891.
Rolfs, A. et al., 1991, In PCR Topics. Usage of Polymerase Chain reaction in Genetic and Infectious Disease. Berlin: Springer-Verlag.
Sambrook, J. et al., 1989, In Molecular cloning: A Laboratory Manual. Cold Spring Harbor, N.Y.: Cold Spring Harbor Laboratory Press.
Sanchez-Pescador, R., 1988, J. Clin. Microbiol., 26(10): 1934-1938.
Segev D., 1992, in "Non-radioactive Labeling and Detection of Biomolecules". Kessler C. Springer Verlag, Berlin, N.Y.: 197-205.
Shiver, J. W., 1995, in Vaccines 1995, eds Chanock, R. M. Brown, F. Ginsberg, H. S. & Norrby, E., pp. 95-98, Cold Spring Harbor Laboratory Press, Cold Spring Harbor, N.Y.
Tascon, R. E. et al., 1996, Nature Medicine, 2(8): 888-892.
Tischer, I. et al., 1982, Nature, 295: 64-66.
Tischer, I. et al., 1986, Arch. Virol., 91: 271-276.
Tischer, I. et al., 1988, Zentralbl Bakteriol Mikrobiol Hyg [A] 270: 280-287.
Tischer, I. et al., 1995, Arch. Virol., 140: 737-743.
Urdea, M. S., 1988, Nucleic Acids Research, II: 4937-4957.
Walker, G. T. et al., 1992, NAR 20: 1691-1696.
Walker, G. T. et al., 1992, PNAS. USA, 89: 392-396.
White, B. A. et al., 1997, Methods in Molecular Biology, 67, Humana Press, Towota.
Zhao, T. M. et al., 1996, Proc. Natl. Acad. Sci., USA 93(13): 6653-6648.

SEQUENCE LISTING

```
<160> NUMBER OF SEQ ID NOS: 170

<210> SEQ ID NO 1
<211> LENGTH: 1759
<212> TYPE: DNA
<213> ORGANISM: Type A PWD circovirus
<220> FEATURE:
<221> NAME/KEY: CDS
<222> LOCATION: (1)..(78)
<220> FEATURE:
<221> NAME/KEY: CDS
<222> LOCATION: (82)..(99)
<220> FEATURE:
<221> NAME/KEY: CDS
<222> LOCATION: (106)..(156)
```

```
<220> FEATURE:
<221> NAME/KEY: CDS
<222> LOCATION: (160)..(195)
<220> FEATURE:
<221> NAME/KEY: CDS
<222> LOCATION: (199)..(231)
<220> FEATURE:
<221> NAME/KEY: CDS
<222> LOCATION: (235)..(246)
<220> FEATURE:
<221> NAME/KEY: CDS
<222> LOCATION: (250)..(315)
<220> FEATURE:
<221> NAME/KEY: CDS
<222> LOCATION: (319)..(330)
<220> FEATURE:
<221> NAME/KEY: CDS
<222> LOCATION: (334)..(489)
<220> FEATURE:
<221> NAME/KEY: CDS
<222> LOCATION: (493)..(525)
<220> FEATURE:
<221> NAME/KEY: CDS
<222> LOCATION: (529)..(591)
<220> FEATURE:
<221> NAME/KEY: CDS
<222> LOCATION: (595)..(600)
<220> FEATURE:
<221> NAME/KEY: CDS
<222> LOCATION: (604)..(606)
<220> FEATURE:
<221> NAME/KEY: CDS
<222> LOCATION: (610)..(627)
<220> FEATURE:
<221> NAME/KEY: CDS
<222> LOCATION: (634)..(636)
<220> FEATURE:
<221> NAME/KEY: CDS
<222> LOCATION: (640)..(681)
<220> FEATURE:
<221> NAME/KEY: CDS
<222> LOCATION: (685)..(708)
<220> FEATURE:
<221> NAME/KEY: CDS
<222> LOCATION: (712)..(726)
<220> FEATURE:
<221> NAME/KEY: CDS
<222> LOCATION: (730)..(753)
<220> FEATURE:
<221> NAME/KEY: CDS
<222> LOCATION: (757)..(933)
<220> FEATURE:
<221> NAME/KEY: CDS
<222> LOCATION: (937)..(969)
<220> FEATURE:
<221> NAME/KEY: CDS
<222> LOCATION: (973)..(1047)
<220> FEATURE:
<221> NAME/KEY: CDS
<222> LOCATION: (1051)..(1056)
<220> FEATURE:
<221> NAME/KEY: CDS
<222> LOCATION: (1060)..(1071)
<220> FEATURE:
<221> NAME/KEY: CDS
<222> LOCATION: (1075)..(1236)
<220> FEATURE:
<221> NAME/KEY: CDS
<222> LOCATION: (1240)..(1257)
<220> FEATURE:
<221> NAME/KEY: CDS
<222> LOCATION: (1261)..(1293)
<220> FEATURE:
<221> NAME/KEY: CDS
<222> LOCATION: (1297)..(1350)
<220> FEATURE:
<221> NAME/KEY: CDS
<222> LOCATION: (1354)..(1380)
```

```
<220> FEATURE:
<221> NAME/KEY: CDS
<222> LOCATION: (1384)..(1386)
<220> FEATURE:
<221> NAME/KEY: CDS
<222> LOCATION: (1390)..(1416)
<220> FEATURE:
<221> NAME/KEY: CDS
<222> LOCATION: (1420)..(1425)
<220> FEATURE:
<221> NAME/KEY: CDS
<222> LOCATION: (1429)..(1497)
<220> FEATURE:
<221> NAME/KEY: CDS
<222> LOCATION: (1501)..(1512)
<220> FEATURE:
<221> NAME/KEY: CDS
<222> LOCATION: (1516)..(1551)
<220> FEATURE:
<221> NAME/KEY: CDS
<222> LOCATION: (1555)..(1566)
<220> FEATURE:
<221> NAME/KEY: CDS
<222> LOCATION: (1570)..(1581)
<220> FEATURE:
<221> NAME/KEY: CDS
<222> LOCATION: (1585)..(1620)
<220> FEATURE:
<221> NAME/KEY: CDS
<222> LOCATION: (1624)..(1752)
<220> FEATURE:
<221> NAME/KEY: CDS
<222> LOCATION: (1756)..(1758)

<400> SEQUENCE: 1 acc agc gca ctt cgg cag cgg cag cac ctc ggc agc gtc agt gaa aat      48
Thr Ser Ala Leu Arg Gln Arg Gln His Leu Gly Ser Val Ser Glu Asn
1               5                   10                  15 gcc aag caa gaa aag cgg ccc gca acc cca taa gag gtg ggt gtt cac      96
Ala Lys Gln Glu Lys Arg Pro Ala Thr Pro     Glu Val Gly Val His
            20                  25                  30 cct taataa tcc ttc cga gga gga gaa aaa caa aat acg gga gct tcc      144
Pro        Ser Phe Arg Gly Gly Glu Lys Gln Asn Thr Gly Ala Ser
               35                  40                  45 aat ctc cct ttt tga tta ttt tgt ttg tgg cga gga agg ttt gga aga     192
Asn Leu Pro Phe     Leu Phe Cys Leu Trp Arg Gly Arg Phe Gly Arg
            50                  55                  60 ggg tag aac tcc tca cct cca ggg gtt tgc gaa ttt tgc taa gaa gca     240
Gly     Asn Ser Ser Pro Pro Gly Val Cys Glu Phe Cys     Glu Ala
                65                  70 gac ttt taa caa ggt gaa gtg gta ttt tgg tgc ccg ctg cca cat cga     288
Asp Phe     Gln Gly Glu Val Val Phe Trp Cys Pro Leu Pro His Arg
75                  80                  85 gaa agc gaa agg aac cga cca gca gaa taa aga ata ctg cag taa aga     336
Glu Ser Glu Arg Asn Arg Pro Ala Glu     Arg Ile Leu Gln     Arg
90                  95                  100 agg cca cat act tat cga gtg tgg agc tcc gcg aaa cca ggg gaa gcg     384
Arg Pro His Thr Tyr Arg Val Trp Ser Ser Ala Glu Pro Gly Glu Ala
        105                 110                 115 cag cga cct gtc tac tgc tgt gag tac cct ttt gga gac ggg gtc ttt     432
Gln Arg Pro Val Tyr Cys Cys Glu Tyr Pro Phe Gly Asp Gly Val Phe
120                 125                 130                 135 ggt gac tgt agc cga gca gtt tcc tgt aac gta tgt gag aaa ttt ccg     480
Gly Asp Cys Ser Arg Ala Val Ser Cys Asn Val Cys Glu Lys Phe Pro
            140                 145                 150 cgg gct ggc tga act ttt gaa agt gag cgg gaa gat gca gaa gcg tga     528
Arg Ala Gly     Thr Phe Glu Ser Glu Arg Glu Asp Ala Glu Ala
                155                 160                 165
```

```
ttg gaa gac agc tgt aca cgt cat agt ggg ccc gcc cgg ttg tgg gaa    576
Leu Glu Asp Ser Cys Thr Arg His Ser Gly Pro Ala Arg Leu Trp Glu
            170                 175                 180 gag cca gtg ggc ccg taa ttt tgc tga gcc tag gga cac cta ctg gaa    624
Glu Pro Val Gly Pro     Phe Cys     Ala     Gly His Leu Leu Glu
                185                             190 gcc tagtag aaa taa gtg gtg gga tgg ata tca tgg aga aga agt tgt    672
Ala        Lys     Val Val Gly Trp Ile Ser Trp Arg Arg Ser Cys
195                            200                 205 tgt ttt gga tga ttt tta tgg ctg gtt acc ttg gga tga tct act gag    720
Cys Phe Gly     Phe Leu Trp Leu Val Thr Leu Gly     Ser Thr Glu
        210                 215                         220 act gtg tga ccg gta tcc att gac tgt aga gac taa agg ggg tac tgt    768
Thr Val     Pro Val Ser Ile Asp Cys Arg Asp     Arg Gly Tyr Cys
                225                 230                     235 tcc ttt ttt ggc ccg cag tat ttt gat tac cag caa tca ggc ccc cca    816
Ser Phe Phe Gly Pro Gln Tyr Phe Asp Tyr Gln Gln Ser Gly Pro Pro
                240                 245                 250 gga atg gta ctc ctc aac tgc tgt ccc agc tgt aga agc tct cta tcg    864
Gly Met Val Leu Leu Asn Cys Cys Pro Ser Cys Arg Ser Ser Leu Ser
                255                 260                 265 gag gat tac tac ttt gca att ttg gaa gac tgc tgg aga aca atc cac    912
Glu Asp Tyr Tyr Phe Ala Ile Leu Glu Asp Cys Trp Arg Thr Ile His
            270                 275                 280 gga ggt acc cga agg ccg att tga agc agt gga ccc acc ctg tgc cct    960
Gly Gly Thr Arg Arg Pro Ile     Ser Ser Gly Pro Thr Leu Cys Pro
285                 290                         295 ttt ccc ata taa aat aaa tta ctg agt ctt ttt tgt tat cac atc gta   1008
Phe Pro Ile     Asn Lys Leu Leu Ser Leu Phe Cys Tyr His Ile Val
        300                 305                 310 atg gtt ttt att ttt att cat tta gag ggt ctt tca gga taa att ctc   1056
Met Val Phe Ile Phe Ile His Leu Glu Gly Leu Ser Gly     Ile Leu
        315                 320                 325 tga att gta cat aaa tag tca acc tta cca cat aat ttt ggg ctg tgg   1104
    Ile Val His Lys     Ser Thr Leu Pro His Asn Phe Gly Leu Trp
            330                 335                 340 ttg cat ttt gga gcg cat agc cca ggc ctg tgt gct cga cat tgg tgt   1152
Leu His Phe Gly Ala His Ser Pro Gly Leu Cys Ala Arg His Trp Cys
            345                 350                 355 ggg tat tta aat gga gcc aca gct ggt ttc ttt tat tat ttg gct gga   1200
Gly Tyr Leu Asn Gly Ala Thr Ala Gly Phe Phe Tyr Tyr Leu Ala Gly
        360                 365                 370 acc aat caa ttg ttt ggt cta gct ctg gtt tgg ggg tga agt acc tgg   1248
Thr Asn Gln Leu Phe Gly Leu Ala Leu Val Trp Gly     Ser Thr Trp
375                 380                 385 agt ggt agg taa agg gct gcc tta tgg tgt ggc ggg agg agt agt taa   1296
Ser Gly Arg     Arg Ala Ala Leu Trp Cys Gly Gly Arg Ser Ser
390                 395                 400 tat agg ggt cat agg cca agt tgg tgg agg ggg tta caa agt tgg cat   1344
Tyr Arg Gly His Arg Pro Ser Trp Trp Arg Gly Leu Gln Ser Trp His
    405                 410                 415 cca aga taa caa cag tgg acc caa cac ctc ttt gat tag agg tga tgg   1392
Pro Arg     Gln Gln Trp Thr Gln His Leu Phe Asp     Arg     Trp
420                 425                 430 ggt ctc tgg ggt aaa att cat att tag cct ttc taa tac ggt agt att   1440
Gly Leu Trp Gly Lys Ile His Ile     Pro Phe     Tyr Gly Ser Ile
                435                 440                 445 gga aag gta ggg gta ggg ggt tgg tgc cgc ctg agg ggg gga gga act   1488
Gly Lys Val Gly Val Gly Gly Trp Cys Arg Leu Arg Gly Gly Gly Thr
            450                 455                 460
```

```
ggc cga tgt tga atc tca gct cgt taa cat tcc aag atg gct gcg agt     1536
Gly Arg Cys     Ile Ser Ala Arg     His Ser Lys Met Ala Ala Ser
        465                             470                 475 gtc ctc ctc tta tgg tga gta caa att ctc tag aaa ggc ggg aat tga     1584
Val Leu Leu Leu Trp     Val Gln Ile Leu     Lys Gly Gly Asn
            480                     485 aga tac ccg tct ttc ggc gcc atc tgt aac ggt ttc tga agg cgg ggt     1632
Arg Tyr Pro Ser Phe Gly Ala Ile Cys Asn Gly Phe     Arg Arg Gly
490             495                 500 gta cca aat atg gtc ttc tcc gga gga tgt ttc caa gat ggc tgc ggg     1680
Val Pro Asn Met Val Phe Ser Gly Gly Cys Phe Gln Asp Gly Cys Gly
505             510              515                 520 ggc ggg tcc gtc ttc tgc ggt aac gcc tcc ttg gcc acg tca tcc tat     1728
Gly Gly Ser Val Phe Cys Gly Asn Ala Ser Leu Ala Thr Ser Ser Tyr
            525             530                 535 aaa agt gaa aga agt gcg ctg ctg tag tat t                           1759
Lys Ser Glu Arg Ser Ala Leu Leu     Tyr
540                         545

<210> SEQ ID NO 2
<211> LENGTH: 545
<212> TYPE: PRT
<213> ORGANISM: Type A PWD circovirus

<400> SEQUENCE: 2

Thr Ser Ala Leu Arg Gln Arg Gln His Leu Gly Ser Val Ser Glu Asn
1               5                   10                  15

Ala Lys Gln Glu Lys Arg Pro Ala Thr Pro Glu Val Gly Val His Pro
            20                  25                  30

Ser Phe Arg Gly Gly Glu Lys Gln Asn Thr Gly Ala Ser Asn Leu Pro
        35                  40                  45

Phe Leu Phe Cys Leu Trp Arg Gly Arg Phe Gly Arg Gly Asn Ser Ser
    50                  55                  60

Pro Pro Gly Val Cys Glu Phe Cys Glu Ala Asp Phe Gln Gly Glu Val
65                  70                  75                  80

Val Phe Trp Cys Pro Leu Pro His Arg Glu Ser Glu Arg Asn Arg Pro
                85                  90                  95

Ala Glu Arg Ile Leu Gln Arg Arg Pro His Thr Tyr Arg Val Trp Ser
            100                 105                 110

Ser Ala Glu Pro Gly Glu Ala Gln Arg Pro Val Tyr Cys Cys Glu Tyr
        115                 120                 125

Pro Phe Gly Asp Gly Val Phe Gly Asp Cys Ser Arg Ala Val Ser Cys
    130                 135                 140

Asn Val Cys Glu Lys Phe Pro Arg Ala Gly Thr Phe Glu Ser Glu Arg
145                 150                 155                 160

Glu Asp Ala Glu Ala Leu Glu Asp Ser Cys Thr Arg His Ser Gly Pro
                165                 170                 175

Ala Arg Leu Trp Glu Glu Pro Val Gly Pro Phe Cys Ala Gly His Leu
            180                 185                 190

Leu Glu Ala Lys Val Val Gly Trp Ile Ser Trp Arg Arg Ser Cys Cys
        195                 200                 205

Phe Gly Phe Leu Trp Leu Val Thr Leu Gly Ser Thr Glu Thr Val Pro
    210                 215                 220

Val Ser Ile Asp Cys Arg Asp Arg Gly Tyr Cys Ser Phe Phe Gly Pro
225                 230                 235                 240

Gln Tyr Phe Asp Tyr Gln Gln Ser Gly Pro Pro Gly Met Val Leu Leu
                245                 250                 255
```

-continued

```
Asn Cys Cys Pro Ser Cys Arg Ser Ser Leu Ser Glu Asp Tyr Tyr Phe
            260                 265                 270

Ala Ile Leu Glu Asp Cys Trp Arg Thr Ile His Gly Gly Thr Arg Arg
        275                 280                 285

Pro Ile Ser Ser Gly Pro Thr Leu Cys Pro Phe Pro Ile Asn Lys Leu
    290                 295                 300

Leu Ser Leu Phe Cys Tyr His Ile Val Met Val Phe Ile Phe Ile His
305                 310                 315                 320

Leu Glu Gly Leu Ser Gly Ile Leu Ile Val His Lys Ser Thr Leu Pro
                325                 330                 335

His Asn Phe Gly Leu Trp Leu His Phe Gly Ala His Ser Pro Gly Leu
            340                 345                 350

Cys Ala Arg His Trp Cys Gly Tyr Leu Asn Gly Ala Thr Ala Gly Phe
        355                 360                 365

Phe Tyr Tyr Leu Ala Gly Thr Asn Gln Leu Phe Gly Leu Ala Leu Val
    370                 375                 380

Trp Gly Ser Thr Trp Ser Gly Arg Arg Ala Ala Leu Trp Cys Gly Gly
385                 390                 395                 400

Arg Ser Ser Tyr Arg Gly His Arg Pro Ser Trp Trp Arg Gly Leu Gln
                405                 410                 415

Ser Trp His Pro Arg Gln Gln Trp Thr Gln His Leu Phe Asp Arg Trp
            420                 425                 430

Gly Leu Trp Gly Lys Ile His Ile Pro Phe Tyr Gly Ser Ile Gly Lys
        435                 440                 445

Val Gly Val Gly Gly Trp Cys Arg Leu Arg Gly Gly Gly Thr Gly Arg
    450                 455                 460

Cys Ile Ser Ala Arg His Ser Lys Met Ala Ala Ser Val Leu Leu Leu
465                 470                 475                 480

Trp Val Gln Ile Leu Lys Gly Gly Asn Arg Tyr Pro Ser Phe Gly Ala
                485                 490                 495

Ile Cys Asn Gly Phe Arg Arg Gly Val Pro Asn Met Val Phe Ser Gly
            500                 505                 510

Gly Cys Phe Gln Asp Gly Cys Gly Gly Gly Ser Val Phe Cys Gly Asn
        515                 520                 525

Ala Ser Leu Ala Thr Ser Ser Tyr Lys Ser Glu Arg Ser Ala Leu Leu
    530                 535                 540

Tyr
545

<210> SEQ ID NO 3
<211> LENGTH: 577
<212> TYPE: PRT
<213> ORGANISM: Type A PWD circovirus

<400> SEQUENCE: 3

Pro Ala His Phe Gly Ser Gly Ser Thr Ser Ala Ala Ser Val Lys Met
1               5                   10                  15

Pro Ser Lys Lys Ser Gly Pro Gln Pro His Lys Arg Trp Val Phe Thr
            20                  25                  30

Leu Asn Asn Pro Ser Glu Glu Glu Lys Asn Lys Ile Arg Glu Leu Pro
        35                  40                  45

Ile Ser Leu Phe Asp Tyr Phe Val Cys Gly Glu Glu Gly Leu Glu Glu
    50                  55                  60

Gly Arg Thr Pro His Leu Gln Gly Phe Ala Asn Phe Ala Lys Lys Gln
```

```
                65                  70                  75                  80
Thr Phe Asn Lys Val Lys Trp Tyr Phe Gly Ala Arg Cys His Ile Glu
                        85                  90                  95
Lys Ala Lys Gly Thr Asp Gln Gln Asn Lys Glu Tyr Cys Ser Lys Glu
            100                 105                 110
Gly His Ile Leu Ile Glu Cys Gly Ala Pro Arg Asn Gln Gly Lys Arg
            115                 120                 125
Ser Asp Leu Ser Thr Ala Val Ser Thr Leu Leu Glu Thr Gly Ser Leu
        130                 135                 140
Val Thr Val Ala Glu Gln Phe Pro Val Thr Tyr Val Arg Asn Phe Arg
145                 150                 155                 160
Gly Leu Ala Glu Leu Leu Lys Val Ser Gly Lys Met Gln Lys Arg Asp
                165                 170                 175
Trp Lys Thr Ala Val His Val Ile Val Gly Pro Gly Cys Gly Lys
            180                 185                 190
Ser Gln Trp Ala Arg Asn Phe Ala Glu Pro Arg Asp Thr Tyr Trp Lys
        195                 200                 205
Pro Ser Arg Asn Lys Trp Trp Asp Gly Tyr His Gly Glu Glu Val Val
210                 215                 220
Val Leu Asp Asp Phe Tyr Gly Trp Leu Pro Trp Asp Asp Leu Leu Arg
225                 230                 235                 240
Leu Cys Asp Arg Tyr Pro Leu Thr Val Glu Thr Lys Gly Gly Thr Val
                245                 250                 255
Pro Phe Leu Ala Arg Ser Ile Leu Ile Thr Ser Asn Gln Ala Pro Gln
            260                 265                 270
Glu Trp Tyr Ser Ser Thr Ala Val Pro Ala Val Glu Ala Leu Tyr Arg
        275                 280                 285
Arg Ile Thr Thr Leu Gln Phe Trp Lys Thr Ala Gly Glu Gln Ser Thr
    290                 295                 300
Glu Val Pro Glu Gly Arg Phe Glu Ala Val Asp Pro Pro Cys Ala Leu
305                 310                 315                 320
Phe Pro Tyr Lys Ile Asn Tyr Val Phe Val Ile Thr Ser Trp Phe
                325                 330                 335
Leu Phe Leu Phe Ile Arg Val Phe Gln Asp Lys Phe Ser Glu Leu Tyr
            340                 345                 350
Ile Asn Ser Gln Pro Tyr His Ile Ile Leu Gly Cys Gly Cys Ile Leu
        355                 360                 365
Glu Arg Ile Ala Gln Ala Cys Val Leu Asp Ile Gly Val Gly Ile Met
    370                 375                 380
Glu Pro Gln Leu Val Ser Phe Ile Ile Trp Leu Glu Pro Ile Asn Cys
385                 390                 395                 400
Leu Val Leu Trp Phe Gly Gly Glu Val Pro Gly Val Gly Lys Gly
                405                 410                 415
Leu Pro Tyr Gly Val Ala Gly Val Val Asn Ile Gly Val Ile Gly
            420                 425                 430
Gln Val Gly Gly Gly Tyr Lys Val Gly Ile Gln Asp Asn Asn Ser
        435                 440                 445
Gly Pro Asn Thr Ser Leu Ile Arg Gly Asp Gly Val Ser Gly Val Lys
    450                 455                 460
Phe Ile Phe Ser Leu Ser Asn Thr Val Val Leu Glu Arg Gly Val Gly
465                 470                 475                 480
Ala Ala Gly Gly Glu Glu Leu Ala Asp Val Glu Ser Gln Leu Val Asn
                485                 490                 495
```

-continued

```
Ile Pro Arg Trp Leu Arg Val Ser Ser Ser Tyr Gly Glu Tyr Lys Phe
            500                 505                 510

Ser Arg Lys Ala Gly Ile Glu Asp Thr Arg Leu Ser Ala Pro Ser Val
        515                 520                 525

Thr Val Ser Glu Gly Gly Val Tyr Gln Ile Trp Ser Ser Pro Glu Asp
    530                 535                 540

Val Ser Lys Met Ala Ala Gly Ala Gly Pro Ser Ser Ala Val Thr Pro
545                 550                 555                 560

Pro Trp Pro Arg His Pro Ile Lys Val Lys Glu Val Arg Cys Cys Ser
                565                 570                 575

Ile

<210> SEQ ID NO 4
<211> LENGTH: 553
<212> TYPE: PRT
<213> ORGANISM: Type A PWD circovirus

<400> SEQUENCE: 4

Gln Arg Thr Ser Ala Ala Ala Ala Pro Arg Gln Arg Gln Lys Cys Gln
1               5                   10                  15

Ala Arg Lys Ala Ala Arg Asn Pro Ile Arg Gly Gly Cys Ser Pro Leu
            20                  25                  30

Leu Pro Arg Arg Arg Lys Thr Lys Tyr Gly Ser Phe Gln Ser Pro Phe
        35                  40                  45

Leu Ile Ile Leu Phe Val Ala Arg Lys Val Trp Lys Arg Val Glu Leu
    50                  55                  60

Leu Thr Ser Arg Gly Leu Arg Ile Leu Leu Arg Ser Arg Leu Leu Thr
65                  70                  75                  80

Arg Ser Gly Ile Leu Val Pro Ala Ala Thr Ser Arg Lys Arg Lys Glu
                85                  90                  95

Pro Thr Ser Arg Ile Lys Asn Thr Ala Val Lys Lys Ala Thr Tyr Leu
            100                 105                 110

Ser Ser Val Glu Leu Arg Gly Thr Arg Gly Ser Ala Ala Thr Cys Leu
        115                 120                 125

Leu Leu Val Pro Phe Trp Arg Arg Gly Leu Trp Leu Pro Ser Ser Phe
    130                 135                 140

Leu Arg Met Glu Ile Ser Ala Gly Trp Leu Asn Phe Lys Ala Gly Arg
145                 150                 155                 160

Cys Arg Ser Val Ile Gly Arg Gln Leu Tyr Thr Ser Trp Ala Arg Pro
                165                 170                 175

Val Val Gly Arg Ala Ser Gly Pro Val Ile Leu Leu Ser Leu Gly Thr
            180                 185                 190

Pro Thr Gly Ser Leu Val Glu Ile Ser Gly Gly Met Asp Ile Met Glu
        195                 200                 205

Lys Lys Leu Leu Phe Trp Met Ile Phe Met Ala Gly Tyr Leu Gly Met
    210                 215                 220

Ile Tyr Asp Cys Val Thr Gly Ile His Leu Arg Leu Lys Gly Val Leu
225                 230                 235                 240

Phe Leu Phe Trp Pro Ala Val Phe Leu Pro Ala Ile Arg Pro Pro Arg
                245                 250                 255

Asn Gly Thr Pro Gln Leu Leu Ser Gln Leu Lys Leu Ser Ile Gly Gly
            260                 265                 270

Leu Leu Leu Cys Asn Phe Gly Arg Leu Leu Glu Asn Asn Pro Arg Arg
        275                 280                 285
```

-continued

Tyr Pro Lys Ala Asp Leu Lys Gln Trp Thr His Pro Val Pro Phe Ser
290 295 300

His Ile Lys Ile Thr Glu Ser Phe Leu Leu Ser His Arg Asn Gly Phe
305 310 315 320

Tyr Phe Tyr Ser Phe Arg Gly Ser Phe Arg Ile Asn Ser Leu Asn Cys
325 330 335

Thr Ile Val Asn Leu Thr Thr Phe Trp Ala Val Val Ala Phe Trp Ser
340 345 350

Ala Pro Arg Pro Val Cys Ser Thr Leu Val Trp Val Phe Lys Trp Ser
355 360 365

His Ser Trp Phe Leu Leu Leu Phe Gly Trp Asn Gln Ser Ile Val Trp
370 375 380

Ser Ser Ser Gly Leu Gly Val Lys Tyr Leu Glu Trp Val Lys Gly Cys
385 390 395 400

Leu Met Val Trp Arg Glu Glu Leu Ile Gly Ser Ala Lys Leu Val Glu
405 410 415

Gly Val Thr Lys Leu Ala Ser Lys Ile Thr Thr Val Asp Pro Thr Pro
420 425 430

Leu Leu Glu Val Met Gly Ser Leu Gly Asn Ser Tyr Leu Ala Phe Leu
435 440 445

Ile Arg Tyr Trp Lys Gly Arg Gly Arg Gly Leu Val Pro Pro Glu Gly
450 455 460

Gly Arg Asn Trp Pro Met Leu Asn Leu Ser Ser Leu Thr Phe Gln Asp
465 470 475 480

Gly Cys Glu Cys Pro Pro Leu Met Val Ser Thr Asn Ser Leu Glu Arg
485 490 495

Arg Glu Leu Lys Ile Pro Val Phe Arg Arg His Leu Arg Phe Leu Lys
500 505 510

Ala Gly Cys Thr Lys Tyr Gly Leu Leu Arg Arg Met Phe Pro Arg Trp
515 520 525

Leu Arg Gly Arg Val Arg Leu Leu Arg Arg Leu Leu Gly His Val Ile
530 535 540

Leu Lys Lys Lys Cys Ala Ala Val Val
545 550

<210> SEQ ID NO 5
<211> LENGTH: 1759
<212> TYPE: DNA
<213> ORGANISM: Type A PWD circovirus

<400> SEQUENCE: 5
aatactacag cagcgcactt ctttcacttt tataggatga cgtggccaag gaggcgttac 60
cgcagaagac ggacccgccc ccgcagccat cttggaaacg tcctccggag aagaccatat 120
ttggtacacc ccgccttcag aaaccgttac agatggcgcc gaaagacggg tatcttcaat 180
tcccgccttt ctagagaatt tgtactcacc ataagaggag gacactcgca gccatcttgg 240
aatgttaacg agctgagatt caacatcggc cagttcctcc ccccctcagg cggcaccaac 300
cccctacccc tacctttcca atactaccgt attagaaagg ctaaatatga attttacccc 360
agagacccca tcacctctaa tcaaagaggt gttgggtcca ctgttgttat cttggatgcc 420
aactttgtaa ccccctccac caacttggcc tatgacccct atattaacta ctcctcccgc 480
cacaccataa ggcagccctt tacctaccac tccaggtact tcacccccaa accagagcta 540
gaccaaacaa ttgattggtt ccagccaaat aataaaagaa accagctgtg gctccattta 600

```
aatacccaca ccaatgtcga gcacacaggc ctgggctatg cgctccaaaa tgcaaccaca    660
gcccaaaatt atgtggtaag gttgactatt tatgtacaat tcagagaatt tatcctgaaa    720
gaccctctaa atgaataaaa ataaaaacca ttacgatgtg ataacaaaaa agactcagta    780
atttatttta tatgggaaaa gggcacaggg tgggtccact gcttcaaatc ggccttcggg    840
tacctccgtg gattgttctc cagcagtctt ccaaaattgc aaagtagtaa tcctccgata    900
gagagcttct acagctggga cagcagttga ggagtaccat tcctgggggg cctgattgct    960
ggtaatcaaa atactgcggg ccaaaaaagg aacagtaccc cctttagtct ctacagtcaa   1020
tggataccgg tcacacagtc tcagtagatc atcccaaggt aaccagccat aaaaatcatc   1080
caaaacaaca acttcttctc catgatatcc atcccaccac ttatttctac taggcttcca   1140
gtaggtgtcc ctaggctcag caaaattacg ggcccactgg ctcttcccac aaccgggcgg   1200
gcccactatg acgtgtacag ctgtcttcca atcacgctgc tgcatcttcc cgctcacttt   1260
caaaagttca gccagcccgc ggaaatttct cacatacgtt acaggaaact gctcggctac   1320
agtcaccaaa gaccccgtct ccaaaagggg actcacagca gtagacaggt cgctgcgctt   1380
cccctggttc cgcggagctc cacactcgat aagtatgtgg ccttctttac tgcagtattc   1440
tttattctgc tggtcggttc ctttcgcttt ctcgatgtgg cagcgggcac caaaatacca   1500
cttcaccttg ttaaaagtct gcttcttagc aaaattcgca aaccctggaa ggtgaggagt   1560
tctaccctct tccaaacctt cctcgccaca aacaaaataa tcaaaagggg agattggaag   1620
ctcccgtatt ttgttttct cctcctcgga aggattatta agggtgaaca cccacctctt    1680
atggggttgc gggccgcttt tcttgcttgg cattttcact gacgctgccg aggtgctgcc   1740
gctgccgaag tgcgctggt                                                1759
```

<210> SEQ ID NO 6
<211> LENGTH: 567
<212> TYPE: PRT
<213> ORGANISM: Type A PWD circovirus

<400> SEQUENCE: 6

```
Gly Ala Cys Lys Pro Leu Pro Leu Val Glu Ala Ala Asp Thr Phe Ile
1               5                   10                  15

Gly Leu Leu Phe Leu Pro Gly Cys Gly Trp Leu Leu His Thr Asn Val
            20                  25                  30

Arg Leu Leu Gly Glu Ser Ser Phe Phe Leu Ile Arg Ser Ser Gly
        35                  40                  45

Ile Glu Arg Lys Ser Lys Thr Gln Pro Ser Ser Pro Lys Ser Ser Pro
    50                  55                  60

Leu Val Gly Arg Trp Pro Asn Ala Phe Lys Ala Leu Phe Cys Val Lys
65                  70                  75                  80

Leu Leu Thr Phe His Tyr Lys Pro Ala Arg Gln Trp Met Ser Phe Ala
                85                  90                  95

Phe Pro Val Ser Trp Cys Phe Leu Ser Tyr Gln Leu Leu Ser Pro Trp
            100                 105                 110

Met Ser Ile Ser His Pro Ala Gly Arg Phe Trp Pro Phe Arg Leu Ser
        115                 120                 125

Arg Asp Val Ala Thr Leu Val Arg Lys Ser Val Pro Asp Lys Thr Val
    130                 135                 140

Thr Ala Ser Cys Asn Gly Thr Val Tyr Thr Leu Phe Lys Arg Pro Ser
145                 150                 155                 160
```

-continued

```
Ala Ser Ser Lys Phe Thr Leu Pro Phe Ile Cys Cys Arg Ser Gln Phe
            165                 170                 175

Val Ala Thr Cys Thr Met Thr Pro Gly Gly Pro Gln Pro Phe Leu Trp
            180                 185                 190

His Ala Arg Leu Lys Ala Ser Gly Leu Ser Val Gln Phe Gly Leu Leu
            195                 200                 205

Phe Leu His His Ser Pro Tyr Pro Ser Ser Thr Thr Lys Ser Ser
210                 215                 220

Lys Pro Gln Asn Gly Gln Ser Ser Arg Ser Leu Ser His Ser Arg Tyr
225                 230                 235                 240

Gly Asn Val Thr Ser Val Leu Pro Pro Val Thr Gly Lys Lys Ala Arg
                    245                 250                 255

Leu Ile Lys Ile Val Leu Leu Ala Gly Trp Ser His Tyr Glu Glu Val
                260                 265                 270

Ala Thr Gly Ala Thr Ser Ala Arg Arg Leu Ile Val Val Lys Cys Asn
                275                 280                 285

Gln Phe Val Ala Pro Ser Cys Asp Val Ser Thr Gly Ser Pro Arg Asn
290                 295                 300

Ser Ala Thr Ser Gly Gly Gln Ala Arg Lys Gly Tyr Leu Ile Phe Gln
305                 310                 315                 320

Thr Lys Lys Thr Ile Val Asp Tyr His Asn Lys Asn Lys Asn Met Leu
                    325                 330                 335

Thr Lys Ser Leu Asn Glu Ser Asn Tyr Met Phe Leu Gly Trp Met Ile
                340                 345                 350

Lys Pro Gln Pro Gln Met Lys Ser Arg Met Ala Trp Ala Gln Thr Ser
                355                 360                 365

Ser Met Pro Thr Pro Ile Ile Ser Gly Cys Ser Thr Glu Lys Ile Ile
370                 375                 380

Gln Ser Ser Gly Ile Leu Gln Lys Thr Ser Gln Asn Pro Pro Ser Thr
385                 390                 395                 400

Gly Pro Thr Thr Pro Leu Pro Ser Gly Pro Thr Ala Pro Pro Thr Thr
                    405                 410                 415

Leu Ile Pro Thr Met Pro Trp Thr Pro Pro Pro Leu Thr Pro Met
                420                 425                 430

Trp Ser Leu Leu Leu Pro Gly Leu Val Glu Lys Ile Leu Pro Ser Pro
                435                 440                 445

Thr Glu Pro Thr Phe Asn Met Asn Leu Arg Glu Leu Val Thr Thr Asn
450                 455                 460

Ser Leu Tyr Pro Tyr Pro Thr Pro Ala Ala Gln Pro Pro Ser Ser Ser
465                 470                 475                 480

Ala Ser Thr Ser Asp Ser Thr Leu Met Gly Leu His Ser Arg Thr Asp
                    485                 490                 495

Glu Glu Pro Ser Tyr Leu Asn Glu Leu Phe Ala Pro Ile Ser Ser Val
                500                 505                 510

Arg Arg Glu Ala Gly Asp Thr Val Thr Glu Ser Pro Thr Tyr Trp
                515                 520                 525

Ile His Asp Glu Gly Ser Ser Thr Glu Leu Ile Ala Ala Pro Ala Pro
                530                 535                 540

Gly Asp Glu Ala Thr Val Gly Gly Gln Gly Arg Gly Ile Phe Thr Phe
545                 550                 555                 560

Ser Thr Arg Gln Gln Leu Ile
                565
```

<210> SEQ ID NO 7
<211> LENGTH: 580
<212> TYPE: PRT
<213> ORGANISM: Type A PWD circovirus

<400> SEQUENCE: 7

```
Trp Arg Val Glu Ala Ala Ala Ala Gly Arg Cys Arg His Phe His Trp
1               5                   10                  15

Ala Leu Phe Ala Ala Arg Leu Gly Met Leu Pro Pro His Glu Gly Lys
            20                  25                  30

Ile Ile Arg Gly Leu Leu Leu Phe Val Phe Tyr Pro Leu Lys Trp Asp
        35                  40                  45

Gly Lys Lys Ile Ile Lys Asn Thr Ala Leu Phe Thr Gln Phe Leu Thr
    50                  55                  60

Ser Ser Arg Val Glu Leu Pro Lys Arg Ile Lys Ser Leu Leu Leu Ser
65                  70                  75                  80

Lys Val Leu His Leu Pro Ile Lys Thr Gly Ala Ala Val Asp Leu Phe
                85                  90                  95

Arg Phe Ser Gly Val Leu Leu Ile Phe Phe Val Ala Thr Phe Phe Ala
            100                 105                 110

Val Tyr Lys Asp Leu Thr Ser Ser Arg Pro Val Leu Pro Leu Ala Ala
        115                 120                 125

Val Gln Arg Ser Ser His Thr Gly Lys Gln Leu Arg Pro Arg Gln His
    130                 135                 140

Ser Tyr Gly Leu Leu Lys Arg Tyr Arg Ile His Ser Ile Glu Ala Pro
145                 150                 155                 160

Gln Ser Phe Lys Gln Phe His Ala Pro Leu His Leu Leu Thr Ile Pro
                165                 170                 175

Leu Cys Ser Tyr Val Asp Tyr His Ala Arg Gly Thr Thr Pro Leu Ala
            180                 185                 190

Leu Pro Gly Thr Ile Lys Ser Leu Arg Pro Val Gly Val Pro Leu Arg
        195                 200                 205

Thr Ser Ile Leu Pro Pro Ile Ser Ile Met Ser Phe Phe Asn Asn Asn
    210                 215                 220

Gln Ile Ile Lys Ile Ala Pro Arg Pro Ile Ile Gln Ser Gln Thr Val
225                 230                 235                 240

Pro Ile Trp Gln Ser Tyr Leu Ser Phe Pro Thr Ser Asn Arg Lys Gln
                245                 250                 255

Gly Ala Thr Asn Gln Asn Gly Ala Ile Leu Gly Gly Leu Phe Pro Val
            260                 265                 270

Gly Ser Ser Asp Trp Ser Tyr Phe Ser Glu Ile Pro Pro Asn Ser Ser
        275                 280                 285

Gln Leu Lys Pro Leu Ser Ser Ser Phe Leu Gly Arg Leu Tyr Gly Phe
    290                 295                 300

Ala Ser Lys Phe Cys His Val Trp Gly Thr Gly Lys Glu Trp Ile Phe
305                 310                 315                 320

Tyr Ile Val Ser Asp Lys Lys Asn Asp Cys Arg Leu Pro Lys Lys Glu
                325                 330                 335

Asn Leu Pro Asp Lys Leu Ile Phe Glu Arg Phe Gln Val Tyr Ile Thr
            340                 345                 350

Leu Arg Val Val Tyr Asn Gln Ala Thr Thr Ala Asn Gln Leu Ala Tyr
        355                 360                 365

Gly Leu Gly Thr His Glu Val Asn Thr His Thr Asn Leu His Leu Trp
    370                 375                 380
```

```
Leu Gln Asn Arg Lys Asn Asn Pro Gln Phe Trp Asp Ile Thr Gln Asp
385                 390                 395                 400

Leu Glu Pro Lys Pro Thr Phe Tyr Arg Ser His Tyr Thr Phe Pro Gln
                405                 410                 415

Arg Ile Thr His Arg Ser Ser Tyr Asn Ile His Pro Asp Tyr Ala Leu
            420                 425                 430

Asn Thr Ser Pro Thr Val Phe Asn Ala Asp Leu Ile Val Val Thr Ser
        435                 440                 445

Gly Val Gly Arg Gln Asn Ser Thr Ile Pro Asp Arg Pro Tyr Phe Glu
    450                 455                 460

Tyr Lys Ala Lys Arg Ile Arg Tyr Tyr Gln Phe Pro Leu Pro Leu Pro
465                 470                 475                 480

Asn Thr Gly Gly Ser Pro Pro Leu Phe Gln Gly Ile Asn Phe Arg Leu
                485                 490                 495

Glu Asn Val Asn Trp Ser Pro Gln Ser His Gly Gly Arg Ile Thr Leu
                500                 505                 510

Val Phe Glu Arg Ser Leu Arg Ser Asn Phe Ile Gly Thr Lys Arg Arg
            515                 520                 525

Trp Arg Tyr Arg Asn Arg Phe Ala Pro His Val Leu Tyr Pro Arg Arg
        530                 535                 540

Arg Leu Ile Asn Gly Leu His Ser Arg Pro Arg Thr Arg Arg Arg Arg
545                 550                 555                 560

Tyr Arg Arg Arg Pro Trp Thr Met Arg Tyr Phe His Phe Phe His Ala
                565                 570                 575

Ala Thr Thr Asn
            580

<210> SEQ ID NO 8
<211> LENGTH: 557
<212> TYPE: PRT
<213> ORGANISM: Type A PWD circovirus

<400> SEQUENCE: 8

Leu Ala Ser Arg Cys Arg Cys Cys Arg Pro Leu Thr Leu Ser Phe Ala
1               5                   10                  15

Leu Cys Ser Phe Arg Gly Ala Val Gly Tyr Ser Thr Pro Thr Gly Tyr
                20                  25                  30

Asp Lys Arg Pro Pro Ser Phe Cys Phe Val Pro Ala Glu Leu Arg Gly
            35                  40                  45

Lys Gln Asn Asn Gln Lys His Arg Pro Leu Asn Pro Leu Pro Tyr Phe
        50                  55                  60

Glu Glu Gly Gly Pro Thr Gln Ser Asn Gln Ser Ala Ser Lys Cys Pro
65                  70                  75                  80

Ser Thr Thr Asn Gly His Gly Ser Gly Cys Arg Ser Leu Ser Leu Phe
                85                  90                  95

Arg Gly Ala Ser Tyr Leu Ile Ser Cys Tyr Leu Leu Gly Cys Val Arg
                100                 105                 110

Thr His Leu Glu Ala Ser Gly Pro Ser Ala Cys Arg Gly Thr Gln Gln
            115                 120                 125

Ser Tyr Gly Lys Pro Ser Pro Thr Lys Pro Ser Gln Leu Arg Ala Thr
        130                 135                 140

Glu Gln Leu Thr His Ser Phe Asn Gly Arg Ala Pro Gln Val Lys Ser
145                 150                 155                 160

Leu Ser Arg Ser Ser Ala Ala His Asn Ser Ser Leu Gln Val Arg
                165                 170                 175
```

Leu Pro Gly Ala Arg Asn His Ser Ser Gly Thr Pro Gly Tyr Asn Gln
                180                 185                 190

Gln Ala Pro Cys Arg Ser Ser Ala Tyr Phe Tyr Thr Thr Pro His Ile
            195                 200                 205

Asp His Leu Leu Leu Gln Gln Lys Pro His Asn Lys His Ser Thr Val
        210                 215                 220

Lys Pro His Asp Val Ser Val Thr His Gly Thr Asp Met Ser Gln Leu
225                 230                 235                 240

Ser Leu Pro Tyr Gln Glu Lys Lys Pro Gly Cys Tyr Lys Ser Trp Cys
                245                 250                 255

Asp Pro Gly Gly Pro Ile Thr Ser Arg Leu Gln Gln Gly Leu Gln Leu
            260                 265                 270

Leu Glu Arg Asp Ser Ser Lys Ala Ile Lys Ser Ser Gln Gln Leu Val
        275                 280                 285

Ile Trp Pro Pro Val Arg Leu Gly Ile Gln Leu Leu Pro Gly Val Arg
290                 295                 300

His Gly Lys Gly Met Tyr Phe Leu Asn Ser Leu Arg Lys Gln Met Thr
305                 310                 315                 320

Ile Thr Lys Ile Lys Ile Lys Ser Pro Arg Glu Pro Tyr Ile Arg Gln
                325                 330                 335

Ile Thr Cys Leu Tyr Asp Val Lys Gly Cys Leu Lys Pro Ser His Asn
            340                 345                 350

Cys Lys Pro Ala Cys Leu Gly Pro Arg His Ala Arg Cys Gln His Pro
        355                 360                 365

Tyr Lys Phe Pro Ala Val Val Pro Lys Lys Ala Pro Val Leu Asn
370                 375                 380

Asn Pro Arg Ala Arg Thr Gln Pro His Leu Val Gln Leu Pro Leu Tyr
385                 390                 395                 400

Leu Ala Ala Lys His His Pro Pro Leu Leu Tyr Leu Pro Leu Gly
                405                 410                 415

Leu Gln His Leu Pro Asn Cys Leu Gln Cys Gly Leu Tyr Cys Cys His
            420                 425                 430

Val Trp Cys Arg Lys Ser Leu His His Pro Arg Gln Pro Leu Ile Ile
        435                 440                 445

Gly Lys Tyr Pro Leu Ile Pro Phe Thr Pro Thr Pro Gln His Arg
450                 455                 460

Arg Leu Pro Pro Val Pro Arg His Gln Ile Glu Ala Arg Cys Glu
465                 470                 475                 480

Leu Ile Ala Ala Leu Thr Arg Arg Lys His His Thr Cys Ile Arg Phe
                485                 490                 495

Pro Pro Phe Gln Leu Tyr Gly Asp Lys Pro Ala Met Gln Leu Pro Lys
            500                 505                 510

Gln Leu Arg Pro Thr Gly Phe Ile Thr Lys Glu Pro Pro His Lys Trp
        515                 520                 525

Ser Pro Gln Pro Pro Asp Thr Lys Gln Pro Leu Ala Glu Lys Ala
530                 535                 540

Val Asp Asp Leu Leu Ser Leu Leu Ala Ser Ser Tyr Tyr
545                 550                 555

<210> SEQ ID NO 9
<211> LENGTH: 939
<212> TYPE: DNA
<213> ORGANISM: Type A PWD circovirus
<220> FEATURE:

<221> NAME/KEY: CDS
<222> LOCATION: (1)..(936)

<400> SEQUENCE: 9

```
atg cca agc aag aaa agc ggc ccg caa ccc cat aag agg tgg gtg ttc      48
Met Pro Ser Lys Lys Ser Gly Pro Gln Pro His Lys Arg Trp Val Phe
1               5                   10                  15 acc ctt aat aat cct tcc gag gag gag aaa aac aaa ata cgg gag ctt      96
Thr Leu Asn Asn Pro Ser Glu Glu Glu Lys Asn Lys Ile Arg Glu Leu
            20                  25                  30 cca atc tcc ctt ttt gat tat ttt gtt tgt ggc gag gaa ggt ttg gaa     144
Pro Ile Ser Leu Phe Asp Tyr Phe Val Cys Gly Glu Glu Gly Leu Glu
        35                  40                  45 gag ggt aga act cct cac ctc cag ggg ttt gcg aat ttt gct aag aag     192
Glu Gly Arg Thr Pro His Leu Gln Gly Phe Ala Asn Phe Ala Lys Lys
    50                  55                  60 cag act ttt aac aag gtg aag tgg tat ttt ggt gcc cgc tgc cac atc     240
Gln Thr Phe Asn Lys Val Lys Trp Tyr Phe Gly Ala Arg Cys His Ile
65                  70                  75                  80 gag aaa gcg aaa gga acc gac cag cag aat aaa gaa tac tgc agt aaa     288
Glu Lys Ala Lys Gly Thr Asp Gln Gln Asn Lys Glu Tyr Cys Ser Lys
                85                  90                  95 gaa ggc cac ata ctt atc gag tgt gga gct ccg cgg aac cag ggg aag     336
Glu Gly His Ile Leu Ile Glu Cys Gly Ala Pro Arg Asn Gln Gly Lys
            100                 105                 110 cgc agc gac ctg tct act gct gtg agt acc ctt ttg gag acg ggg tct     384
Arg Ser Asp Leu Ser Thr Ala Val Ser Thr Leu Leu Glu Thr Gly Ser
        115                 120                 125 ttg gtg act gta gcc gag cag ttt cct gta acg tat gtg aga aat ttc     432
Leu Val Thr Val Ala Glu Gln Phe Pro Val Thr Tyr Val Arg Asn Phe
    130                 135                 140 cgc ggg ctg gct gaa ctt ttg aaa gtg agc ggg aag atg cag cag cgt     480
Arg Gly Leu Ala Glu Leu Leu Lys Val Ser Gly Lys Met Gln Gln Arg
145                 150                 155                 160 gat tgg aag aca gct gta cac gtc ata gtg ggc ccg ccc ggt tgt ggg     528
Asp Trp Lys Thr Ala Val His Val Ile Val Gly Pro Pro Gly Cys Gly
                165                 170                 175 aag agc cag tgg gcc cgt aat ttt gct gag cct agg gac acc tac tgg     576
Lys Ser Gln Trp Ala Arg Asn Phe Ala Glu Pro Arg Asp Thr Tyr Trp
            180                 185                 190 aag cct agt aga aat aag tgg tgg gat gga tat cat gga gaa gaa gtt     624
Lys Pro Ser Arg Asn Lys Trp Trp Asp Gly Tyr His Gly Glu Glu Val
        195                 200                 205 gtt gtt ttg gat gat ttt tat ggc tgg tta cct tgg gat gat cta ctg     672
Val Val Leu Asp Asp Phe Tyr Gly Trp Leu Pro Trp Asp Asp Leu Leu
    210                 215                 220 aga ctg tgt gac cgg tat cca ttg act gta gag act aaa ggg ggt act     720
Arg Leu Cys Asp Arg Tyr Pro Leu Thr Val Glu Thr Lys Gly Gly Thr
225                 230                 235                 240 gtt cct ttt ttg gcc cgc agt att ttg att acc agc aat cag gcc ccc     768
Val Pro Phe Leu Ala Arg Ser Ile Leu Ile Thr Ser Asn Gln Ala Pro
                245                 250                 255 cag gaa tgg tac tcc tca act gct gtc cca gct gta gaa gct ctc tat     816
Gln Glu Trp Tyr Ser Ser Thr Ala Val Pro Ala Val Glu Ala Leu Tyr
            260                 265                 270 cgg agg att act act ttg caa ttt tgg aag act gct gga gaa caa tcc     864
Arg Arg Ile Thr Thr Leu Gln Phe Trp Lys Thr Ala Gly Glu Gln Ser
        275                 280                 285 acg gag gta ccc gaa ggc cga ttt gaa gca gtg gac cca ccc tgt gcc     912
Thr Glu Val Pro Glu Gly Arg Phe Glu Ala Val Asp Pro Pro Cys Ala
```

```
                290                 295                 300
ctt ttc cca tat aaa ata aat tac tga                                       939
Leu Phe Pro Tyr Lys Ile Asn Tyr
305                 310
```

<210> SEQ ID NO 10
<211> LENGTH: 312
<212> TYPE: PRT
<213> ORGANISM: Type A PWD circovirus

<400> SEQUENCE: 10

```
Met Pro Ser Lys Lys Ser Gly Pro Gln Pro His Lys Arg Trp Val Phe
1               5                   10                  15

Thr Leu Asn Asn Pro Ser Glu Glu Lys Asn Lys Ile Arg Glu Leu
            20                  25                  30

Pro Ile Ser Leu Phe Asp Tyr Phe Val Cys Gly Glu Glu Gly Leu Glu
            35                  40                  45

Glu Gly Arg Thr Pro His Leu Gln Gly Phe Ala Asn Phe Ala Lys Lys
50                  55                  60

Gln Thr Phe Asn Lys Val Lys Trp Tyr Phe Gly Ala Arg Cys His Ile
65                  70                  75                  80

Glu Lys Ala Lys Gly Thr Asp Gln Gln Asn Lys Glu Tyr Cys Ser Lys
                85                  90                  95

Glu Gly His Ile Leu Ile Glu Cys Gly Ala Pro Arg Asn Gln Gly Lys
            100                 105                 110

Arg Ser Asp Leu Ser Thr Ala Val Ser Thr Leu Leu Glu Thr Gly Ser
            115                 120                 125

Leu Val Thr Val Ala Glu Gln Phe Pro Val Thr Tyr Val Arg Asn Phe
130                 135                 140

Arg Gly Leu Ala Glu Leu Leu Lys Val Ser Gly Lys Met Gln Gln Arg
145                 150                 155                 160

Asp Trp Lys Thr Ala Val His Val Ile Val Gly Pro Pro Gly Cys Gly
                165                 170                 175

Lys Ser Gln Trp Ala Arg Asn Phe Ala Glu Pro Arg Asp Thr Tyr Trp
            180                 185                 190

Lys Pro Ser Arg Asn Lys Trp Trp Asp Gly Tyr His Gly Glu Glu Val
            195                 200                 205

Val Val Leu Asp Asp Phe Tyr Gly Trp Leu Pro Trp Asp Asp Leu Leu
210                 215                 220

Arg Leu Cys Asp Arg Tyr Pro Leu Thr Val Glu Thr Lys Gly Gly Thr
225                 230                 235                 240

Val Pro Phe Leu Ala Arg Ser Ile Leu Ile Thr Ser Asn Gln Ala Pro
                245                 250                 255

Gln Glu Trp Tyr Ser Ser Thr Ala Val Pro Ala Val Glu Ala Leu Tyr
            260                 265                 270

Arg Arg Ile Thr Thr Leu Gln Phe Trp Lys Thr Ala Gly Glu Gln Ser
            275                 280                 285

Thr Glu Val Pro Glu Gly Arg Phe Glu Ala Val Asp Pro Pro Cys Ala
290                 295                 300

Leu Phe Pro Tyr Lys Ile Asn Tyr
305                 310
```

<210> SEQ ID NO 11
<211> LENGTH: 702
<212> TYPE: DNA
<213> ORGANISM: Type A PWD circovirus

<220> FEATURE:
<221> NAME/KEY: CDS
<222> LOCATION: (1)..(699)

<400> SEQUENCE: 11

```
atg acg tgg cca agg agg cgt tac cgc aga aga cgg acc cgc ccc cgc      48
Met Thr Trp Pro Arg Arg Arg Tyr Arg Arg Arg Thr Arg Pro Arg
1               5                   10                  15 agc cat ctt gga aac atc ctc cgg aga aga cca tat ttg gta cac ccc      96
Ser His Leu Gly Asn Ile Leu Arg Arg Arg Pro Tyr Leu Val His Pro
            20                  25                  30 gcc ttc aga aac cgt tac aga tgg cgc gaa aag acg ggt atc ttc aat     144
Ala Phe Arg Asn Arg Tyr Arg Trp Arg Arg Lys Thr Gly Ile Phe Asn
        35                  40                  45 tcc cgc ctt tct aga gaa ttt gta ctc acc ata aga gga gga cac tcg     192
Ser Arg Leu Ser Arg Glu Phe Val Leu Thr Ile Arg Gly Gly His Ser
    50                  55                  60 cag cca tct tgg aat gtt aac gag ctg aga ttc aac atc ggc cag ttc     240
Gln Pro Ser Trp Asn Val Asn Glu Leu Arg Phe Asn Ile Gly Gln Phe
65                  70                  75                  80 ctc ccc ccc tca ggc ggc acc aac ccc cta ccc cta cct ttc caa tac     288
Leu Pro Pro Ser Gly Gly Thr Asn Pro Leu Pro Leu Pro Phe Gln Tyr
                85                  90                  95 tac cgt att aga aag gct aaa tat gaa ttt tac ccc aga gac ccc atc     336
Tyr Arg Ile Arg Lys Ala Lys Tyr Glu Phe Tyr Pro Arg Asp Pro Ile
            100                 105                 110 acc tct aat caa aga ggt gtt ggg tcc act gtt gtt atc ttg gat gcc     384
Thr Ser Asn Gln Arg Gly Val Gly Ser Thr Val Val Ile Leu Asp Ala
        115                 120                 125 aac ttt gta acc ccc tcc acc aac ttg gcc tat gac ccc tat att aac     432
Asn Phe Val Thr Pro Ser Thr Asn Leu Ala Tyr Asp Pro Tyr Ile Asn
    130                 135                 140 tac tcc tcc cgc cac acc ata agg cag ccc ttt acc tac cac tcc agg     480
Tyr Ser Ser Arg His Thr Ile Arg Gln Pro Phe Thr Tyr His Ser Arg
145                 150                 155                 160 tac ttc acc ccc aaa cca gag cta gac caa aca att gat tgg ttc cag     528
Tyr Phe Thr Pro Lys Pro Glu Leu Asp Gln Thr Ile Asp Trp Phe Gln
                165                 170                 175 cca aat aat aaa aga aac cag ctg tgg ctc cat tta aat acc cac acc     576
Pro Asn Asn Lys Arg Asn Gln Leu Trp Leu His Leu Asn Thr His Thr
            180                 185                 190 aat gtc gag cac aca ggc ctg ggc tat gcg ctc caa aat gca acc aca     624
Asn Val Glu His Thr Gly Leu Gly Tyr Ala Leu Gln Asn Ala Thr Thr
        195                 200                 205 gcc caa aat tat gtg gta agg ttg act att tat gta caa ttc aga gaa     672
Ala Gln Asn Tyr Val Val Arg Leu Thr Ile Tyr Val Gln Phe Arg Glu
    210                 215                 220 ttt atc ctg aaa gac cct cta aat gaa taa                             702
Phe Ile Leu Lys Asp Pro Leu Asn Glu
225                 230
```

<210> SEQ ID NO 12
<211> LENGTH: 233
<212> TYPE: PRT
<213> ORGANISM: Type A PWD circovirus

<400> SEQUENCE: 12

```
Met Thr Trp Pro Arg Arg Arg Tyr Arg Arg Arg Thr Arg Pro Arg
1               5                   10                  15

Ser His Leu Gly Asn Ile Leu Arg Arg Arg Pro Tyr Leu Val His Pro
            20                  25                  30
```

```
Ala Phe Arg Asn Arg Tyr Arg Trp Arg Arg Lys Thr Gly Ile Phe Asn
             35                  40                  45

Ser Ar

```
ttc ttt att ctg ctg gtc ggt tcc ttt cgc ttt ctc gat gtg gca gcg      384
Phe Phe Ile Leu Leu Val Gly Ser Phe Arg Phe Leu Asp Val Ala Ala
        115                 120                 125 ggc acc aaa ata cca ctt cac ctt gtt aaa agt ctg ctt ctt agc aaa      432
Gly Thr Lys Ile Pro Leu His Leu Val Lys Ser Leu Leu Leu Ser Lys
130                 135                 140 att cgc aaa ccc ctg gag gtg agg agt tct acc ctc ttc caa acc ttc      480
Ile Arg Lys Pro Leu Glu Val Arg Ser Ser Thr Leu Phe Gln Thr Phe
145                 150                 155                 160 ctc gcc aca aac aaa ata atc aaa aag gga gat tgg aag ctc ccg tat      528
Leu Ala Thr Asn Lys Ile Ile Lys Lys Gly Asp Trp Lys Leu Pro Tyr
                165                 170                 175 ttt gtt ttt ctc ctc ctc gga agg att att aag ggt gaa cac cca cct      576
Phe Val Phe Leu Leu Leu Gly Arg Ile Ile Lys Gly Glu His Pro Pro
            180                 185                 190 ctt atg ggg ttg cgg gcc gct ttt ctt gct tgg cat ttt cac tga          621
Leu Met Gly Leu Arg Ala Ala Phe Leu Ala Trp His Phe His
        195                 200                 205
```

<210> SEQ ID NO 14
<211> LENGTH: 206
<212> TYPE: PRT
<213> ORGANISM: Type A PW

```
<220> FEATURE:
<221> NAME/KEY: CDS
<222> LOCATION: (115)..(243)
<220> FEATURE:
<221> NAME/KEY: CDS
<222> LOCATION: (247)..(267)
<220> FEATURE:
<221> NAME/KEY: CDS
<222> LOCATION: (271)..(360)
<220> FEATURE:
<221> NAME/KEY: CDS
<222> LOCATION: (364)..(417)
<220> FEATURE:
<221> NAME/KEY: CDS
<222> LOCATION: (421)..(447)
<220> FEATURE:
<221> NAME/KEY: CDS
<222> LOCATION: (451)..(471)
<220> FEATURE:
<221> NAME/KEY: CDS
<222> LOCATION: (475)..(510)
<220> FEATURE:
<221> NAME/KEY: CDS
<222> LOCATION: (514)..(516)
<220> FEATURE:
<221> NAME/KEY: CDS
<222> LOCATION: (520)..(729)
<220> FEATURE:
<221> NAME/KEY: CDS
<222> LOCATION: (733)..(753)
<220> FEATURE:
<221> NAME/KEY: CDS
<222> LOCATION: (757)..(759)
<220> FEATURE:
<221> NAME/KEY: CDS
<222> LOCATION: (763)..(804)
<220> FEATURE:
<221> NAME/KEY: CDS
<222> LOCATION: (808)..(861)
<220> FEATURE:
<221> NAME/KEY: CDS
<222> LOCATION: (865)..(984)
<220> FEATURE:
<221> NAME/KEY: CDS
<222> LOCATION: (988)..(1173)
<220> FEATURE:
<221> NAME/KEY: CDS
<222> LOCATION: (1177)..(1233)
<220> FEATURE:
<221> NAME/KEY: CDS
<222> LOCATION: (1237)..(1359)
<220> FEATURE:
<221> NAME/KEY: CDS
<222> LOCATION: (1363)..(1476)
<220> FEATURE:
<221> NAME/KEY: CDS
<222> LOCATION: (1480)..(1737)
<220> FEATURE:
<221> NAME/KEY: CDS
<222> LOCATION: (1741)..(1767)

<400> SEQUENCE: 15 acc agc gca ctt cgg cag cgg cag cac ctc ggc agc acc tca gca gca      48
Thr Ser Ala Leu Arg Gln Arg Gln His Leu Gly Ser Thr Ser Ala Ala
1               5                   10                  15 aca tgc cca gca aga aga atg gaa gaa gcg gac ccc aac ccc ata aaa      96
Thr Cys Pro Ala Arg Arg Met Glu Glu Ala Asp Pro Asn Pro Ile Lys
            20                  25                  30 ggt ggg tgt tca ctc tga ata atc ctt ccg aag acg agc gca aga aaa     144
Gly Gly Cys Ser Leu     Ile Ile Leu Pro Lys Thr Ser Ala Arg Lys
        35                      40                  45 tac ggg atc ttc caa tat ccc tat ttg att att tta ttg ttg gcg agg     192
Tyr Gly Ile Phe Gln Tyr Pro Tyr Leu Ile Ile Leu Leu Leu Ala Arg
    50                  55                  60
```

```
agg gta atg agg aag gac gaa cac ctc acc tcc agg ggt tcg cta att    240
Arg Val Met Arg Lys Asp Glu His Leu Thr Ser Arg Gly Ser Leu Ile
 65                  70                  75 ttg tga aga agc aga ctt tta ata aag tga agt ggt att tgg gtg ccc    288
Leu     Arg Ser Arg Leu Leu Ile Lys     Ser Gly Ile Trp Val Pro
 80                  85                  90 gct gcc aca tcg aga aag cga aag gaa cag atc agc aga ata aag aat    336
Ala Ala Thr Ser Arg Lys Arg Lys Glu Gln Ile Ser Arg Ile Lys Asn
         95                 100                 105 act gca gta aag aag gca act tac tga tgg agt gtg gag ctc cta gat    384
Thr Ala Val Lys Lys Ala Thr Tyr     Trp Ser Val Glu Leu Leu Asp
110                 115                 120 ctc agg gac aac gga gtg acc tgt cta ctg ctg tga gta cct tgt tgg    432
Leu Arg Asp Asn Gly Val Thr Cys Leu Leu Leu     Val Pro Cys Trp
125                 130                 135 aga gcg gga gtc tgg tga ccg ttg cag agc agc acc ctg taa cgt ttg    480
Arg Ala Gly Val Trp     Pro Leu Gln Ser Ser Thr Leu     Arg Leu
140                 145                 150 tca gaa att tcc gcg ggc tgg ctg aac ttt tga aag tga gcg gga aaa    528
Ser Glu Ile Ser Ala Gly Trp Leu Asn Phe     Lys     Ala Gly Lys
        155                 160                 165 tgc aga agc gtg att gga aga cta atg tac acg tca ttg tgg ggc cac    576
Cys Arg Ser Val Ile Gly Arg Leu Met Tyr Thr Ser Leu Trp Gly His
            170                 175                 180 ctg ggt gtg gta aaa gca aat ggg ctg cta att ttg cag acc cgg aaa    624
Leu Gly Val Val Lys Ala Asn Gly Leu Leu Ile Leu Gln Thr Arg Lys
                185                 190                 195 cca cat act gga aac cac cta gaa aca agt ggt ggg atg gtt acc atg    672
Pro His Thr Gly Asn His Leu Glu Thr Ser Gly Gly Met Val Thr Met
200                 205                 210                 215 gtg aag aag tgg ttg tta ttg atg act ttt atg gct ggc tgc cct ggg    720
Val Lys Lys Trp Leu Leu Met Thr Phe Met Ala Gly Cys Pro Gly
                220                 225                 230 atg atc tac tga gac tgt gtg atc gat atc cat tga ctg tag aga cta    768
Met Ile Tyr     Asp Cys Val Ile Asp Ile His     Leu     Arg Leu
                235                 240 aag gtg gaa ctg tac ctt ttt tgg ccc gca gta ttc tga tta cca gca    816
Lys Val Glu Leu Tyr Leu Phe Trp Pro Ala Val Phe     Leu Pro Ala
245                 250                 255 atc aga ccc cgt tgg aat ggt act cct caa ctg ctg tcc cag ctg tag    864
Ile Arg Pro Arg Trp Asn Gly Thr Pro Gln Leu Leu Ser Gln Leu
260                 265                 270 aag ctc ttt atc gga gga tta ctt cct tgg tat ttt gga aga atg cta    912
Lys Leu Phe Ile Gly Gly Leu Leu Pro Trp Tyr Phe Gly Arg Met Leu
275                 280                 285                 290 cag aac aat cca cgg agg aag ggg gcc agt tcg tca ccc ttt ccc ccc    960
Gln Asn Asn Pro Arg Arg Lys Gly Ala Ser Ser Ser Pro Phe Pro Pro
                295                 300                 305 cat gcc ctg aat ttc cat atg aaa taa att act gag tct ttt tta tca   1008
His Ala Leu Asn Phe His Met Lys     Ile Thr Glu Ser Phe Leu Ser
                310                 315                 320 ctt cgt aat ggt ttt tat tat tca tta agg gtt aag tgg ggg gtc ttt   1056
Leu Arg Asn Gly Phe Tyr Tyr Ser Leu Arg Val Lys Trp Gly Val Phe
                325                 330                 335 aaa att aaa ttc tct gaa ttg tac ata cat ggt tac acg gat att gta   1104
Lys Ile Lys Phe Ser Glu Leu Tyr Ile His Gly Tyr Thr Asp Ile Val
                340                 345                 350 ttc ctg gtc gta tat act gtt ttc gaa cgc agt gcc gag gcc tac gtg   1152
Phe Leu Val Val Tyr Thr Val Phe Glu Arg Ser Ala Glu Ala Tyr Val
            355                 360                 365
```

| | | | | | | | | | | | | | | |
|---|---|---|---|---|---|---|---|---|---|---|---|---|---|---|
| gtc | tac | att | tcc | agc | agt | ttg | tag | tct | cag | cca | cag | ctg | gtt tct ttt | 1200 |
| Val | Tyr | Ile | Ser | Ser | Ser | Leu | | Ser | Gln | Pro | Gln | Leu | Val Ser Phe | |
| 370 | | | | | 375 | | | | | | 380 | | | |
| gtt | gtt | tgg | ttg | gaa | gta | atc | aat | agt | gaa | atc | tag | gac | agg ttt ggg | 1248 |
| Val | Val | Trp | Leu | Glu | Val | Ile | Asn | Ser | Glu | Ile | | Asp | Arg Phe Gly | |
| 385 | | | | | 390 | | | | | 395 | | | | |
| ggt | aaa | gta | ccg | gga | gtg | gta | gga | gaa | ggg | ctg | ggt | tat | ggt atg gcg | 1296 |
| Gly | Lys | Val | Pro | Gly | Val | Val | Gly | Glu | Gly | Leu | Gly | Tyr | Gly Met Ala | |
| 400 | | | | | 405 | | | | | 410 | | | | 415 |
| gga | gga | gta | gtt | tac | ata | ggg | gtc | ata | ggt | gag | ggc | tgt | ggc ctt tgt | 1344 |
| Gly | Gly | Val | Val | Tyr | Ile | Gly | Val | Ile | Gly | Glu | Gly | Cys | Gly Leu Cys | |
| | | | | 420 | | | | | 425 | | | | | 430 |
| tac | aaa | gtt | atc | atc | taa | aat | aac | agc | act | gga | gcc | cac | tcc cct gtc | 1392 |
| Tyr | Lys | Val | Ile | Ile | | Asn | Asn | Ser | Thr | Gly | Ala | His | Ser Pro Val | |
| | | | 435 | | | | | 440 | | | | | | 445 |
| acc | ctg | ggt | gat | cgg | gga | gca | ggg | cca | gaa | ttc | aac | ctt | aac ctt tct | 1440 |
| Thr | Leu | Gly | Asp | Arg | Gly | Ala | Gly | Pro | Glu | Phe | Asn | Leu | Asn Leu Ser | |
| | | | | 450 | | | | | 455 | | | | 460 | |
| tat | tct | gta | gta | ttc | aaa | ggg | cac | aga | gcg | ggg | gtt | tga | ccc ccc tcc | 1488 |
| Tyr | Ser | Val | Val | Phe | Lys | Gly | His | Arg | Ala | Gly | Val | | Pro Pro Ser | |
| | | | 465 | | | | | 470 | | | | | 475 | |
| tgg | ggg | aag | aaa | gtc | att | aat | att | gaa | tct | cat | cat | gtc | cac cgc cca | 1536 |
| Trp | Gly | Lys | Lys | Val | Ile | Asn | Ile | Glu | Ser | His | His | Val | His Arg Pro | |
| | | | 480 | | | | | 485 | | | | | 490 | |
| gga | ggg | cgt | tct | gac | tgt | ggt | tcg | ctt | gac | agt | ata | tcc | gaa ggt gcg | 1584 |
| Gly | Gly | Arg | Ser | Asp | Cys | Gly | Ser | Leu | Asp | Ser | Ile | Ser | Glu Gly Ala | |
| | | | 495 | | | | | 500 | | | | | 505 | |
| gga | gag | gcg | ggt | gtt | gaa | gat | gcc | att | ttt | cct | tct | cca | gcg gta acg | 1632 |
| Gly | Glu | Ala | Gly | Val | Glu | Asp | Ala | Ile | Phe | Pro | Ser | Pro | Ala Val Thr | |
| 510 | | | | | 515 | | | | | 520 | | | | 525 |
| gtg | gcg | ggg | gtg | gac | gag | cca | ggg | gcg | gcg | gcg | gag | gat | ctg gcc aag | 1680 |
| Val | Ala | Gly | Val | Asp | Glu | Pro | Gly | Ala | Ala | Ala | Glu | Asp | Leu Ala Lys | |
| | | | | 530 | | | | | 535 | | | | 540 | |
| atg | gct | gcg | ggg | gcg | gtg | tct | tct | tct | tcg | gta | acg | cct | cct tgg ata | 1728 |
| Met | Ala | Ala | Gly | Ala | Val | Ser | Ser | Ser | Ser | Val | Thr | Pro | Pro Trp Ile | |
| | | | | 545 | | | | | 550 | | | | 555 | |
| cgt | cat | atc | tga | aaa | cga | aag | aag | tgc | gct | gta | agt | att | | 1767 |
| Arg | His | Ile | | Lys | Arg | Lys | Lys | Cys | Ala | Val | Ser | Ile | | |
| | | | 560 | | | | | 565 | | | | | | |

<210> SEQ ID NO 16
<211> LENGTH: 569
<212> TYPE: PRT
<213> ORGANISM: Type B PWD circovirus

<400> SEQUENCE: 16

Thr Ser Ala Leu Arg Gln Arg Gln His Leu Gly Ser Thr Ser Ala Ala
1               5                   10                  15

Thr Cys Pro Ala Arg Arg Met Glu Glu Ala Asp Pro Asn Pro Ile Lys
            20                  25                  30

Gly Gly Cys Ser Leu Ile Ile Leu Pro Lys Thr Ser Ala Arg Lys Tyr
        35                  40                  45

Gly Ile Phe Gln Tyr Pro Tyr Leu Ile Ile Leu Leu Ala Arg Arg
    50                  55                  60

Val Met Arg Lys Asp Glu His Leu Thr Ser Arg Gly Ser Leu Ile Leu
65                  70                  75                  80

Arg Ser Arg Leu Leu Ile Lys Ser Gly Ile Trp Val Pro Ala Ala Thr
                85                  90                  95

```
Ser Arg Lys Arg Lys Glu Gln Ile Ser Arg Ile Lys Asn Thr Ala Val
            100                 105                 110

Lys Lys Ala Thr Tyr Trp Ser Val Glu Leu Leu Asp Leu Arg Asp Asn
        115                 120                 125

Gly Val Thr Cys Leu Leu Leu Val Pro Cys Trp Arg Ala Gly Val Trp
    130                 135                 140

Pro Leu Gln Ser Ser Thr Leu Arg Leu Ser Glu Ile Ser Ala Gly Trp
145                 150                 155                 160

Leu Asn Phe Lys Ala Gly Lys Cys Arg Ser Val Ile Gly Arg Leu Met
            165                 170                 175

Tyr Thr Ser Leu Trp Gly His Leu Gly Val Val Lys Ala Asn Gly Leu
        180                 185                 190

Leu Ile Leu Gln Thr Arg Lys Pro His Thr Gly Asn His Leu Glu Thr
        195                 200                 205

Ser Gly Gly Met Val Thr Met Val Lys Lys Trp Leu Leu Leu Met Thr
    210                 215                 220

Phe Met Ala Gly Cys Pro Gly Met Ile Tyr Asp Cys Val Ile Asp Ile
225                 230                 235                 240

His Leu Arg Leu Lys Val Glu Leu Tyr Leu Phe Trp Pro Ala Val Phe
            245                 250                 255

Leu Pro Ala Ile Arg Pro Arg Trp Asn Gly Thr Pro Gln Leu Leu Ser
        260                 265                 270

Gln Leu Lys Leu Phe Ile Gly Gly Leu Leu Pro Trp Tyr Phe Gly Arg
        275                 280                 285

Met Leu Gln Asn Asn Pro Arg Arg Lys Gly Ala Ser Ser Ser Pro Phe
    290                 295                 300

Pro Pro His Ala Leu Asn Phe His Met Lys Ile Thr Glu Ser Phe Leu
305                 310                 315                 320

Ser Leu Arg Asn Gly Phe Tyr Tyr Ser Leu Arg Val Lys Trp Gly Val
            325                 330                 335

Phe Lys Ile Lys Phe Ser Glu Leu Tyr Ile His Gly Tyr Thr Asp Ile
        340                 345                 350

Val Phe Leu Val Val Tyr Thr Val Phe Glu Arg Ser Ala Glu Ala Tyr
        355                 360                 365

Val Val Tyr Ile Ser Ser Leu Ser Gln Pro Gln Leu Val Ser Phe
    370                 375                 380

Val Val Trp Leu Glu Val Ile Asn Ser Glu Ile Asp Arg Phe Gly Gly
385                 390                 395                 400

Lys Val Pro Gly Val Val Gly Glu Gly Leu Gly Tyr Gly Met Ala Gly
            405                 410                 415

Gly Val Val Tyr Ile Gly Val Ile Gly Glu Gly Cys Gly Leu Cys Tyr
        420                 425                 430

Lys Val Ile Ile Asn Asn Ser Thr Gly Ala His Ser Pro Val Thr Leu
        435                 440                 445

Gly Asp Arg Gly Ala Gly Pro Glu Phe Asn Leu Asn Leu Ser Tyr Ser
    450                 455                 460

Val Val Phe Lys Gly His Arg Ala Gly Val Pro Ser Trp Gly Lys
465                 470                 475                 480

Lys Val Ile Asn Ile Glu Ser His His Val His Arg Pro Gly Gly Arg
            485                 490                 495

Ser Asp Cys Gly Ser Leu Asp Ser Ile Ser Glu Gly Ala Gly Glu Ala
        500                 505                 510

Gly Val Glu Asp Ala Ile Phe Pro Ser Pro Ala Val Thr Val Ala Gly
```

-continued

```
        515                 520                 525

Val Asp Glu Pro Gly Ala Ala Ala Glu Asp Leu Ala Lys Met Ala Ala
    530                 535                 540

Gly Ala Val Ser Ser Ser Ser Val Thr Pro Pro Trp Ile Arg His Ile
545                 550                 555                 560

Lys Arg Lys Lys Cys Ala Val Ser Ile
                565

<210> SEQ ID NO 17
<211> LENGTH: 542
<212> TYPE: PRT
<213> ORGANISM: Type B PWD circovirus

<400> SEQUENCE: 17

Pro Ala His Phe Gly Ser Gly Ser Thr Ser Ala Ala Pro Gln Gln Gln
1               5                   10                  15

His Ala Gln Gln Glu Glu Trp Lys Lys Arg Thr Pro Thr Pro Lys Val
            20                  25                  30

Gly Val His Ser Glu Ser Phe Arg Arg Arg Ala Gln Glu Asn Thr Gly
        35                  40                  45

Ser Ser Asn Ile Pro Ile Leu Phe Tyr Cys Trp Arg Gly Gly Gly Arg
    50                  55                  60

Thr Asn Thr Ser Pro Pro Gly Val Arg Phe Cys Glu Glu Ala Asp Phe
65                  70                  75                  80

Ser Glu Val Val Phe Gly Cys Pro Leu Pro His Arg Glu Ser Glu Arg
                85                  90                  95

Asn Arg Ser Ala Glu Arg Ile Leu Gln Arg Arg Gln Leu Thr Asp Gly
            100                 105                 110

Val Trp Ser Ser Ile Ser Gly Thr Thr Glu Pro Val Tyr Cys Cys Glu
        115                 120                 125

Tyr Leu Val Gly Glu Arg Glu Ser Gly Asp Arg Cys Arg Ala Ala Pro
    130                 135                 140

Cys Asn Val Cys Gln Lys Phe Pro Arg Ala Gly Thr Phe Glu Ser Glu
145                 150                 155                 160

Arg Glu Asn Ala Glu Ala Cys Thr Arg His Cys Gly Ala Thr Trp Val
                165                 170                 175

Trp Lys Gln Met Gly Cys Phe Cys Arg Pro Gly Asn His Ile Leu Glu
            180                 185                 190

Thr Thr Lys Gln Val Val Gly Trp Leu Pro Trp Arg Ser Gly Cys Tyr
        195                 200                 205

Leu Leu Trp Leu Ala Ala Leu Gly Ser Thr Glu Thr Val Ser Ile Ser
    210                 215                 220

Ile Asp Cys Arg Asp Arg Trp Asn Cys Thr Phe Phe Gly Pro Gln Tyr
225                 230                 235                 240

Ser Asp Tyr Gln Gln Ser Asp Pro Val Gly Met Val Leu Leu Asn Cys
                245                 250                 255

Cys Pro Ser Cys Arg Ser Ser Leu Ser Glu Asp Tyr Phe Leu Gly Ile
            260                 265                 270

Leu Glu Glu Cys Tyr Arg Thr Ile His Gly Gly Arg Gly Pro Val Arg
        275                 280                 285

His Pro Phe Pro Pro Met Pro Asn Lys Leu Leu Ser Leu Phe Tyr His
    290                 295                 300

Phe Val Met Val Phe Ile Ile His Gly Leu Ser Gly Gly Ser Leu Lys
305                 310                 315                 320

-continued

```
Leu Asn Ser Leu Asn Cys Thr Tyr Met Val Thr Arg Ile Leu Tyr Ser
            325                 330                 335

Trp Ser Tyr Ile Leu Phe Ser Asn Ala Val Pro Arg Pro Thr Trp Ser
        340                 345                 350

Thr Phe Pro Ala Val Cys Ser Leu Ser His Ser Trp Phe Leu Leu Leu
    355                 360                 365

Phe Gly Trp Lys Ser Ile Val Lys Ser Arg Thr Gly Leu Gly Val Lys
370                 375                 380

Tyr Arg Glu Trp Glu Lys Gly Trp Val Met Val Trp Arg Glu Glu Val
385                 390                 395                 400

Arg Ala Val Ala Phe Val Thr Lys Leu Ser Ser Lys Ile Thr Ala Leu
                405                 410                 415

Glu Pro Thr Pro Leu Ser Pro Trp Val Ile Gly Glu Gln Gly Gln Asn
            420                 425                 430

Ser Thr Leu Thr Phe Leu Ile Leu Tyr Ser Lys Gly Thr Glu Arg Gly
        435                 440                 445

Phe Asp Pro Pro Gly Gly Arg Lys Ser Leu Ile Leu Asn Leu Ile
    450                 455                 460

Met Ser Thr Ala Gln Glu Gly Val Leu Thr Val Val Arg Leu Thr Val
465                 470                 475                 480

Tyr Pro Lys Val Arg Glu Arg Val Leu Lys Met Pro Phe Phe Leu
                485                 490                 495

Leu Gln Arg Arg Trp Arg Gly Trp Thr Ser Gln Gly Arg Arg Arg Arg
            500                 505                 510

Ile Trp Pro Arg Trp Leu Arg Gly Arg Cys Leu Leu Leu Arg Arg Leu
        515                 520                 525

Leu Gly Tyr Val Ile Ser Glu Asn Glu Arg Ser Ala Leu Val
    530                 535                 540

<210> SEQ ID NO 18
<211> LENGTH: 566
<212> TYPE: PRT
<213> ORGANISM: Type B PWD circovirus

<400> SEQUENCE: 18

Gln Arg Thr Ser Ala Ala Ala Pro Arg Gln His Leu Ser Ser Asn
1               5                   10                  15

Met Pro Ser Lys Lys Asn Gly Arg Ser Gly Pro Gln Pro His Lys Arg
            20                  25                  30

Trp Val Phe Thr Leu Asn Asn Pro Ser Glu Asp Glu Arg Lys Lys Ile
        35                  40                  45

Arg Asp Leu Pro Ile Ser Leu Phe Asp Tyr Phe Ile Val Gly Glu Glu
50                  55                  60

Gly Asn Glu Glu Gly Arg Thr Pro His Leu Gln Gly Phe Ala Asn Phe
65                  70                  75                  80

Val Lys Lys Gln Thr Phe Asn Lys Val Lys Trp Tyr Leu Gly Ala Arg
                85                  90                  95

Cys His Ile Glu Lys Ala Lys Gly Thr Asp Gln Gln Asn Lys Glu Tyr
            100                 105                 110

Cys Ser Lys Glu Gly Asn Leu Leu Met Glu Cys Gly Ala Pro Arg Ser
        115                 120                 125

Gln Gly Gln Arg Ser Asp Leu Ser Thr Ala Val Ser Thr Leu Leu Glu
    130                 135                 140

Ser Gly Ser Leu Val Thr Val Ala Glu Gln His Pro Val Thr Phe Val
145                 150                 155                 160
```

-continued

```
Arg Asn Phe Arg Gly Leu Ala Glu Leu Leu Lys Val Ser Gly Lys Met
            165                 170                 175

Gln Lys Arg Asp Trp Lys Thr Asn Val His Val Ile Val Gly Pro Pro
        180                 185                 190

Gly Cys Gly Lys Ser Lys Trp Ala Ala Asn Phe Ala Asp Pro Glu Thr
    195                 200                 205

Thr Tyr Trp Lys Pro Pro Arg Asn Lys Trp Asp Gly Tyr His Gly
210                 215                 220

Glu Glu Val Val Val Ile Asp Asp Phe Tyr Gly Trp Leu Pro Trp Asp
225                 230                 235                 240

Asp Leu Leu Arg Leu Cys Asp Arg Tyr Pro Leu Thr Val Glu Thr Lys
                245                 250                 255

Gly Gly Thr Val Pro Phe Leu Ala Arg Ser Ile Leu Ile Thr Ser Asn
            260                 265                 270

Gln Thr Pro Leu Glu Trp Tyr Ser Ser Thr Ala Val Pro Ala Val Glu
        275                 280                 285

Ala Leu Tyr Arg Arg Ile Thr Ser Leu Val Phe Trp Lys Asn Ala Thr
    290                 295                 300

Glu Gln Ser Thr Glu Glu Gly Gln Phe Val Thr Leu Ser Pro Pro
305                 310                 315                 320

Cys Pro Glu Phe Pro Tyr Glu Ile Asn Tyr Val Phe Phe Ile Thr Ser
                325                 330                 335

Trp Phe Leu Leu Phe Ile Lys Gly Val Gly Gly Leu Ile Val His Thr
            340                 345                 350

Trp Leu His Gly Tyr Cys Ile Pro Gly Arg Ile Tyr Cys Phe Arg Thr
        355                 360                 365

Gln Cys Arg Gly Leu Arg Gly Leu His Phe Gln Gln Phe Val Val Ser
    370                 375                 380

Ala Thr Ala Gly Phe Phe Cys Cys Leu Val Gly Ser Asn Gln Asn Leu
385                 390                 395                 400

Gly Gln Val Trp Gly Ser Thr Gly Ser Gly Arg Arg Arg Ala Gly Leu
                405                 410                 415

Trp Tyr Gly Gly Arg Ser Ser Leu His Arg Gly His Arg Gly Leu Trp
            420                 425                 430

Pro Leu Leu Gln Ser Tyr His Leu Lys Gln His Trp Ser Pro Leu Pro
        435                 440                 445

Cys His Pro Gly Ser Gly Ser Arg Ala Arg Ile Gln Pro Pro Phe Leu
    450                 455                 460

Phe Cys Ser Ile Gln Arg Ala Gln Ser Gly Gly Leu Thr Pro Leu Leu
465                 470                 475                 480

Gly Glu Glu Ser His Ile Ser Ser Cys Pro Pro Arg Arg Ala Phe
                485                 490                 495

Leu Trp Phe Ala Gln Tyr Ile Arg Arg Cys Gly Arg Gly Gly Cys Arg
            500                 505                 510

Cys His Phe Ser Phe Ser Ser Gly Asn Gly Gly Gly Gly Arg Ala
        515                 520                 525

Arg Gly Gly Gly Gly Ser Gly Gln Asp Gly Cys Gly Gly Val
    530                 535                 540

Phe Phe Phe Gly Asn Ala Ser Leu Asp Thr Ser Tyr Leu Lys Thr Lys
545                 550                 555                 560

Glu Val Arg Cys Lys Tyr
                565
```

<210> SEQ ID NO 19
<211> LENGTH: 1767
<212> TYPE: DNA
<213> ORGANISM: Type B PWD circovirus

<400> SEQUENCE: 19

```
aatacttaca gcgcacttct ttcgttttca gatatgacgt atccaaggag gcgttaccga      60
agaagaagac accgcccccg cagccatctt ggccagatcc tccgccgccg ccctggctc     120
gtccaccccc gccaccgtta ccgctggaga aggaaaaatg gcatcttcaa cacccgcctc    180
tcccgcacct tcggatatac tgtcaagcga accacagtca gaacgccctc ctgggcggtg    240
gacatgatga gattcaatat taatgacttt cttcccccag gagggggtc aaaccccgc      300
tctgtgccct ttgaatacta cagaataaga aggttaagg ttgaattctg gccctgctcc     360
ccgatcaccc agggtgacag gggagtgggc tccagtgctg ttatttaga tgataacttt    420
gtaacaaagg ccacagccct cacctatgac ccctatgtaa actactcctc ccgccatacc    480
ataacccagc ccttctccta ccactcccgg tactttaccc ccaaacctgt cctagatttc    540
actattgatt acttccaacc aaacaacaaa agaaaccagc tgtggctgag actacaaact    600
gctggaaatg tagaccacgt aggcctcggc actgcgttcg aaaacagtat atacgaccag    660
gaatacaata tccgtgtaac catgtatgta caattcagag aatttaattt taaagacccc    720
ccacttaacc cttaatgaat aataaaaacc attacgaagt gataaaaaag actcagtaat    780
ttatttcata tggaaattca gggcatgggg gggaaagggt gacgaactgg ccccttcct    840
ccgtggattg ttctgtagca ttcttccaaa ataccaagga agtaatcctc cgataaagag    900
cttctacagc tgggacagca gttgaggagt accattccaa cggggtctga ttgctggtaa    960
tcagaatact gcgggccaaa aaaggtacag ttccacctttt agtctctaca gtcaatggat   1020
atcgatcaca cagtctcagt agatcatccc agggcagcca gccataaaag tcatcaataa   1080
caaccacttc ttcaccatgg taaccatccc accacttgtt tctaggtggt ttccagtatg   1140
tggtttccgg gtctgcaaaa ttagcagccc atttgctttt accacaccca ggtggcccca   1200
caatgacgtg tacattagtc ttccaatcac gcttctgcat tttcccgctc actttcaaaa   1260
gttcagccag cccgcggaaa tttctgacaa acgttacagg gtgctgctct gcaacggtca   1320
ccagactccc gctctccaac aaggtactca cagcagtaga caggtcactc cgttgtccct   1380
gagatctagg agctccacac tccatcagta agttgcctcc tttactgcag tattctttat   1440
tctgctgatc tgttcctttc gctttctcga tgtggcagcg ggcacccaaa taccacttca   1500
ctttattaaa agtctgcttc ttcacaaaat tagcgaaccc ctggaggtga ggtgttcgtc   1560
cttcctcatt accctcctcg ccaacaataa aataatcaaa tagggatatt ggaagatccc   1620
gtattttctt gcgctcgtct tcggaaggat tattcagagt gaacacccac cttttatggg   1680
gttggggtcc gcttcttcca ttcttcttgc tgggcatgtt gctgctgagg tgctgccgag   1740
gtgctgccgc tgccgaagtg cgctggt                                       1767
```

<210> SEQ ID NO 20
<211> LENGTH: 567
<212> TYPE: PRT
<213> ORGANISM: Type B PWD circovirus

<400> SEQUENCE: 20

```
Gly Ala Cys Lys Pro Leu Pro Leu Val Glu Ala Ala Gly Cys Cys Cys
 1               5                  10                  15
```

-continued

```
Ala Trp Cys Ser Ser His Phe Arg Val Gly Val Gly Tyr Phe Thr
             20                  25                  30

Pro Thr Glu Ser Tyr Asp Lys Arg Leu Arg Ala Cys Ser Phe Val Pro
         35                  40                  45

Asp Glu Leu Ile Gly Ile Gln Asn Asn Gln Gln Arg Pro Pro Tyr His
     50                  55                  60

Pro Leu Val Phe Val Glu Gly Pro Thr Arg Asn Gln Ser Ser Ala
65                  70                  75                  80

Ser Lys Tyr Leu Ser Thr Thr Asn Pro His Gly Ser Gly Cys Arg Ser
                 85                  90                  95

Leu Ser Leu Phe Leu Asp Ala Ser Tyr Leu Ile Ser Cys Tyr Leu Leu
             100                 105                 110

Cys Ser Val Ser Pro Thr His Leu Glu Ile Glu Pro Val Val Ser His
             115                 120                 125

Gly Thr Gln Gln Ser Tyr Arg Thr Pro Ser Arg Ser Asp Pro Ser Arg
     130                 135                 140

Gln Leu Ala Ala Gly Gln Leu Thr Gln Phe Asn Gly Arg Ala Pro Gln
145                 150                 155                 160

Val Lys Ser Leu Ser Arg Ser Phe Ala Ser Ala His Asn Ser Ser His
                 165                 170                 175

Val Arg Gln Pro Ala Val Gln Thr His Tyr Phe Cys Ile Pro Gln Asn
             180                 185                 190

Gln Leu Gly Pro Phe Trp Met Ser Val Val Phe Cys Thr Thr Pro
         195                 200                 205

His Asn Gly His His Leu Leu Pro Gln Gln His Ser Lys His Ser Ala
     210                 215                 220

Ala Arg Pro His Asp Val Ser Val Thr His Asp Ile Asp Met Ser Gln
225                 230                 235                 240

Leu Ser Leu His Phe Gln Val Lys Lys Pro Gly Cys Tyr Glu Ser Trp
             245                 250                 255

Cys Asp Ser Gly Thr Pro Ile Thr Ser Arg Leu Gln Gln Gly Leu Gln
             260                 265                 270

Leu Leu Glu Lys Asp Ser Ser Lys Arg Pro Ile Lys Ser Ser His Leu
         275                 280                 285

Val Ile Trp Pro Pro Leu Pro Gly Thr Arg Gly Lys Gly Gly Met Gly
     290                 295                 300

Gln Ile Glu Met His Phe Leu Asn Ser Leu Arg Lys Lys Thr Ile Thr
305                 310                 315                 320

Lys Ile Ile Pro Asn Leu Pro Pro Asp Lys Phe Asn Phe Glu Arg Phe
             325                 330                 335

Gln Val Tyr Met Thr Val Arg Ile Asn Tyr Glu Gln Asp Tyr Ile Ser
             340                 345                 350

Asn Glu Phe Ala Thr Gly Leu Gly Val His Asp Val Asn Gly Ala Thr
             355                 360                 365

Gln Leu Arg Leu Trp Leu Gln Asn Arg Lys Asn Asn Pro Gln Phe Tyr
     370                 375                 380

Asp Ile Thr Phe Asp Leu Val Pro Lys Pro Thr Phe Tyr Arg Ser His
385                 390                 395                 400

Tyr Ser Phe Pro Gln Thr Ile Thr His Arg Ser Ser Tyr Asn Val Tyr
                 405                 410                 415

Pro Asp Tyr Thr Leu Ala Thr Ala Lys Thr Val Pro Asn Asp Asp Leu
             420                 425                 430

Ile Val Ala Ser Ser Gly Val Gly Arg Asp Gly Gln Thr Ile Pro Ser
```

```
                435                 440                 445
Cys Pro Trp Phe Glu Val Lys Val Lys Arg Ile Arg Tyr Tyr Glu Phe
    450                 455                 460

Pro Val Ser Arg Pro Asn Ser Gly Gly Pro Pro Leu Phe Asp Asn
465                 470                 475                 480

Ile Asn Phe Arg Met Met Asp Val Ala Trp Ser Pro Thr Arg Val Thr
                485                 490                 495

Thr Arg Lys Val Thr Tyr Gly Phe Thr Arg Ser Leu Arg Thr Asn Phe
                500                 505                 510

Ile Gly Asn Lys Arg Arg Trp Arg Tyr Arg His Arg Pro His Val Leu
            515                 520                 525

Trp Pro Arg Arg Arg Leu Ile Gln Gly Leu His Ser Arg Pro Arg His
530                 535                 540

Arg Arg Arg Arg Tyr Arg Arg Pro Tyr Thr Met Asp Ser Phe Ser
545                 550                 555                 560

Leu Leu Ala Ser Tyr Thr Asn
                565

<210> SEQ ID NO 21
<211> LENGTH: 566
<212> TYPE: PRT
<213> ORGANISM: Type B PWD circovirus

<400> SEQUENCE: 21

Trp Arg Val Glu Ala Ala Ala Gly Arg Cys Cys Arg Leu Leu Leu
1               5                   10                  15

Met Gly Leu Leu Phe Phe Pro Leu Leu Pro Gly Trp Gly Trp Leu Leu
                20                  25                  30

His Thr Asn Val Arg Phe Leu Gly Glu Ser Ser Ser Arg Leu Phe Ile
            35                  40                  45

Arg Ser Arg Gly Ile Asp Arg Asn Ser Lys Ile Thr Pro Ser Ser Pro
50                  55                  60

Leu Ser Ser Pro Arg Val Gly Arg Trp Pro Asn Ala Leu Lys Thr Phe
65                  70                  75                  80

Phe Cys Val Lys Leu Leu Thr Phe His Tyr Lys Pro Ala Arg Gln Trp
                85                  90                  95

Met Ser Phe Ala Phe Pro Val Ser Cys Phe Leu Ser Tyr Gln Leu Leu
                100                 105                 110

Ser Pro Leu Lys Ser Ile Ser His Pro Ala Gly Leu Asp Pro Cys Arg
            115                 120                 125

Leu Ser Arg Asp Val Ala Thr Leu Val Lys Asn Ser Leu Pro Leu Arg
130                 135                 140

Thr Val Thr Ala Ser Cys Cys Gly Thr Val Asn Thr Leu Phe Lys Arg
145                 150                 155                 160

Pro Ser Ala Ser Ser Lys Phe Thr Leu Pro Phe Ile Cys Phe Arg Ser
                165                 170                 175

Gln Phe Val Leu Thr Cys Thr Met Thr Pro Gly Gly Pro His Pro Leu
                180                 185                 190

Leu Leu His Ala Ala Leu Lys Ala Ser Gly Ser Val Val Tyr Gln Phe
            195                 200                 205

Gly Gly Leu Phe Leu His His Ser Pro Trp Pro Ser Thr Thr Thr
            210                 215                 220

Ile Ser Ser Lys Pro Gln Ser Gly Gln Ser Ser Arg Ser Leu Ser His
225                 230                 235                 240
```

-continued

```
Ser Arg Tyr Gly Asn Val Thr Ser Val Leu Pro Pro Val Thr Gly Lys
                245                 250                 255

Lys Ala Arg Leu Ile Arg Ile Val Leu Leu Val Gly Asn Ser His Tyr
            260                 265                 270

Glu Glu Val Ala Thr Gly Ala Thr Ser Ala Arg Arg Leu Ile Val Glu
        275                 280                 285

Lys Thr Asn Gln Phe Phe Ala Val Ser Cys Asp Val Ser Ser Pro Pro
    290                 295                 300

Trp Asn Thr Val Arg Glu Gly Gly His Gly Ser Asn Gly Tyr Ser Ile
305                 310                 315                 320

Phe Gln Thr Lys Lys Ile Val Glu Tyr His Asn Lys Asn Asn Met Leu
                325                 330                 335

Pro Thr Pro Pro Arg Phe Ile Arg Gln Ile Thr Cys Val His Asn Cys
            340                 345                 350

Pro Tyr Gln Ile Gly Pro Arg Ile Tyr Gln Lys Arg Val Cys His Arg
        355                 360                 365

Pro Arg Arg Pro Arg Cys Lys Trp Cys Asn Thr Thr Glu Ala Val Ala
    370                 375                 380

Pro Lys Lys Gln Gln Lys Thr Pro Leu Leu Tyr His Phe Arg Pro Cys
385                 390                 395                 400

Thr Gln Pro Tyr Leu Val Pro Leu Pro Leu Leu Leu Ala Pro Asn His
                405                 410                 415

Tyr Pro Pro Leu Leu Leu Lys Cys Leu Pro Leu His Pro Ser His Gly
            420                 425                 430

Lys Asn Cys Leu Arg Phe Tyr Cys Cys Gln Leu Gly Ser Gly Gln Gly
        435                 440                 445

Pro His Asp Pro Leu Leu Ala Leu Ile Gly Gly Lys Lys Asn Gln Leu
    450                 455                 460

Ile Leu Ala Cys Leu Pro Pro Lys Val Gly Arg Arg Pro Ser Ser Leu
465                 470                 475                 480

Tyr Gln Ile Glu Asp His Gly Gly Gly Leu Leu Ala Asn Gln Ser His
                485                 490                 495

Asn Ala Gln Cys Tyr Ile Arg Leu His Pro Leu Pro Pro His Gln Leu
            500                 505                 510

His Trp Lys Glu Lys Glu Leu Pro Leu Pro Pro Pro Pro Pro Arg Ala
        515                 520                 525

Leu Pro Pro Pro Pro Pro Asp Pro Trp Ser Pro Gln Pro Pro Pro Thr
    530                 535                 540

Lys Lys Lys Pro Leu Ala Glu Lys Ser Val Asp Tyr Arg Phe Val Phe
545                 550                 555                 560

Ser Thr Arg Gln Leu Tyr
                565
```

<210> SEQ ID NO 22
<211> LENGTH: 569
<212> TYPE: PRT
<213> ORGANISM: Type B PWD circovirus

<400> SEQUENCE: 22

```
Leu Ala Ser Arg Cys Arg Cys Cys Arg Pro Leu Val Glu Ala Ala Val
1               5                   10                  15

His Gly Ala Leu Leu Ile Ser Ser Ala Ser Gly Leu Gly Met Phe Pro
            20                  25                  30

Pro His Glu Ser Gln Ile Ile Arg Gly Phe Val Leu Ala Leu Phe Tyr
        35                  40                  45
```

```
Pro Ile Lys Trp Tyr Gly Lys Ile Ile Lys Asn Asn Ala Leu Leu Thr
    50                  55                  60
Ile Leu Phe Ser Ser Cys Arg Val Glu Leu Pro Glu Ser Ile Lys His
65                  70                  75                  80
Leu Leu Leu Ser Lys Ile Phe His Leu Pro Ile Gln Thr Gly Ala Ala
                85                  90                  95
Val Asp Leu Phe Arg Phe Ser Cys Ile Leu Leu Ile Phe Phe Val Ala
            100                 105                 110
Thr Phe Phe Ala Val Gln His Leu Thr Ser Ser Arg Ser Arg Leu Ser
        115                 120                 125
Leu Pro Thr Val Gln Arg Ser Ser His Thr Gly Gln Gln Leu Ala Pro
    130                 135                 140
Thr Gln His Gly Asn Cys Leu Leu Val Arg Tyr Arg Lys Asp Ser Ile
145                 150                 155                 160
Glu Ala Pro Gln Ser Phe Lys Gln Phe His Ala Pro Phe His Leu Leu
                165                 170                 175
Thr Ile Pro Leu Ser Ile Tyr Val Asp Asn His Pro Trp Arg Pro Thr
            180                 185                 190
Thr Phe Ala Phe Pro Ser Ser Ile Lys Cys Val Arg Phe Gly Cys Val
        195                 200                 205
Pro Phe Trp Arg Ser Val Leu Pro Pro Ile Thr Val Met Thr Phe Phe
    210                 215                 220
His Asn Asn Asn Ile Val Lys Ile Ala Pro Gln Gly Pro Ile Ile Gln
225                 230                 235                 240
Ser Gln Thr Ser Ser Ile Trp Gln Ser Tyr Leu Ser Phe Thr Ser Ser
                245                 250                 255
Tyr Arg Lys Gln Gly Ala Thr Asn Gln Asn Gly Ala Ile Leu Gly Arg
            260                 265                 270
Gln Phe Pro Val Gly Ser Ser Asp Trp Ser Tyr Phe Ser Lys Ile Pro
        275                 280                 285
Pro Asn Ser Gly Gln Tyr Lys Pro Leu Ile Ser Cys Phe Leu Gly Arg
    290                 295                 300
Leu Phe Pro Ala Leu Glu Asp Gly Lys Gly Gly Trp Ala Arg Phe Lys
305                 310                 315                 320
Trp Ile Phe Trp Ile Val Ser Asp Lys Lys Asp Ser Arg Leu Pro Lys
                325                 330                 335
Glu Asn Leu Thr Leu His Pro Thr Lys Leu Ile Leu Asn Glu Ser Asn
            340                 345                 350
Tyr Met Cys Pro Val Ser Ile Thr Asn Arg Thr Thr Tyr Val Thr Lys
        355                 360                 365
Ser Arg Leu Ala Ser Ala Thr Thr Met Glu Leu Leu Lys Tyr Asp Gly
    370                 375                 380
Cys Ser Thr Glu Lys Thr Thr Gln Asn Ser Thr Ile Leu Leu Ser Ile
385                 390                 395                 400
Ser Leu Asn Pro Pro Leu Thr Gly Pro Thr Pro Ser Pro Ser Pro
                405                 410                 415
Pro Ile Ala Pro Pro Thr Thr Met Pro Thr Met Pro Ser Pro Gln Pro
            420                 425                 430
Arg Gln Leu Thr Ile Met Phe Leu Leu Val Pro Ala Trp Glu Gly Thr
        435                 440                 445
Val Arg Pro Ser Arg Pro Ala Pro Gly Ser Asn Leu Arg Leu Arg Glu
    450                 455                 460
```

```
Glu Thr Thr Asn Leu Pro Cys Leu Ala Pro Thr Gln Gly Gly Glu Gln
465                 470                 475                 480

Pro Phe Phe Thr Met Leu Ile Ser Asp Thr Trp Arg Gly Pro Pro Arg
            485                 490                 495

Glu Ser Gln Pro Glu Ser Ser Leu Ile Asp Ser Pro Ala Pro Ser Ala
        500                 505                 510

Pro Thr Ser Ser Ala Met Lys Gly Glu Gly Ala Thr Val Thr Ala Pro
        515                 520                 525

Thr Ser Ser Gly Pro Ala Ala Ala Ser Ser Arg Ala Leu Ile Ala Ala
        530                 535                 540

Pro Ala Thr Asp Glu Glu Thr Val Gly Gly Gln Ile Arg Ile Gln
545                 550                 555                 560

Phe Arg Phe Phe His Ala Thr Leu Ile
                565

<210> SEQ ID NO 23
<211> LENGTH: 945
<212> TYPE: DNA
<213> ORGANISM: Type B PWD circovirus
<220> FEATURE:
<221> NAME/KEY: CDS
<222> LOCATION: (1)..(942)

<400> SEQUENCE: 23 atg ccc agc aag aag aat gga aga ag

-continued

```
aca tac tgg aaa cca cct aga aac aag tgg tgg gat ggt tac cat ggt    624
Thr Tyr Trp Lys Pro Pro Arg Asn Lys Trp Trp Asp Gly Tyr His Gly
        195                 200                 205 gaa gaa gtg gtt gtt att gat gac ttt tat ggc tgg ctg ccc tgg gat    672
Glu Glu Val Val Val Ile Asp Asp Phe Tyr Gly Trp Leu Pro Trp Asp
210                 215                 220 gat cta ctg aga ctg tgt gat cga tat cca ttg act gta gag act aaa    720
Asp Leu Leu Arg Leu Cys Asp Arg Tyr Pro Leu Thr Val Glu Thr Lys
225                 230                 235                 240 ggt gga act gta cct ttt ttg gcc cgc agt att ctg att acc agc aat    768
Gly Gly Thr Val Pro Phe Leu Ala Arg Ser Ile Leu Ile Thr Ser Asn
                245                 250                 255 cag acc ccg ttg gaa tgg tac tcc tca act gct gtc cca gct gta gaa    816
Gln Thr Pro Leu Glu Trp Tyr Ser Ser Thr Ala Val Pro Ala Val Glu
            260                 265                 270 gct ctt tat cgg agg att act tcc ttg gta ttt tgg aag aat gct aca    864
Ala Leu Tyr Arg Arg Ile Thr Ser Leu Val Phe Trp Lys Asn Ala Thr
        275                 280                 285 gaa caa tcc acg gag gaa ggg ggc cag ttc gtc acc ctt tcc ccc cca    912
Glu Gln Ser Thr Glu Glu Gly Gly Gln Phe Val Thr Leu Ser Pro Pro
    290                 295                 300 tgc cct gaa ttt cca tat gaa ata aat tac tga                        945
Cys Pro Glu Phe Pro Tyr Glu Ile Asn Tyr
305                 310
```

<210> SEQ ID NO 24
<211> LENGTH: 314
<212> TYPE: PRT
<213> ORGANISM: Type B PWD circovirus

<400> SEQUENCE: 24

```
Met Pro Ser Lys Lys Asn Gly Arg Ser Gly Pro Gln Pro His Lys Arg
1               5                   10                  15

Trp Val Phe Thr Leu Asn Asn Pro Ser Glu Asp Glu Arg Lys Lys Ile
                20                  25                  30

Arg Asp Leu Pro Ile Ser Leu Phe Asp Tyr Phe Ile Val Gly Glu Glu
            35                  40                  45

Gly Asn Glu Glu Gly Arg Thr Pro His Leu Gln Gly Phe Ala Asn Phe
        50                  55                  60

Val Lys Lys Gln Thr Phe Asn Lys Val Lys Trp Tyr Leu Gly Ala Arg
65                  70                  75                  80

Cys His Ile Glu Lys Ala Lys Gly Thr Asp Gln Gln Asn Lys Glu Tyr
                85                  90                  95

Cys Ser Lys Glu Gly Asn Leu Leu Met Glu Cys Gly Ala Pro Arg Ser
            100                 105                 110

Gln Gly Gln Arg Ser Asp Leu Ser Thr Ala Val Ser Thr Leu Leu Glu
        115                 120                 125

Ser Gly Ser Leu Val Thr Val Ala Glu Gln His Pro Val Thr Phe Val
    130                 135                 140

Arg Asn Phe Arg Gly Leu Ala Glu Leu Leu Lys Val Ser Gly Lys Met
145                 150                 155                 160

Gln Lys Arg Asp Trp Lys Thr Asn Val His Val Ile Val Gly Pro Pro
                165                 170                 175

Gly Cys Gly Lys Ser Lys Trp Ala Ala Asn Phe Ala Asp Pro Glu Thr
            180                 185                 190

Thr Tyr Trp Lys Pro Pro Arg Asn Lys Trp Trp Asp Gly Tyr His Gly
        195                 200                 205
```

```
Glu Glu Val Val Val Ile Asp Asp Phe Tyr Gly Trp Leu Pro Trp Asp
    210                 215                 220
Asp Leu Leu Arg Leu Cys Asp Arg Tyr Pro Leu Thr Val Glu Thr Lys
225                 230                 235                 240
Gly Gly Thr Val Pro Phe Leu Ala Arg Ser Ile Leu Ile Thr Ser Asn
                245                 250                 255
Gln Thr Pro Leu Glu Trp Tyr Ser Ser Thr Ala Val Pro Ala Val Glu
            260                 265                 270
Ala Leu Tyr Arg Arg Ile Thr Ser Leu Val Phe Trp Lys Asn Ala Thr
        275                 280                 285
Glu Gln Ser Thr Glu Glu Gly Gly Gln Phe Val Thr Leu Ser Pro Pro
    290                 295                 300
Cys Pro Glu Phe Pro Tyr Glu Ile Asn Tyr
305                 310

<210> SEQ ID NO 25
<211> LENGTH: 702
<212> TYPE: DNA
<213> ORGANISM: Type B PWD circovirus
<220> FEATURE:
<221> NAME/KEY: CDS
<222> LOCATION: (1)..(699)

<400> SEQUENCE: 25 atg acg tat cca agg agg cgt tac cga aga aga aga cac cgc ccc cgc      48
Met Thr Tyr Pro Arg Arg Arg Tyr Arg Arg Arg Arg His Arg Pro Arg
1               5                   10                  15 agc cat ctt ggc cag atc ctc cgc cgc cgc ccc tgg ctc gtc cac ccc      96
Ser His Leu Gly Gln Ile Leu Arg Arg Arg Pro Trp Leu Val His Pro
            20                  25                  30 cgc cac cgt tac cgc tgg aga agg aaa aat ggc atc ttc aac acc cgc     144
Arg His Arg Tyr Arg Trp Arg Arg Lys Asn Gly Ile Phe Asn Thr Arg
        35                  40                  45 ctc tcc cgc acc ttc gga tat act gtc aag cga acc aca gtc aga acg     192
Leu Ser Arg Thr Phe Gly Tyr Thr Val Lys Arg Thr Thr Val Arg Thr
    50                  55                  60 ccc tcc tgg gcg gtg gac atg atg aga ttc aat att aat gac ttt ctt     240
Pro Ser Trp Ala Val Asp Met Met Arg Phe Asn Ile Asn Asp Phe Leu
65                  70                  75                  80 ccc cca gga ggg ggg tca aac ccc cgc tct gtg ccc ttt gaa tac tac     288
Pro Pro Gly Gly Gly Ser Asn Pro Arg Ser Val Pro Phe Glu Tyr Tyr
                85                  90                  95 aga ata aga aag gtt aag gtt gaa ttc tgg ccc tgc tcc ccg atc acc     336
Arg Ile Arg Lys Val Lys Val Glu Phe Trp Pro Cys Ser Pro Ile Thr
            100                 105                 110 cag ggt gac agg gga gtg ggc tcc agt gct gtt att tta gat gat aac     384
Gln Gly Asp Arg Gly Val Gly Ser Ser Ala Val Ile Leu Asp Asp Asn
        115                 120                 125 ttt gta aca aag gcc aca gcc ctc acc tat gac ccc tat gta aac tac     432
Phe Val Thr Lys Ala Thr Ala Leu Thr Tyr Asp Pro Tyr Val Asn Tyr
    130                 135                 140 tcc tcc cgc cat acc ata acc cag ccc ttc tcc tac cac tcc cgg tac     480
Ser Ser Arg His Thr Ile Thr Gln Pro Phe Ser Tyr His Ser Arg Tyr
145                 150                 155                 160 ttt acc ccc aaa cct gtc cta gat ttc act att gat tac ttc caa cca     528
Phe Thr Pro Lys Pro Val Leu Asp Phe Thr Ile Asp Tyr Phe Gln Pro
                165                 170                 175 aac aac aaa aga aac cag ctg tgg ctg aga cta caa act gct gga aat     576
Asn Asn Lys Arg Asn Gln Leu Trp Leu Arg Leu Gln Thr Ala Gly Asn
```

```
                    180                 185                 190
gta gac cac gta ggc ctc ggc act gcg ttc gaa aac agt ata tac gac     624
Val Asp His Val Gly Leu Gly Thr Ala Phe Glu Asn Ser Ile Tyr Asp
        195                 200                 205 cag gaa tac aat atc cgt gta acc atg tat gta caa ttc aga gaa ttt     672
Gln Glu Tyr Asn Ile Arg Val Thr Met Tyr Val Gln Phe Arg Glu Phe
    210                 215                 220 aat ttt aaa gac ccc cca ctt aac cct taa                             702
Asn Phe Lys Asp Pro Pro Leu Asn Pro
225                 230

<210> SEQ ID NO 26
<211> LENGTH: 233
<212> TYPE: PRT
<213> ORGANISM: Type B PWD circovirus

<400> SEQUENCE: 26

Met Thr Tyr Pro Arg Arg Tyr Arg Arg Arg His Arg Pro Arg
1               5                   10

```
Met Val Thr Ile Pro Pro Leu Val Ser Arg Trp Phe Pro Val Cys Gly
1               5                   10                  15 ttc cgg gtc tgc aaa att agc agc cca ttt gct ttt acc aca ccc agg       96
Phe Arg Val Cys Lys Ile Ser Ser Pro Phe Ala Phe Thr Thr Pro Arg
            20                  25                  30 tgg ccc cac aat gac gtg tac att agt ctt cca atc acg ctt ctg cat       144
Trp Pro His Asn Asp Val Tyr Ile Ser Leu Pro Ile Thr Leu Leu His
                35                  40                  45 ttt ccc gct cac ttt caa aag ttc agc cag ccc gcg gaa att tct gac       192
Phe Pro Ala His Phe Gln Lys Phe Ser Gln Pro Ala Glu Ile Ser Asp
50                  55                  60 aaa cgt tac agg gtg ctg ctc tgc aac ggt cac cag act ccc gct ctc       240
Lys Arg Tyr Arg Val Leu Leu Cys Asn Gly His Gln Thr Pro Ala Leu
65                  70                  75                  80 caa caa ggt act cac agc agt aga cag gtc act ccg ttg tcc ctg aga       288
Gln Gln Gly Thr His Ser Ser Arg Gln Val Thr Pro Leu Ser Leu Arg
                85                  90                  95 tct agg agc tcc aca ctc cat cag taa                                   315
Ser Arg Ser Ser Thr Leu His Gln
                100

<210> SEQ ID NO 28
<211> LENGTH: 104
<212> TYPE: PRT
<213> ORGANISM: Type B PWD circovirus

<400> SEQUENCE: 28

Met Val Thr Ile Pro Pro Leu Val Ser Arg Trp Phe Pro Val Cys Gly
1               5                   10                  15

Phe Arg Val Cys Lys Ile Ser Ser Pro Phe Ala Phe Thr Thr Pro Arg
            20                  25                  30

Trp Pro His Asn Asp Val Tyr Ile Ser Leu Pro Ile Thr Leu Leu His
                35                  40                  45

Phe Pro Ala His Phe Gln Lys Phe Ser Gln Pro Ala Glu Ile Ser Asp
50                  55                  60

Lys Arg Tyr Arg Val Leu Leu Cys Asn Gly His Gln Thr Pro Ala Leu
65                  70                  75                  80

Gln Gln Gly Thr His Ser Ser Arg Gln Val Thr Pro Leu Ser Leu Arg
                85                  90                  95

Ser Arg Ser Ser Thr Leu His Gln
                100

<210> SEQ ID NO 29
<211> LENGTH: 15
<212> TYPE: PRT
<213> ORGANISM: Type B PWD circovirus

<400> SEQUENCE: 29

Val Asp Met Met Arg Phe Asn Ile Asn Asp Phe Leu Pro Pro Gly
1               5                   10                  15

<210> SEQ ID NO 30
<211> LENGTH: 15
<212> TYPE: PRT
<213> ORGANISM: Type B PWD circovirus

<400> SEQUENCE: 30

Gln Gly Asp Arg Gly Val Gly Ser Ser Ala Val Ile Leu Asp Asp
1               5                   10                  15
```

```
<210> SEQ ID NO 31
<211> LENGTH: 15
<212> TYPE: PRT
<213> ORGANISM: Type B PWD circovirus

<400> SEQUENCE: 31

Gly Val Gly Ser Ser Ala Val Ile Leu Asp Asp Asn Phe Val Thr
1               5                   10                  15

<210> SEQ ID NO 32
<211> LENGTH: 15
<212> TYPE: PRT
<213> ORGANISM: Type B PWD circovirus

<400> SEQUENCE: 32

Val Asp His Val Gly Leu Gly Thr Ala Phe Glu Asn Ser Ile Tyr
1               5                   10                  15

<210> SEQ ID NO 33
<211> LENGTH: 8
<212> TYPE: DNA
<213> ORGANISM: Type A PWD circovirus

<400> SEQUENCE: 33 tgtggcga                                                                  8

<210> SEQ ID NO 34
<211> LENGTH: 8
<212> TYPE: DNA
<213> ORGANISM: Type A PWD circovirus

<400> SEQUENCE: 34 agtttcct                                                                  8

<210> SEQ ID NO 35
<211> LENGTH: 20
<212> TYPE: DNA
<213> ORGANISM: Type A PWD circovirus

<400> SEQUENCE: 35
tcatttagag ggtctttcag                                                    20

<210> SEQ ID NO 36
<211> LENGTH: 8
<212> TYPE: DNA
<213> ORGANISM: Type A PWD circovirus

<400> SEQUENCE: 36 gtcaacct                                                                  8

<210> SEQ ID NO 37
<211> LENGTH: 8
<212> TYPE: DNA
<213> ORGANISM: Type A PWD circovirus

<400> SEQUENCE: 37 gtggttgc                                                                  8

<210> SEQ ID NO 38
<211> LENGTH: 8
<212> TYPE: DNA
<213> ORGANISM: Type A PWD circovirus

<400> SEQUENCE: 38
```

```
agcccagg                                                            8

<210> SEQ ID NO 39
<211> LENGTH: 8
<212> TYPE: DNA
<213> ORGANISM: Type A PWD circovirus

<400> SEQUENCE: 39 ttggctgg                                                            8

<210> SEQ ID NO 40
<211> LENGTH: 12
<212> TYPE: DNA
<213> ORGANISM: Type A PWD circovirus

<400> SEQUENCE: 40
tctagctctg gt                                                      12

<210> SEQ ID NO 41
<211> LENGTH: 12
<212> TYPE: DNA
<213> ORGANISM: Type A PWD circovirus

<400> SEQUENCE: 41
atctcagctc gt                                                      12

<210> SEQ ID NO 42
<211> LENGTH: 12
<212> TYPE: DNA
<213> ORGANISM: Type A PWD circovirus

<400> SEQUENCE: 42
tgtcctcctc tt                                                      12

<210> SEQ ID NO 43
<211> LENGTH: 8
<212> TYPE: DNA
<213> ORGANISM: Type A PWD circovirus

<400> SEQUENCE: 43 tctctaga                                                            8

<210> SEQ ID NO 44
<211> LENGTH: 8
<212> TYPE: DNA
<213> ORGANISM: Type A PWD circovirus

<400> SEQUENCE: 44 tgtaccaa                                                            8

<210> SEQ ID NO 45
<211> LENGTH: 8
<212> TYPE: DNA
<213> ORGANISM: Type A PWD circovirus

<400> SEQUENCE: 45 tccgtctt                                                            8

<210> SEQ ID NO 46
<211> LENGTH: 20
<212> TYPE: DNA
<213> ORGANISM: Primer

<400> SEQUENCE: 46
```

```
gtgtgctcga cattggtgtg                                              20

<210> SEQ ID NO 47
<211> LENGTH: 20
<212> TYPE: DNA
<213> ORGANISM: Primer

<400> SEQUENCE: 47
tggaatgtta acgagctgag                                              20

<210> SEQ ID NO 48
<211> LENGTH: 20
<212> TYPE: DNA
<213> ORGANISM: Primer

<400> SEQUENCE: 48
ctcgcagcca tcttggaatg                                              20

<210> SEQ ID NO 49
<211> LENGTH: 20
<212> TYPE: DNA
<213> ORGANISM: Primer

<400> SEQUENCE: 49
cgcgcgtaat acgactcact                                              20

<210> SEQ ID NO 50
<211> LENGTH: 26
<212> TYPE: DNA
<213> ORGANISM: Primer

<400> SEQUENCE: 50
cctgtctact gctgtgagta ccttgt                                       26

<210> SEQ ID NO 51
<211> LENGTH: 26
<212> TYPE: DNA
<213> ORGANISM: Primer

<400> SEQUENCE: 51
gcagtagaca ggtcactccg ttgtcc                                       26

<210> SEQ ID NO 52
<211> LENGTH: 20
<212> TYPE: DNA
<213> ORGANISM: Primer

<400> SEQUENCE: 52
tggaatgtta actacctcaa                                              20

<210> SEQ ID NO 53
<211> LENGTH: 23
<212> TYPE: DNA
<213> ORGANISM: Primer

<400> SEQUENCE: 53
ggcggcgcca tctgtaacgg ttt                                          23

<210> SEQ ID NO 54
<211> LENGTH: 23
<212> TYPE: DNA
<213> ORGANISM: Primer
```

-continued

<400> SEQUENCE: 54
gatggcgccg aaagacgggt atc					23

<210> SEQ ID NO 55
<211> LENGTH: 15
<212> TYPE: PRT
<213> ORGANISM: Type B PWD circovirus

<400> SEQUENCE: 55

Asn Val Asn Glu Leu Arg Phe Asn Ile Gly Gln Phe Leu Pro Pro
1               5                   10                  15

<210> SEQ ID NO 56
<211> LENGTH: 14
<212> TYPE: PRT
<213> ORGANISM: Type A PWD circovirus

<400> SEQUENCE: 56

Thr Ser Asn Gln Arg Gly Val Gly Ser Thr Val Val Ile Leu
1               5                   10

<210> SEQ ID NO 57
<211> LENGTH: 15
<212> TYPE: PRT
<213> ORGANISM: Type A PWD circovirus

<400> SEQUENCE: 57

Arg Gly Val Gly Ser Thr Val Val Ile Leu Asp Ala Asn Phe Val
1               5                   10                  15

<210> SEQ ID NO 58
<211> LENGTH: 15
<212> TYPE: PRT
<213> ORGANISM: Type B PWD circovirus

<400> SEQUENCE: 58

Phe Thr Ile Asp Tyr Phe Gln Pro Asn Asn Lys Arg Asn Gln Leu
1               5                   10                  15

<210> SEQ ID NO 59
<211> LENGTH: 15
<212> TYPE: PRT
<213> ORGANISM: Type A PWD circovirus

<400> SEQUENCE: 59

Asp Gln Thr Ile Asp Trp Phe Gln Pro Asn Asn Lys Arg Asn Gln
1               5                   10                  15

<210> SEQ ID NO 60
<211> LENGTH: 15
<212> TYPE: PRT
<213> ORGANISM: Type A PWD circovirus

<400> SEQUENCE: 60

Asn Val Glu His Thr Gly Leu Gly Tyr Ala Leu Gln Asn Ala Thr
1               5                   10                  15

<210> SEQ ID NO 61
<211> LENGTH: 15
<212> TYPE: PRT
<213> ORGANISM: Type B PWD circovirus

<400> SEQUENCE: 61

His Arg Pro Arg Ser His Leu Gly Gln Ile Leu Arg Arg Arg Pro

-continued

<210> SEQ ID NO 62
<211> LENGTH: 15
<212> TYPE: PRT
<213> ORGANISM: Type B PWD circovirus

<400> SEQUENCE: 62

Ser His Leu Gly Gln Ile Leu Arg Arg Arg Pro Trp Leu Val His
1               5                   10                  15

<210> SEQ ID NO 63
<211> LENGTH: 15
<212> TYPE: PRT
<213> ORGANISM: Type B PWD circovirus

<400> SEQUENCE: 63

Gln Ile Leu Arg Arg Arg Pro Trp Leu Val His Pro Arg His Arg
1 5 10 15

<210> SEQ ID NO 64
<211> LENGTH: 15
<212> TYPE: PRT
<213> ORGANISM: Type B PWD circovirus

<400> SEQUENCE: 64

Arg Arg Pro Trp Leu Val His Pro Arg His Arg Tyr Arg Trp Arg
1 5 10 15

<210> SEQ ID NO 65
<211> LENGTH: 15
<212> TYPE: PRT
<213> ORGANISM: Type B PWD circovirus

<400> SEQUENCE: 65

Leu Val His Pro Arg His Arg Tyr Arg Trp Arg Arg Lys Asn Gly
1 5 10 15

<210> SEQ ID NO 66
<211> LENGTH: 15
<212> TYPE: PRT
<213> ORGANISM: Type B PWD circovirus

<400> SEQUENCE: 66

Arg His Arg Tyr Arg Trp Arg Arg Lys Asn Gly Ile Phe Asn Thr
1 5 10 15

<210> SEQ ID NO 67
<211> LENGTH: 15
<212> TYPE: PRT
<213> ORGANISM: Type B PWD circovirus

<400> SEQUENCE: 67

Arg Trp Arg Arg Lys Asn Gly Ile Phe Asn Thr Arg Leu Ser Arg
1 5 10 15

<210> SEQ ID NO 68
<211> LENGTH: 15
<212> TYPE: PRT
<213> ORGANISM: Type B PWD circovirus

<400> SEQUENCE: 68

Lys Asn Gly Ile Phe Asn Thr Arg Leu Ser Arg Thr Phe Gly Tyr
1 5 10 15

<210> SEQ ID NO 69
<211> LENGTH: 15
<212> TYPE: PRT
<213> ORGANISM: Type B PWD circovirus

<400> SEQUENCE: 69

Phe Asn Thr Arg Leu Ser Arg Thr Phe Gly Tyr Thr Val Lys Arg
1               5                   10                  15

<210> SEQ ID NO 70
<211> LENGTH: 15
<212> TYPE: PRT
<213> ORGANISM: Type B PWD circovirus

<400> SEQUENCE: 70

Leu Ser Arg Thr Phe Gly Tyr Thr Val Lys Arg Thr Thr Val Arg
1               5                   10                  15

<210> SEQ ID NO 71
<211> LENGTH: 15
<212> TYPE: PRT
<213> ORGANISM: Type B PWD circovirus

<400> SEQUENCE: 71

```
Phe Gly Tyr Thr Val Lys Arg Thr Thr Val Arg Thr Pro Ser Trp
1               5                   10                  15
```

<210> SEQ ID NO 72
<211> LENGTH: 15
<212> TYPE: PRT
<213> ORGANISM: Type B PWD circovirus

<400> SEQUENCE: 72

```
Val Lys Arg Thr Thr Val Arg Thr Pro Ser Trp Ala Val Asp Met
1               5                   10                  15
```

<210> SEQ ID NO 73
<211> LENGTH: 15
<212> TYPE: PRT
<213> ORGANISM: Type B PWD circovirus

<400> SEQUENCE: 73

```
Thr Val Arg Thr Pro Ser Trp Ala Val Asp Met Met Arg Phe Asn
1               5                   10                  15
```

<210> SEQ ID NO 74
<211> LENGTH: 15
<212> TYPE: PRT
<213> ORGANISM: Type B PWD circovirus

<400> SEQUENCE: 74

```
Pro Ser Trp Ala Val Asp Met Met Arg Phe Asn Ile Asn Asp Phe
1               5                   10                  15
```

<210> SEQ ID NO 75
<211> LENGTH: 15
<212> TYPE: PRT
<213> ORGANISM: Type B PWD circovirus

<400> SEQUENCE: 75

```
Arg Phe Asn Ile Asn Asp Phe Leu Pro Pro Gly Gly Gly Ser Asn
1               5                   10                  15
```

<210> SEQ ID NO 76

```
<211> LENGTH: 15
<212> TYPE: PRT
<213> ORGANISM: Type B PWD circovirus

<400> SEQUENCE: 76

Asn Asp Phe Leu Pro Pro Gly Gly Gly Ser Asn Pro Arg Ser Val
1               5                   10                  15

<210> SEQ ID NO 77
<211> LENGTH: 15
<212> TYPE: PRT
<213> ORGANISM: Type B PWD circovirus

<400> SEQUENCE: 77

Pro Pro Gly Gly Gly Ser Asn Pro Arg Ser Val Pro Phe Glu Tyr
1               5                   10                  15

<210> SEQ ID NO 78
<211> LENGTH: 15
<212> TYPE: PRT
<213> ORGANISM: Type B PWD circovirus

<400> SEQUENCE: 78

Gly Ser Asn Pro Arg Ser Val Pro Phe Glu Tyr Tyr Arg Ile Arg
1               5                   10                  15

<210> SEQ ID NO 79
<211> LENGTH: 15
<212> TYPE: PRT
<213> ORGANISM: Type B PWD circovirus

<400> SEQUENCE: 79

Arg Ser Val Pro Phe Glu Tyr Tyr Arg Ile Arg Lys Val Lys Val
1               5                   10                  15

<210> SEQ ID NO 80
<211> LENGTH: 15
<212> TYPE: PRT
<213> ORGANISM: Type B PWD circovirus

<400> SEQUENCE: 80

Phe Glu Tyr Tyr Arg Ile Arg Lys Val Lys Val Glu Phe Trp Pro
1               5                   10                  15

<210> SEQ ID NO 81
<211> LENGTH: 15
<212> TYPE: PRT
<213> ORGANISM: Type B PWD circovirus

<400> SEQUENCE: 81

Arg Ile Arg Lys Val Lys Val Glu Phe Trp Pro Cys Ser Pro Ile
1               5                   10                  15

<210> SEQ ID NO 82
<211> LENGTH: 15
<212> TYPE: PRT
<213> ORGANISM: Type B PWD circovirus

<400> SEQUENCE: 82

Val Lys Val Glu Phe Trp Pro Cys Ser Pro Ile Thr Gln Gly Asp
1               5                   10                  15

<210> SEQ ID NO 83
<211> LENGTH: 15
<212> TYPE: PRT
```

-continued

<213> ORGANISM: Type B PWD circovirus

<400> SEQUENCE: 83

Phe Trp Pro Cys Ser Pro Ile Thr Gln Gly Asp Arg Gly Val Gly
1               5                   10                  15

<210> SEQ ID NO 84
<211> LENGTH: 15
<212> TYPE: PRT
<213> ORGANISM: Type A PWD circovirus

<400> SEQUENCE: 84

Thr Arg Pro Arg Ser His Leu Gly Asn Ile Leu Arg Arg Arg Pro
1               5                   10                  15

<210> SEQ ID NO 85
<211> LENGTH: 15
<212> TYPE: PRT
<213> ORGANISM: Type A PWD circovirus

<400> SEQUENCE: 85

Ser His Leu Gly Asn Ile Leu Arg Arg Arg Pro Tyr Leu Val His
1               5                   10                  15

<210> SEQ ID NO 86
<211> LENGTH: 15
<212> TYPE: PRT
<213> ORGANISM: Type A PWD circovirus

<400> SEQUENCE: 86

Asn Ile Leu Arg Arg Arg Pro Tyr Leu Val His Pro Ala Phe Arg
1               5                   10                  15

<210> SEQ ID NO 87
<211> LENGTH: 15
<212> TYPE: PRT
<213> ORGANISM: Type A PWD circovirus

<400> SEQUENCE: 87

Arg Arg Pro Tyr Leu Val His Pro Ala Phe Arg Asn Arg Tyr Arg
1               5                   10                  15

<210> SEQ ID NO 88
<211> LENGTH: 15
<212> TYPE: PRT
<213> ORGANISM: Type A PWD circovirus

<400> SEQUENCE: 88

Leu Val His Pro Ala Phe Arg Asn Arg Tyr Arg Trp Arg Arg Lys
1               5                   10                  15

<210> SEQ ID NO 89
<211> LENGTH: 15
<212> TYPE: PRT
<213> ORGANISM: Type A PWD circovirus

<400> SEQUENCE: 89

Ala Phe Arg Asn Arg Tyr Arg Trp Arg Arg Lys Thr Gly Ile Phe
1               5                   10                  15

<210> SEQ ID NO 90
<211> LENGTH: 15
<212> TYPE: PRT
<213> ORGANISM: Type A PWD circovirus

```
<400> SEQUENCE: 90

Arg Tyr Arg Trp Arg Arg Lys Thr Gly Ile Phe Asn Ser Arg Leu
1               5                   10                  15

<210> SEQ ID NO 91
<211> LENGTH: 15
<212> TYPE: PRT
<213> ORGANISM: Type A PWD circovirus

<400> SEQUENCE: 91

Arg Arg Lys Thr Gly Ile Phe Asn Ser Arg Leu Ser Arg Glu Phe
1               5                   10                  15

<210> SEQ ID NO 92
<211> LENGTH: 15
<212> TYPE: PRT
<213> ORGANISM: Type A PWD circovirus

<400> SEQUENCE: 92

Gly Ile Phe Asn Ser Arg Leu Ser Arg Glu Phe Val Leu Thr Ile
1               5                   10                  15

<210> SEQ ID NO 93
<211> LENGTH: 15
<212> TYPE: PRT
<213> ORGANISM: Type A PWD circovirus

<400> SEQUENCE: 93

Ser Arg Leu Ser Arg Glu Phe Val Leu Thr Ile Arg Gly Gly His
1               5                   10                  15

<210> SEQ ID NO 94
<211> LENGTH: 15
<212> TYPE: PRT
<213> ORGANISM: Type A PWD circovirus

<400> SEQUENCE: 94

Arg Glu Phe Val Leu Thr Ile Arg Gly Gly His Ser Gln Pro Ser
1               5                   10                  15

<210> SEQ ID NO 95
<211> LENGTH: 15
<212> TYPE: PRT
<213> ORGANISM: Type A PWD circovirus

<400> SEQUENCE: 95

Leu Thr Ile Arg Gly Gly His Ser Gln Pro Ser Trp Asn Val Asn
1               5                   10                  15

<210> SEQ ID NO 96
<211> LENGTH: 15
<212> TYPE: PRT
<213> ORGANISM: Type A PWD circovirus

<400> SEQUENCE: 96

Gly Gly His Ser Gln Pro Ser Trp Asn Val Asn Glu Leu Arg Phe
1               5                   10                  15

<210> SEQ ID NO 97
<211> LENGTH: 15
<212> TYPE: PRT
<213> ORGANISM: Type A PWD circovirus

<400> SEQUENCE: 97
```

```
Gln Pro Ser Trp Asn Val Asn Glu Leu Arg Phe Asn Ile Gly Gln
1               5                   10                  15

<210> SEQ ID NO 98
<211> LENGTH: 15
<212> TYPE: PRT
<213> ORGANISM: Type A PWD circovirus

<400> SEQUENCE: 98

Asn Val Asn Glu Leu Arg Phe Asn Ile Gly Gln Phe Leu Pro Pro
1               5                   10                  15

<210> SEQ ID NO 99
<211> LENGTH: 15
<212> TYPE: PRT
<213> ORGANISM: Type A PWD circovirus

<400> SEQUENCE: 99

Leu Arg Phe Asn Ile Gly Gln Phe Leu Pro Pro Ser Gly Gly Thr
1               5                   10                  15

<210> SEQ ID NO 100
<211> LENGTH: 15
<212> TYPE: PRT
<213> ORGANISM: Type A PWD circovirus

<400> SEQUENCE: 100

Ile Gly Gln Phe Leu Pro Pro Ser Gly Gly Thr Asn Pro Leu Pro
1               5                   10                  15

<210> SEQ ID NO 101
<211> LENGTH: 15
<212> TYPE: PRT
<213> ORGANISM: Type A PWD circovirus

<400> SEQUENCE: 101

Leu Pro Pro Ser Gly Gly Thr Asn Pro Leu Pro Leu Pro Phe Gln
1               5                   10                  15

<210> SEQ ID NO 102
<211> LENGTH: 15
<212> TYPE: PRT
<213> ORGANISM: Type A PWD circovirus

<400> SEQUENCE: 102

Gly Gly Thr Asn Pro Leu Pro Leu Pro Phe Gln Tyr Tyr Arg Ile
1               5                   10                  15

<210> SEQ ID NO 103
<211> LENGTH: 15
<212> TYPE: PRT
<213> ORGANISM: Type A PWD circovirus

<400> SEQUENCE: 103

Pro Leu Pro Leu Pro Phe Gln Tyr Tyr Arg Ile Arg Lys Ala Lys
1               5                   10                  15

<210> SEQ ID NO 104
<211> LENGTH: 15
<212> TYPE: PRT
<213> ORGANISM: Type A PWD circovirus

<400> SEQUENCE: 104

Pro Phe Gln Tyr Tyr Arg Ile Arg Lys Ala Lys Tyr Glu Phe Tyr
1               5                   10                  15
```

<210> SEQ ID NO 105
<211> LENGTH: 15
<212> TYPE: PRT
<213> ORGANISM: Type A PWD circovirus

<400> SEQUENCE: 105

Tyr Arg Ile Arg Lys Ala Lys Tyr Glu Phe Tyr Pro Arg Asp Pro
1               5                   10                  15

<210> SEQ ID NO 106
<211> LENGTH: 15
<212> TYPE: PRT
<213> ORGANISM: Type A PWD circovirus

<400> SEQUENCE: 106

Lys Ala Lys Tyr Glu Phe Tyr Pro Arg Asp Pro Ile Thr Ser Asn
1               5                   10                  15

<210> SEQ ID NO 107
<211> LENGTH: 15
<212> TYPE: PRT
<213> ORGANISM: Type A PWD circovirus

<400> SEQUENCE: 107

Glu Phe Tyr Pro Arg Asp Pro Ile Thr Ser Asn Gln Arg Gly Val
1               5                   10                  15

<210> SEQ ID NO 108
<211> LENGTH: 15
<212> TYPE: PRT
<213> ORGANISM: Type A PWD circovirus

<400> SEQUENCE: 108

Arg Asp Pro Ile Thr Ser Asn Gln Arg Gly Val Gly Ser Thr Val
1               5                   10                  15

<210> SEQ ID NO 109
<211> LENGTH: 15
<212> TYPE: PRT
<213> ORGANISM: Type A PWD circovirus

<400> SEQUENCE: 109

Thr Ser Asn Gln Arg Gly Val Gly Ser Thr Val Val Ile Leu Asp
1               5                   10                  15

<210> SEQ ID NO 110
<211> LENGTH: 15
<212> TYPE: PRT
<213> ORGANISM: Type B PWD circovirus

<400> SEQUENCE: 110

Gly Val Gly Ser Ser Ala Val Ile Leu Asp Asp Asn Phe Val Thr
1               5                   10                  15

<210> SEQ ID NO 111
<211> LENGTH: 15
<212> TYPE: PRT
<213> ORGANISM: Type B PWD circovirus

<400> SEQUENCE: 111

Ser Ala Val Ile Leu Asp Asp Asn Phe Val Thr Lys Ala Thr Ala
1               5                   10                  15

```
<210> SEQ ID NO 112
<211> LENGTH: 15
<212> TYPE: PRT
<213> ORGANISM: Type B PWD circovirus

<400> SEQUENCE: 112

Leu Asp Asp Asn Phe Val Thr Lys Ala Thr Ala Leu Thr Tyr Asp
1               5                   10                  15

<210> SEQ ID NO 113
<211> LENGTH: 15
<212> TYPE: PRT
<213> ORGANISM: Type B PWD circovirus

<400> SEQUENCE: 113

Phe Val Thr Lys Ala Thr Ala Leu Thr Tyr Asp Pro Tyr Val Asn
1               5                   10                  15

<210> SEQ ID NO 114
<211> LENGTH: 15
<212> TYPE: PRT
<213> ORGANISM: Type B PWD circovirus

<400> SEQUENCE: 114

Ala Thr Ala Leu Thr Tyr Asp Pro Tyr Val Asn Tyr Ser Ser Arg
1               5                   10                  15

<210> SEQ ID NO 115
<211> LENGTH: 15
<212> TYPE: PRT
<213> ORGANISM: Type B PWD circovirus

<400> SEQUENCE: 115

Thr Tyr Asp Pro Tyr Val Asn Tyr Ser Ser Arg His Thr Ile Thr
1               5                   10                  15

<210> SEQ ID NO 116
<211> LENGTH: 15
<212> TYPE: PRT
<213> ORGANISM: Type B PWD circovirus

<400> SEQUENCE: 116

Tyr Val Asn Tyr Ser Ser Arg His Thr Ile Thr Gln Pro Phe Ser
1               5                   10                  15

<210> SEQ ID NO 117
<211> LENGTH: 15
<212> TYPE: PRT
<213> ORGANISM: Type B PWD circovirus

<400> SEQUENCE: 117

Ser Ser Arg His Thr Ile Thr Gln Pro Phe Ser Tyr His Ser Arg
1               5                   10                  15

<210> SEQ ID NO 118
<211> LENGTH: 15
<212> TYPE: PRT
<213> ORGANISM: Type B PWD circovirus

<400> SEQUENCE: 118

Thr Ile Thr Gln Pro Phe Ser Tyr His Ser Arg Tyr Phe Thr Pro
1               5                   10                  15

<210> SEQ ID NO 119
<211> LENGTH: 15
```

<210> SEQ ID NO 119
<211> LENGTH: 15
<212> TYPE: PRT
<213> ORGANISM: Type B PWD circovirus

<400> SEQUENCE: 119

Pro Phe Ser Tyr His Ser Arg Tyr Phe Thr Pro Lys Pro Val Leu
1               5                   10                  15

<210> SEQ ID NO 120
<211> LENGTH: 15
<212> TYPE: PRT
<213> ORGANISM: Type B PWD circovirus

<400> SEQUENCE: 120

His Ser Arg Tyr Phe Thr Pro Lys Pro Val Leu Asp Phe Thr Ile
1               5                   10                  15

<210> SEQ ID NO 121
<211> LENGTH: 15
<212> TYPE: PRT
<213> ORGANISM: Type B PWD circovirus

<400> SEQUENCE: 121

Phe Thr Pro Lys Pro Val Leu Asp Phe Thr Ile Asp Tyr Phe Gln
1               5                   10                  15

<210> SEQ ID NO 122
<211> LENGTH: 15
<212> TYPE: PRT
<213> ORGANISM: Type B PWD circovirus

<400> SEQUENCE: 122

Pro Val Leu Asp Phe Thr Ile Asp Tyr Phe Gln Pro Asn Asn Lys
1               5                   10                  15

<210> SEQ ID NO 123
<211> LENGTH: 15
<212> TYPE: PRT
<213> ORGANISM: Type B PWD circovirus

<400> SEQUENCE: 123

Phe Thr Ile Asp Tyr Phe Gln Pro Asn Asn Lys Arg Asn Gln Leu
1               5                   10                  15

<210> SEQ ID NO 124
<211> LENGTH: 15
<212> TYPE: PRT
<213> ORGANISM: Type B PWD circovirus

<400> SEQUENCE: 124

Tyr Phe Gln Pro Asn Asn Lys Arg Asn Gln Leu Trp Leu Arg Leu
1               5                   10                  15

<210> SEQ ID NO 125
<211> LENGTH: 15
<212> TYPE: PRT
<213> ORGANISM: Type B PWD circovirus

<400> SEQUENCE: 125

Asn Asn Lys Arg Asn Gln Leu Trp Leu Arg Leu Gln Thr Ala Gly
1               5                   10                  15

<210> SEQ ID NO 126
<211> LENGTH: 15
<212> TYPE: PRT
<213> ORGANISM: Type B PWD circovirus

<400> SEQUENCE: 126

Asn Gln Leu Trp Leu Arg Leu Gln Thr Ala Gly Asn Val Asp His
1               5                   10                  15

<210> SEQ ID NO 127
<211> LENGTH: 15
<212> TYPE: PRT
<213> ORGANISM: Type B PWD circovirus

<400> SEQUENCE: 127

Leu Arg Leu Gln Thr Ala Gly Asn Val Asp His Val Gly Leu Gly
1               5                   10                  15

<210> SEQ ID NO 128
<211> LENGTH: 15
<212> TYPE: PRT
<213> ORGANISM: Type B PWD circovirus

<400> SEQUENCE: 128

Thr Ala Gly Asn Val Asp His Val Gly Leu Gly Thr Ala Phe Glu
1               5                   10                  15

<210> SEQ ID NO 129
<211> LENGTH: 15
<212> TYPE: PRT
<213> ORGANISM: Type B PWD circovirus

<400> SEQUENCE: 129

Gly Leu Gly Thr Ala Phe Glu Asn Ser Ile Tyr Asp Gln Glu Tyr
1               5                   10                  15

<210> SEQ ID NO 130
<211> LENGTH: 15
<212> TYPE: PRT
<213> ORGANISM: Type B PWD circovirus

<400> SEQUENCE: 130

Ala Phe Glu Asn Ser Ile Tyr Asp Gln Glu Tyr Asn Ile Arg Val
1               5                   10                  15

<210> SEQ ID NO 131
<211> LENGTH: 15
<212> TYPE: PRT
<213> ORGANISM: Type B PWD circovirus

<400> SEQUENCE: 131

Ser Ile Tyr Asp Gln Glu Tyr Asn Ile Arg Val Thr Met Tyr Val
1               5                   10                  15

<210> SEQ ID NO 132
<211> LENGTH: 15
<212> TYPE: PRT
<213> ORGANISM: Type B PWD circovirus

<400> SEQUENCE: 132

Gln Glu Tyr Asn Ile Arg Val Thr Met Tyr Val Gln Phe Arg Glu
1               5                   10                  15

<210> SEQ ID NO 133
<211> LENGTH: 15
<212> TYPE: PRT
<213> ORGANISM: Type B PWD circovirus

<400> SEQUENCE: 133

Ile Arg Val Thr Met Tyr Val Gln Phe Arg Glu Phe Asn Phe Lys
1               5                   10                  15

<210> SEQ ID NO 134
<211> LENGTH: 15
<212> TYPE: PRT
<213> ORGANISM: Type B PWD circovirus

<400> SEQUENCE: 134

Met Tyr Val Gln Phe Arg Glu Phe Asn Phe Lys Asp Pro Pro Leu
1               5                   10                  15

<210> SEQ ID NO 135
<211> LENGTH: 15
<212> TYPE: PRT
<213> ORGANISM: Type B PWD circovirus

<400> SEQUENCE: 135

Val Gln Phe Arg Glu Phe Asn Phe Lys Asp Pro Pro Leu Asn Pro
1               5                   10                  15

<210> SEQ ID NO 136
<211> LENGTH: 15
<212> TYPE: PRT
<213> ORGANISM: Type A PWD circovirus

<400> SEQUENCE: 136

Arg Gly Val Gly Ser Thr Val Val Ile Leu Asp Ala Asn Phe Val
1               5                   10                  15

<210> SEQ ID NO 137
<211> LENGTH: 15
<212> TYPE: PRT
<213> ORGANISM: Type A PWD circovirus

<400> SEQUENCE: 137

Ser Thr Val Val Ile Leu Asp Ala Asn Phe Val Thr Pro Ser Thr
1               5                   10                  15

<210> SEQ ID NO 138
<211> LENGTH: 15
<212> TYPE: PRT
<213> ORGANISM: Type A PWD circovirus

<400> SEQUENCE: 138

Ile Leu Asp Ala Asn Phe Val Thr Pro Ser Thr Asn Leu Ala Tyr
1               5                   10                  15

<210> SEQ ID NO 139
<211> LENGTH: 15
<212> TYPE: PRT
<213> ORGANISM: Type A PWD circovirus

<400> SEQUENCE: 139

Asn Phe Val Thr Pro Ser Thr Asn Leu Ala Tyr Asp Pro Tyr Ile
1               5                   10                  15

<210> SEQ ID NO 140
<211> LENGTH: 15
<212> TYPE: PRT
<213> ORGANISM: Type A PWD circovirus

<400> SEQUENCE: 140

Pro Ser Thr Asn Leu Ala Tyr Asp Pro Tyr Ile Asn Tyr Ser Ser

```
            1               5                  10                  15
```

<210> SEQ ID NO 141
<211> LENGTH: 15
<212> TYPE: PRT
<213> ORGANISM: Type A PWD circovirus

<400> SEQUENCE: 141

```
Leu Ala Tyr Asp Pro Tyr Ile Asn Tyr Ser Ser Arg His Thr Ile
1               5                  10                  15
```

<210> SEQ ID NO 142
<211> LENGTH: 15
<212> TYPE: PRT
<213> ORGANISM: Type A PWD circovirus

<400> SEQUENCE: 142

```
Pro Tyr Ile Asn Tyr Ser Ser Arg His Thr Ile Arg Gln Pro Phe
1               5                  10                  15
```

<210> SEQ ID NO 143
<211> LENGTH: 15
<212> TYPE: PRT
<213> ORGANISM: Type A PWD circovirus

<400> SEQUENCE: 143

```
Tyr Ser Ser Arg His Thr Ile Arg Gln Pro Phe Thr Tyr His Ser
1               5                  10                  15
```

<210> SEQ ID NO 144
<211> LENGTH: 15
<212> TYPE: PRT
<213> ORGANISM: Type A PWD circovirus

<400> SEQUENCE: 144

```
His Thr Ile Arg Gln Pro Phe Thr Tyr His Ser Arg Tyr Phe Thr
1               5                  10                  15
```

<210> SEQ ID NO 145
<211> LENGTH: 15
<212> TYPE: PRT
<213> ORGANISM: Type A PWD circovirus

<400> SEQUENCE: 145

```
Gln Pro Phe Thr Tyr His Ser Arg Tyr Phe Thr Pro Lys Pro Glu
1               5                  10                  15
```

<210> SEQ ID NO 146
<211> LENGTH: 15
<212> TYPE: PRT
<213> ORGANISM: Type A PWD circovirus

<400> SEQUENCE: 146

```
Tyr His Ser Arg Tyr Phe Thr Pro Lys Pro Glu Leu Asp Gln Thr
1               5                  10                  15
```

<210> SEQ ID NO 147
<211> LENGTH: 15
<212> TYPE: PRT
<213> ORGANISM: Type A PWD circovirus

<400> SEQUENCE: 147

```
Tyr Phe Thr Pro Lys Pro Glu Leu Asp Gln Thr Ile Asp Trp Phe
1               5                  10                  15
```

```
<210> SEQ ID NO 148
<211> LENGTH: 15
<212> TYPE: PRT
<213> ORGANISM: Type A PWD circovirus

<400> SEQUENCE: 148

Lys Pro Glu Leu Asp Gln Thr Ile Asp Trp Phe Gln Pro Asn Asn
1               5                   10                  15

<210> SEQ ID NO 149
<211> LENGTH: 15
<212> TYPE: PRT
<213> ORGANISM: Type A PWD circovirus

<400> SEQUENCE: 149

Asp Gln Thr Ile Asp Trp Phe Gln Pro Asn Asn Lys Arg Asn Gln
1               5                   10                  15

<210> SEQ ID NO 150
<211> LENGTH: 15
<212> TYPE: PRT
<213> ORGANISM: Type A PWD circovirus

<400> SEQUENCE: 150

Asp Trp Phe Gln Pro Asn Asn Lys Arg Asn Gln Leu Trp Leu His
1               5                   10                  15

<210> SEQ ID NO 151
<211> LENGTH: 15
<212> TYPE: PRT
<213> ORGANISM: Type A PWD circovirus

<400> SEQUENCE: 151

Pro Asn Asn Lys Arg Asn Gln Leu Trp Leu His Leu Asn Thr His
1               5                   10                  15

<210> SEQ ID NO 152
<211> LENGTH: 15
<212> TYPE: PRT
<213> ORGANISM: Type A PWD circovirus

<400> SEQUENCE: 152

Arg Asn Gln Leu Trp Leu His Leu Asn Thr His Thr Asn Val Glu
1               5                   10                  15

<210> SEQ ID NO 153
<211> LENGTH: 15
<212> TYPE: PRT
<213> ORGANISM: Type A PWD circovirus

<400> SEQUENCE: 153

Trp Leu His Leu Asn Thr His Thr Asn Val Glu His Thr Gly Leu
1               5                   10                  15

<210> SEQ ID NO 154
<211> LENGTH: 15
<212> TYPE: PRT
<213> ORGANISM: Type A PWD circovirus

<400> SEQUENCE: 154

Asn Thr His Thr Asn Val Glu His Thr Gly Leu Gly Tyr Ala Leu
1               5                   10                  15

<210> SEQ ID NO 155
```

```
<211> LENGTH: 15
<212> TYPE: PRT
<213> ORGANISM: Type A PWD circovirus

<400> SEQUENCE: 155

Asn Val Glu His Thr Gly Leu Gly Tyr Ala Leu Gln Asn Ala Thr
1               5                   10                  15

<210> SEQ ID NO 156
<211> LENGTH: 15
<212> TYPE: PRT
<213> ORGANISM: Type A PWD circovirus

<400> SEQUENCE: 156

Thr Gly Leu Gly Tyr Ala Leu Gln Asn Ala Thr Thr Ala Gln Asn
1               5                   10                  15

<210> SEQ ID NO 157
<211> LENGTH: 15
<212> TYPE: PRT
<213> ORGANISM: Type A PWD circovirus

<400> SEQUENCE: 157

Tyr Ala Leu Gln Asn Ala Thr Thr Ala Gln Asn Tyr Val Val Arg
1               5                   10                  15

<210> SEQ ID NO 158
<211> LENGTH: 15
<212> TYPE: PRT
<213> ORGANISM: Type A PWD circovirus

<400> SEQUENCE: 158

Asn Ala Thr Thr Ala Gln Asn Tyr Val Val Arg Leu Thr Ile Tyr
1               5                   10                  15

<210> SEQ ID NO 159
<211> LENGTH: 15
<212> TYPE: PRT
<213> ORGANISM: Type A PWD circovirus

<400> SEQUENCE: 159

Ala Gln Asn Tyr Val Val Arg Leu Thr Ile Tyr Val Gln Phe Arg
1               5                   10                  15

<210> SEQ ID NO 160
<211> LENGTH: 15
<212> TYPE: PRT
<213> ORGANISM: Type A PWD circovirus

<400> SEQUENCE: 160

Val Val Arg Leu Thr Ile Tyr Val Gln Phe Arg Glu Phe Ile Leu
1               5                   10                  15

<210> SEQ ID NO 161
<211> LENGTH: 15
<212> TYPE: PRT
<213> ORGANISM: Type A PWD circovirus

<400> SEQUENCE: 161

Thr Ile Tyr Val Gln Phe Arg Glu Phe Ile Leu Lys Asp Pro Leu
1               5                   10                  15

<210> SEQ ID NO 162
<211> LENGTH: 15
<212> TYPE: PRT
```

<210> SEQ ID NO 162
<211> LENGTH: 15
<212> TYPE: PRT
<213> ORGANISM: Type A PWD circovirus

<400> SEQUENCE: 162

Tyr Val Gln Phe Arg Glu Phe Ile Leu Lys Asp Pro Leu Asn Glu
1               5                   10                  15

<210> SEQ ID NO 163
<211> LENGTH: 1759
<212> TYPE: DNA
<213> ORGANISM: Type A PWD circovirus

<400> SEQUENCE: 163

```
accagcgcac ttcggcagcg gcagcacctc ggcagcgtca gtgaaaatgc caagcaagaa        60
aagcggcccg caaccccata agaggtgggt gttcacccct aataatcctt ccgaggagga       120
gaaaaacaaa atacgggagc ttccaatctc ccttttttgat tattttgttt gcggagagga     180
aggtttggaa gagggtagaa ctcctcacct ccagggggttt gcgaattttg ctaagaagca     240
gacttttaac aaggtgaagt ggtatttttgg tgcccgctgc cacatcgaga aagcgaaagg     300
aaccgaccag cagaataaag aatactgcag taaagaaggc cacatactta tcgagtgtgg     360
agctccgcgg aaccagggga agcgcagcga cctgtctact gctgtgagta cccttttgga     420
gacggggtct ttggtgactg tagccgagca gttccctgta acgtatgtga aaatttccg       480
cgggctggct gaacttttga aagtgagcgg gaagatgcag aagcgtgatt ggaagacagc      540
tgtacacgtc atagtgggcc cgcccggttg tgggaagagc cagtgggccc gtaattttgc     600
tgagcctagg gacacctact ggaagcctag tagaaataag tggtgggatg gatatcatgg     660
agaagaagtt gttgttttgg atgatttttta tggctggtta ccttgggatg atctactgag    720
actgtgtgac cggtatccat tgactgtaga gactaaaggg ggtactgttc ctttttttggc   780
ccgcagtatt ttgattacca gcaatcaggc ccccaggaa tggtactcct caactgctgt       840
cccagctgta gaagctctct atcggaggat tactactttg caattttgga agactgctgg     900
agaacaatcc acggaggtac ccgaaggccg atttgaagca gtggacccac cctgtgccct     960
tttcccatat aaaataaatt actgagtctt ttttgttatc acatcgtaat ggttttatt    1020
tttatttatt tagagggtct tttaggataa attctctgaa ttgtacataa atagtcagcc    1080
ttaccacata attttgggct gtggttgcat tttggagcgc atagcccagg cctgtgtgct    1140
cgacattggt gtgggtattt aaatggagcc acagctggtt tctttttatta tttgggtgga   1200
accaatcaat tgttttggtcc agctcaggtt tgggggtgaa gtacctggag tggtaggtaa   1260
agggctgcct tatggtgtgg cgggaggagt agttaatata ggggtcatag gccaagttgg    1320
tggaggggt tacaaagttg gcatccaaga taacaacagt ggacccaaca cctctttgat     1380
tagaggtgat ggggtctctg ggtaaaatt catatttagc ctttctaata cggtagtatt     1440
ggaaaggtag gggtagggggg ttggtgccgc ctgaggggg gaggaactgg ccgatgttga     1500
atttcagcta gttaacattc caagatggct gcgagtatcc tccttttatg gtgagtacaa     1560
attctgtaga aaggcgggaa ttgaagatac ccgtctttcg gcgccatctg taacggtttc     1620
tgaaggcggg gtgtgccaaa tatggtcttc tccggaggat gtttccaaga tggctgcggg     1680
ggcgggtcct tcttctgcgg taacgcctcc ttggccacgt catcctataa aagtgaaaga    1740
agtgcgctgc tgtagtatt                                                 1759
```

<210> SEQ ID NO 164
<211> LENGTH: 1759
<212> TYPE: DNA

<213> ORGANISM: Type A PWD circovirus

<400> SEQUENCE: 164

| | | | | | |
|---|---|---|---|---|---|
| accagcgcac | ttcggcagcg | gcagcacctc | ggcagcgtca | gtgaaaatgc | caagcaagaa | 60 |
| aagcggcccg | caaccccata | agaggtgggt | gttcacccct | aataatcctt | ccgaggagga | 120 |
| gaaaaacaaa | atacgggagc | ttccaatctc | ccttttgat | tattttgttt | gcggagagga | 180 |
| aggtttggaa | gagggtagaa | ctcctcacct | ccagggtt | gctaattttg | ctaagaagca | 240 |
| gacttttaac | aaggtgaagt | ggtattttgg | tgcccgctgc | cacatcgaga | aagcgaaagg | 300 |
| aaccgaccag | cagaataaag | aatactgcag | taaagaaggc | cacatactta | tcgagtgtgg | 360 |
| agctccgcgg | aaccagggga | agcgcagcga | cctgtctact | gctgtgagta | ccctttgga | 420 |
| gacgggtct | ttggtgactg | tagccgagca | gttccctgta | acgtatgtga | aaatttccg | 480 |
| cgggctggct | gaacttttga | aagtgagcgg | aagatgcag | aagcgtgatt | ggaagacagc | 540 |
| tgtacacgtc | atagtgggcc | cgcccggttg | tgggaagagc | cagtgggccc | gtaattttgc | 600 |
| tgagcctagc | gacacctact | ggaagcctag | tagaaataag | tggtgggatg | gatatcatgg | 660 |
| agaagaagtt | gttgttttgg | atgattttta | tggctggtta | ccttgggatg | atctactgag | 720 |
| actgtgtgac | cggtatccat | tgactgtaga | gactaaaggc | ggtactgttc | ctttttggc | 780 |
| tcgcagtatt | ttgattacca | gcaatcaggc | cccccaggaa | tggtactcct | caactgctgt | 840 |
| cccagctgta | gaagctctct | atcggaggat | tactacttg | caattttgga | agactgctgg | 900 |
| agaacaatca | acggaggtac | ccgaaggccg | atttgaagca | gtggaccccac | cctgtgccct | 960 |
| tttcccatat | aaaataaatt | actgagtctt | tttgttatc | acatcgtaat | ggtttttatt | 1020 |
| tttatttatt | tagagggtct | tttaggataa | attctctgaa | ttgtacataa | atagtcagcc | 1080 |
| ttaccacata | attttgggct | gtggttgcat | tttggagcgc | atagcccagg | cctgtgtgct | 1140 |
| cgacattggt | gtgggtattt | aaatggagcc | acagctggtt | tcttttatta | tttgggtgga | 1200 |
| accattcaat | tgtttggtcc | agctcaggtt | tgggggtgaa | gtacctggag | tggtaggtaa | 1260 |
| agggctgcct | tatggtgtgg | cgggaggagt | agttaatata | gggtcatag | gccaagttgg | 1320 |
| tggagggggt | tacaaagttg | gcatccaaga | taacaacagt | ggacccaaca | cctctttcat | 1380 |
| tagaggtgat | ggggtctctg | gggtaaaatt | catatttagc | ctttctaata | cggtagtatt | 1440 |
| ggaaaggtag | gggtagggg | ttggtgccgc | ctgagggggg | gaggaactgg | ccgatgttga | 1500 |
| atctgaggtg | gttaacatgc | caagatggct | gcgagtatcc | tccttttatg | gtgattacaa | 1560 |
| attctttaga | aaggcggcaa | ttgaagatac | ccgtctttcg | gcgccatctg | taacggtttc | 1620 |
| tgaaggcggg | gtgtgccaaa | tatggtcttc | tccggaggat | gttccaagga | tggctgcggg | 1680 |
| ggcgggtcct | tcttctgcgg | taacgcctcc | ttggccacgt | catcctataa | aagtgaaaga | 1740 |
| agtgcgctgc | tgtagtatt | | | | | 1759 |

<210> SEQ ID NO 165
<211> LENGTH: 312
<212> TYPE: PRT
<213> ORGANISM: Type A PWD circovirus

<400> SEQUENCE: 165

Met Pro Ser Lys Lys Ser Gly Pro Gln Pro His Lys Arg Trp Val Phe
1               5                   10                  15

Thr Leu Asn Asn Pro Ser Gly Gly Gly Lys Asn Lys Ile Arg Gly Leu
            20                  25                  30

Pro Ile Ser Leu Phe Asp Tyr Phe Val Cys Gly Gly Gly Leu Gly

-continued

```
                35                  40                  45
Gly Gly Arg Thr Pro His Leu Gln Gly Phe Ala Asn Phe Ala Lys Lys
 50                  55                  60
Gln Thr Phe Asn Lys Val Lys Trp Tyr Phe Gly Ala Arg Cys His Ile
 65                  70                  75                  80
Gly Lys Ala Lys Gly Thr Asp Gln Gln Asn Lys Gly Tyr Cys Ser Lys
                 85                  90                  95
Gly Gly His Ile Leu Ile Gly Cys Gly Ala Pro Arg Asn Gln Gly Lys
                100                 105                 110
Arg Ser Asp Leu Ser Thr Ala Val Ser Thr Leu Gly Thr Gly Ser
                115                 120                 125
Leu Val Thr Val Ala Gly Gln Phe Pro Val Thr Tyr Val Arg Asn Phe
130                 135                 140
Arg Gly Leu Ala Gly Leu Leu Lys Val Ser Gly Lys Met Gln Gln Arg
145                 150                 155                 160
Asp Trp Lys Thr Ala Val His Val Ile Val Gly Pro Pro Gly Cys Gly
                165                 170                 175
Lys Ser Gln Trp Ala Arg Asn Phe Ala Gly Pro Arg Asp Thr Tyr Trp
                180                 185                 190
Lys Pro Ser Arg Asn Lys Trp Trp Asp Gly Tyr His Gly Gly Gly Val
                195                 200                 205
Val Val Leu Asp Asp Phe Tyr Gly Trp Leu Pro Trp Asp Asp Leu Leu
                210                 215                 220
Arg Leu Cys Asp Arg Tyr Pro Leu Thr Val Gly Thr Lys Gly Gly Thr
225                 230                 235                 240
Val Pro Phe Leu Ala Arg Ser Ile Leu Ile Thr Ser Asn Gln Ala Pro
                245                 250                 255
Gln Gly Trp Tyr Ser Ser Thr Ala Val Pro Ala Val Gly Ala Leu Tyr
                260                 265                 270
Arg Arg Ile Thr Thr Leu Gln Phe Trp Lys Thr Ala Gly Gly Gln Ser
                275                 280                 285
Thr Gly Val Pro Gly Gly Arg Phe Gly Ala Val Asp Pro Pro Cys Ala
                290                 295                 300
Leu Phe Pro Tyr Lys Ile Asn Tyr
305                 310

<210> SEQ ID NO 166
<211> LENGTH: 312
<212> TYPE: PRT
<213> ORGANISM: Type A PWD circovirus

<400> SEQUENCE: 166

Met Pro Ser Lys Lys Ser Gly Pro Gln Pro His Lys Arg Trp Val Phe
 1                   5

Gly Gly His Ile Leu Ile Gly Cys Gly Ala Pro Arg Asn Gln Gly Lys
                100                 105                 110

Arg Ser Asp Leu Ser Thr Ala Val Ser Thr Leu Leu Gly Thr Gly Ser
            115                 120                 125

Leu Val Thr Val Ala Gly Gln Phe Pro Val Thr Tyr Val Arg Asn Phe
        130                 135                 140

Arg Gly Leu Ala Gly Leu Leu Lys Val Ser Gly Lys Met Gln Gln Arg
145                 150                 155                 160

Asp Trp Lys Thr Ala Val His Val Ile Val Gly Pro Pro Gly Cys Gly
                165                 170                 175

Lys Ser Gln Trp Ala Arg Asn Phe Ala Gly Pro Ser Asp Thr Tyr Trp
            180                 185                 190

Lys Pro Ser Arg Asn Lys Trp Trp Asp Gly Tyr His Gly Gly Gly Val
        195                 200                 205

Val Val Leu Asp Asp Phe Tyr Gly Trp Leu Pro Trp Asp Asp Leu Leu
        210                 215                 220

Arg Leu Cys Asp Arg Tyr Pro Leu Thr Val Gly Thr Lys Gly Gly Thr
225                 230                 235                 240

Val Pro Phe Leu Ala Arg Ser Ile Leu Ile Thr Ser Asn Gln Ala Pro
                245                 250                 255

Gln Gly Trp Tyr Ser Ser Thr Ala Val Pro Ala Val Gly Ala Leu Tyr
            260                 265                 270

Arg Arg Ile Thr Thr Leu Gln Phe Trp Lys Thr Ala Gly Gly Gln Ser
        275                 280                 285

Thr Gly Val Pro Gly Gly Arg Phe Gly Ala Val Asp Pro Pro Cys Ala
        290                 295                 300

Leu Phe Pro Tyr Lys Ile Asn Tyr
305                 310

<210> SEQ ID NO 167
<211> LENGTH: 233
<212> TYPE: PRT
<213> ORGANISM: Type A PWD circovirus

<400> SEQUENCE: 167

Met Thr Trp Pro Arg Arg Tyr Arg Arg Arg Thr Arg Pro Arg
1               5                   10                  15

Ser His Leu Gly Asn Ile Leu Arg Arg Pro Tyr Leu Ala His Pro
            20                  25                  30

Ala Phe Arg Asn Arg Tyr Arg Trp Arg Arg Lys Thr Gly Ile Phe Asn
        35                  40                  45

Ser Arg Leu Ser Thr Glu Phe Val Leu Thr Ile Arg Gly Gly His Ser
50                  55                  60

Gln Pro Ser Trp Asn Val Asn Tyr Leu Lys Phe Asn Ile Gly Gln Phe
65                  70                  75                  80

Leu Pro Pro Ser Gly Gly Thr Asn Pro Leu Pro Phe Gln Tyr
        85                  90                  95

Tyr Arg Ile Arg Lys Ala Lys Tyr Glu Phe Tyr Pro Arg Asp Pro Ile
                100                 105                 110

Thr Ser Asn Gln Arg Gly Val Gly Ser Thr Val Val Ile Leu Asp Ala
            115                 120                 125

Asn Phe Val Thr Pro Ser Thr Asn Leu Ala Tyr Asp Pro Tyr Ile Asn
        130                 135                 140

Tyr Ser Ser Arg His Thr Ile Arg Gln Pro Phe Thr Tyr His Ser Arg
145                 150                 155                 160

-continued

Tyr Phe Thr Pro Lys Pro Glu Leu Asp Gln Thr Ile Asp Trp Phe His
                165                 170                 175

Pro Asn Asn Lys Arg Asn Gln Leu Trp Leu His Leu Asn Thr His Thr
            180                 185                 190

Asn Val Glu His Thr Gly Leu Gly Tyr Ala Leu Gln Asn Ala Ala Thr
        195                 200                 205

Ala Gln Asn Tyr Val Val Arg Leu Thr Ile Tyr Val Gln Phe Arg Glu
    210                 215                 220

Phe Ile Leu Lys Asp Pro Leu Asn Lys
225                 230

<210> SEQ ID NO 168
<211> LENGTH: 233
<212> TYPE: PRT
<213> ORGANISM: Type A PWD circovirus

<400> SEQUENCE: 168

Met Thr Trp Pro Arg Arg Arg Tyr Arg Arg Arg Thr Arg Pro Arg
1               5                   10                  15

Ser His Leu Gly Asn Ile Leu Arg Arg Arg Pro Tyr Leu Val His Pro
            20                  25                  30

Ala Phe Arg Asn Arg Tyr Arg Trp Arg Arg Lys Thr Gly Ile Phe Asn
        35                  40                  45

Cys Arg Leu Ser Lys Glu Phe Val Ile Thr Ile Arg Gly Gly His Ser
    50                  55                  60

Gln Pro Ser Trp Ile Val Asn Ile Leu Arg Phe Asn Ile Gly Gln Phe
65                  70                  75                  80

Leu Pro Pro Ser Gly Gly Thr Asn Pro Leu Pro Leu Pro Phe Gln Tyr
                85                  90                  95

Tyr Arg Ile Arg Lys Ala Lys Tyr Glu Phe Tyr Pro Arg Asp Pro Ile
            100                 105                 110

Thr Ser Asn Glu Arg Gly Val Gly Ser Thr Val Val Ile Leu Asp Ala
        115                 120                 125

Asn Phe Val Thr Pro Ser Thr Asn Leu Ala Tyr Asp Pro Tyr Ile Asn
    130                 135                 140

Tyr Ser Ser Arg His Thr Ile Arg Gln Pro Phe Thr Tyr His Ser Arg
145                 150                 155                 160

Tyr Phe Thr Pro Lys Pro Glu Leu Asp Gln Thr Ile Glu Trp Phe His
                165                 170                 175

Pro Asn Asn Lys Arg Asn Gln Leu Trp Leu His Leu Asn Thr His Thr
            180                 185                 190

Asn Val Glu His Thr Gly Leu Gly Tyr Ala Leu Gln Asn Ala Ala Thr
        195                 200                 205

Ala Gln Asn Tyr Val Val Arg Leu Thr Ile Tyr Val Gln Phe Arg Glu
    210                 215                 220

Phe Ile Leu Lys Asp Pro Leu Asn Lys
225                 230

<210> SEQ ID NO 169
<211> LENGTH: 206
<212> TYPE: PRT
<213> ORGANISM: Type A PWD circovirus

<400> SEQUENCE: 169

Met Ile Ser Ile Pro Pro Leu Ile Ser Thr Arg Leu Pro Val Gly Val
1               5                   10                  15

```
Pro Arg Leu Ser Lys Ile Thr Gly Pro Leu Ala Leu Pro Thr Thr Gly
            20                  25                  30

Arg Ala His Tyr Asp Val Tyr Ser Cys Leu Pro Ile Thr Leu Leu His
        35                  40                  45

Leu Pro Ala His Phe Gln Lys Phe Ser Gln Pro Ala Glu Ile Ser His
    50                  55                  60

Ile Arg Tyr Arg Glu Leu Leu Gly Tyr Ser His Gln Arg Pro Arg Leu
65                  70                  75                  80

Gln Lys Gly Thr His Ser Ser Arg Gln Val Ala Ala Leu Pro Leu Val
                85                  90                  95

Pro Arg Ser Ser Thr Leu Asp Lys Tyr Val Ala Phe Phe Thr Ala Val
            100                 105                 110

Phe Phe Ile Leu Leu Val Gly Ser Phe Arg Phe Leu Asp Val Ala Ala
        115                 120                 125

Gly Thr Lys Ile Pro Leu His Leu Val Lys Ser Leu Leu Leu Ser Lys
    130                 135                 140

Ile Arg Lys Pro Leu Glu Val Arg Ser Ser Thr Leu Phe Gln Thr Phe
145                 150                 155                 160

Leu Ser Ala Asn Lys Ile Ile Lys Lys Gly Asp Trp Lys Leu Pro Tyr
                165                 170                 175

Phe Val Phe Leu Leu Gly Arg Ile Ile Lys Gly Glu His Pro Pro
            180                 185                 190

Leu Met Gly Leu Arg Ala Ala Phe Leu Ala Trp His Phe His
        195                 200                 205

<210> SEQ ID NO 170
<211> LENGTH: 206
<212> TYPE: PRT
<213> ORGANISM: Type A PWD circovirus

<400> SEQUENCE: 170

Met Ile Ser Ile Pro Pro Leu Ile Ser Thr Arg Leu Pro Val Gly Val
1               5                   10                  15

Ala Arg Leu Ser Lys Ile Thr Gly Pro Leu Ala Leu Pro Thr Thr Gly
            20                  25                  30

Arg Ala His Tyr Asp Val Tyr Ser Cys Leu Pro Ile Thr Leu Leu His
        35                  40                  45

Leu Pro Ala His Phe Gln Lys Phe Ser Gln Pro Ala Glu Ile Ser His
    50                  55                  60

Ile Arg Tyr Arg Glu Leu Leu Gly Tyr Ser His Gln Arg Pro Arg Leu
65                  70                  75                  80

Gln Lys Gly Thr His Ser Ser Arg Gln Val Ala Ala Leu Pro Leu Val
                85                  90                  95

Pro Arg Ser Ser Thr Leu Asp Lys Tyr Val Ala Phe Phe Thr Ala Val
            100                 105                 110

Phe Phe Ile Leu Leu Val Gly Ser Phe Arg Phe Leu Asp Val Ala Ala
        115                 120                 125

Gly Thr Lys Ile Pro Leu His Leu Val Lys Ser Leu Leu Leu Ser Lys
    130                 135                 140

Ile Ser Lys Pro Leu Glu Val Ser Ser Ser Thr Leu Phe Gln Thr Phe
145                 150                 155                 160

Leu Ser Ala Asn Lys Ile Ile Lys Lys Gly Asp Trp Lys Leu Pro Tyr
                165                 170                 175
```

```
                              -continued
Phe Val Phe Leu Leu Leu Gly Arg Ile Ile Lys Gly Glu His Pro Pro
            180                 185                 190

Leu Met Gly Leu Arg Ala Ala Phe Leu Ala Trp His Phe His
        195                 200                 205
```

We claim:

1. A vector capable of expressing at least one polypeptide encoded by a nucleic acid sequence comprising a sequence having at least 90% sequence identity to SEQ ID NO: 25 and at least one polypeptide encoded by a nucleic acid sequence comprising a sequence having at least 90% sequence identity to SEQ ID NO: 23.

2. The vector of claim 1, wherein the vector is a baculovirus vector.

3. A vector capable of expressing at least one polypeptide encoded by a nucleic acid sequence comprising a sequence having at least 95% sequence identity to SEQ ID NO: 25 and at least one polypeptide encoded by a nucleic acid sequence comprising a sequence having at least 90% sequence identity to SEQ ID NO: 23.

4. The vector of claim 3, wherein the vector is a baculovirus vector.

5. A vector capable of expressing at least one polypeptide encoded by a nucleic acid sequence comprising a sequence having at least 90% sequence identity to SEQ ID NO: 25 and at least one polypeptide encoded by a nucleic acid sequence comprising a sequence having at least 95% sequence identity to SEQ ID NO: 23.

6. The vector of claim 5, wherein the vector is a baculovirus vector.

7. A vector capable of expressing at least one polypeptide encoded by a nucleic acid sequence comprising a sequence having at least 95% sequence identity to SEQ ID NO: 25 and at least one polypeptide encoded by a nucleic acid sequence comprising a sequence having at least 95% sequence identity to SEQ ID NO: 23.

8. The vector of claim 7, wherein the vector is a baculovirus vector.

9. A vaccine composition, comprising the vector of claim 1 and a pharmaceutically or veterinarily acceptable carrier, wherein said nucleic acid sequence encodes an immunogenic protein that induces a protective response effective against infection by a piglet weight loss disease virus.

10. A vaccine composition, comprising the vector of claim 2 and a pharmaceutically or veterinarily acceptable carrier, wherein said nucleic acid sequence encodes an immunogenic protein that induces a protective response effective against infection by a piglet weight loss disease virus.

11. A vaccine composition, comprising the vector of claim 3 and a pharmaceutically or veterinarily acceptable carrier, wherein said nucleic acid sequence encodes an immunogenic protein that induces a protective response effective against infection by a piglet weight loss disease virus.

12. A vaccine composition, comprising the vector of claim 4 and a pharmaceutically or veterinarily acceptable carrier, wherein said nucleic acid sequence encodes an immunogenic protein that induces a protective response effective against infection by a piglet weight loss disease virus.

13. A vaccine composition, comprising the vector of claim 5 and a pharmaceutically or veterinarily acceptable carrier, wherein said nucleic acid sequence encodes an immunogenic protein that induces a protective response effective against infection by a piglet weight loss disease virus.

14. A vaccine composition, comprising the vector of claim 6 and a pharmaceutically or veterinarily acceptable carrier, wherein said nucleic acid sequence encodes an immunogenic protein that induces a protective response effective against infection by a piglet weight loss disease virus.

15. A vaccine composition, comprising the vector of claim 7 and a pharmaceutically or veterinarily acceptable carrier, wherein said nucleic acid sequence encodes an immunogenic protein that induces a protective response effective against infection by a piglet weight loss disease virus.

16. A vaccine composition, comprising the vector of claim 8 and a pharmaceutically or veterinarily acceptable carrier, wherein said nucleic acid sequence encodes an immunogenic protein that induces a protective response effective against infection by a piglet weight loss disease virus.

17. An immunogenic composition, comprising an immunizing amount of the vector of claim 1 and a pharmaceutically or veterinarily acceptable carrier.

18. An immunogenic composition, comprising an immunizing amount of the vector of claim 2 and a pharmaceutically or veterinarily acceptable carrier.

19. An immunogenic composition, comprising an immunizing amount of the vector of claim 3 and a pharmaceutically or veterinarily acceptable carrier.

20. An immunogenic composition, comprising an immunizing amount of the vector of claim 4 and a pharmaceutically or veterinarily acceptable carrier.

21. An immunogenic composition, comprising an immunizing amount of the vector of claim 5 and a pharmaceutically or veterinarily acceptable carrier.

22. An immunogenic composition, comprising an immunizing amount of the vector of claim 6 and a pharmaceutically or veterinarily acceptable carrier.

23. An immunogenic composition, comprising an immunizing amount of the vector of claim 7 and a pharmaceutically or veterinarily acceptable carrier.

24. An immunogenic composition, comprising an immunizing amount of the vector of claim 8 and a pharmaceutically or veterinarily acceptable carrier.

25. A method for treating or preventing porcine circovirus type B infection in a mammalian subject, comprising administering to said subject a therapeutically effective amount of a vaccine according to claim 9.

26. A method for treating or preventing porcine circovirus type B infection in a mammalian subject, comprising administering to said subject a therapeutically effective amount of a vaccine according to claim 10.

27. A method for treating or preventing porcine circovirus type B infection in a mammalian subject, comprising administering to said subject a therapeutically effective amount of a vaccine according to claim 11.

28. A method for treating or preventing porcine circovirus type B infection in a mammalian subject, comprising administering to said subject a therapeutically effective amount of a vaccine according to claim 12.

29. A method for treating or preventing porcine circovirus type B infection in a mammalian subject, comprising administering to said subject a therapeutically effective amount of a vaccine according to claim 13.

30. A method for treating or preventing porcine circovirus type B infection in a mammalian subject, comprising administering to said subject a therapeutically effective amount of a vaccine according to claim 14.

31. A method for treating or preventing porcine circovirus type B infection in a mammalian subject, comprising administering to said subject a therapeutically effective amount of a vaccine according to claim 15.

32. A method for treating or preventing porcine circovirus type B infection in a mammalian subject, comprising administering to said subject a therapeutically effective amount of a vaccine according to claim 16.

33. A recombinant polynucleotide comprising a sequence having at least 90% sequence identity to SEQ ID NO: 25 and at least 90% sequence identity to SEQ ID NO: 23.

34. A recombinant polynucleotide comprising a sequence having at least 95% sequence identity to SEQ ID NO: 25 and at least 90% sequence identity to SEQ ID NO: 23.

35. A recombinant polynucleotide comprising a sequence having at least 90% sequence identity to SEQ ID NO: 25 and at least 95% sequence identity to SEQ ID NO: 23.

36. A recombinant polynucleotide comprising a sequence having at least 95% sequence identity to SEQ ID NO: 25 and at least 95% sequence identity to SEQ ID NO: 23.

37. A method for detecting and quantifying at least one polynucleotide of a porcine circovirus type B (PCVB) by a hybridization method, wherein said polynucleotide comprises a sequence with at least 90% identity to SEQ ID NO: 25 and at least 90% sequence identity to SEQ ID NO: 23.

38. A method for detecting and quantifying at least one polynucleotide of a porcine circovirus type B (PCVB) by a hybridization method, wherein said polynucleotide comprises a sequence with at least 95% identity to SEQ ID NO: 25 and at least 90% sequence identity to SEQ ID NO: 23.

39. A method for detecting and quantifying at least one polynucleotide of a porcine circovirus type B (PCVB) by a hybridization method, wherein said polynucleotide comprises a sequence with at least 90% identity to SEQ ID NO: 25 and at least 95% sequence identity to SEQ ID NO: 23.

40. A method for detecting and quantifying at least one polynucleotide of a porcine circovirus type B (PCVB) by a hybridization method, wherein said polynucleotide comprises a sequence with at least 95% identity to SEQ ID NO: 25 and at least 95% sequence identity to SEQ ID NO: 23.

41. A method for expressing ORF'1 and ORF'2 of a porcine circovirus type B (PCVB) in vitro, comprising transfecting cells in culture with the vector of claim 1.

42. A method for expressing ORF'1 and ORF'2 of a porcine circovirus type B (PCVB) in vitro, comprising transfecting cells in culture with the vector of claim 2.

43. The method of claim 42, wherein the cells are SF9 cells.

44. A method for expressing ORF'1 and ORF'2 of a porcine circovirus type B (PCVB) in vitro, comprising transfecting cells in culture with the vector of claim 3.

45. A method for expressing ORF'1 and ORF'2 of a porcine circovirus type B (PCVB) in vitro, comprising transfecting cells in culture with the vector of claim 4.

46. The method of claim 45, wherein the cells are SF9 cells.

47. A method for expressing ORF'1 and ORF'2 of a porcine circovirus type B (PCVB) in vitro, comprising transfecting cells in culture with the vector of claim 5.

48. A method for expressing ORF'1 and ORF'2 of a porcine circovirus type B (PCVB) in vitro, comprising transfecting cells in culture with the vector of claim 6.

49. The method of claim 48, wherein the cells are SF9 cells.

50. A method for expressing ORF'1 and ORF'2 of a porcine circovirus type B (PCVB) in vitro, comprising transfecting cells in culture with the vector of claim 7.

51. A method for expressing ORF'1 and ORF'2 of a porcine circovirus type B (PCVB) in vitro, comprising transfecting cells in culture with the vector of claim 8.

52. The method of claim 51, wherein the cells are SF9 cells.

53. A method for expressing ORF'1 and ORF'2 of a porcine circovirus type B (PCVB) in vivo, comprising administering the vector of claim 1 to a mammal.

54. The method of claim 53, wherein the mammal is a pig.

55. A method for expressing ORF'1 and ORF'2 of a porcine circovirus type B (PCVB) in vivo, comprising administering the vector of claim 2 to a mammal.

56. The method of claim 55, wherein the mammal is a pig.

57. A method for expressing ORF'1 and ORF'2 of a porcine circovirus type B (PCVB) in vivo, comprising administering the vector of claim 3 to a mammal.

58. The method of claim 57, wherein the mammal is a pig.

59. A method for expressing ORF'1 and ORF'2 of a porcine circovirus type B (PCVB) in vivo, comprising administering the vector of claim 4 to a mammal.

60. The method of claim 59, wherein the mammal is a pig.

61. A method for expressing ORF'1 and ORF'2 of a porcine circovirus type B (PCVB) in vivo, comprising administering the vector of claim 5 to a mammal.

62. The method of claim 61, wherein the mammal is a pig.

63. A method for expressing ORF'1 and ORF'2 of a porcine circovirus type B (PCVB) in vivo, comprising administering the vector of claim 6 to a mammal.

64. The method of claim 63, wherein the mammal is a pig.

65. A method for expressing ORF'1 and ORF'2 of a porcine circovirus type B (PCVB) in vivo, comprising administering the vector of claim 7 to a mammal.

66. The method of claim 65, wherein the mammal is a pig.

67. A method for expressing ORF'1 and ORF'2 of a porcine circovirus type B (PCVB) in vivo, comprising administering the vector of claim 66 to a mammal.

68. The method of claim 67, wherein the mammal is a pig.

* * * * *

UNITED STATES PATENT AND TRADEMARK OFFICE
CERTIFICATE OF CORRECTION

PATENT NO. : 7,425,444 B2 Page 1 of 1
APPLICATION NO. : 11/588306
DATED : September 16, 2008
INVENTOR(S) : Andre Jestin et al.

It is certified that error appears in the above-identified patent and that said Letters Patent is hereby corrected as shown below:

On the Title Page, Item [73] Assignee, after "Wyeth" please insert --Madison, New Jersey--.

Signed and Sealed this

Second Day of December, 2008

JON W. DUDAS
*Director of the United States Patent and Trademark Office*